(12) United States Patent
Law et al.

(10) Patent No.: US 11,357,873 B2
(45) Date of Patent: Jun. 14, 2022

(54) CHIRAL CYCLEN COMPOUNDS AND THEIR USES

(71) Applicant: THE HONG KONG POLYTECHNIC UNIVERSITY, Hong Kong (CN)

(72) Inventors: Ga-Lai Law, Hong Kong (CN); Lixiong Dai, Hong Kong (CN)

(73) Assignee: THE HONG KONG POLYTECHNIC UNIVERSITY, Hong Kong (CN)

( * ) Notice: Subject to any disclaimer, the term of this patent is extended or adjusted under 35 U.S.C. 154(b) by 579 days.

(21) Appl. No.: 16/334,464

(22) PCT Filed: Jun. 23, 2017

(86) PCT No.: PCT/IB2017/053771
§ 371 (c)(1),
(2) Date: Mar. 19, 2019

(87) PCT Pub. No.: WO2018/051197
PCT Pub. Date: Mar. 22, 2018

(65) Prior Publication Data
US 2021/0283278 A1    Sep. 16, 2021

Related U.S. Application Data

(60) Provisional application No. 62/396,785, filed on Sep. 19, 2016.

(51) Int. Cl.
| | |
|---|---|
| *A61K 51/00* | (2006.01) |
| *A61M 36/14* | (2006.01) |
| *A61K 51/04* | (2006.01) |
| *A61K 51/08* | (2006.01) |
| *C07D 257/02* | (2006.01) |
| *C07F 5/00* | (2006.01) |

(52) U.S. Cl.
CPC ........ *A61K 51/0482* (2013.01); *A61K 51/088* (2013.01); *C07D 257/02* (2013.01); *C07F 5/003* (2013.01)

(58) Field of Classification Search
CPC .............. A61K 51/0482; A61K 51/088; C07D 257/02; C07F 5/003
USPC ........................................................ 424/1.69
See application file for complete search history.

(56) References Cited

U.S. PATENT DOCUMENTS

2006/0210479 A1*  9/2006  Young ................... C07F 9/6561
                                                      424/9.363

FOREIGN PATENT DOCUMENTS

| CN | 1795015 A | 6/2006 |
|---|---|---|
| CN | 1809386 A | 7/2006 |
| CN | 100999495 A | 7/2007 |
| CN | 101400371 A | 4/2009 |
| CN | 102827149 A | 12/2012 |
| CN | 103242255 A | 8/2013 |
| CN | 104447598 A | 3/2015 |
| EP | 0872479 A1 | 10/1998 |
| JP | 2007521254 A | 8/2007 |
| WO | 1995031444 A1 | 11/1995 |
| WO | 2016/046793 A3 | 6/2016 |

OTHER PUBLICATIONS

Extended European Search Report of EP application No. 17850361.1 issued from the European Patent Office dated Aug. 12, 2020.
Atsarkin et al.; Direct Measurement of Fast Electron Spin-Lattice Relaxation: Method and Application to Nitroxide Radical Solutions and Gd3+ Contrast Agents; The Journal of Physical Chemistry A; Oct. 18, 2001; vol. 105, No. 41; pp. 9323-9327; American Chemical Society.
Kobayashi et al.; HBF4 and HBr Salts of New Chiral Cyclens; Acta Crystallographica Section C; Feb. 15, 1994; pp. 306-312; vol. C50, Part 2; International Union of Crystallography.
Kobayashi et al.; Crystal Structure of 2(S),5(S),8(S), 11(S)-1,4,7,10-tetraethyl-2,5,8,11-tetraisobutyl-1,4,7,10-tetraazacyclododecane and Its Analog; Analytical Sciences; Dec. 1996; pp. 1003-1004; vol. 12. No. 6; The Japan Society for Analytical Chemistry.
Dai et al.; Synthesis of Water-soluble Chiral DOTA Lanthanide Complexes with Predominantly Twisted Square Antiprism Isomers; Mar. 26, 2018; State Key Laboratory of Chemical Biology and Drug Discovery, Department of Applied Biology and Chemical Technology, The Hong Kong Polytechnic University.
Dai et al.; New Class of Bright and Highly Stable Chiral Cyclen Europium Complexes for Circularly Polarized Luminescence Applications; Inorganic Chemistry; Aug. 18, 2016; pp. 9065-9070; vol. 55, Issue 17; ACS Publications.
Ranganathan et al.; Polymethylated DOTA Ligands. 1. Synthesis of Rigidified Ligands and Studies on the Effects of Alkyl Substitution on Acid-Base Properties and Conformational Mobility; Inorganic Chemistry; Nov. 15, 2002; pp. 6846-6855; vol. 41, Issue 25; ACS Publications.
Ranganathan et al.; Polymethylated DOTA Ligands. 2. Synthesis of Rigidified Lanthanide Chelates and Studies on the Effect of Alkyl Substitution on Conformational Mobility and Relaxivity; Inorganic Chemistry; Nov. 15, 2002; pp. 6856-6866; vol. 41, Issue 25; ACS Publications.

(Continued)

*Primary Examiner* — Michael G. Hartley
*Assistant Examiner* — Sean R Donohue
(74) *Attorney, Agent, or Firm* — Spruson & Ferguson (Hong Kong) Limited

(57) ABSTRACT

The present invention relates to the preparation of a series of chiral DOTA, DO3A, DO2A, DO1A, cyclen and their metal complexes, which display properties superior to those of previous DOTA-based compounds, and hence are potentially valuable as a platform for diagnostic applications. The chiral DOTAs reveal a high abundance of twisted square antiprism (TSA) geometry favoring them to be used as potential MRI contrast agents, whereas their rapid labelling properties at mild conditions make them excellent candidates for use as radiometal chelators.

9 Claims, 57 Drawing Sheets

(56) References Cited

OTHER PUBLICATIONS

Tashiro et al.; Chiral Recognition of r-Amino Acids by an Optically Active (2S,5S,8S,11S)-2,5,8,11-Tetraethyl Cyclen Cobalt(III) Complex; Inorganic Chemistry; Nov. 29, 2010; pp. 4-6; vol. 50, Issue 1; ACS Publications.

Anelli et al.; Gd(III) complexes of poly(hydroxymethyl)substituted derivatives of 1,4,7,10-tetraazacyclododecane-1,4,7,10-tetraacetic acid; Inorganica Chimica Acta; May 28, 2011; pp. 218-229; vol. 317, Issues 1-2; Elsevier.

Kamioka et al.; Synthesis of chiral polyazamacrocycles of variable ring size; Organic & Biomolecular Chemistry; Apr. 1, 2010; pp. 2529-2536; vol. 8, Issue 11; The Royal Society of Chemistry.

Kamioka et al.; Chiral Tetraazamacrocycles Having Four Pendant-Arms; Organic Letters; May 11, 2009; pp. 2289-2292; vol. 11, Issue 11; ACS Publications.

Dai et al.; Chiral DOTA chelators as an improved platform for biomedical imaging and therapy applications; Nature Communications; Feb. 27, 2018; vol. 9, Article No. 857; Nature.

Tsuboyama et al.; Cyclic tetramers of chiral aziridines. III. Ring conformation.; Tetrahedron Letters; 1977; pp. 4603-4606; vol. 18, Issue 52; Elsevier.

Office Action of JP2019-515409 issued from the Japan Patent Office dated May 13, 2021.

\* cited by examiner

Figure 11
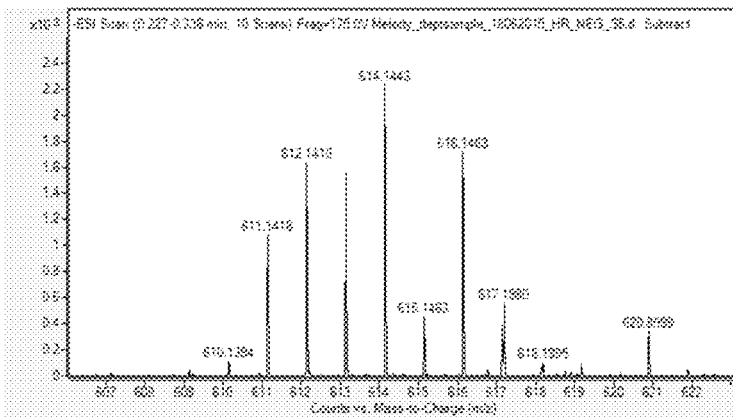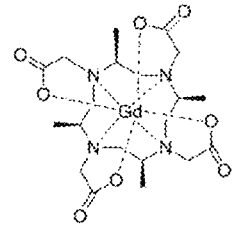
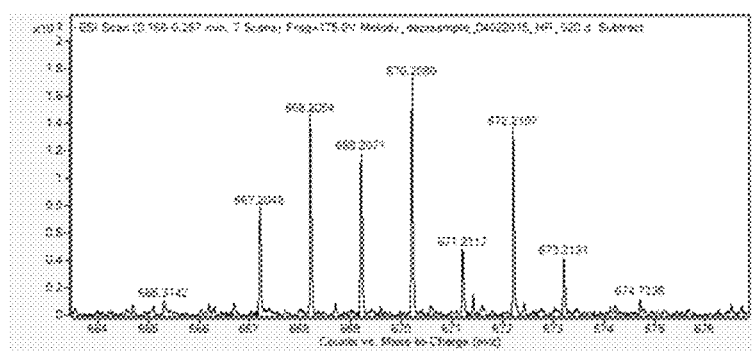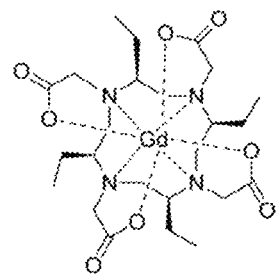
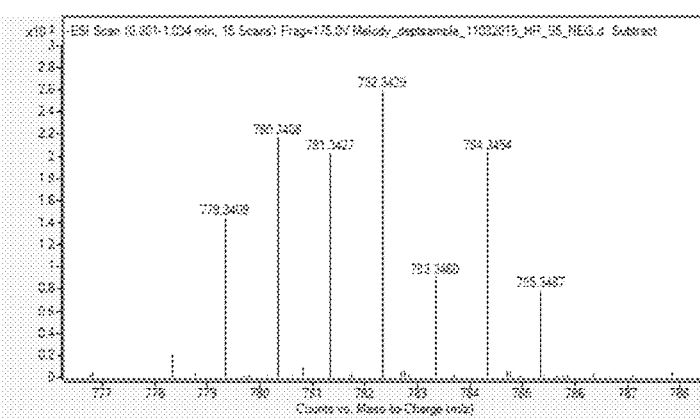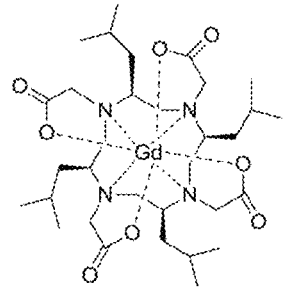
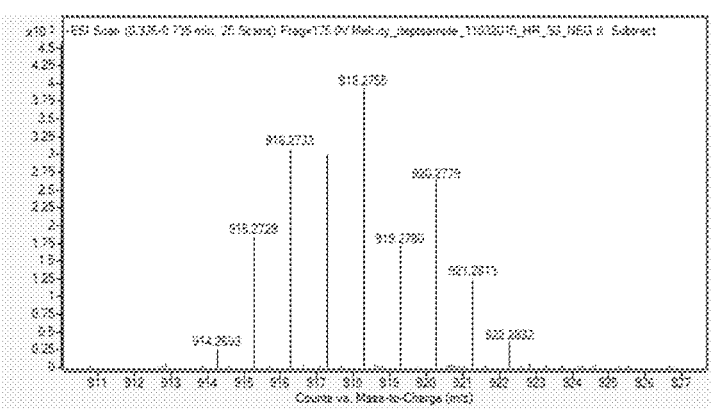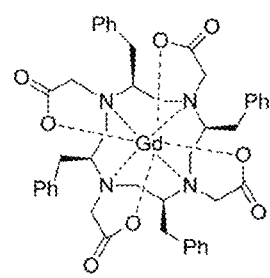

Figure 12
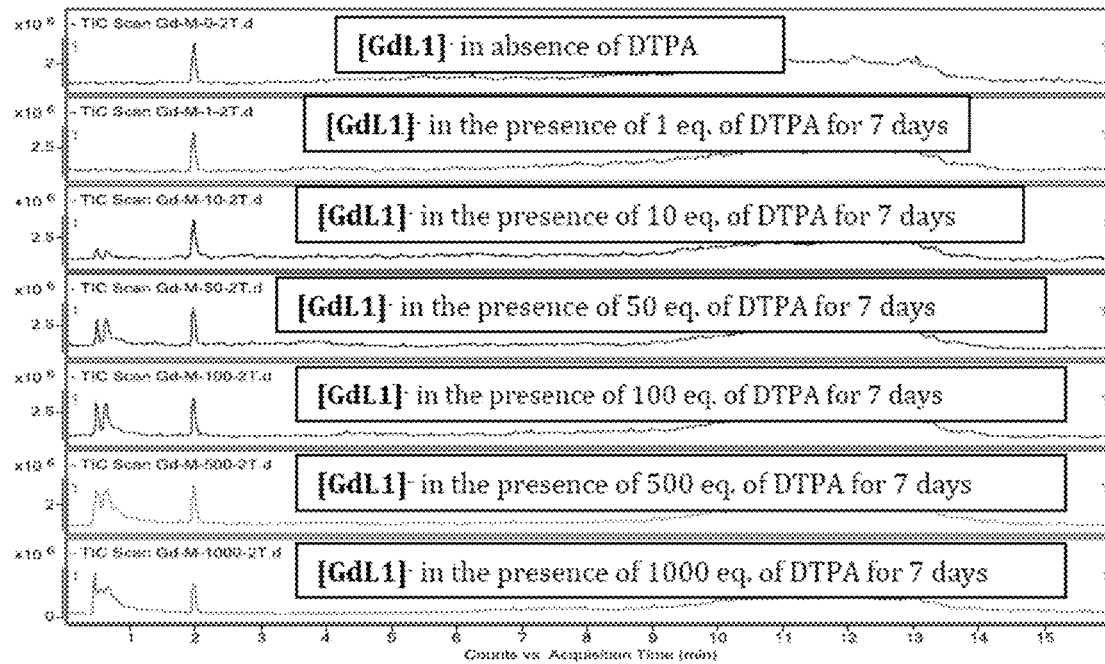
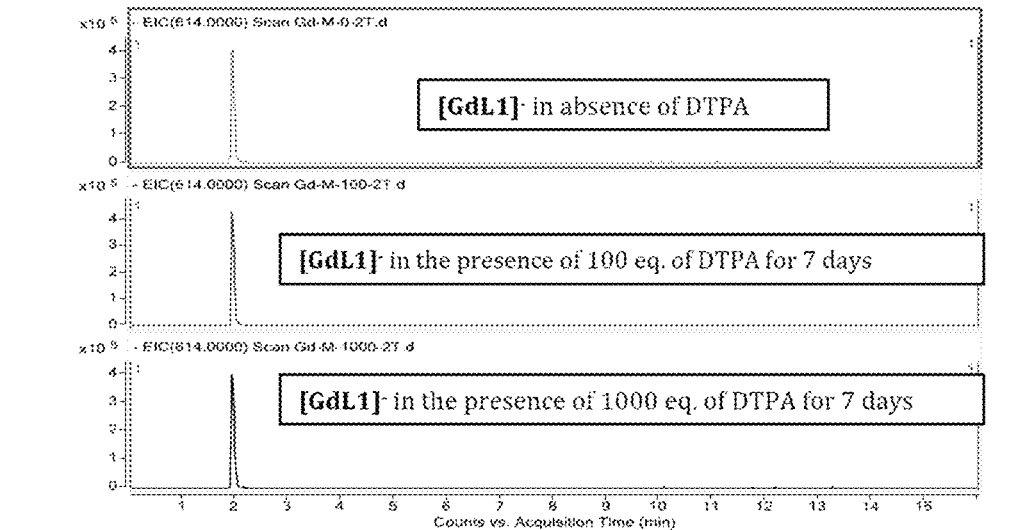
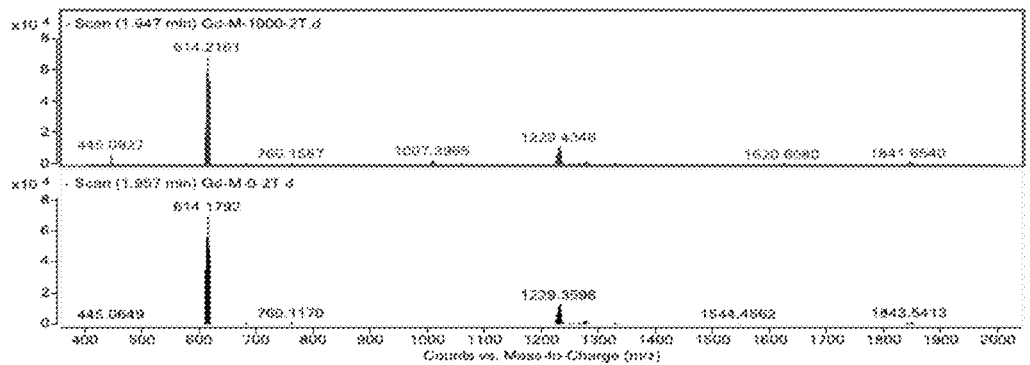

Figure 13
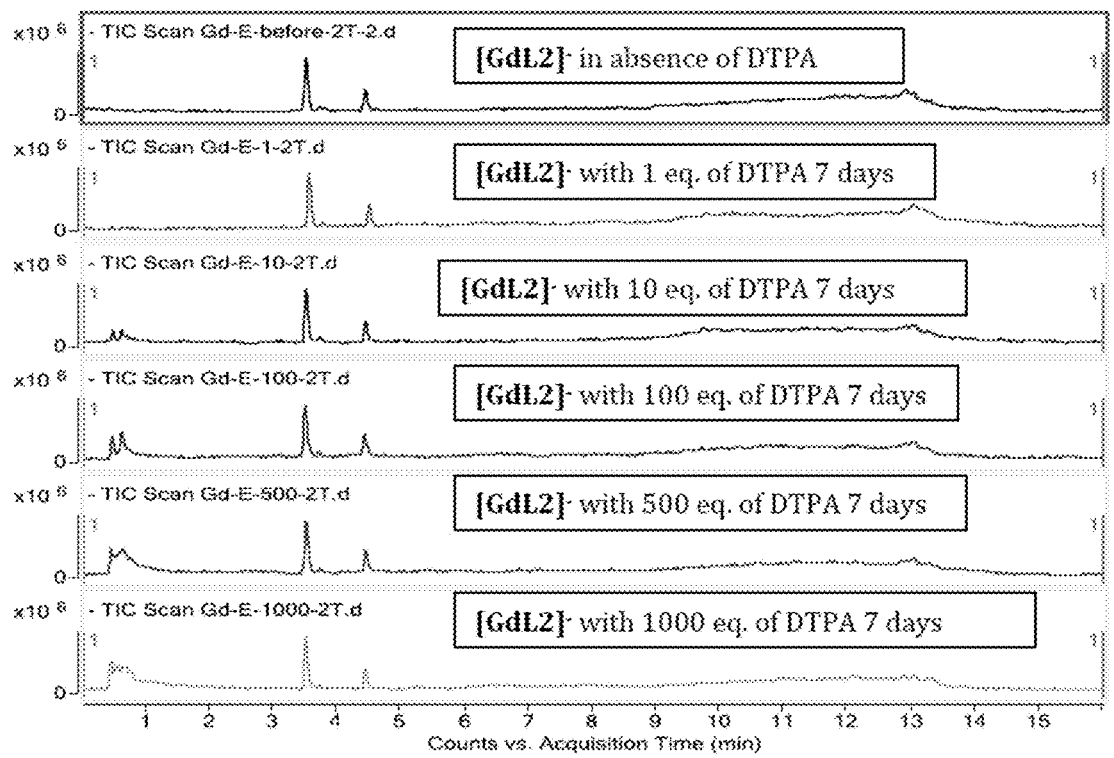
Extracted spectra with MS: 670.00
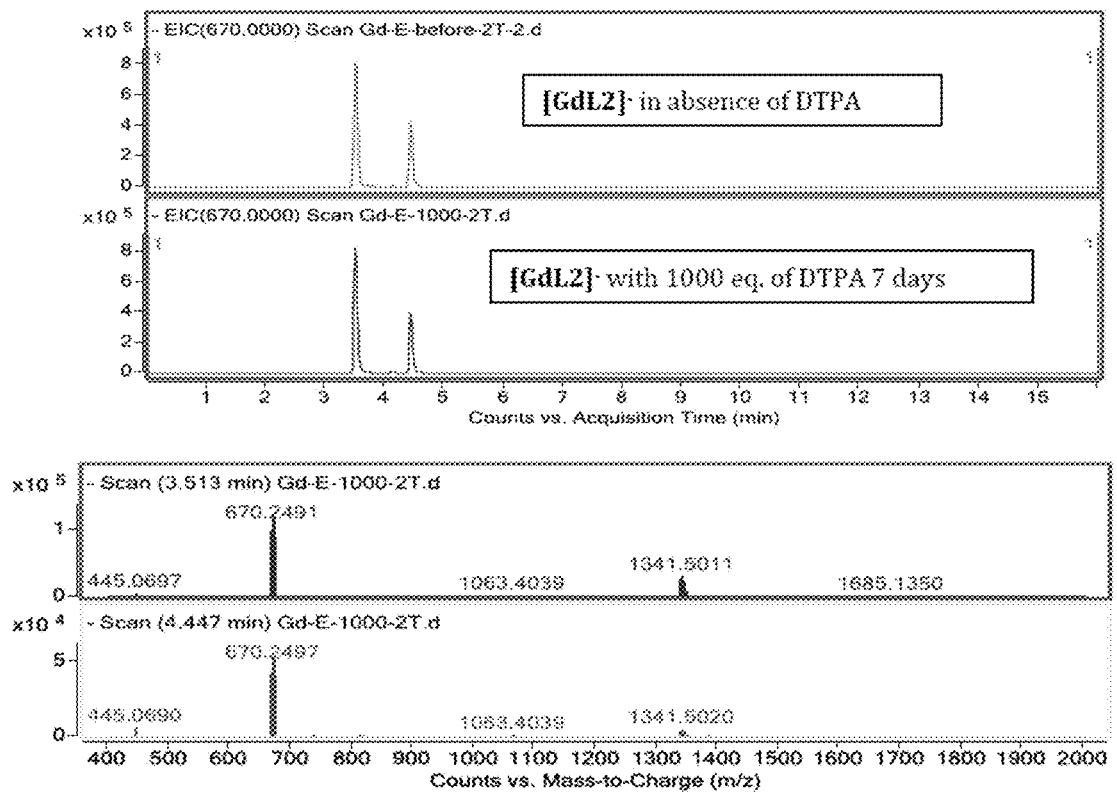

Complex 11

Figure 35
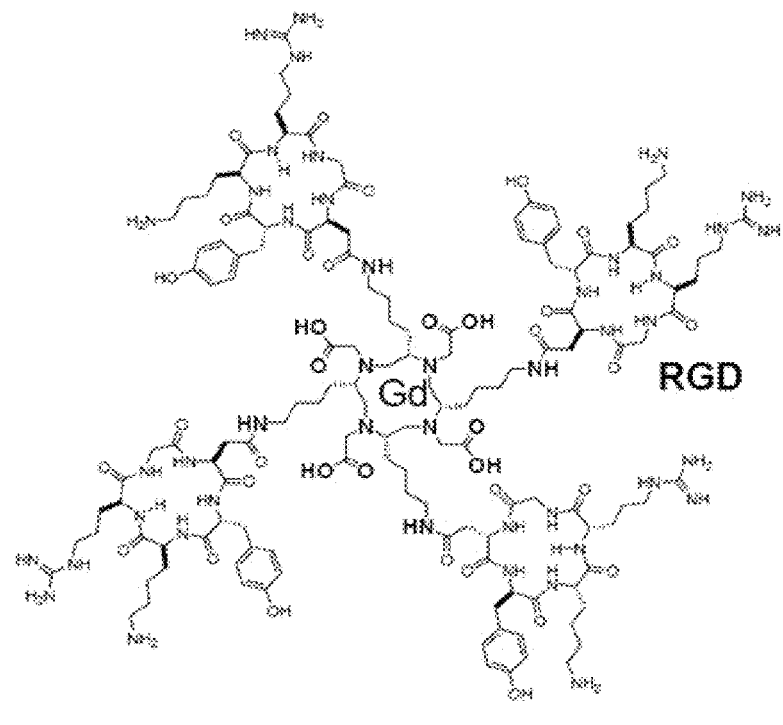
Chiral DOTA-RGD
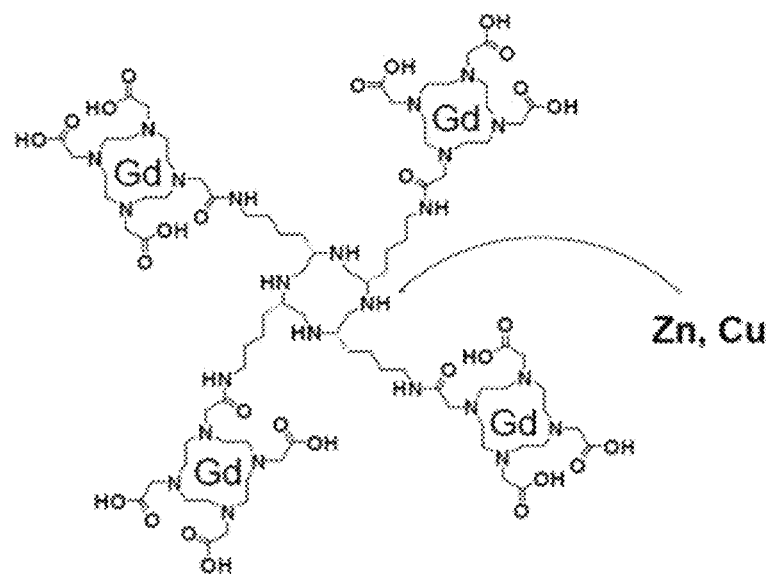
Chiral Cyclen-DOTA

Figure 36B
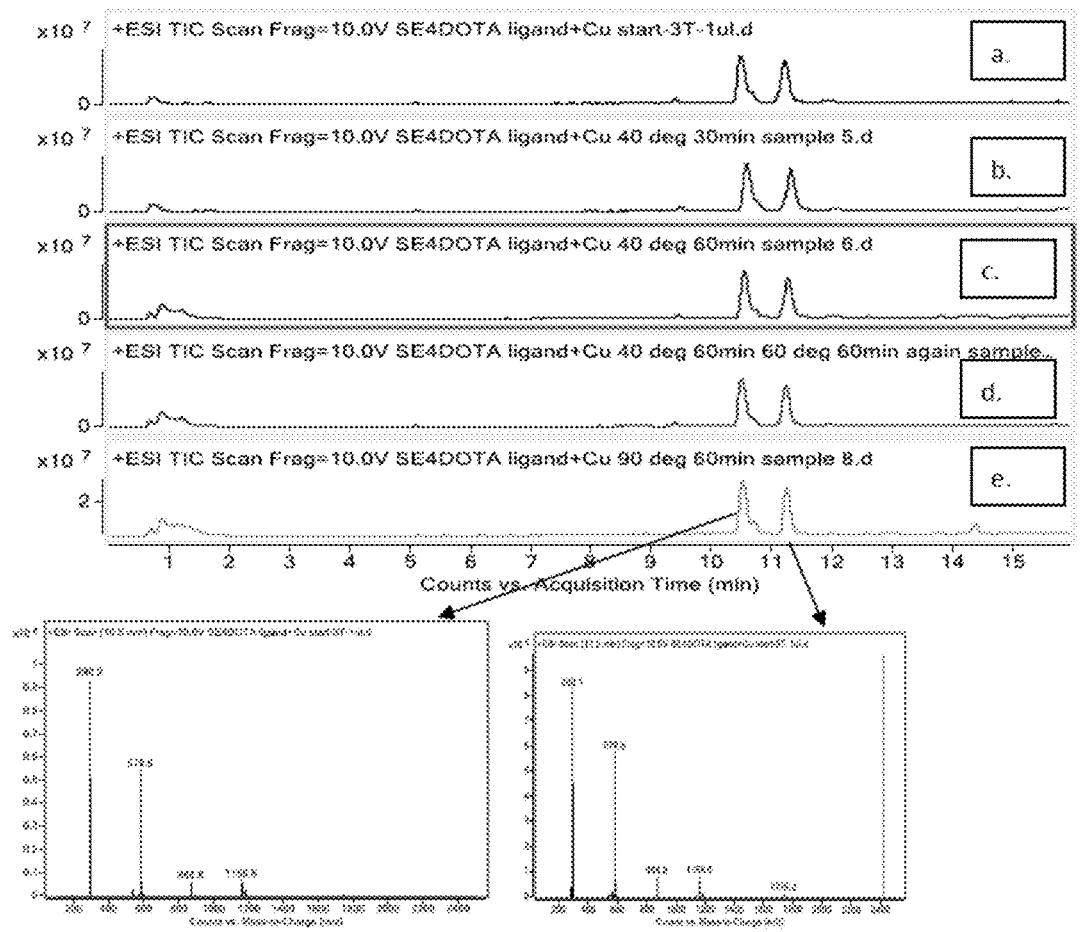
Comparison a. and d.
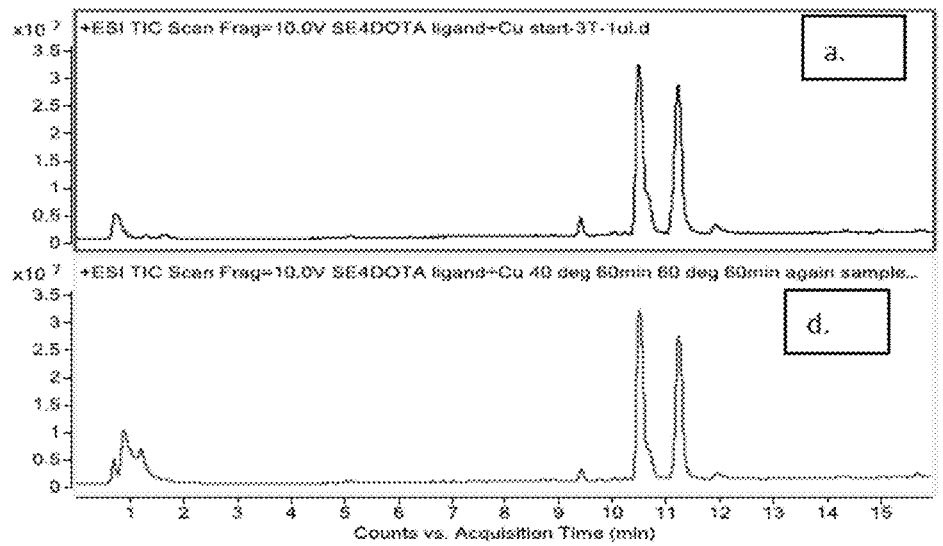

Figure 38A
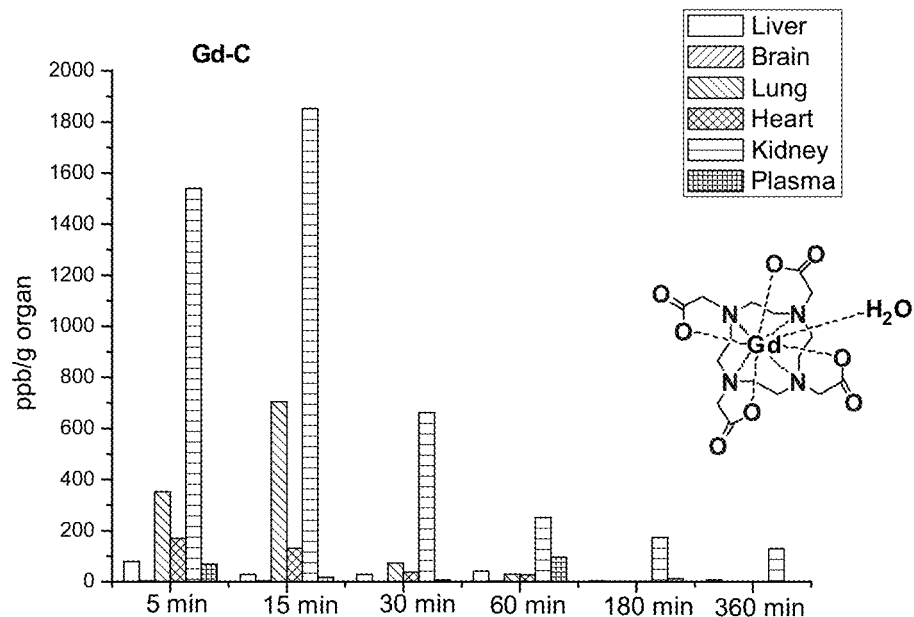
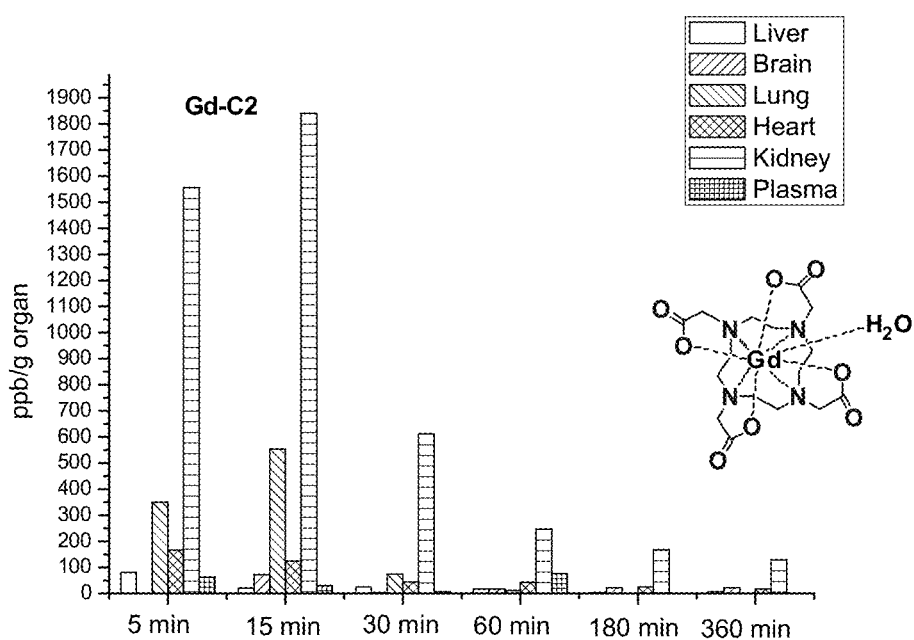

Figure 38B
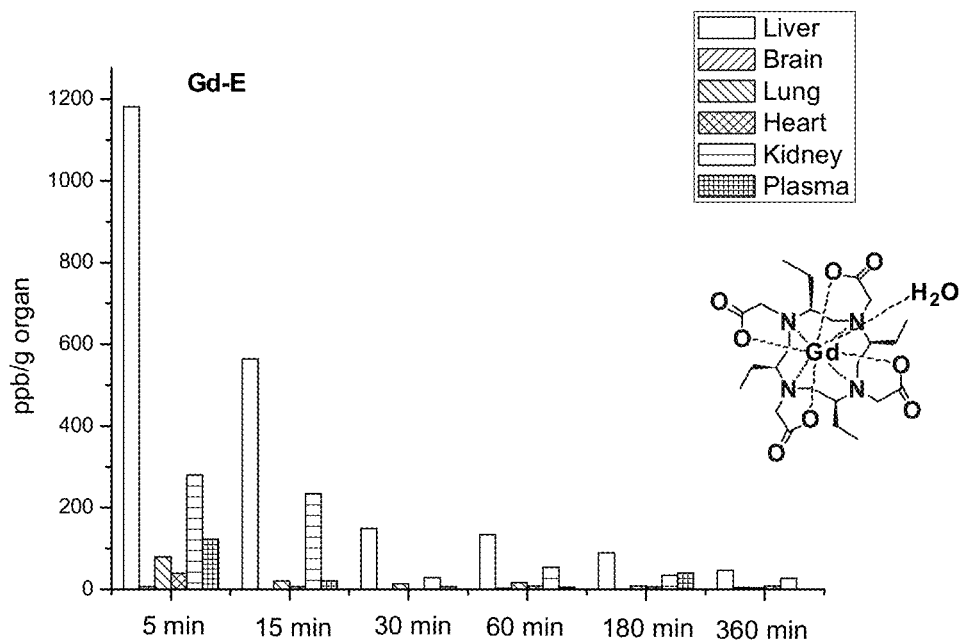
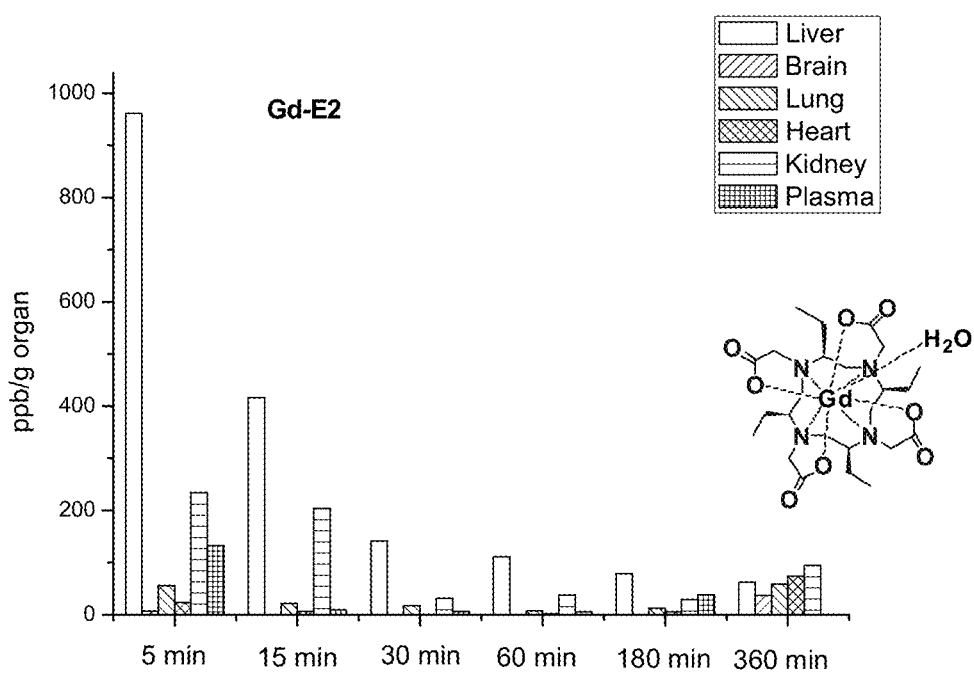

Figure 38C
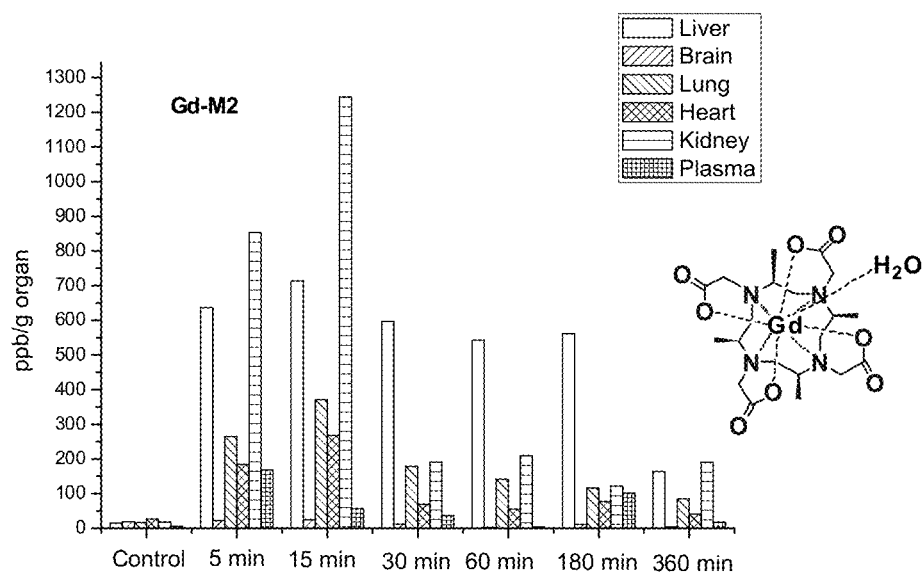
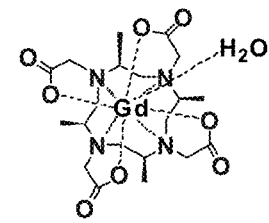
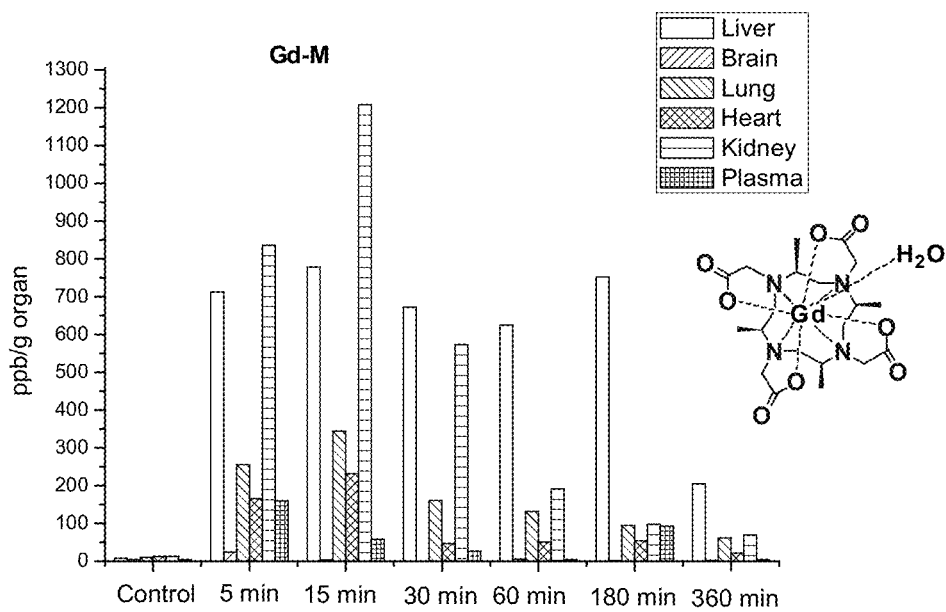
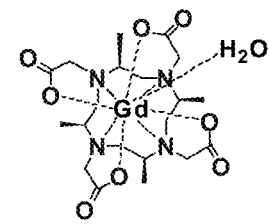

Figure 46A

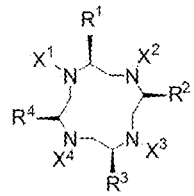

| $R^1, R^2, R^3, R^4$ (S configuration) | $X^1, X^2, X^3, X^4 =$ $-CH_2CO_2H$ | $X^1 = H;$ $X^2, X^3, X^4 =$ $-CH_2CO_2H$ | $X^1, X^3 = H;$ $X^2, X^4 =$ $-CH_2CO_2H$ | $X^1, X^2, X^3 = H;$ $X^4 =$ $-CH_2CO_2H$ |
|---|---|---|---|---|
| Me | L1 | L1_DO3A | L1_DO2A | L1_DO1A |
| Et | L2 | L2_DO3A | L2_DO2A | L2_DO1A |
| Isobutyl | L3 | L3_DO3A | L3_DO2A | L3_DO1A |
| Benzyl | L4 | L4_DO3A | L4_DO2A | L4_DO1A |
| 4-methoxybenzyl | 40-d_DOTA | 40-d_DO3A | 40-d_DO2A | 40-d_DO1A |
| $-[CH_2]_4NH_2$ | 41-d_DOTA | 41-d_DO3A | 41-d_DO2A | 41-d_DO1A |
| Isopropyl | 44-h_DOTA | 44-h_DO3A | 44-h_DO2A | 44-h_DO1A |
| $-CH_2SH$ | 45-h_DOTA | 45-h_DO3A | 45-h_DO2A | 45-h_DO1A |
| 4-Hydroxybenzyl | 46-b_DOTA | 46-b_DO3A | 46-b_DO2A | 46-b_DO1A |
| 4-Aminobenzyl | 46-c_DOTA | 46-c_DO3A | 46-c_DO2A | 46-c_DO1A |
| $-CH_2(C_6H_4)OCH_2CONH-[CH_2]_3SO_3H$ | 46-d_DOTA | 46-d_DO3A | 46-d_DO2A | 46-d_DO1A |
| $-CH_2(C_6H_4)O[CH_2]_3SO_3H$ | 46-e_DOTA | 46-e_DO3A | 46-e_DO2A | 46-e_DO1A |
| $-CH_2(C_6H_4)N(CH_2CO_2H)_2$ | 46-f_DOTA | 46-f_DO3A | 46-f_DO2A | 46-f_DO1A |
| (structure) | 46-g_DOTA | 46-g_DO3A | 46-g_DO2A | 46-g_DO1A |
| (structure) | 46-h_DOTA | 46-h_DO3A | 46-h_DO2A | 46-h_DO1A |
| (structure) | 46-i_DOTA | 46-i_DO3A | 46-i_DO2A | 46-i_DO1A |
| (structure) | 46-j_DOTA | 46-j_DO3A | 46-j_DO2A | 46-j_DO1A |
| $-CH_2OH$ | 46-k_DOTA | 46-k_DO3A | 46-k_DO2A | 46-k_DO1A |
| (structure) | 46-l_DOTA | 46-l_DO3A | 46-l_DO2A | 46-l_DO1A |
| $-[CH_2]_2SCH_3$ | 46-m_DOTA | 46-m_DO3A | 46-m_DO2A | 46-m_DO1A |
| (structure) | 46-n_DOTA | 46-n_DO3A | 46-n_DO2A | 46-n_DO1A |
| $-CH_2CO_2H$ | 46-o_DOTA | 46-o_DO3A | 46-o_DO2A | 46-o_DO1A |
| $-CH_2CONH_2$ | 46-p_DOTA | 46-p_DO3A | 46-p_DO2A | 46-p_DO1A |
| $-[CH_2]_2CO_2H$ | 46-q_DOTA | 46-q_DO3A | 46-q_DO2A | 46-q_DO1A |
| $-[CH_2]_2CONH_2$ | 46-r_DOTA | 46-r_DO3A | 46-r_DO2A | 46-r_DO1A |

Figure 46B

| R¹, R², R³, R⁴ (S configuration) | X¹, X², X³, X⁴ = –CH₂CO₂H | X¹ = H; X², X³, X⁴ = –CH₂CO₂H | X¹, X³ = H; X², X⁴ = –CH₂CO₂H | X¹, X², X³ = H; X⁴ = –CH₂CO₂H |
|---|---|---|---|---|
| 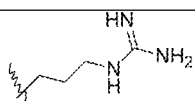 | 46-s_DOTA | 46-s_DO3A | 46-s_DO2A | 46-s_DO1A |
| 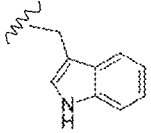 | 46-t_DOTA | 46-t_DO3A | 46-t_DO2A | 46-t_DO1A |
| 4-Bromobenzyl | 46-u_DOTA | 46-u_DO3A | 46-u_DO2A | 46-u_DO1A |
| 4-Nitrobenzyl | 46-v_DOTA | 46-v_DO3A | 46-v_DO2A | 46-v_DO1A |

Figure 46C

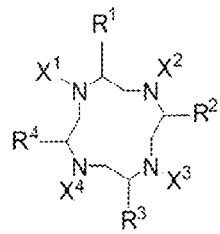

| R¹, R², R³, R⁴ (R configuration) | X¹, X², X³, X⁴ = –CH₂CO₂H | X¹ = H; X², X³, X⁴ = –CH₂CO₂H | X¹, X³ = H; X², X⁴ = –CH₂CO₂H | X¹, X², X³ = H; X⁴ = –CH₂CO₂H |
|---|---|---|---|---|
| Me | (R)-L1 | (R)-L1_DO3A | (R)-L1_DO2A | (R)-L1_DO1A |
| Et | (R)-46a_DOTA | (R)-46a_DO3A | (R)-46a_DO2A | (R)-46a_DO1A |
| Isobutyl | (R)-L3 | (R)-L3_DO3A | (R)-L3_DO2A | (R)-L3_DO1A |
| Benzyl | (R)-L4 | (R)-L4_DO3A | (R)-L4_DO2A | (R)-L4_DO1A |

Figure 66

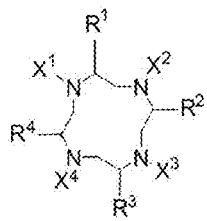

$X^1, X^2, X^3, X^4 = H$

| Compound | $R^1, R^2, R^3, R^4$ (S configuration) | Compound | $R^1, R^2, R^3, R^4$ (R configuration) |
|---|---|---|---|
| 66-a | Me | (R)-66-a | Me |
| 66-b | Et | (R)-66-b | Et |
| 66-c | Isopropyl | (R)-66-c | Isopropyl |
| 66-d | s-Butyl | (R)-66-d | s-Butyl |
| 66-e | –CH$_2$CO$_2$H | (R)-66-e | –CH$_2$CO$_2$H |
| 66-f | –CH$_2$CONH$_2$ | (R)-66-f | –CH$_2$CONH$_2$ |
| 66-g | –[CH$_2$]$_2$CO$_2$H | (R)-66-g | –[CH$_2$]$_2$CO$_2$H |
| 66-h | –[CH$_2$]$_2$CONH$_2$ | (R)-66-h | –[CH$_2$]$_2$CONH$_2$ |
| 66-i | –CH(OH)Me | (R)-66-i | –CH(OH)Me |
| 66-j | Isobutyl | (R)-66-j | Isobutyl |
| 66-k | –[CH$_2$]$_2$SCH$_3$ | (R)-66-k | –[CH$_2$]$_2$SCH$_3$ |
| 66-l | –CH$_2$SCH$_3$ | (R)-66-l | –CH$_2$SCH$_3$ |
| 66-m | –CH$_2$OH | (R)-66-m | –CH$_2$OH |
| 66-n | Benzyl | (R)-66-n | Benzyl |
| 66-o | –[CH$_2$]$_4$NH$_2$ | (R)-66-o | –[CH$_2$]$_4$NH$_2$ |
| 66-p | –(CH$_2$)$_3$NHC(=NH)NH$_2$ | (R)-66-p | –(CH$_2$)$_3$NHC(=NH)NH$_2$ |
| 66-q | 4-Methoxybenzyl | (R)-66-q | 4-Methoxybenzyl |
| 66-r | 4-Hydroxybenzyl | (R)-66-r | 4-Hydroxybenzyl |
| 66-s | 4-Bromobenzyl | (R)-66-s | 4-Bromobenzyl |
| 66-t | 4-Nitrobenzyl | (R)-66-t | 4-Nitrobenzyl |
| 66-u | 4-Aminobenzyl | (R)-66-u | 4-Aminobenzyl |
| 66-v | (methoxy/sulfonic acid substituted benzyl) | (R)-66-v | (methoxy/sulfonic acid substituted benzyl) |
| 66-w | imidazolylmethyl | (R)-66-w | imidazolylmethyl |
| 66-x | indolylmethyl | (R)-66-x | indolylmethyl |

CHIRAL CYCLEN COMPOUNDS AND THEIR USES

CROSS-REFERENCE TO RELATED APPLICATIONS

This application claims the benefit, of U.S. Provisional Application No. 62/396,785, filed Sep. 19, 2016. The entire contents and disclosures of the preceding application are incorporated by reference into this application.

Throughout this application, various publications are cited. The disclosures of these publications in their entireties are hereby incorporated by reference into this application to more fully describe the state of the art to which this invention pertains.

FIELD OF THE INVENTION

The present invention relates to synthetic strategies to gain steric control of the chiral cyclen ligands, which have increased rigidity, higher stability and water solubility to be used in various biomedical applications.

BACKGROUND OF THE INVENTION

Tetraazacycloalkanes and especially cyclen (1, 4, 7, 10-tetraazacyclododecane) derivatives are known to form very stable lanthanide complexes that are well-suited to a wide range of biological applications. The cyclen derivatives, DOTA (1,4,7,10-tetraazacyclododecane-1,4,7,10-tetraacetic acid), DO3A (1, 4, 7, 10-tetraazacyclododecane-1, 4, 7-triacetic acid), DO2A (1, 4, 7, 10-tetraazacyclododecane-1, 7-bis(acetic acid)) and DO1A (1,4,7,10-tetraazacyclododecane-1-acetic acid), are well-known and widely studied macrocyclic ligands in coordination chemistry.[1,37,38]

Numerous kinds of metal-DOTA complexes are known to show excellent stability under physiological conditions, hence making them preeminent for use in biomedical applications.[2] Notable examples are the use of [GdDOTA]⁻ as a contrast agent in magnetic resonance imaging (MRI), with diverse literature studies showing its use in radiopharmaceuticals as well as fluorescence microscopy for diagnosis and therapy.[3]

The conformational structures of lanthanide (III) complexes, [LnDOTA]⁻, have been extensively studied,[4] and the control of their stereoisomers has always been an active research area in coordination chemistry to improve its practical value. The development of pure chiral luminescent lanthanide complexes is also an area of burgeoning interest and crucial for the development in circularly polarized luminescence (CPL) studies.[5] It is recognized that different conformations of [LnDOTA]⁻ with different properties are key parameters for determining their applications.[4,6] In general, there are four different isomers formed in the process of complexation with DOTA. Two pairs of enantiomers result in four stereoisomers which are able to interconvert in solution by either ring inversion or acetate arm rotation to give the capped square antiprism CSAP (SA) and twisted CSAP (TSA) geometries in solution.[4]

The introduction of chiral substituents at the carbon positions of the cyclen ring of DOTA has been established as a general approach to control the formation of isomers. If one chiral substituent was introduced, four convertible isomers in the DOTA-based systems are then restricted to form two pairs of 'intraconvertible' but not interconvertible isomers at different ratios.[7] The locked 12-N-4 approach was investigated by Desreux[8] to control the formation of a preferred stereoisomer. Desreux found that by introducing four chiral side arms onto the cyclen ring, three isomers of [YbM₄DOTA]⁻ typically formed and were easily characterized by ¹H NMR in the ratio of 1:0.095:0.013. They also stated that when another four extra chiral substituents were added onto the acetate arms in a chiral DOTA, only one isomer—a [YbM₄DOTMA]⁻ complex—was formed. The configuration of these isomers is crucial as it is well-known that water exchange rate ($\tau M$), a key parameter in the function of MRI contrast agents, is dependent on the abundance of the TSA/SA isomers.[2,9-11] It has been shown that the water molecule is exchanged 10-100 times faster in the TSA configuration than in the SA isomer.[12] Controlling a Gd(III) chelate to predominantly form the TSA isomer would be desirable in developing MRI contrast agents.[13] There are indeed examples of tetraamide complex [Eu-DOTTA]³⁺ (TSA/SA=2)[14] and DOTA-based complexes with chiral substituents on the acetate side arms[15] with a high ratio of TSA/SA; however, the stability of the DOTA-tetraamide complexes is much lower than that of the DOTA complexes,[16] and chiral substituents on the acetate side arms always contain racemic isomers which are formed in substitution reactions.[15]

Sherry et al found that chiral substituents on the acetate arms, and one chiral benzyl group on the cyclen ring were necessary to induce single isomer formation.[42] Parker et al subsequently designed a DOTA-based ligand that formed a series of lanthanide (III) complexes as predominantly one isomer in solution[43] when the ligand carried four chiral tetraamide moieties but no stereogenic center on the cyclen ring. Parker et al reported "complete stereocontrol" by a mono-C-substitution on the triazacyclononane backbone with three bidentate chromophores without any chiral acetate coordinating groups.[57]

The chiral DOTA-based compounds have favorable hepatic biodistribution; however, their lifetime in the liver is quite short, about 5-10 mins after administration. Therefore, quick imaging technology is required.

Lanthanide complexes of cyclen derivatives may be used for CPL studies.[27a,39] CPL spectroscopy has several advantages over other chiroptical techniques in the study of chiral molecules and chiral systems.[27] This is the emission analogy of circular dichroism (CD),[28] which measures the difference in absorption between the left- and right-handed circularly polarized light, giving chiroptical information on the electronic ground state of molecules.[29] CPL spectroscopy measures the differential emission of the left- and right-handed circularly polarized light and provides information on the excited-state properties of the compounds.[4] The degree of CPL is commonly reported as a luminescence dissymmetry factor ($g_{lum}$) value, which is defined as $g_{lum}=2(I_L-I_R)/(I_L+I_R)$, where $I_L$ and $I_R$ are the emission intensity of the left- and right-handed circularly polarized light.[31-33] Most chiral organic fluorophores have low $|g_{lum}|$ values (~10-5-10-2), despite brilliant fluorescence quantum yields.[34] Lanthanide (III) cations are considered to be good candidates due to their spherical nature, which avoids the problem of anisotropy, and their magnetic dipole allowed f-f transitions could give rise to larger $g_{lum}$ values.[35] Chiral lanthanide complexes with $g_{lum}$ values within the range of 0.05 to 0.5 are reported,[35,36] but most of these complexes have low luminescence and are formed from multicomponent ligands, making them less stable for CPL application in biological environments.

The rigidity of the complex directly determines the average of local helicity of metal ion coordination and the degree of mixing of the electric and magnetic dipole transition moments, which was shown to increase the magnitude of DOTA-based lanthanide complexes' $g_{lum}$ values.[27a,32]

Europium (III) is often used for studying CPL due to its generally decent luminescence quantum yields,[45] allowing the magnetic dipole allowed $^5D_0 \rightarrow {}^7F_1$ transition to be observed relatively easily.[46] Muller et al. reported an exceptional $g_{lum}$ of +1.38 ($\Delta J$=1,595 nm, in $CHCl_3$) for a heterobimetallic tetrakis(diketonate) europium (III) adduct.[35b] Nevertheless, in order to improve the candidates further, more factors have to be considered.[47]

The luminescence quantum yields ($\Phi$) should be high enough for practical applications.[47] Moreover, the stability and water solubility of the complexes are pivotal for biological applications. Lanthanide (III) adducts, despite their large $g_{lum}$ values, are generally water-sensitive and stable only in nonpolar solutions.[49,50] Parker's group reported a racemic europium(III) complex with induced CPL properties upon binding with α1-AGP protein, reaching a $g_{lum}$ of −0.23 ($\Delta J$=1,598 nm),[51] the largest obtained thus far for a macrocyclic (including NOTA and DOTA derivatives)[52] lanthanide complex in water.

The present invention is directed to chiral cyclen complexes having a prolonged lifetime in a target organ such as the heart, brain, pancreas, spleen, or liver so that antibodies or peptides and metals carried by these complexes can be used to treat or diagnose diseases such as cancer in these organs. The resulting chiral cyclen complexes show increased rigidity, higher stability and water solubility, and can be used in various biomedical applications. The present invention provides an efficient chromophore ($\varepsilon \approx 19\,000 M^{-1} cm^{-1}$)[48] for achieving conformational rigidity (vide supra) and excellent luminescence properties in a series of Lanthanide complexes, in terms of $g_{lum}$ and $\Phi$ values.

SUMMARY OF THE INVENTION

The present invention relates to synthetic strategies to gain steric control of chiral cyclen ligands. The present invention discloses the synthesis of chiral cyclen ligands comprising one or more of the following features: (a) one or more chiral groups placed at the carbon positions of the cyclen ring; (b) one or more substituents on the tetraaza ring; (c) the substituents on the tetraaza ring are monodentate, bidentate, tridentate, tetradentate or polydentate; (d) the substituents on the tetraaza ring are achiral or chiral; (e) the substituents on the tetraaza ring contain a chromophore.

The present invention further discloses complexes formed between the chiral cyclen ligands and a metal selected from d-block metal or f-block metal. The resulting chiral cyclen metal complexes are extremely rigid and the conformation can be controlled.

The present invention provides a chiral cyclen of formula (1):

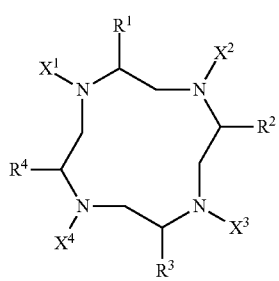

(I)

The present invention also provides a composition for imaging, comprising the chiral cyclen of formula (I), one or more metals, and optionally pharmaceutically acceptable excipients, wherein a metal complex is formed between the chiral cyclen and one or more metals.

The present invention discloses a method of using the composition of the present invention comprising the chiral cyclen of formula (I) for imaging, comprising the steps of (a) administering the composition to a subject in need thereof; (b) detecting radiation emitted by the metal complex; and (c) forming an image therefrom.

The present invention further discloses a method of using the composition of the present invention comprising the chiral cyclen of formula (I), comprising the steps of (a) contacting a target with the composition; (b) detecting radiation emitted by the metal complex; and (c) measuring the amount and/or concentration of the metal complex in the target.

In addition, the properties and biomedical applications of the chiral cyclen ligands are disclosed in the present invention.

BRIEF DESCRIPTION OF THE DRAWINGS

FIG. 11 shows the HRMS spectra of Gd(III) complexes of [GdL1]$^-$, [GdL2]$^-$, [GdL3]$^-$ and [GdL4]$^-$.

FIG. 12 shows the UPLC-HRMS spectra of [GdL1]$^-$ in the absence of DPTA and in the presence of different amounts of DTPA after shaking for 7 days.

FIG. 13 shows the UPLC-HRMS spectra of [GdL2]⁻ in the absence of DPTA and in the presence of different amounts of DTPA after shaking for 7 days.

FIG. 35 shows additional examples of chiral DOTA-based metal complexes and chiral cyclen metal complexes.

FIG. 36B shows LC-MS copper complexation with lithium salt 29-c under various conditions.

FIG. 38A shows biodistribution data of complexes Gd-C and Gd-C2.

FIG. 38B shows biodistribution data of complexes Gd-E and Gd-E2.

FIG. 38C shows biodistribution data of complexes Gd-M and Gd-M2.

FIGS. 46A, 46B and 46C show additional examples of chiral DO1A, DO2A, DO3A and DOTA-based ligands.

FIG. 66 shows additional examples of chiral cyclen ligands.

DETAILED DESCRIPTION OF THE INVENTION

Figure 1A:
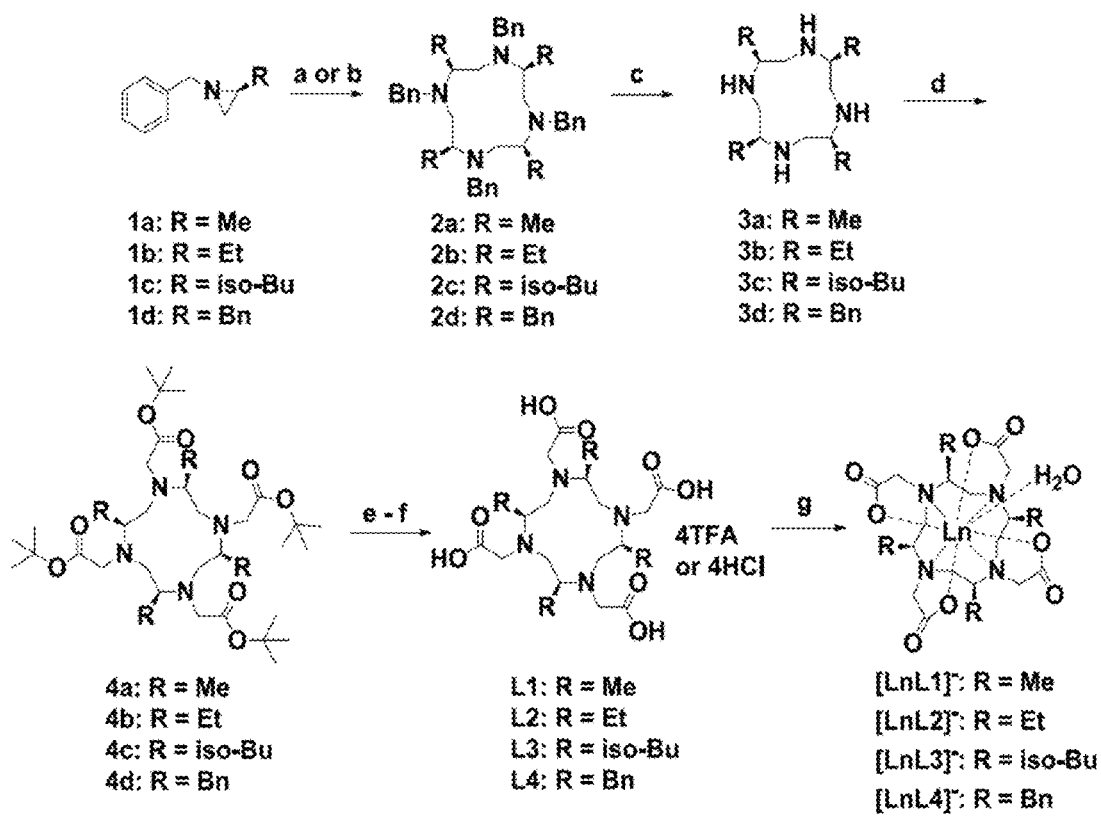
FIG. 1A shows a synthetic route of chiral cyclen ligands L1-L4 and DOTA-based complexes. Step (a): TsOH/EtOH, RT (1a); Step (b): $BF_3 \cdot Et_2O$/Benzene, reflux (1b-1d), 24 h; Step (c): $Pd(OH)_2/C$, ammonium formate, EtOH, reflux, 2 days; Step (d): tert-butyl 2-bromoacetate, $K_2CO_3$, dry acetonitrile, 16 h; Step (e): TFA/DCM (1:1), 24 h; Step (f) 1 M HCl (L2-L4); g): $LnCl_3 \cdot 6H_2O$, pH 7.0, 16 h (Ln=Eu (III), Yb(III) and Gd(III)) (for clarity, the counterions are not depicted).

The present invention relates to synthetic strategies to gain steric control of chiral cyclen ligands. The present invention discloses the synthesis of chiral cyclen ligands comprising one or more of following features: (a) one or more chiral substituents placed at the carbon positions of the cyclen ring; (b) one or more substituents on the tetraaza ring; (c) the substituents on the tetraaza ring are monodentate, bidentate, tridentate, tetradentate or polydentate; (d) the substituents on the tetraaza ring are achiral or chiral; (e) the substituents on the tetraaza ring contain a chromophore.

In one embodiment, the chiral cyclen ligands of the present invention are generally of the structure below:

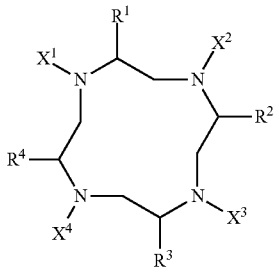

Chirality can be introduced into the cyclen ligands in two ways. Firstly, a substituent can be added to the carbon atoms of the cyclen ring, converting these carbon atoms into chiral centers. Secondly, a chiral substituent may be added to the nitrogen atoms of the cyclen ring. In one embodiment, the substituents at the nitrogen atoms are acetates. Introducing chirality in these two ways could lead to steric locking. In one embodiment, cyclen complexes having one or more chiral elements can be synthesized. In one embodiment, DOTA-, DO3A-, DO2A- and DO1A-based ligands have chirality at the carbon positions of the cyclen ring and chiral acetate substituents at the nitrogen atoms of the cyclen ring. In another embodiment, the cyclen ligands have chirality at the carbon positions of the cyclen ring without any substituent at the nitrogen atoms of the cyclen ring.

The DOTA-, DO3A-, DO2A-, DO1A- and cyclen based ligands of the present invention are of the general structures below:

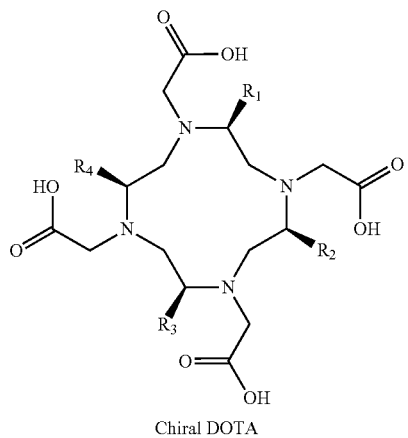

Chiral DOTA

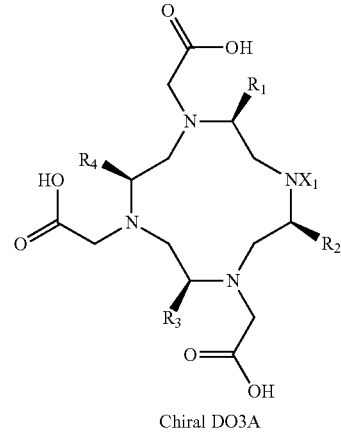

Chiral DO3A

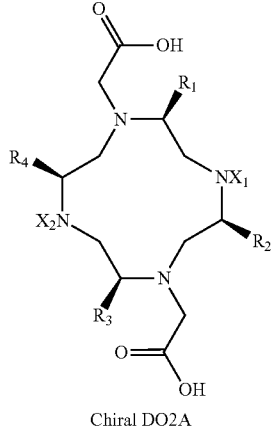

Chiral DO2A

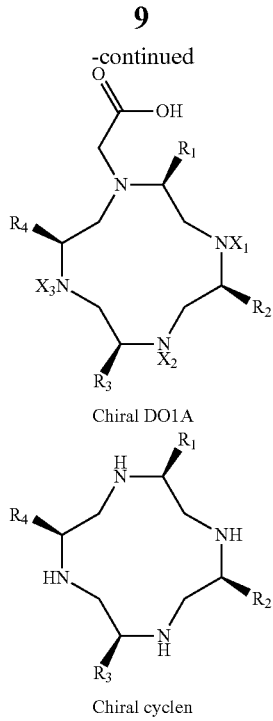

Chiral DO1A

Chiral cyclen

Examples of the DOTA-, DO3A-, DO2A-, DO1A- and cyclen based ligands include, but are not limited to, the structures shown in FIGS. 1A, 2, 15, 27, 29, 30-35 and 39-66.

For DOTA-based ligands with acetate arms, chirality on the cyclic backbone is required, and the steric locking property is complemented by having chiral coordinating acetate arms.

For chiral cyclen, DO3A-, DO2A- and DO1A-based ligands of the present invention, one or more of the substituents on the tetraaza ring can be other functional groups, such as amino-linker, peptide, vector and chromophores. Examples of the substituents on the tetraaza ring include, but are not limited to, the structures shown in FIGS. 2, 15, 27, 30, 32-33 and 46A-C.

For chiral cyclen, DOTA-, DO3A-, DO2A- and DO1A-based ligands of the present invention, one or more of the substituents placed at the carbon positions of the cyclen ring can further comprise other functional groups, such as alcohol, phenol, carboxylic acid, amine, alkylamine, aniline, optionally substituted benzyl, sulfonate, and thiol. Examples of the substituents on the tetraaza ring include, but are not limited to, the structures shown in FIGS. 1A, 2, 27, 28, 30, 35 and 39-66.

In one embodiment, the chiral cyclen ligands of the present invention, including DOTA-, DO3A-DO2A-, DO1A- and cyclen based ligands, can form complexes with metals selected from the group consisting of p-block elements, d-block elements and f-block elements. In a preferred embodiment, the p-block element is selected from the group consisting of Aluminium, Gallium and Indium. In a preferred embodiment, the d-block element can be selected from the group consisting of Iron, Nickel, Manganese, Cobalt, Chromium, Yttrium, Zirconium, Zinc and Copper. In another preferred embodiment, the f-block element can be selected from the group consisting of lanthanides. The lanthanides can be selected from the group consisting of Lanthanum, Cerium, Praseodymium, Neodymium, Promethium, Samarium, Europium, Gadolinium, Terbium, Dysprosium, Holmium, Erbium, Thulium Ytterbium and Lutetium. In another preferred embodiment, the f-block element can be selected from the group consisting of actinides. The actinides can be selected from the group consisting of Thorium, Uranium, Americium, Curium and Berkelium.

Examples of the chiral metal cyclen complexes include, but are not limited to, the structures shown in FIGS. 1A, 2, 15, 28, 29, 32, 33, 35, 39-45, 47-50 and 54.

In the present invention, a series of chiral cyclen ligands, DOTA, having different chiral groups symmetrically placed at the carbon positions of the cyclen ring, and their metal complexes are synthesized.

A synthetic route to prepare the chiral cyclens and DOTA-based complexes is outlined in FIG. 1A. In step (a) or (b), aziridine 1 can be used as starting material in the presence of one or more catalysts to give cyclized product 2. The R group of aziridine 1 is selected from the group consisting of alkyl having 1-5 carbon atoms, benzyl, substituted benzyl and $[CH_2]_m$—$N(R')(R'')$, wherein m is an integer selected from 2, 3, 4, 5, 6, 7, 8, 9 and 10, and each of R' and R'' is independently selected from hydrogen, alkyl having 1-10 carbon atoms, and optionally substituted benzyl. In another embodiment, the R group of aziridine 1 is methyl, ethyl, iso-butyl or benzyl. The catalysts can be selected from TsOH or a Lewis acid (such as boron trifluoride and diethyl etherate complex). The cyclized tetramer product can be purified by either column chromatography or recrystallization. In step (c), deprotection of the four benzyl groups in 2 resulted in the chiral cyclen 3. In step (d), the chiral cyclen 3 can react with tert-butyl 2-bromoacetate to afford chiral cyclen 4. In step (e) and (f), the tert-butyl groups in chiral cyclen 3 can be deprotected by acid.

In step (g), the chiral cyclen metal complexes can be synthesized according to the classical procedures known in the art. The metal can be selected from the group consisting of p-block elements, d-block elements and f-block elements. In a preferred embodiment, the p-block element is selected from the group consisting of Aluminium, Gallium and Indium. In a preferred embodiment, the d-block element can be selected from the group consisting of Iron, Nickel, Manganese, Cobalt, Chromium, Yttrium, Zirconium, Zinc and Copper. In another preferred embodiment, the f-block element can be selected from the group consisting of lanthanides. The lanthanides can be selected from the group consisting of Lanthanum, Cerium, Praseodymium, Neodymium, Promethium, Samarium, Europium, Gadolinium, Terbium, Dysprosium, Holmium, Erbium, Thulium Ytterbium and Lutetium. In another preferred embodiment, the f-block element can be selected from the group consisting of actinides. The actinides can be selected from the group consisting of Thorium, Uranium, Americium, Curium and Berkelium.

More synthetic approaches to prepare DOTA-base ligands for metal complexes formation have been shown in FIGS. 29, 39-45 and 47-56. As shown in FIGS. 44, 45, 47, 48, 50 and 57-65, natural amino acids can be used as starting material. The amino acid can be selected from but not limited to lysine, Tyrosine, valine, cysteine, histidine, serine, threonine, methionine, isoleucine, aspartic acid, asparagine, glutamic acid, glutamine, arginine and tryptophan. The resulting chiral DOTA ligand 41-d_DOTA having four amino group can be used to conjugate with molecules having carboxylic groups.

In another embodiment, aromatic substituents can be placed on carbon positions of the cyclen ring. These aromatic substituents with high steric hindrance can induce the lanthanide complexes into predominantly TSAP geometry, with the water exchange rate close to the optimal range for use as MRI agents. In addition, using phenol and aniline substituents on carbon positions of the cyclen ring would provide synthetic handles for further modifications on these aromatic rings, and therefore desired properties of the resulting chiral DOTA ligands and metal complexes can be tailored conveniently. Examples have been shown in FIGS. 1A, 28, 39-40, 42-43, 48-55.

To investigate the properties of the chiral cyclen metal complexes, the ratio of TSA/SA isomers can be determined by $^1$H NMR. In addition, the conformational properties of chiral cyclen metal complexes can be studied by both HPLC and NMR spectroscopy. To check if the abundance of TSA and SA isomers of these chiral cyclen metal complexes is temperature dependent and stable, variable temperature studies and stability in the presence of a competitive ligand can be investigated with $^1$H NMR experiments under different temperature and monitored by UPLC-HRMS.

The chiral cyclen metal complexes of the present invention have significant properties superior to those of these parent DOTAs, showcasing potential value as a platform for diagnostic applications.

Further structural modifications on the four pendant acetate side arms of the chiral DOTA-based ligands can be obtained. One to four carboxylate groups can be modified with either the same or different conjugates. In one embodiment, N-hydroxysulfosuccinimide (Sulfo-NHS) and EDCl can be used to activate the carboxylate group on DOTA ligand for conjugation with primary amines.

Figure 56:
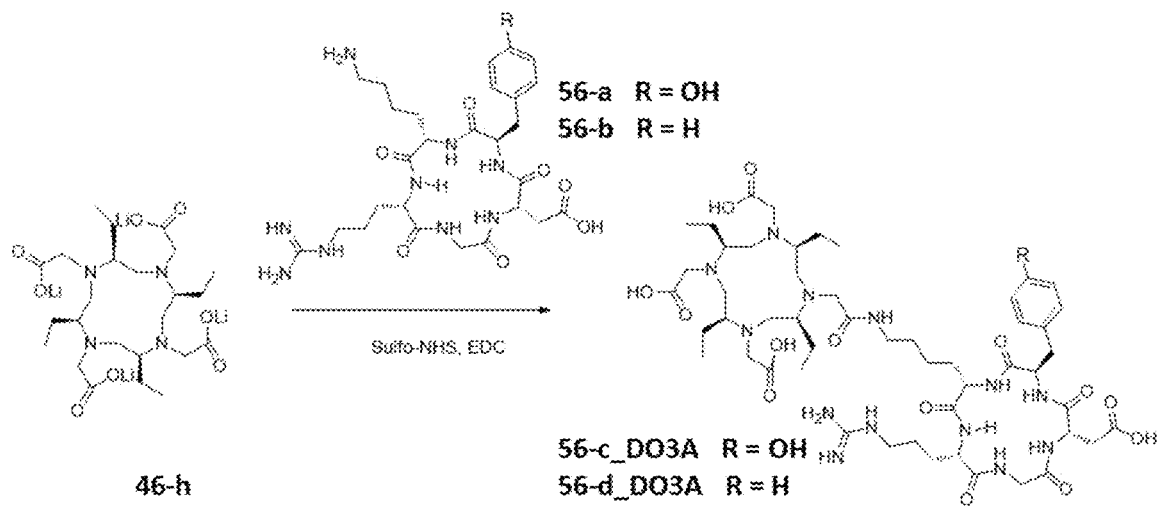
FIG. 56 shows a synthetic route of chiral DOTA-based ligand 56-c_DO3A and 56-d_DO3A.
Figure 57:
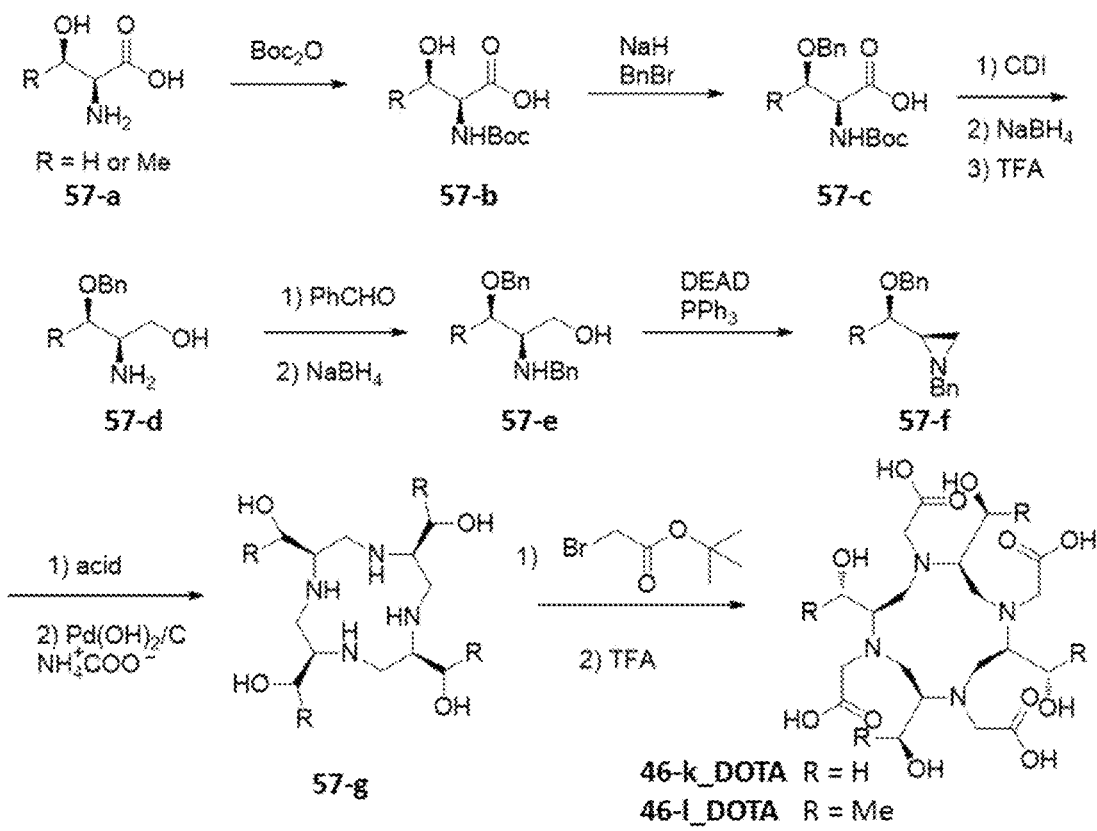
FIG. 57 shows a synthetic route of chiral DOTA-based ligands 46-k_DOTA and 46-1_DOTA.
Figure 58:
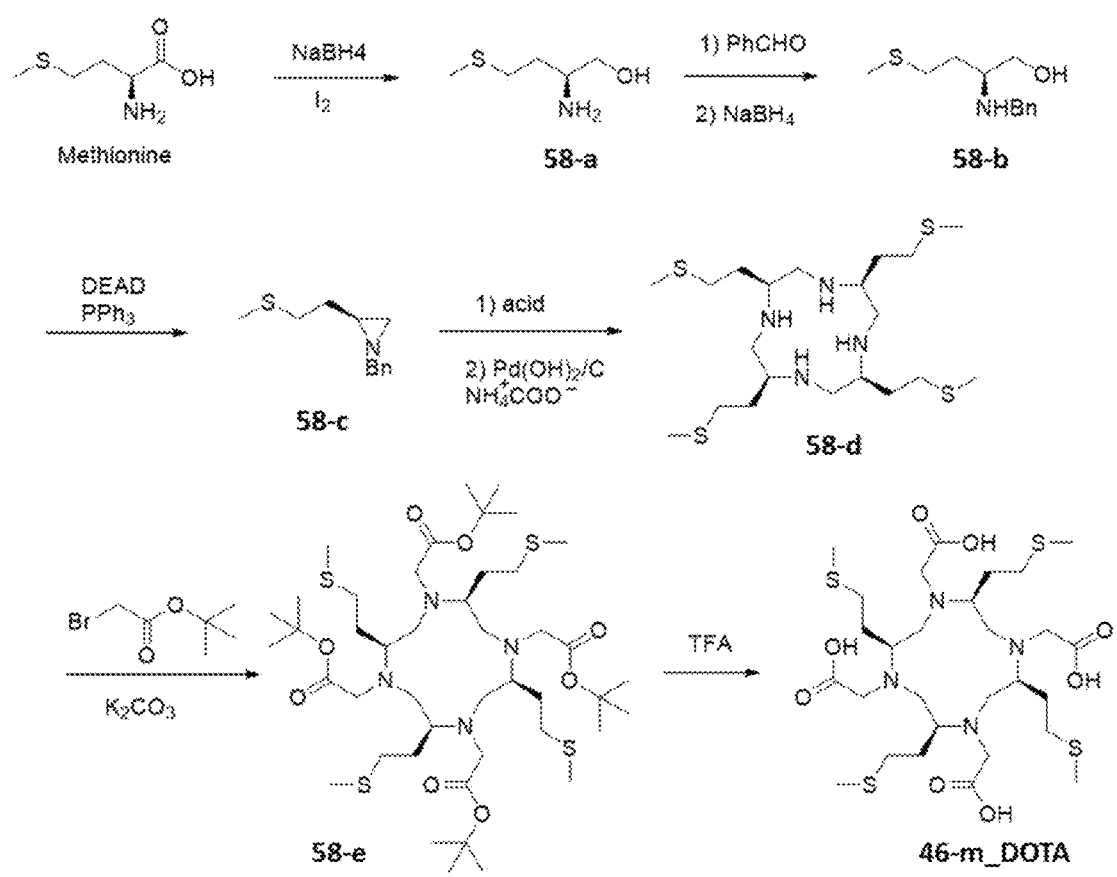
FIG. 58 shows a synthetic route of chiral DOTA-based ligand 46-m_DOTA.
Figure 59:
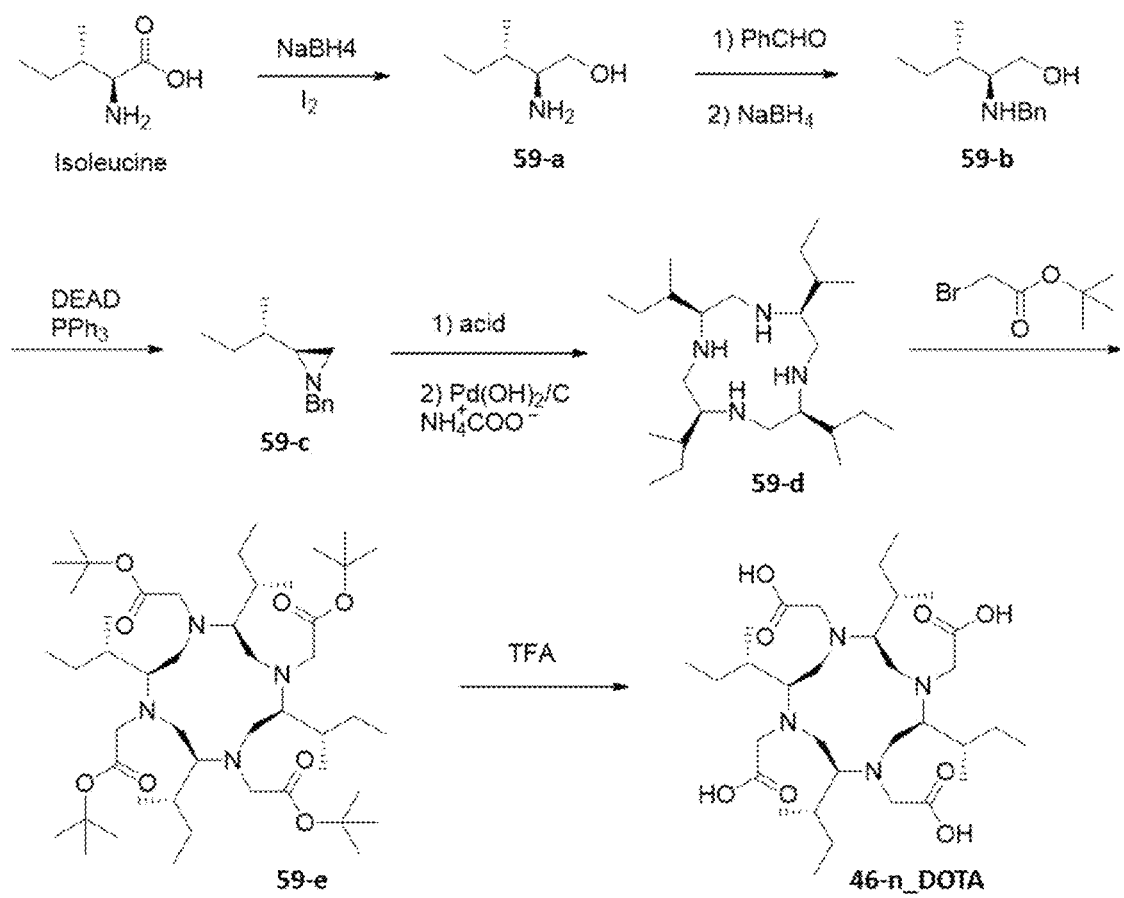
FIG. 59 shows a synthetic route of chiral DOTA-based ligand 46-n_DOTA.
Figure 60:
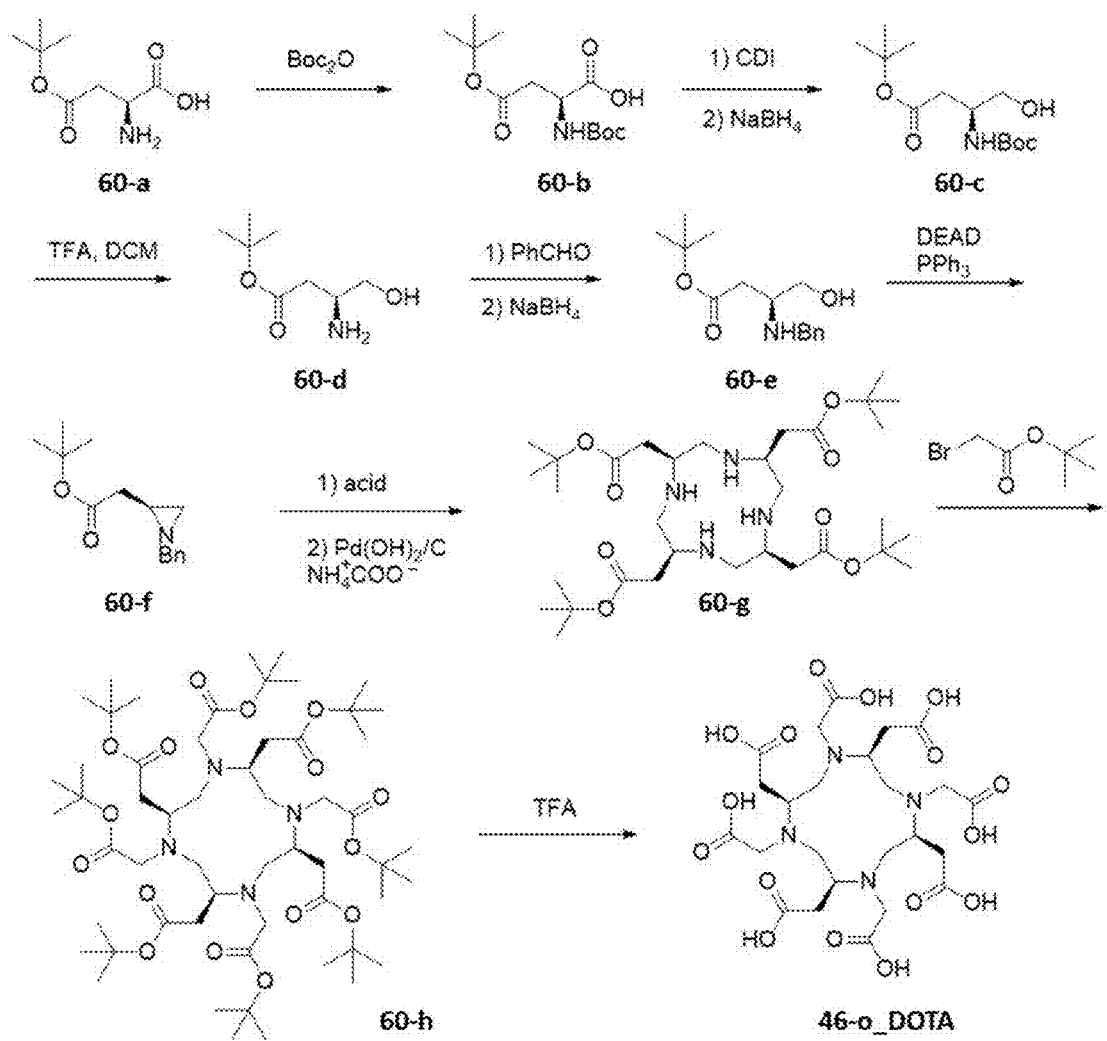
FIG. 60 shows a synthetic route of chiral DOTA-based ligand 46-o_DOTA.
Figure 61:
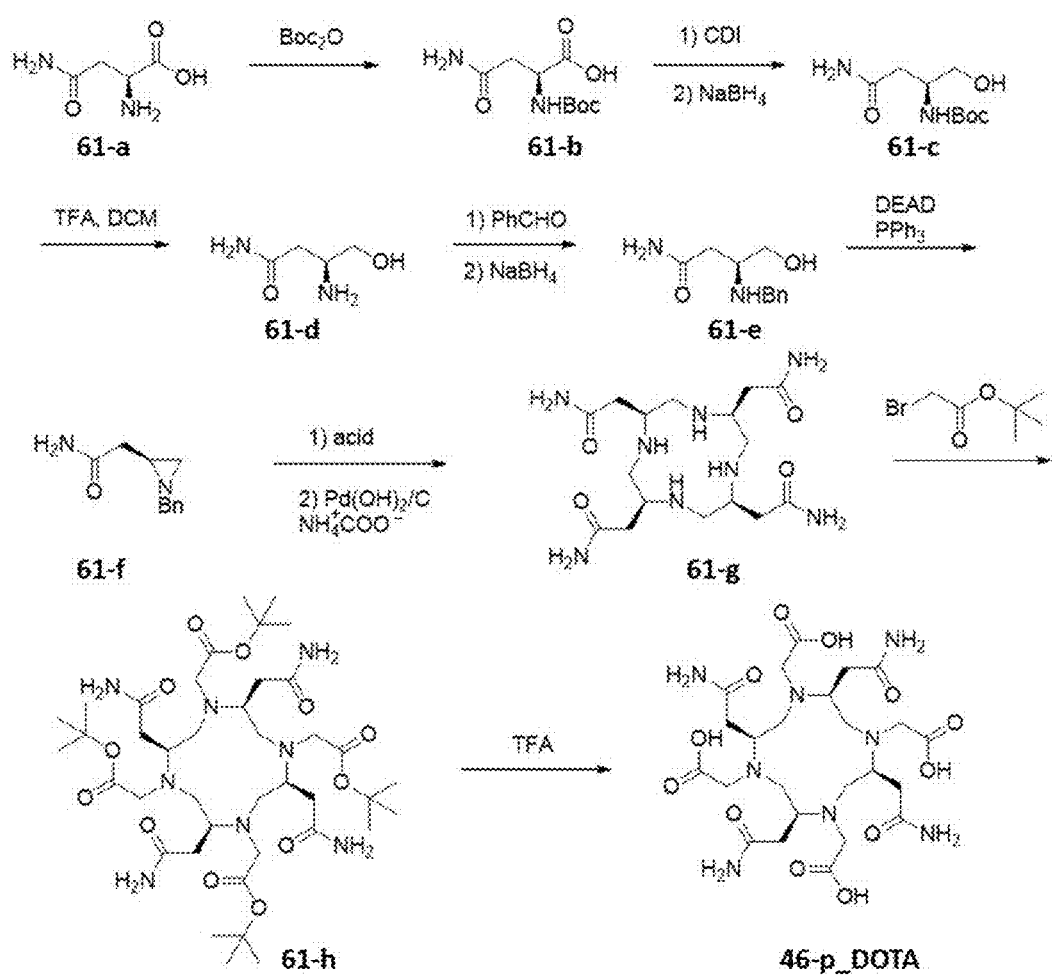
FIG. 61 shows a synthetic route of chiral DOTA-based ligand 46-p_DOTA.
Figure 62:
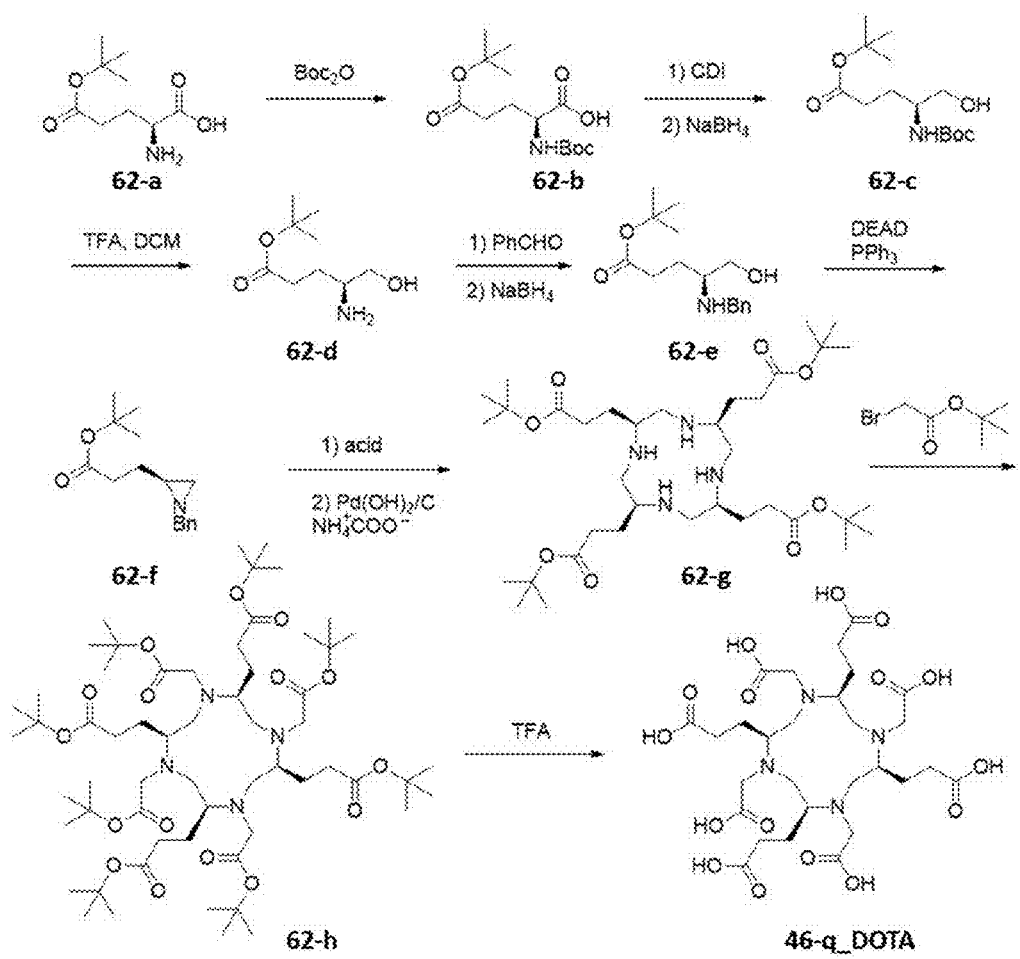
FIG. 62 shows a synthetic route of chiral DOTA-based ligand 46-q_DOTA.
Figure 63:
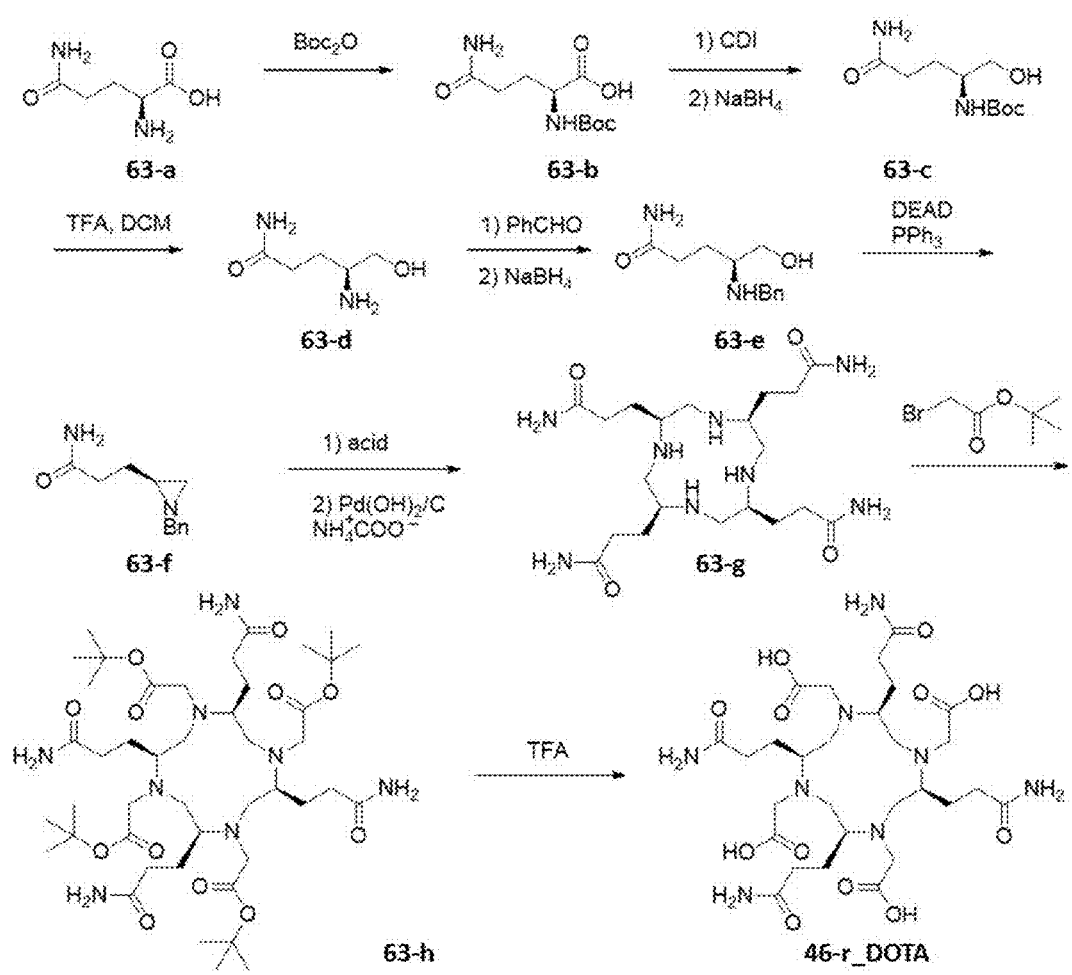
FIG. 63 shows a synthetic route of chiral DOTA-based ligand 46-r_DOTA.
Figure 64:
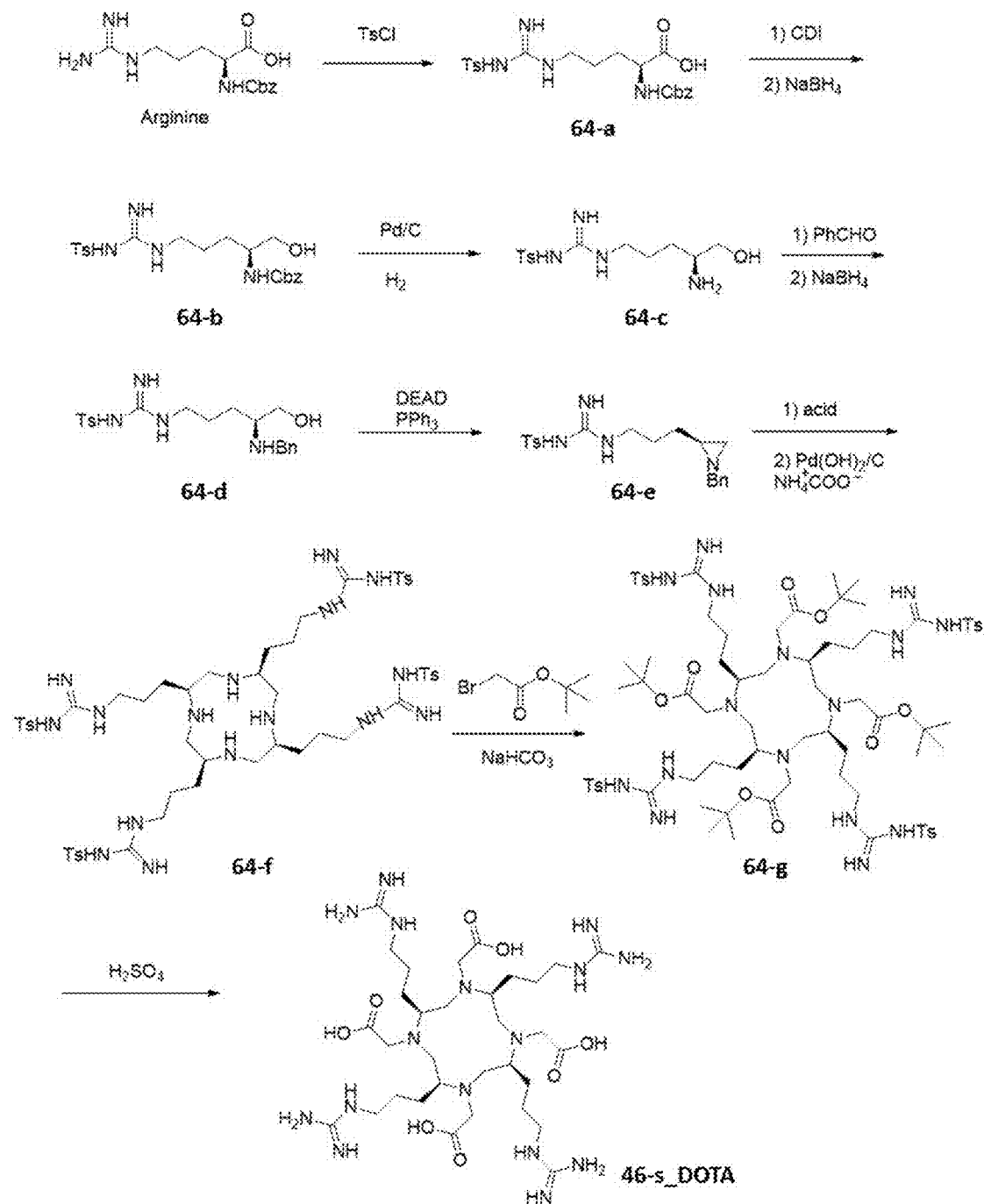
FIG. 64 shows a synthetic route of chiral DOTA-based ligand 46-s_DOTA.
Figure 65:
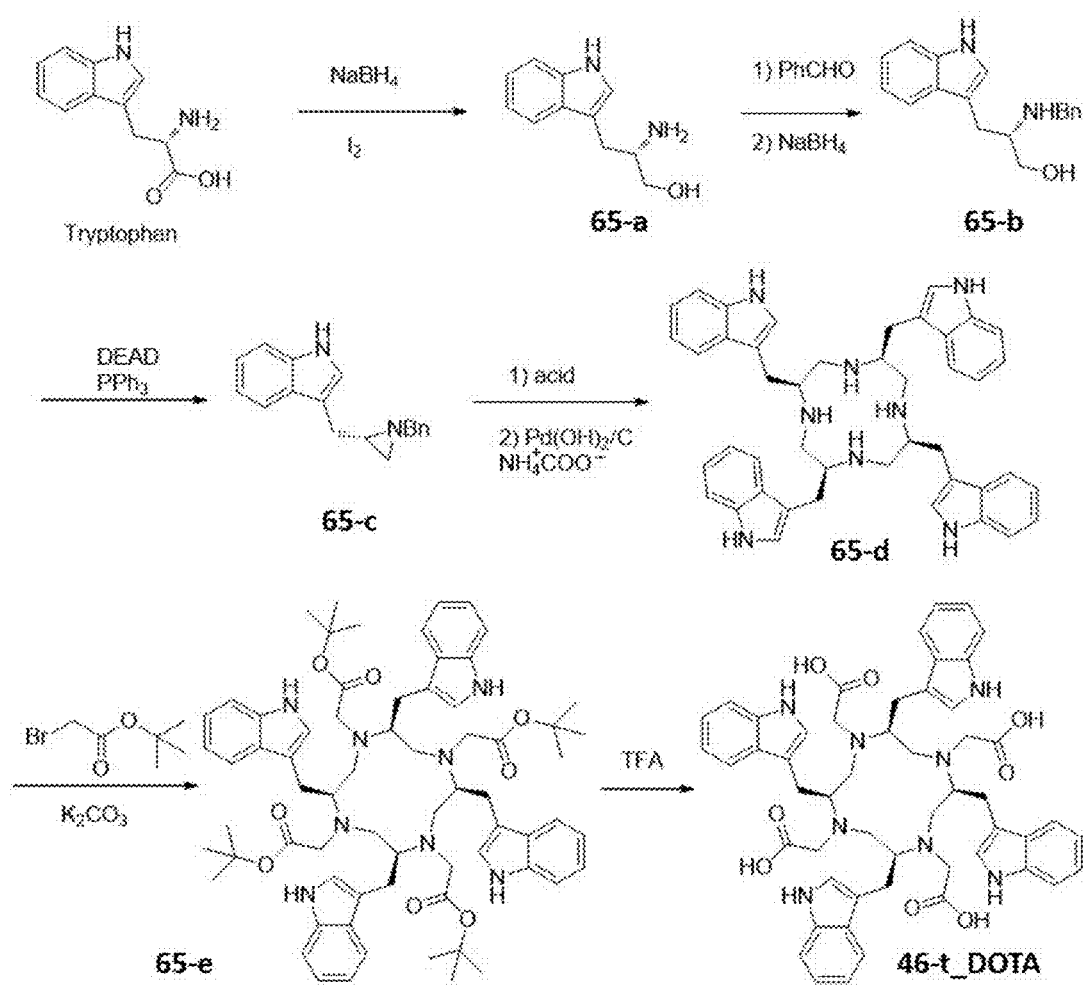
FIG. 65 shows a synthetic route of chiral DOTA-based ligand 46-t_DOTA.

As shown in FIG. 56, one of the carboxylate groups of 46-h can be activated with Sulfo-NHS and EDCl for conjugation with the primary amine in RGD peptide 56-a and 56-b to afford conjugates 56-c_DO3A and 56-d_DO3A respectively.

Figure 2:
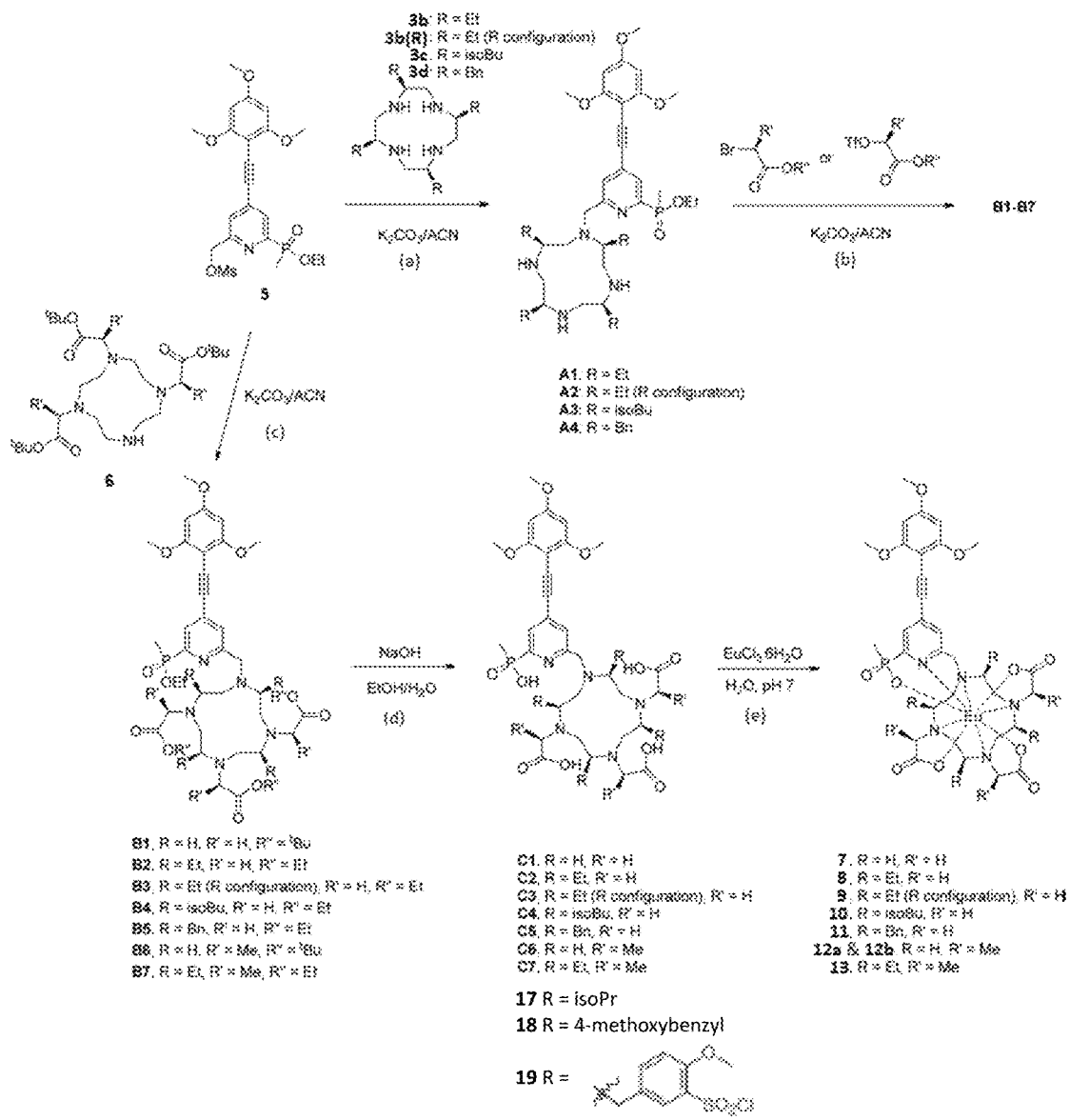
FIG. 2 shows a synthetic route of chiral cyclen ligands C1-C7 and DO3A-based complexes.

A synthetic route to prepare the chiral cyclens and DO3A-based complexes is outlined in FIG. 2. There are two approaches to afford B1-B7. The first approach comprises steps (a) and (b), where amine groups of cyclen derivatives is mono-substituted first and then tri-alkylated to incorporate the acetate groups. The second approaches as shown in step (c) involves substitution of the remaining amine group in the DO3A derivatives.

In step (c), B1-B7 are deprotected to give DO3A-based ligands C1-C7.

In step (d), chiral DO3A-based metal complexes can be synthesized according to the classical procedures known in the art. The metal can be selected from the group consisting of metals selected from the group consisting of p-block elements, d-block elements and f-block elements. In a preferred embodiment, the p-block element is selected from the group consisting of Aluminium, Gallium and Indium. In a preferred embodiment, the d-block element can be selected from the group consisting of Iron, Nickel, Manganese, Cobalt, Chromium, Yttrium, Zirconium, Zinc and Copper. In another preferred embodiment, the f-block element can be selected from the group consisting of lanthanides. The lanthanides can be selected from the group consisting of Lanthanum, Cerium, Praseodymium, Neodymium, Promethium, Samarium, Europium, Gadolinium, Terbium, Dysprosium, Holmium, Erbium, Thulium Ytterbium and Lutetium. In another preferred embodiment, the f-block element can be selected from the group consisting of actinides. The actinides can be selected from the group consisting of Thorium, Uranium, Americium, Curium and Berkelium.

More synthetic approaches to prepare DO3A-based ligands for metal complexes formation are shown in FIGS. 15 and 30-32. More examples of DO3A-based ligands for metal complexes formation are shown in FIGS. 46A, 46B and 46C.

Figure 34:
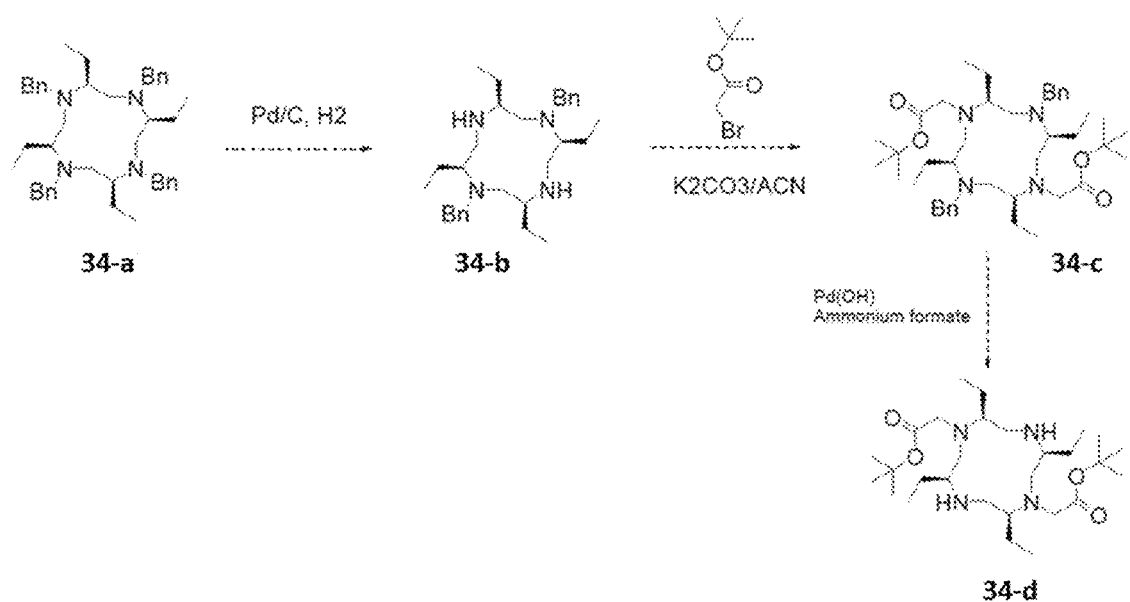
FIG. 34 shows a synthetic route of chiral DO2A-based ligands 34-d.

A general synthetic route to prepare DO2A-based complexes is outlined in FIG. 34. More examples of DO2A-based ligands for metal complexes formation are shown in FIGS. 46A, 46B and 46C.

More examples of DO1A-based ligands for metal complexes formation are shown in FIGS. 46A, 46B and 46C.

Examples of chiral cyclen ligands for metal complexes formation are shown in FIG. 66.

The chiral cyclen metal complexes of the present invention are extremely rigid and the conformation can be controlled.

Cyclen metal complexes may exist as two pairs of stereoisomers due to ring inversion ($\lambda$, or $\delta$) and rotation of the acetate arm ($\Lambda$ or $\Delta$), leading to four dynamically interconvertible geometries in solution.[40] The $\Delta$ and $\Lambda$ helicities interconvert rapidly in solution, while that between $\delta$ and $\lambda$ occurs at a rate of around 50 Hz for unsubstituted DOTA[52] complexes;[27a,40b] For the chiral cyclen metal complexes of present invention, the preferential formation of one chiral isomer Can be controlled in order to maximize the CPL performance.

The chiral cyclen metal complexes of present invention exhibit good luminescent quantum yields, large dissymmetry factors, better water solubility, and high stability. By modifying the chiral cyclen ligands for complexes formation with metal, a trend in the CPL properties can be observed, laying down a definitive blueprint for designing and synthesizing practical lanthanide-based CPL probes for recognition of chiral biomolecules.

The chiral cyclen metal complexes of present invention has feasible biomedical applications to be used as imaging or multi-imaging agents and can be used for studying protein interactions as well as an optical platform for cellular studies.

The chiral cyclen metal complexes reveal a high abundance of twisted square antiprism (TSA) geometry favoring them to be used as potential MRI contrast agents. The chiral cyclen metal complexes synthesized with high isomeric control show predominantly one isomer, which can enhance their application in current technique of Magnetic Resonance Imaging (MRI).

For chiral cyclen metal complexes comprising Gd metal ion, having selective hepatic biodistribution would enable their use without the concern for Nephrogenic Systemic Fibrosis (NSF). The highly stable complexes can alleviate the concerns about transmetallation effects.

The chiral cyclen metal complexes of the present invention can improve retention time in the liver. Furthermore, the metal complexes can be designed for investigation of selectivity to other organs. In addition, the chiral cyclen metal complexes of the present invention can be used as radiopharmaceutical drugs to conjugate target groups, and can be used as chelators for alpha emitters.

Also, the rapid labelling properties of the chiral cyclen metal complexes at mild conditions make them excellent candidates for use as radiometal chelators. The ease of radiolabeling under mild conditions is demonstrated by "cold" studies using non-radioactive metals as the surrogate.

The chiral cyclen metal complexes of the present invention can be used in any imaging platforms, and the versatility in the backbone modification has the potential to add any directing and biological targeting vectors, resulting in a platform for multimodal imaging. The chiral cyclen metal complexes can provide a platform to create dual or multimodal imaging for combined diagnosis; for example, combining the imaging technique of MRI and PET. As a result, patients' discomfort and high cost for diagnosis can be reduced.

Advantages of the present invention include (a) Enhanced dominance of the favored isomer for MRI imaging—TSA/SA; (b) Ease of labeling with metal used for radioimaging (Lu and Ga), such as SPECT and PET, at mild conditions; (c) Highly stable complexes; (d) potential hepatic MRI contrast agents which can be used without any concern for Nephrogenic Systemic Fibrosis (NSF).

In one embodiment, the present invention provides a chiral cyclen of formula (1):

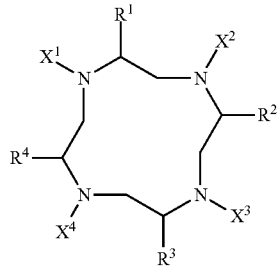

wherein each of $R^1$, $R^2$, $R^3$, $R^4$, $X^1$, $X^2$, $X^3$ and $X^4$ is independently selected from the group consisting of hydrogen, alkyl having 1-10 carbon atoms, benzyl, substituted benzyl, acetate, α-substituted acetate, —[CH$_2$]$_m$—N(R$^5$)(R$^6$), —[CH$_2$]$_m$(C$_6$H$_4$)N(R$^5$)(R$^6$), —[CH$_2$]$_m$(C$_6$H$_4$)N(R$^5$)[CH$_2$]$_n$SO$_3$R$^7$, —[CH$_2$]$_m$—[CH$_2$]$_m$OH, —CHOHCH$_3$, —[CH$_2$]$_m$CO$_2$H, —[CH$_2$]$_m$CON(R$^5$)(R$^6$), —[CH$_2$]$_m$(C$_6$H$_4$)O[CH$_2$]$_n$CO$_2$H, —CH$_2$(C$_6$H$_4$)O[CH$_2$]$_m$SO$_3$H, —CH$_2$(C$_6$H$_4$)OCH$_2$CONH—[CH$_2$]$_m$SO$_3$H, —[CH$_2$]$_m$—NHTs, 6-(substituted methyl)picolinic acid,

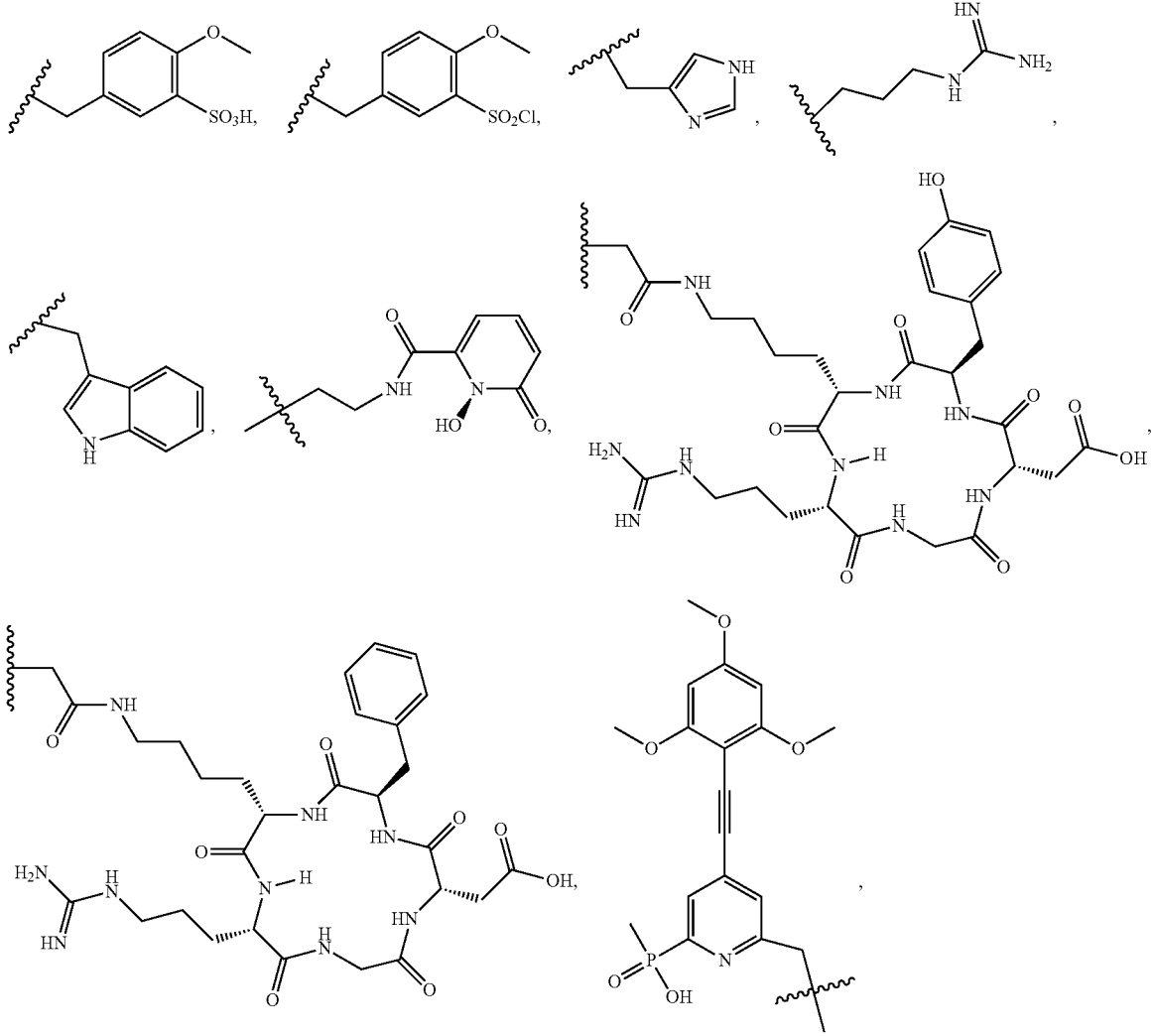

15
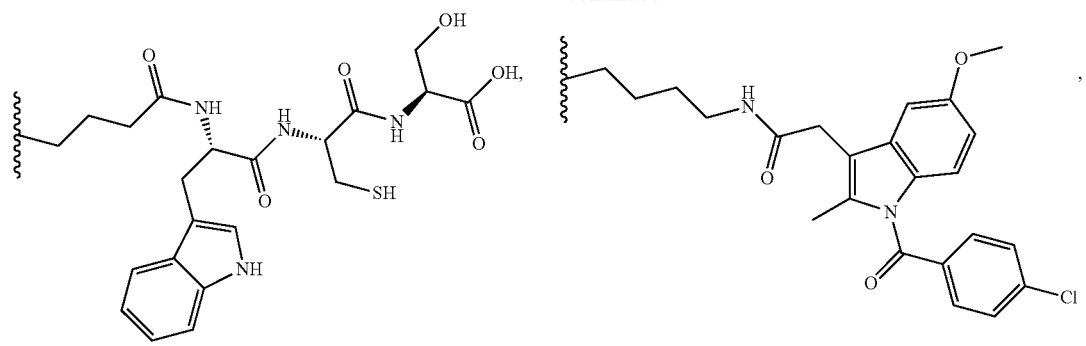
16
-continued
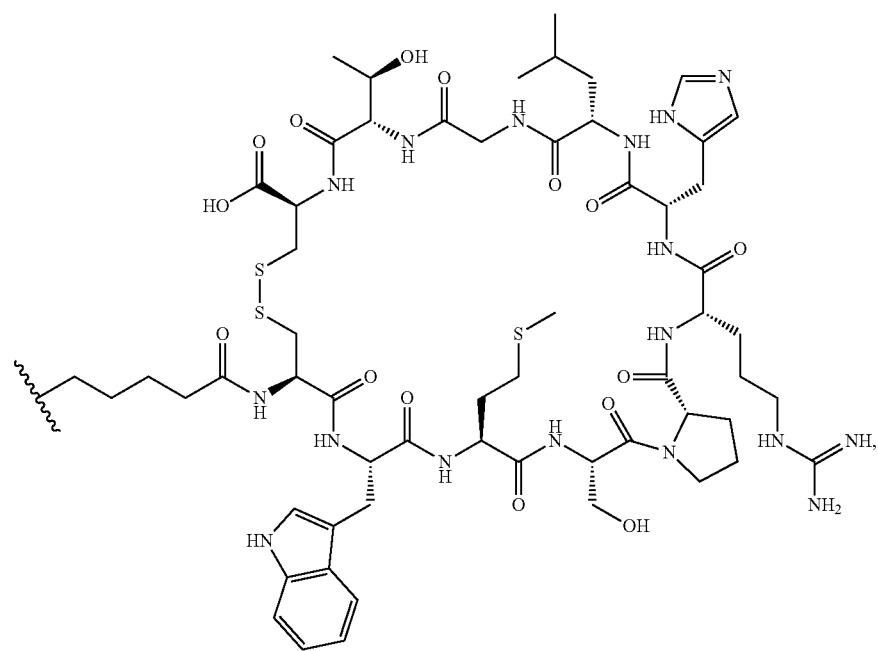
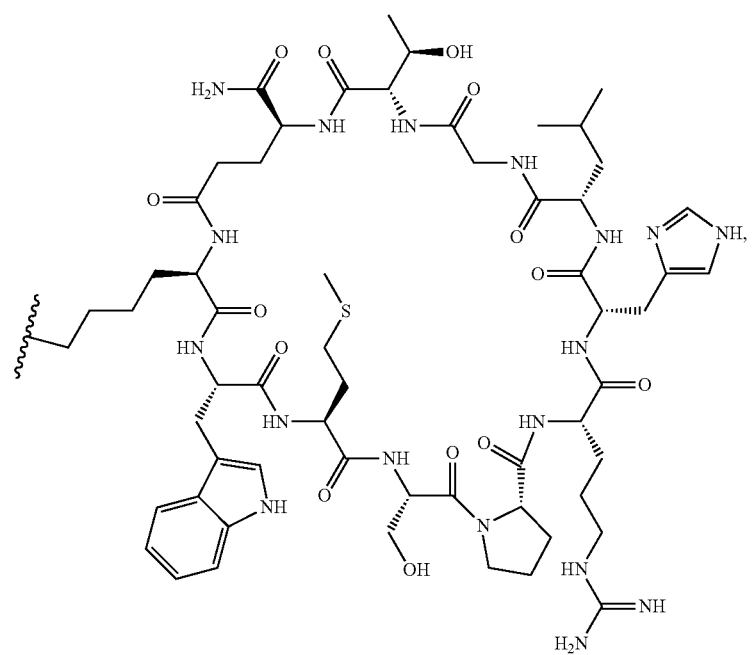

-continued
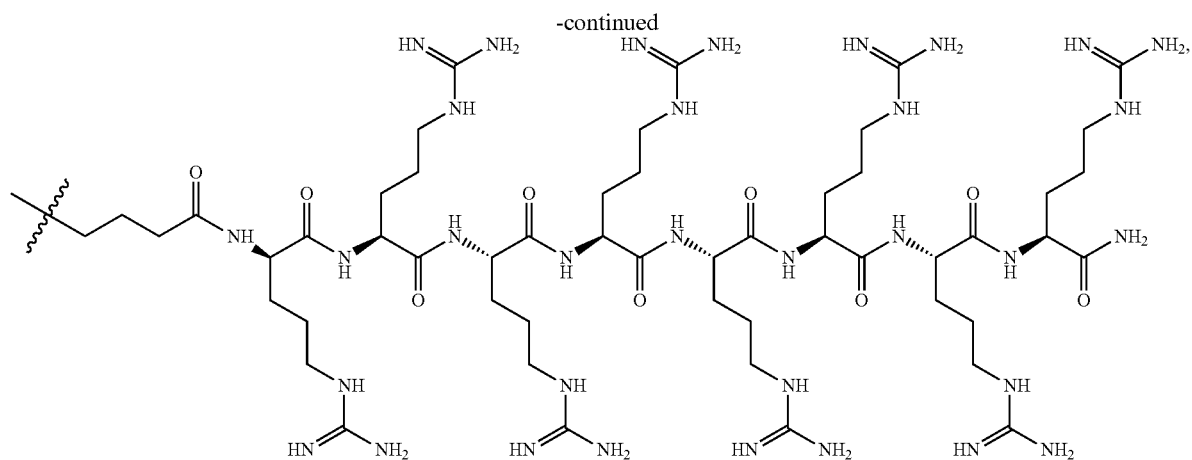
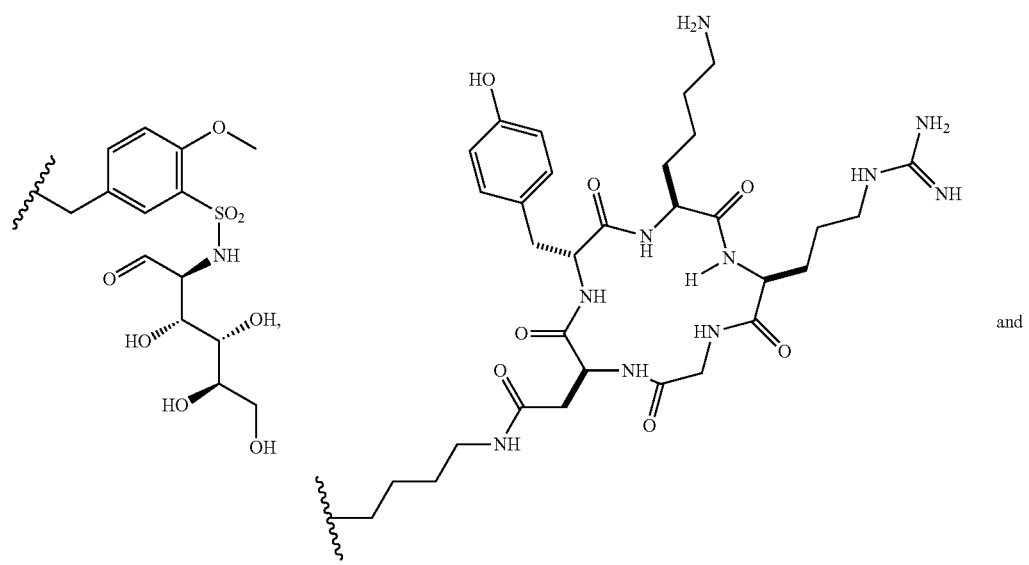
and
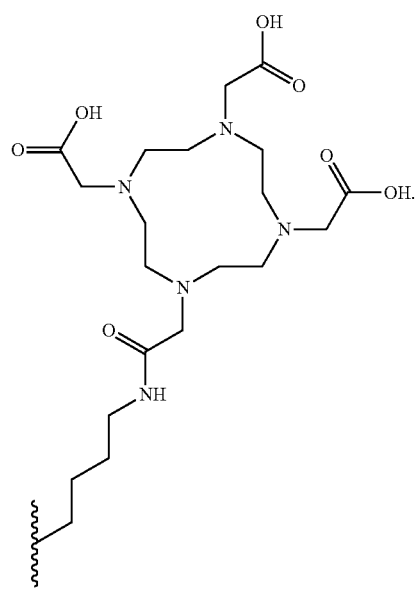

wherein m and n are integer selected from 1-10, and each of $R^5$, $R^6$ and $R^7$ is independently selected from hydrogen, acetate, alkyl having 1-10 carbon atoms, and optionally substituted benzyl.

In some embodiments, the chiral cyclen of formula (I) has each of $R^1$, $R^2$, $R^3$ and $R^4$ independently selected from the group consisting of methyl, ethyl, isopropyl, isobutyl, s-butyl, benzyl, —[CH$_2$]$_m$OH, —CHOHCH$_3$, —[CH$_2$]$_m$CO$_2$H, —[CH$_2$]$_m$CONH$_2$, —[CH$_2$]$_m$SH, —[CH$_2$]$_m$SCH$_3$, 4-bromobenzyl, 4-nitrobenzyl, 4-aminobenzyl, —CH$_2$(C$_6$H$_4$)NH—CH$_2$CO$_2$H, —CH$_2$(C$_6$H$_4$)N(CH$_2$CO$_2$H)$_2$, —CH$_2$(C$_6$H$_4$)NH[CH$_2$]$_m$SO$_3$H, —[CH$_2$]$_m$—NH$_2$, 4-hydroxybenzyl, 4-methoxybenzyl, —CH$_2$(C$_6$H$_4$)OCH$_2$CO$_2$H, —CH$_2$(C$_6$H$_4$)O[CH$_2$]$_m$SO$_3$H, —CH$_2$(C$_6$H$_4$)OCH$_2$CONH—[CH$_2$]$_m$SO$_3$H,

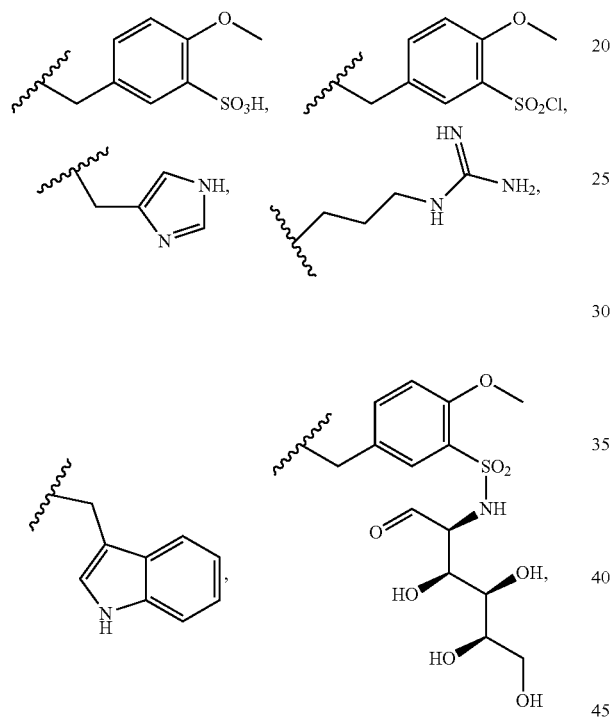

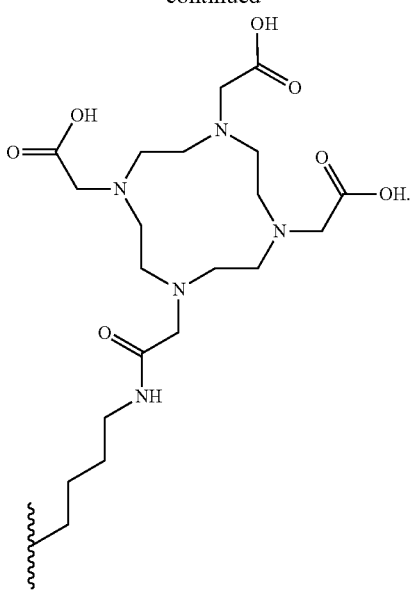

In another embodiment, the chiral cyclen of formula (I) has each of $X^1$, $X^2$, $X^3$ and $X^4$ independently selected from the group consisting of hydrogen, methyl, ethyl, isopropyl, isobutyl, s-butyl, —[CH$_2$]$_m$OH, —CHOHCH$_3$, —CH$_2$CO$_2$H, —CH(CH$_3$)CO$_2$H, —[CH$_2$]$_m$CO$_2$H, —[CH$_2$]$_m$CONH$_2$, —[CH$_2$]$_m$—NH$_2$, —[CH$_2$]$_m$SCH$_3$, benzyl, 4-hydroxybenzyl, 4-methoxybenzyl, 4-bromobenzyl, 4-nitrobenzyl, 4-aminobenzyl, —[CH$_2$]$_m$—NHTs, 6-(substituted methyl)picolinic acid,

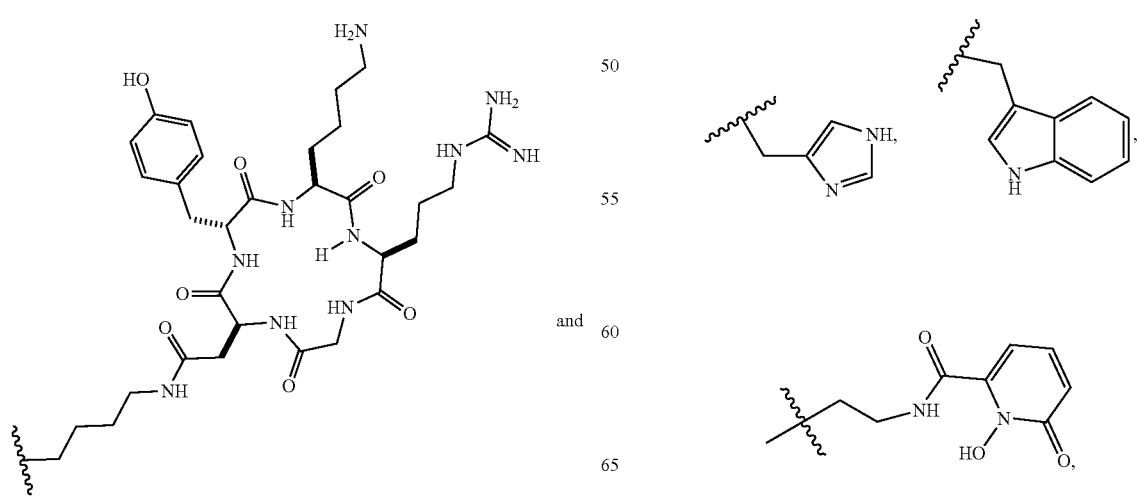

and

In some embodiments, the $R^1$, $R^2$, $R^3$, $R^4$, $X^1$, $X^2$, $X^3$ and $X^4$ of formula (I) can be independently selected from nanoparticles, targeting vectors and chromophores. In one embodiment, the nanoparticles include but not limited to gold, silver and silica nanoparticles. In one embodiment, targeting vectors include but not limited to macro- or supramolecular structures of peptides, proteins, DNA, RNA and polymers.

In one embodiment, the chiral cyclen having the structure of formula (1) is selected from the group consisting of:
(2S,5S,8S,11S)-2,5,8,11-tetramethyl-1,4,7,10-tetraazacyclododecane (66-a);
(2R,5R,8R,11R)-2,5,8,11-tetramethyl-1,4,7,10-tetraazacyclododecane ((R)-66-a);
(2S,5S,8S,11S)-2,5,8,11-tetraethyl-1,4,7,10-tetraazacyclododecane ((R)-66-b);
(2R,5R,8R,11R)-2,5,8,11-tetraethyl-1,4,7,10-tetraazacyclododecane ((R)-66-b);
(2S,5S,8S,11S)-2,5,8,11-tetraisopropyl-1,4,7,10-tetraazacyclododecane (66-c);
(2S,5R,8R,11R)-2,5,8,11-tetraisopropyl-1,4,7,10-tetraazacyclododecane ((R)-66-c);
(2S,5S,8S,11S)-2,5,8,11-tetra((S)-sec-butyl)-1,4,7,10-tetraazacyclododecane (66-d);
(2R,5R,8R,11R)-2,5,8,11-tetra((R)-sec-butyl)-1,4,7,10-tetraazacyclododecane ((R)-66-d);
2,2',2'',2'''-((2S,5S,8S,11S)-1,4,7,10-tetraazacyclododecane-2,5,8,11-tetrayl)tetraacetic acid (66-e);
2,2',2'',2'''-((2R,5R,8R,11R)-1,4,7,10-tetraazacyclododecane-2,5,8,11-tetrayl)tetraacetic acid ((R)-66-e);
2,2',2'',2'''-((2S,5S,8S,11S)-1,4,7,10-tetraazacyclododecane-2,5,8,11-tetrayl)tetraacetamide (66-f);
2,2',2'',2'''-((2R,5R,8R,11R)-1,4,7,10-tetraazacyclododecane-2,5,8,11-tetrayl)tetraacetamide ((R)-66-f);
3,3',3''-((2S,5S,8S,11S)-11-(3-carboxypropyl)-1,4,7,10-tetraazacyclododecane-2,5,8-triyl)tripropanoic acid (66-g);
3,3',3''-((2R,5R,8R,11R)-11-(3-carboxypropyl)-1,4,7,10-tetraazacyclododecane-2,5,8-triyl)tripropanoic acid ((R)-66-g);
3,3',3''-((2S,5S,8S,11S)-11-(4-amino-4-oxobutyl)-1,4,7,10-tetraazacyclododecane-2,5,8-triyl)tripropanamide (66-h);
3,3',3''-((2R,5R,8R,11R)-11-(4-amino-4-oxobutyl)-1,4,7,10-tetraazacyclododecane-2,5,8-triyl)tripropanamide ((R)-66-h);
(1S,1'S,1''S,1'''S)-1,1',1'',1'''-((2R,5R,8R,11R)-1,4,7,10-tetraazacyclododecane-2,5,8,11-tetrayl)tetraethanol (66-i);
(1R,1'R,1''R,1'''R)-1,1',1'',1'''-((2S,5S,8S,11S)-1,4,7,10-tetraazacyclododecane-2,5,8,11-tetrayl)tetraethanol ((R)-66-i);
(2S,5S,8S,11S)-2,5,8,11-tetraisobutyl-1,4,7,10-tetraazacyclododecane (66-j);
(2R,5R,8R,11R)-2,5,8,11-tetraisobutyl-1,4,7,10-tetraazacyclododecane ((R)-66-j);
(2S,5S,8S,11S)-2,5,8,11-tetrakis(2-(methylthio)ethyl)-1,4,7,10-tetraazacyclododecane (66-k);
(2R,5R,8R,11R)-2,5,8,11-tetrakis(2-(methylthio)ethyl)-1,4,7,10-tetraazacyclododecane ((R)-66-k);
((2R,5R,8R,11R)-1,4,7,10-tetraazacyclododecane-2,5,8,11-tetrayl)tetramethanethiol (66-1);
((2S,5S,8S,11S)-1,4,7,10-tetraazacyclododecane-2,5,8,11-tetrayl)tetramethanethiol ((R)-66-1);
((2R,5R,8R,11R)-1,4,7,10-tetraazacyclododecane-2,5,8,11-tetrayl)tetramethanol (66-m);
((2S,5S,8S,11S)-1,4,7,10-tetraazacyclododecane-2,5,8,11-tetrayl)tetramethanol ((R)-66-m);
(2S,5S,8S,11S)-2,5,8,11-tetrabenzyl-1,4,7,10-tetraazacyclododecane (66-n);
(2R,5R,8R,11R)-2,5,8,11-tetrabenzyl-1,4,7,10-tetraazacyclododecane ((R)-66-n);
4,4',4'',4'''-((2S,5S,8S,11S)-1,4,7,10-tetraazacyclododecane-2,5,8,11-tetrayl)tetrakis(butan-1-amine) (66-o);
4,4',4'',4'''-((2R,5R,8R,11R)-1,4,7,10-tetraazacyclododecane-2,5,8,11-tetrayl)tetrakis(butan-1-amine) ((R)-66-o);
1,1',1'',1'''-(((2S,5S,8S,11S)-1,4,7,10-tetraazacyclododecane-2,5,8,11-tetrayl)tetrakis(propane-3,1-diyl))tetraguanidine (66-p);
1,1',1'',1'''-(((2R,5R,8R,11R)-1,4,7,10-tetraazacyclododecane-2,5,8,11-tetrayl)tetrakis(propane-3,1-diyl))tetraguanidine ((R)-66-p);
(2S,5S,8S,11S)-2,5,8,11-tetrakis(4-methoxybenzyl)-1,4,7,10-tetraazacyclododecane triformate (66-q);
(2R,5R,8R,11R)-2,5,8,11-tetrakis(4-methoxybenzyl)-1,4,7,10-tetraazacyclododecane ((R)-66-q);

4,4',4'',4'''-(((2S,5S,8S,11S)-1,4,7,10-tetraazacyclododecane-2,5,8,11-tetrayl)tetrakis(methylene))tetraphenol (66-r);

4,4',4'',4'''-(((2R,5R,8R,11R)-1,4,7,10-tetraazacyclododecane-2,5,8,11-tetrayl)tetrakis(methylene))tetraphenol ((R)-66-r);

(2S,5S,8S,11S)-2,5,8,11-tetrakis(4-bromobenzyl)-1,4,7,10-tetraazacyclododecane (66-s);

(2R,5R,8R,11R)-2,5,8,11-tetrakis(4-bromobenzyl)-1,4,7,10-tetraazacyclododecane ((R)-66-s);

(2S,5S,8S,11S)-2,5,8,11-tetrakis(4-nitrobenzyl)-1,4,7,10-tetraazacyclododecane (66-t);

(2R,5R,8R,11R)-2,5,8,11-tetrakis(4-nitrobenzyl)-1,4,7,10-tetraazacyclododecane ((R)-66-t);

4,4',4'',4'''-(((2S,5S,8S,11S)-1,4,7,10-tetraazacyclododecane-2,5,8,11-tetrayl)tetrakis(methylene))tetraaniline (66-u);

4,4',4'',4'''-(((2R,5R,8R,11R)-1,4,7,10-tetraazacyclododecane-2,5,8,11-tetrayl)tetrakis(methylene))tetraaniline ((R)-66-u);

5,5',5'',5'''-(((2S,5S,8S,11S)-1,4,7,10-tetraazacyclododecane-2,5,8,11-tetrayl)tetrakis(methylene))tetrakis(2-methoxybenzenesulfonic acid) (66-v);

5,5',5'',5'''-(((2R,5R,8R,11R)-1,4,7,10-tetraazacyclododecane-2,5,8,11-tetrayl)tetrakis(methylene))tetrakis(2-methoxybenzenesulfonic acid) ((R)-66-v);

(2S,5S,8S,11S)-2,5,8,11-tetrakis((1H-imidazol-5-yl)methyl)-1,4,7,10-tetraazacyclododecane (66-w);

(2R,5R,8R,11R)-2,5,8,11-tetrakis((1H-imidazol-5-yl)methyl)-1,4,7,10-tetraazacyclododecane ((R)-66-w);

(2S,5S,8S,11S)-2,5,8,11-tetrakis((1H-indol-3-yl)methyl)-1,4,7,10-tetraazacyclododecane (66-x);

(2R,5R,8R,11R)-2,5,8,11-tetrakis((1H-indol-3-yl)methyl)-1,4,7,10-tetraazacyclododecane ((R)-66-x);

2-((2S,5S,8S,11S)-2,5,8,11-tetramethyl-1,4,7,10-tetraazacyclododecan-1-yl)acetic acid (L1_DO1A);

2-((2R,5R,8R,11R)-2,5,8,11-tetramethyl-1,4,7,10-tetraazacyclododecan-1-yl)acetic acid ((R)-L1_DO1A);

2,2'-((2S,5S,8S,11S)-2,5,8,11-tetramethyl-1,4,7,10-tetraazacyclododecane-1,7-diyl)diacetic acid (L1_DO2A);

2,2'-((2R,5R,8R,11R)-2,5,8,11-tetramethyl-1,4,7,10-tetraazacyclododecane-1,7-diyl)diacetic acid ((R)-L1_DO2A);

2,2',2''-((2S,5S,8S,11S)-2,5,8,11-tetramethyl-1,4,7,10-tetraazacyclododecane-1,4,7-triyl)triacetic acid (L1_DO3A);

2,2',2''-((2R,5R,8R,11R)-2,5,8,11-tetramethyl-1,4,7,10-tetraazacyclododecane-1,4,7-triyl)triacetic acid ((k)-L1_DO3A);

2,2',2'',2'''-((2S,5S,8S,11S)-2,5,8,11-tetramethyl-1,4,7,10-tetraazacyclododecane-1,4,7,10-tetrayl)tetraacetic acid (L1);

2,2',2'',2'''-((2R,5R,8R,11R)-2,5,8,11-tetramethyl-1,4,7,10-tetraazacyclododecane-1,4,7,10-tetrayl)tetraacetic acid ((R)-L1);

2-((2S,5S,8S,11S)-2,5,8,11-tetraethyl-1,4,7,10-tetraazacyclododecan-1-yl)acetic acid (L2_DO1A);

2-((2R,5R,8R,11R)-2,5,8,11-tetraethyl-1,4,7,10-tetraazacyclododecan-1-yl)acetic acid ((R)-46-a_DO1A);

2,2'-((2S,5S,8S,11S)-2,5,8,11-tetraethyl-1,4,7,10-tetraazacyclododecane-1,7-diyl)diacetic acid (L2_DO2A);

2,2'-((2R,5R,8R,11R)-2,5,8,11-tetraethyl-1,4,7,10-tetraazacyclododecane-1,7-diyl)diacetic acid ((R)-46-a_DO2A);

2,2',2''-((2S,5S,8S,11S)-2,5,8,11-tetraethyl-1,4,7,10-tetraazacyclododecane-1,4,7-triyl)triacetic acid (L2_DO3A);

2,2',2''-((2R,5R,8R,11R)-2,5,8,11-tetraethyl-1,4,7,10-tetraazacyclododecane-1,4,7-triyl)triacetic acid ((R)-L2_DO3A);

2,2',2'',2'''-((2S,5S,8S,11S)-2,5,8,11-tetraethyl-1,4,7,10-tetraazacyclododecane-1,4,7,10-tetrayl)tetraacetic acid (L2);

2,2',2'',2'''-((2R,5R,8R,11R)-2,5,8,11-tetraethyl-1,4,7,10-tetraazacyclododecane-1,4,7,10-tetrayl)tetraacetic acid ((R)-46-a_DOTA);

2-((2S,5S,8S,11S)-2,5,8,11-tetraisobutyl-1,4,7,10-tetraazacyclododecan-1-yl)acetic acid (L3_DO1A);

2-((2R,5R,8R,11R)-2,5,8,11-tetraisobutyl-1,4,7,10-tetraazacyclododecan-1-yl)acetic acid((R)-L3_DO1A);

2,2'-((2S,5S,8S,11S)-2,5,8,11-tetraisobutyl-1,4,7,10-tetraazacyclododecane-1,7-diyl)diacetic acid (L3_DO2A);

2,2'-((2R,5R,8R,11R)-2,5,8,11-tetraisobutyl-1,4,7,10-tetraazacyclododecane-1,7-diyl)diacetic acid ((R)-L3_DO2A);

2,2',2''-((2S,5S,8S,11S)-2,5,8,11-tetraisobutyl-1,4,7,10-tetraazacyclododecane-1,4,7-triyl)triacetic acid (L3_DO3A);

2,2',2''-((2R,5R,8R,11R)-2,5,8,11-tetraisobutyl-1,4,7,10-tetraazacyclododecane-1,4,7-triyl)triacetic acid ((R)-L3_DO3A);

2,2',2'',2'''-((2S,5S,8S,11S)-2,5,8,11-tetraisobutyl-1,4,7,10-tetraazacyclododecane-1,4,7,10-tetrayl)tetraacetic acid (L3);

2,2',2'',2'''-((2R,5R,8R,11R)-2,5,8,11-tetraisobutyl-1,4,7,10-tetraazacyclododecane-1,4,7,10-tetrayl)tetraacetic acid ((R)-L3);

2-((2S,5S,8S,11S)-2,5,8,11-tetrabenzyl-1,4,7,10-tetraazacyclododecan-1-yl)acetic acid (L4_DO1A);

2,2'-((2S,5S,8S,11S)-2,5,8,11-tetrabenzyl-1,4,7,10-tetraazacyclododecane-1,7-diyl)diacetic acid (L4_DO2A);

2,2',2''-((2S,5S,8S,11S)-2,5,8,11-tetrabenzyl-1,4,7,10-tetraazacyclododecane-1,4,7-triyl)triacetic acid (L4_DO3A);

2,2',2'',2'''-((2S,5S,8S,11S)-2,5,8,11-tetrabenzyl-1,4,7,10-tetraazacyclododecane-1,4,7,10-tetrayl)tetraacetic acid (L4);

2-((2S,5S,8S,11S)-2,5,8,11-tetrakis(4-aminobutyl)-1,4,7,10-tetraazacyclododecan-1-yl)acetic acid (41-d_DO1A);

2,2'-((2S,5S,8S,11S)-2,5,8,11-tetrakis(4-aminobutyl)-1,4,7,10-tetraazacyclododecane-1,7-diyl)diacetic acid (41-d_DO2A);

2,2',2''-((2S,5S,8S,11S)-2,5,8,11-tetrakis(4-aminobutyl)-1,4,7,10-tetraazacyclododecane-1,4,7-triyl)triacetic acid (41-d_DO3A);

2,2',2'',2'''-((2S,5S,8S,11S)-2,5,8,11-tetrakis(4-aminobutyl)-1,4,7,10-tetraazacyclododecane-1,4,7,10-tetrayl)tetraacetic acid (41-d_DOTA);

2-((2S,5S,8S,11S)-2,5,8,11-tetrakis(3-guanidinopropyl)-1,4,7,10-tetraazacyclododecan-1-yl)acetic acid (46-s_DO1A);

2,2'-((2S,5S,8S,11S)-2,5,8,11-tetrakis(3-guanidinopropyl)-1,4,7,10-tetraazacyclododecane-1,7-diyl)diacetic acid (46-s_DO2A);

2,2',2''-((2S,5S,8S,11S)-2,5,8,11-tetrakis(3-guanidinopropyl)-1,4,7,10-tetraazacyclododecane-1,4,7-triyl)triacetic acid (46-s_DO3A);

2,2',2'',2'''-((2S,5S,8S,11S)-2,5,8,11-tetrakis(3-guanidinopropyl)-1,4,7,10-tetraazacyclododecane-1,4,7,10-tetrayl)tetraacetic acid (46-s_DOTA);

2-((2S,5S,8S,11S)-2,5,8,11-tetraisopropyl-1,4,7,10-tetraazacyclododecan-1-yl)acetic acid (44-h_DO1A);

2,2'-((2S,5S,8S,11S)-2,5,8,11-tetraisopropyl-1,4,7,10-tetraazacyclododecane-1,7-diyl)diacetic acid (44-h_DO2A);

2,2',2"-((2S,5S,8S,11S)-2,5,8,11-tetraisopropyl-1,4,7,10-tetraazacyclododecane-1,4,7-triyl)triacetic acid (44-h_DO3A);

2,2',2",2'''-((2S,5S,8S,11S)-2,5,8,11-tetraisopropyl-1,4,7,10-tetraazacyclododecane-1,4,7,10-tetrayl)tetraacetic acid (44-h_DOTA);

2-((2R,5R,8R,11R)-2,5,8,11-tetrakis((S)-1-hydroxyethyl)-1,4,7,10-tetraazacyclododecan-1-yl)acetic acid (46-1_DO1A);

2,2'-((2R,5R,8R,11R)-2,5,8,11-tetrakis((S)-1-hydroxyethyl)-1,4,7,10-tetraazacyclododecane-1,7-diyl)diacetic acid (46-1_DO2A);

2,2',2"-((2R,5R,8R,11R)-2,5,8,11-tetrakis((S)-1-hydroxyethyl)-1,4,7,10-tetraazacyclododecane-1,4,7-triyl)triacetic acid (46-1_DO3A);

2,2',2",2'''-((2R,5R,8R,11R)-2,5,8,11-tetrakis((S)-1-hydroxyethyl)-1,4,7,10-tetraazacyclododecane-1,4,7,10-tetrayl)tetraacetic acid (46-1_DOTA);

2-((2S,5S,8S,11S)-2,5,8,11-tetrakis(2-(methylthio)ethyl)-1,4,7,10-tetraazacyclododecan-1-yl)acetic acid (46-m_DO1A);

2,2'-((2S,5S,8S,11S)-2,5,8,11-tetrakis(2-(methylthio)ethyl)-1,4,7,10-tetraazacyclododecane-1,7-diyl)diacetic acid (46-m_DO2A);

2,2',2"-((2S,5S,8S,11S)-2,5,8,11-tetrakis(2-(methylthio)ethyl)-1,4,7,10-tetraazacyclododecane-1,4,7-triyl)triacetic acid (46-m_DO3A);

2,2',2",2'''-((2S,5S,8S,11S)-2,5,8,11-tetrakis(2-(methylthio)ethyl)-1,4,7,10-tetraazacyclododecane-1,4,7,10-tetrayl)tetraacetic acid (46-*m* DOTA);

2-((2R,5R,8R,11R)-2,5,8,11-tetrakis(mercaptomethyl)-1,4,7,10-tetraazacyclododecan-1-yl)acetic acid (45-h_DO1A);

2,2'-((2R,5R,8R,11R)-2,5,8,11-tetrakis(mercaptomethyl)-1,4,7,10-tetraazacyclododecane-1,7-diyl)diacetic acid (45-h_DO2A);

2,2',2"-((2R,5R,8R,11R)-2,5,8,11-tetrakis(mercaptomethyl)-1,4,7,10-tetraazacyclododecane-1,4,7-triyl)triacetic acid (45-h_DO3A);

2,2',2",2'''-((2R,5R,8R,11R)-2,5,8,11-tetrakis(mercaptomethyl)-1,4,7,10-tetraazacyclododecane-1,4,7,10-tetrayl)tetraacetic acid (45-h_DOTA);

2-((2R,5R,8R,11R)-2,5,8,11-tetrakis(hydroxymethyl)-1,4,7,10-tetraazacyclododecan-1-yl)acetic acid (46-k_DO1A);

2,2'-((2R,5R,8R,11R)-2,5,8,11-tetrakis(hydroxymethyl)-1,4,7,10-tetraazacyclododecane-1,7-diyl)diacetic acid (46-k_DO2A);

2,2',2"-((2R,5R,8R,11R)-2,5,8,11-tetrakis(hydroxymethyl)-1,4,7,10-tetraazacyclododecane-1,4,7-triyl)triacetic acid (46-k_DO3A);

2,2',2",2'''-((2R,5R,8R,11R)-2,5,8,11-tetrakis(hydroxymethyl)-1,4,7,10-tetraazacyclodoclecane-1,4,7,10-tetrayl)tetraacetic acid (46-k_DOTA);

2-((2S,5S,8S,11S)-2,5,8,11-tetra((R)-sec-butyl)-1,4,7,10-tetraazacyclododecan-1-yl)acetic acid (46-n_DO1A);

2,2'-((2S,5S,8S,11S)-2,5,8,11-tetra((R)-sec-butyl)-1,4,7,10-tetraazacyclododecane-1,7-diyl)diacetic acid (46-n_DO2A);

2,2',2"-((2S,5S,8S,11S)-2,5,8,11-tetra((R)-sec-butyl)-1,4,7,10-tetraazacyclododecane-1,4,7-triyl)triacetic acid (46-n_DO3A);

2,2',2",2'''-((2S,5S,8S,11S)-2,5,8,11-tetra((R)-sec-butyl)-1,4,7,10-tetraazacyclododecane-1,4,7,10-tetrayl)tetraacetic acid (46-n_DOTA);

2,2',2",2''',2''''-((2S,5S,8S,11S)-1,4,7,10-tetraazacyclododecane-1,2,5,8,11-pentayl)pentaacetic acid (46-o_DO1A);

2,2',2",2''',2'''',2'''''-((2S,5S,8S,11S)-1,4,7,10-tetraazacyclododecane-1,2,5,7,8,11-hexayl)hexaacetic acid (46-o_DO2A);

2,2',2",2''',2'''',2''''',2''''''-((2S,5S,8S,11S)-1,4,7,10-tetraazacyclododecane-1,2,4,5,7,8,11-heptayl)heptaacetic acid (46-o_DO3A);

2,2',2",2''',2'''',2''''',2'''''',2'''''''-((2S,5S,8S,11S)-1,4,7,10-tetraazacyclododecan-1,2,4,5,7,8,10,11-octayl)octaacetic acid (46-o_DOTA);

2-((2S,5S,8S,11S)-2,5,8,11-tetrakis(2-amino-2-oxoethyl)-1,4,7,10-tetraazacyclododecan-1-yl)acetic acid (46-p_DO1A);

2,2'-((2S,5S,8S,11S)-2,5,8,11-tetrakis(2-amino-2-oxoethyl)-1,4,7,10-tetraazacyclododecane-1,7-diyl)diacetic acid (46-p_DO2A);

2,2',2"-((2S,5S,8S,11S)-2,5,8,11-tetrakis(2-amino-2-oxoethyl)-1,4,7,10-tetraazacyclododecane-1,4,7-triyl)triacetic acid (46-p_DO3A);

2,2',2",2'''-((2S,5S,8S,11S)-2,5,8,11-tetrakis(2-amino-2-oxoethyl)-1,4,7,10-tetraazacyclododecane-1,4,7,10-tetrayl)tetraacetic acid (46-p_DOTA);

3,3',3",3'''-((2S,5S,8S,11S)-1-(carboxymethyl)-1,4,7,10-tetraazacyclododecane-2,5,8,11-tetrayl)tetrapropanoic acid (46-q_DO1A);

3,3',3",3'''-((2S,5S,8S,11S)-1,7-bis(carboxymethyl)-1,4,7,10-tetraazacyclododecane-2,5,8,11-tetrayl)tetrapropanoic acid (46-q_DO2A);

3,3',3",3'''-((2S,5S,8S,11S)-1,4,7-tris(carboxymethyl)-17,10-tetraazacyclododecane-2,5,8,11-tetrayl)tetrapropanoic acid (46-q_DO3A);

3,3',3",3'''-((2S,5S,8S,11S)-1,4,7,10-tetrakis(carboxymethyl)-1,4,7,10 tetraazacyclododecane-2,5,8,11-tetrayl)tetrapropanoic acid (46-q_DOTA);

2-((2S,5S,8S,11S)-2,5,8,11-tetrakis(3-amino-3-oxopropyl)-1,4,7,10-tetraazacyclododecan-1-yl)acetic acid (46-r_DO1A);

2,2'-((2S,5S,8S,11S)-2,5,8,11-tetrakis(3-amino-3-oxopropyl)-1,4,7,10-tetraazacyclododecane-1,7-diyl)diacetic acid (46-r_DO2A);

2,2',2"-((2S,5S,8S,11S)-2,5,8,11-tetrakis(3-amino-3-oxopropyl)-1,4,7,10-tetraazacyclododecane-1,4,7-triyl)triacetic acid (46-r_DO3A);

2,2',2",2'''-((2S,5S,8S,11S)-2,5,8,11-tetrakis(3-amino-3-oxopropyl)-1,4,7,10-tetraazacyclododecane-1,4,7,10-tetrayl)tetraacetic acid (46-r_DOTA);

2-((2S,5S,8S,11S)-2,5,8,11-tetrakis(4-methoxybenzyl)-1,4,7,10-tetraazacyclododecan-1-yl)acetic acid (40-d_DO1A);

2,2'-((2S,5S,8S,11S)-2,5,8,11-tetrakis(4-methoxybenzyl)-1,4,7,10-tetraazacyclododecane-1,7-diyl)diacetic acid (40-d_DO2A);

2,2',2"-((2S,5S,8S,11S)-2,5,8,11-tetrakis(4-methoxybenzyl)-1,4,7,10-tetraazacyclododecane-1,4,7-triyl)triacetic acid (40-d_DO3A);

2,2',2",2'''-((2S,5S,8S,11S)-2,5,8,11-tetrakis(4-methoxybenzyl)-1,4,7,10-tetraazacyclododecane-1,4,7,10-tetrayl)tetraacetic acid (40-d_DOTA);

2-((2S,5S,8S,11S)-2,5,8,11-tetrakis(4-hydroxybenzyl)-1,4,7,10-tetraazacyclododecan-1-yl)acetic acid (46-b_DO1A);

2,2'-((2S,5S,8S,11S)-2,5,8,11-tetrakis(4-hydroxybenzyl)-1,4,7,10-tetraazacyclododecane-1,7-diyl)diacetic acid (46-b_DO2A);

2,2',2"-((2S,5S,8S,11S)-2,5,8,11-tetrakis(4-hydroxybenzyl)-1,4,7,10-tetraazacyclododecane-1,4,7-triyl)triacetic acid (46-b_DO3A);

2,2',2'',2'''-((2S,5S,8S,11S)-2,5,8,11-tetrakis(4-hydroxybenzyl)-1,4,7,10-tetraazacyclododecane-1,4,7,10-tetrayl)tetraacetic acid (46-b_DOTA);

2-((2S,5S,8S,11S)-2,5,8,11-tetrakis(4-bromobenzyl)-1,4,7,10-tetraazacyclododecan-1-yl)acetic acid (46-u_DO1A);

2,2'-((2S,5S,8S,11S)-2,5,8,11-tetrakis(4-bromobenzyl)-1,4,7,10-tetraazacyclododecane-1,7-diyl)diacetic acid (46-u_DO2A);

2,2',2''-((2S,5S,8S,11S)-2,5,8,11-tetrakis(4-bromobenzyl)-1,4,7,10-tetraazacyclododecane-1,4,7-triyl)triacetic acid (46-u_DO3A);

2,2',2'',2'''-((2S,5S,8S,11S)-2,5,8,11-tetrakis(4-bromobenzyl)-1,4,7,10-tetraazacyclododecane-1,4,7,10-tetrayl)tetraacetic acid (46-u_DOTA);

2-((2S,5S,8S,11S)-2,5,8,11-tetrakis(4-nitrobenzyl)-1,4,7,10-tetraazacyclododecan-1-yl)acetic acid (46-v_DO1A);

2,2'-((2S,5S,8S,11S)-2,5,8,11-tetrakis(4-nitrobenzyl)-1,4,7,10-tetraazacyclododecane-1,7-diyl)diacetic acid (46-v_DO2A);

2,2',2''-((2S,5S,8S,11S)-2,5,8,11-tetrakis(4-nitrobenzyl)-1,4,7,10-tetraazacyclododecane-1,4,7-triyl)triacetic acid (46-v_DO3A);

2,2',2'',2'''-((2S,5S,8S,11S)-2,5,8,11-tetrakis(4-nitrobenzyl)-1,4,7,10-tetraazacyclododecane-1,4,7,10-tetrayl)tetraacetic acid (46-v_DOTA);

2-((2S,5S,8S,11S)-2,5,8,11-tetrakis(4-aminobenzyl)-1,4,7,10-tetraazacyclododecan-1-yl)acetic acid (46-c_DO1A);

2,2'-((2S,5S,8S,11S)-2,5,8,11-tetrakis(4-aminobenzyl)-1,4,7,10-tetraazacyclododecane-1,7-diyl)diacetic acid (46-c_DO2A);

2,2',2''-((2S,5S,8S,11S)-2,5,8,11-tetrakis(4-aminobenzyl)-1,4,7,10-tetraazacyclododecane-1,4,7-triyl)triacetic acid (46-c_DO3A);

2,2',2'',2'''-((2S,5S,8S,11S)-2,5,8,11-tetrakis(4-aminobenzyl)-1,4,7,10-tetraazacyclododecane-1,4,7,10-tetrayl)tetraacetic acid (46-c_DOTA);

2-((2S,5S,8S,11S)-2,5,8,11-tetrakis((1H-imidazol-5-yl)methyl)-1,4,7,10-tetraazacyclododecan-1-yl)acetic acid (46-j_DO1A);

2,2'-((2S,5S,8S,11S)-2,5,8,11-tetrakis((1H-imidazol-5-yl)methyl)-17,10-tetraazacyclododecane-1,7-diyl)diacetic acid (46-j_DO2A);

2,2',2''-((2S,5S,8S,11S)-2,5,8,11-tetrakis((1H-imidazol-5-yl)methyl)-1,4,7,10-tetraazacyclododecane-1,4,7-triyl)triacetic acid (46-j_DO3A);

2,2',2'',2'''-((2S,5S,8S,11S)-2,5,8,11-tetrakis((1H-imidazol-5-yl)methyl)-1,4,7,10-tetraazacyclododecane-1,4,7,10-tetrayl)tetraacetic acid (46-j_DOTA);

2-((2S,5S,8S,11S)-2,5,8,11-tetrakis((1H-indol-3-yl)methyl)-1,4,7,10-tetraazacyclododecan-1-yl)acetic acid (46-t_DO1A);

2,2'-((2S,5S,8S,11S)-2,5,8,11-tetrakis((1H-indol-3-yl)methyl)-1,4,7,10-tetraazacyclododecane-1,7-diyl)diacetic acid (46-t_DO2A);

2,2',2''-((2S,5S,8S,11S)-2,5,8,11-tetrakis((1H-indol-3-yl)methyl)-1,4,7,10-tetraazacyclododecane-1,4,7-triyl)triacetic acid (46-t_DO3A);

2,2',2'',2'''-((2S,5S,8S,11S)-2,5,8,11-tetrakis((1H-indol-3-yl)methyl)-1,4,7,10-tetraazacyclododecane-1,4,7,10-tetrayl)tetraacetic acid (46-t_DOTA);

2-((2S,5S,8S,11S)-2,5,8,11-tetrakis(4-methoxy-3-sulfobenzyl)-1,4,7,10-tetraazacyclododecan-1-yl)acetic acid (46-g_DO1A);

2,2'-((2S,5S,8S,11S)-2,5,8,11-tetrakis(4-methoxy-3-sulfobenzyl)-1,4,7,10-tetraazacyclododecane-1,7-diyl)diacetic acid (46-g_DO2A);

2,2',2''-((2S,5S,8S,11S)-2,5,8,11-tetrakis(4-methoxy-3-sulfobenzyl)-1,4,7,10-tetraazacyclododecane-1,4,7-triyl)triacetic acid (46-g_DO3A);

2,2',2'',2'''-((2S,5S,8S,11S)-2,5,8,11-tetrakis(4-methoxy-3-sulfobenzyl)-1,4,7,10-tetraazacyclododecane-1,4,7,10-tetrayl)tetraacetic acid (46-g_DOTA);

2,2',2'',2'''-((2S,5S,8S,11S)-2,5,8,11-tetrakis(4-(2-oxo-2-((3-sulfopropyl)amino)ethoxy)benzyl)-1,4,7,10-tetraazacyclododecane-1,4,7,10-tetrayl)tetraacetic acid (46-d_DOTA);

2,2',2'',2'''-((2S,5S,8S,11S)-2,5,8,11-tetrakis(4-(3-sulfopropoxy)benzyl)-1,4,7,10-tetraazacyclododecane-1,4,7,10-tetrayl)tetraacetic acid (46-e_DOTA);

2,2',2'',2''',2'''',2''''',2'''''',2'''''''-(((((2S,5S,8S,11S)-1,4,7,10-tetrakis(carboxymethyl)-1,4,7,10-tetraazacyclododecane-2,5,8,11-tetrayl)tetrakis(methylene))tetrakis(benzene-4,1-diyl))tetrakis(azanetriyl))octaacetic acid (46-f_DOTA);

2,2',2'',2'''-((2S,5S,8S,11S)-2,5,8,11-tetrakis(3-(chlorosulfonyl)-4-methoxybenzyl)-1,4,7,10-tetraazacyclododecane-1,4,7,10-tetrayl)tetraacetic acid (46-h_DOTA);

2,2',2'',2'''-((2S,5S,8S,11S)-2,5,8,11-tetrakis(4-methoxy-3-(N-((2R,3R,4S,5R)-3,4,5,6-tetrahydroxy-1-oxohexan-2-yl)sulfamoyl)benzyl)-1,4,7,10-tetraazacyclododecane-1,4,7,10-tetrayl)tetraacetic acid (46-i_DOTA);

2,2',2''-((2S,5S,8S,11S)-10-(2-((4-((2S,5S,11S,14R)-11-(carboxymethyl)-5-(3-guanidinopropyl)-14-(4-hydroxybenzyl)-3,6,9,12,15-pentaoxo-1,4,7,10,13-pentaazacyclopentadecan-2-yl)butyl)amino)-2-oxoethyl)-2,5,8,11-tetraethyl-1,4,7,10-tetraazacyclododecane-1,4,7-triyl)triacetic acid (56-b_DO3A);

2,2',2''-((2S,5S,8S,11S)-10-(2-((4-((2S,5S,11S,14R)-14-benzyl-11-(carboxymethyl)-5-(3-guanidinopropyl)-3,6,9,12,15-pentaoxo-1,4,7,10,13-pentaazacyclopentadecan-2-yl)butyl)amino)-2-oxoethyl)-2,5,8,11-tetraethyl-1,4,7,10-tetraazacyclododecane-1,4,7-triyl)triacetic acid (56-c_DO3A);

2,2',2''-((2S,5S,8S,11S)-2,5,8,11-tetraethyl-10-((6-(hydroxy(methyl)phosphoryl)-4-((2,4,6-trimethoxyphenyl)ethynyl)pyridin-2-yl)methyl)-1,4,7,10-tetraazacyclododecane-1,4,7-triyl)triacetic acid (C-2);

2,2',2''-((2R,5R,8R,11R)-2,5,8,11-tetraethyl-10-((6-(hydroxy(methyl)phosphoryl)-4-((2,4,6-trimethoxyphenyl)ethynyl)pyridin-2-yl)methyl)-1,4,7,10-tetraazacyclododecane-1,4,7-triyl)triacetic acid (C-3);

2,2',2''-((2S,5S,8S,11S)-10-((6-(hydroxy(methyl)phosphoryl)-4-((2,4,6-trimethoxyphenyl)ethynyl)pyridin-2-yl)methyl)-2,5,8,11-tetraisobutyl-1,4,7,10-tetraazacyclododecane-1,4,7-triyl)triacetic acid (C-4);

2,2',2''-((2S,5S,8S,11S)-10-((6-(hydroxy(methyl)phosphoryl)-4-((2,4,6-trimethoxyphenyl)ethynyl)pyridin-2-yl)methyl)-2,5,8,11-tetraisopropyl-1,4,7,10-tetraazacyclododecane-1,4,7-triyl)triacetic acid (17);

2,2',2''-((2S,5S,8S,11S)-2,5,8,11-tetrabenzyl-10-((6-(hydroxy(methyl)phosphoryl)-4-((2,4,6-trimethoxyphenyl)ethynyl)pyridin-2-yl)methyl)-1,4,7,10-tetraazacyclododecane-1,4,7-triyl)triacetic acid (C-5);

2,2',2''-((2S,5S,8S,11S)-10-((6-(hydroxy(methyl)phosphoryl)-4-((2,4,6-trimethoxyphenyl)ethynyl)pyridin-2-yl)methyl)-2,5,8,11-tetrakis(4-methoxybenzyl)-1,4,7,10-tetraazacyclododecane-1,4,7-triyl)triacetic acid (18);

2,2',2''-((2S,5S,8S,11S)-10-((6-(hydroxy(methyl)phosphoryl)-4-((2,4,6-trimethoxyphenyl)ethynyl)pyridin-2-yl)methyl)-2,5,8,11-tetrakis(4-methoxy-3-sulfobenzyl)-1,4,7,10-tetraazacyclododecane-1,4,7-triyl)triacetic acid (19);

N,N',N'',N'''-(((2S,5S,8S,11S)-2,5,8,11-tetramethyl-1,4,7,10-tetraazacyclododecane-1,4,7,10-tetrayl)tetrakis(ethane-2,1-diyl))tetrakis(1-hydroxy-6-oxo-1,6-dihydropyridine-2-carboxamide) (33-e)

N,N',N'',N'''-(((2S,5S,8S,11S)-2,5,8,11-tetraethyl-1,4,7,10-tetraazacyclododecane-1,4,7,10-tetrayl)tetrakis(ethane-2,1-diyl))tetrakis(1-hydroxy-6-oxo-1,6-dihydropyridine-2-carboxamide) (33-a); and N,N',N'',N'''-(((2S,5S,8S,11S)-2,5,8,11-tetraisopropyl-1,4,7,10-tetraazacyclododecane-1,4,7,10-tetrayl)tetrakis(ethane-2,1-diyl))tetrakis(1-hydroxy-6-oxo-1,6-dihydropyridine-2-carboxamide) (33-f).

In one embodiment, the present invention provides a composition for imaging, comprising the chiral cyclen of formula (I), one or more metals, and optionally pharmaceutically acceptable excipients, wherein a metal complex is formed between the chiral cyclen and one or more metals.

In another embodiment, one or more metals are selected from the group consisting of Aluminium, Gallium, Indium, Iron, Nickel, Manganese, Cobalt, Chromium, Yttrium, Zirconium, Zinc, Copper, Lanthanum, Cerium, Praseodymium, Neodymium, Promethium, Samarium, Europium, Gadolinium, Terbium, Dysprosium, Holmium, Erbium, Thulium Ytterbium, Lutetium, Thorium, Uranium, Americium, Curium and Berkelium.

In one embodiment, the present invention discloses a method of using the composition of the present invention comprising the chiral cyclen of formula (I) for imaging, comprising the steps of (a) administering the composition to a subject in need thereof; (b) detecting radiation emitted by the metal complex; and (c) forming an image therefrom. In another embodiment, the present invention discloses a method of using the composition of the present invention comprising the chiral cyclen of formula (I) for imaging, comprising the steps of (a) administering the composition to a subject in need thereof; (b) allowing sufficient time to permit the metal complex to distribute within the subject; (c) exposing the subject to a wavelength absorbable by the metal complex; (d) detecting radiation emitted by the metal complex; and (e) forming an image therefrom. In one embodiment, the imaging is optical imaging, magnetic resonance imaging, positron emission tomography, single photon emission computed tomography. In another embodiment, the subject is a vertebrate, a mammal or human. In one embodiment, the composition is administered orally, nasally, aurally, ocularly, sublingually, buccally, systemically, transdermally, mucosally, via cerebral spinal fluid injection, vein injection, muscle injection, peritoneal injection, subcutaneous injection, or by inhalation. In some embodiments, the method is used in in vivo imaging or radiotherapy. In some embodiments, the radiation is visible to near infrared, radiowaves, high energy γ rays, lower energy γ rays, alpha particles, beta minus (electron emission), beta plus (positron emission) and gamma emitting radioisotopes, magnetic resonance and fluorescence.

In one embodiment, the present invention further discloses a method of using the composition of the present invention comprising the chiral cyclen of formula (I), comprising the steps of (a) contacting a target with the composition; (b) detecting radiation emitted by the metal complex; and (c) measuring the amount and/or concentration of the metal complex in the target. In one embodiment, the imaging is fluorescent microscopy, flow cytometry, immunohistochemistry, immunoprecipitation, in situ hybridization and Forster resonance energy transfer. In another embodiment, the target is blood or blood serum, bodily fluids, urine, faeces, sputum, saliva amniotic fluid, duodenal fluid, cerebrospinal fluid, tissue biopsy, cell, cell extract, organ and tissue. In one embodiment, the method is used in in vitro imaging. In some embodiments, the radiation is visible to near infrared, radiowaves, high energy γ rays, lower energy γ rays, alpha particles, beta minus (electron emission), beta plus (positron emission) and gamma emitting radioisotopes, magnetic resonance and fluorescence.

The invention will be better understood by reference to the Experimental Details which follow, but those skilled in the art will readily appreciate that the specific experiments are provided only for illustrative purpose, and are not meant to limit the invention scope as described herein.

Throughout this application, various references or publications are cited. Disclosures of these references or publications in their entireties are hereby incorporated by reference into this application in order to more fully describe the state of the art to which this invention pertains. It is to be noted that the transitional term "comprising", which is synonymous with "including", "containing" or "characterized by", is inclusive or open-ended, and does not exclude additional, un-recited elements or method steps.

Example 1

Synthesis of Chiral DOTA Metal Complexes

1. Synthesis of Chiral DOTA-Based Ligands L1-L4

The synthetic route to prepare the chiral DOTA-based ligands is shown in FIG. 1A. The chiral cyclens (3a-3d) were synthesized from aziridines 1a-1d, in the presence of TsOH (Step (a)) or a Lewis acid (Step (b), boron trifluoride and diethyl etherate complex). The cyclized tetramer products 2a-2d were purified by either column chromatography or recrystallization. In step (c), deprotection of the four benzyl groups in 2a-2d resulted in the chiral cyclens 3a-3d. In step (d), the chiral cyclens 3a-3d reacted with tert-butyl 2-bromoacetate to afford chiral cyclens 4a-4d. In step (e) and (0, the tert-butyl groups in chiral cyclens 4a-4d were deprotected by acid to give DOTA-based ligands L1-L4.

2. Synthesis of Chiral DOTA-Based Metal Complexes from L1-L4

In step (g) of FIG. 1A, the chiral DOTA-based lanthanide complexes were synthesized according to the classical procedures for [LnDOTA]⁻ known in the art. Separately, chiral DOTA-based complexes of Europium (III), Ytterbium (III) and Gadolinium (III) were also synthesized.

3. Experimental Procedure for Preparation of Chiral DOTA-Based Ligands L1-L4 and the Metal Complexes (FIG. 1A)

Compounds 1a-3a were synthesized according to a reported procedure (FIG. 1A).[45]

(2S,5S,8S,11S)-1,4,7,10-tetrabenzyl-2,5,8,11-tetraethyl-1,4,7,10-tetraazacyclododecane (2b): It was synthesized following a reported method.[43] A white solid (1.65 g, yield 27.5%) was obtained. $[\alpha]^{20}_D = -341.57°$, (c=0.01012 g/ml, benzene).

(2S,5S,8S,11S)-1,4,7,10-tetrabenzyl-2,5,8,11-tetraisobutyl-1,4,7,10-tetraazacyclododecane (2c): Similarly prepared as 2b. Purification by recrystallization from benzene and ethyl acetate resulted in a white solid (1.7 g, yield 28.3%). MS: 757, [M+H]⁺.

(2S,5S,8S,11S)-1,2,4,5,7,8,10,11-octabenzyl-1,4,7,10-tetraazacyclododecane (2d): Similarly prepared as 2b. Purification by recrystallization from acetonitrile resulted in a white solid (1.5 g, yield 25.0%). MS: 893, [M+H]⁺.

(2S,5S,8S,11S)-2,5,8,11-tetraethyl-1,4,7,10-tetraazacyclododecane (3b): A light yellow solid (1.5 g, yield 97%). HRMS: 285.3022, [M+H]⁺.

(2S,5S,8S,11S)-2,5,8,11-tetraisobutyl-1,4,7,10-tetraazacyclododecane (3c): A white solid (1.4 g, yield 95%). HRMS: 397.4273, [M+H]+.

(2S,5S,8S,11S)-2,5,8,11-tetrabenzyl-1,4,7,10-tetraazacyclododecane (3d): A light yellow solid (1.2 g, yield 71.9%). HRMS: 533.365, [M+H]+.

tetra-tert-butyl 2,2',2'',2'''-((2S,5S,8S,11S)-2,5,8,11-tetramethyl-1,4,7,10-tetraazacyclododecane-1,4,7,10-tetrayl)tetraacetate (4a): To a solution of 3a (120 mg, 0.53 mmol) in dried acetonitrile (5 ml) was added potassium carbonate (0.73 g, 5.25 mmol) and tert-butyl 2-bromoacetate (512.4 mg, 2.6 mmol), the mixture was stirred at 50° C. for 16 hours. Then cooled to room temperature and filtered, the filtrate was concentrated, the residue was dissolved into 60 ml of 2% HCl, then extracted with ethyl acetate (30 ml) twice, the aqueous solution was adjusted pH to 8 by adding sat.$NaHCO_3$, extracted with dichloromethane (30 ml) twice, combined the dichloromethane phases and dried over anhydrous magnesium sulfate, filtered and the filtrate was concentrated under vacuum, this resulted in the product 4a as a white solid (350 mg, yield 97.2%). MS: 685, [M+H]+.

tetra-tert-butyl 2,2',2'',2'''-((2S,5S,8S,11S)-2,5,8,11-tetraethyl-1,4,7,10-tetraazacyclododecane-1,4,7,10-tetrayl)tetraacetate (4b): It was synthesized following the method of 4a. This resulted in a white solid (530 mg, yield 66.5%). MS: 763.5541, [M+Na]+.

tetra-tert-butyl 2,2',2'',2'''-((2S,5S,8S,11S)-2,5,8,11-tetraisobutyl-1,4,7,10-tetraazacyclododecane-1,4,7,10-tetrayl)tetraacetate (4c): To a solution of 3c (153 mg, 0.39 mmol) in anhydrous acetonitrile (5 ml) was added potassium carbonate (533.1 mg, 3.9 mmol) and tert-butyl 2-bromoacetate (376 mg, 1.9 mmol), the mixture was stirred at 65° C. for 20 hours. Then cooled to room temperature and filtered, the filtrate was concentrated, the residue was purified by column chromatography on silica gel ($CHCl_3$ in EtOH, 1%~5%), this resulted in a white solid (160 mg, yield 48.6%). HRMS: 875.6827, [M+Na]+.

tetra-tert-butyl 2,2',2'',2'''-((2S,5S,8S,11S)-2,5,8,11-tetrabenzyl-1,4,7,10-tetraazacyclododecane-1,4,7,10-tetrayl)tetraacetate (4d): It was synthesized following the method of 4c. A white solid (272 mg, yield 71.8%). HRMS: 1011.6191, [M+Na]+.

2,2',2'',2'''-((2S,5S,8S,11S)-2,5,8,11-tetramethyl-1,4,7,10-tetraazacyclododecane-1,4,7,10-tetrayl)tetraacetic acid (L1): The solution of 4a (350 mg, 0.51 mmol) in dried dichloromethane (2 ml) and trifluoroacetic acid (2 ml) was stirred at room temperature for two days, the solvents were concentrated and resulted the deprotected product as a light yellow solid (in the form of TFA salt) (460 mg, yield 98.2%), it was used directly to the next step without any further purification. $^1$H NMR (400 MHz, $D_2O$) δ 4.41-2.44 (m, 20H), 1.34-1.14 (d, J=6.1 Hz, 6H), 1.05 (d, J=5.2 Hz, 6H).

2,2',2'',2'''-((2S,5S,8S,11S)-2,5,8,11-tetraethyl-1,4,7,10-tetraazacyclododecane-1,4,7,10-tetrayl)tetraacetic acid (L2): The solution of 4b (50 mg, 0.067 mmol) in dried dichloromethane (1 ml) and trifluoroacetic acid (1 ml) was stirred at room temperature for 16 hours, the solvents were concentrated and then added 2 ml of 1 M hydrochloride acid, the acidic solution was concentrated under vacuum and the residue was dissolved in 1 ml of water, the solution was lyophilized, this resulted in the product as an off-white powder (42 mg, yield 94.0%), it was used directly to the next step without any further purification. $^1$H NMR of TFA salt: $^1$H NMR (400 MHz, DMSO) δ 7.50 (br, 2H), 2.74-4.23 (m, 20H), 1.94 (m, 4H), 1.22-1.37 (m, 4H), 0.97 (m, 12H); HCl salt: $^1$H NMR. (400 MHz, $D_2O$) δ 4.33-2.54 (m, 20H), 2.01-1.69 (m, 4H), 1.45-1.10 (m, 4H), 0.90 (dd, J=40.1, 6.5 Hz, 12H).

2,2',2'',2'''-((2S,5S,8S,11S)-2,5,8,11-tetraisobutyl-1,4,7,10-tetraazacyclododecane-1,4,7,10-tetrayl)tetraacetic acid (L3): It was synthesized following the method of L2. An off-white powder (140 mg, yield 96.4%), it was used directly to the next step without any further purification. $^1$H NMR (600 MHz, $D_2O$) δ 4.08 (t, J=15.9 Hz, 2H), 3.84 (t, J=20.6 Hz, 2H), 3.73 (dd, J=22.4, 15.0 Hz, 4H), 3.58 (d, J=11.6 Hz, 2H), 3.18 (t, J=13.8 Hz, 4H), 3.10 (d, J=16.3 Hz, 2H), 2.94-2.76 (m, 4H), 1.60 (m, 6H), 1.46 (dd, J=31.9, 19.8 Hz, 4H), 1.41-1.29 (m, 2H), 1.00-0.80 (m, 24H).

2,2',2'',2'''42S,5S,8S,11S)-2,5,8,11-tetrabenzyl-1,4,7,10-tetraazacyclododecane-1,4,7,10-tetrayl)tetraacetic acid (L4): It was synthesized following the method of L2. A light yellow solid (220 mg, yield 95.6%), it was used directly to the next step without any further purification. $^1$H NMR (600 MHz, MeOD) δ 7.61 (t, J=7.4 Hz, 2H), 7.44 (t, J=7.4 Hz, 4H), 7.35-7.15 (m, 6H), 6.53 (d, J=7.4 Hz, 4H), 6.44-6.34 (m, 4H), 4.44 (d, J=16.6 Hz, 2H), 4.23-4.03 (m, 6H), 3.50 (t, J=15.3 Hz, 2H), 3.32-3.17 (m, 6H), 2.96 (d, J=12.5 Hz, 2H), 2.89 (t, J=10.8 Hz, 2H), 2.81 (d, J=13.3 Hz, 2H), 2.51 (ddd, J=29.5, 23.4, 11.6 Hz, 6H).

General method of synthesis [GdL1]−-[GdL4]−. To a solution of the ligands of L1-L4 (TFA salt or HCl salt) in water was added $GdCl_3.6H_2O$ (~1.05 eq.), then adjusted the pH value to 7.0 by adding 0.01 M NaOH, the mixture was stirred at 80° C. for 12 hours. Cooled to room temperature and the pH was adjusted to 10, filtered and the solution was adjusted pH to 7.0 again, concentrated under vacuum. The salt of NaCl or $CF_3COONa$ was removed by reversed-phase HPLC, with the mobile phases of acetonitrile and the solution of ammonium formate or ammonium acetate.

4. Experimental Procedure for Preparation of Chiral DOTA-Based Ligand 47-d and the Metal Complexes 47-k (FIG. 47)

Figure 47:
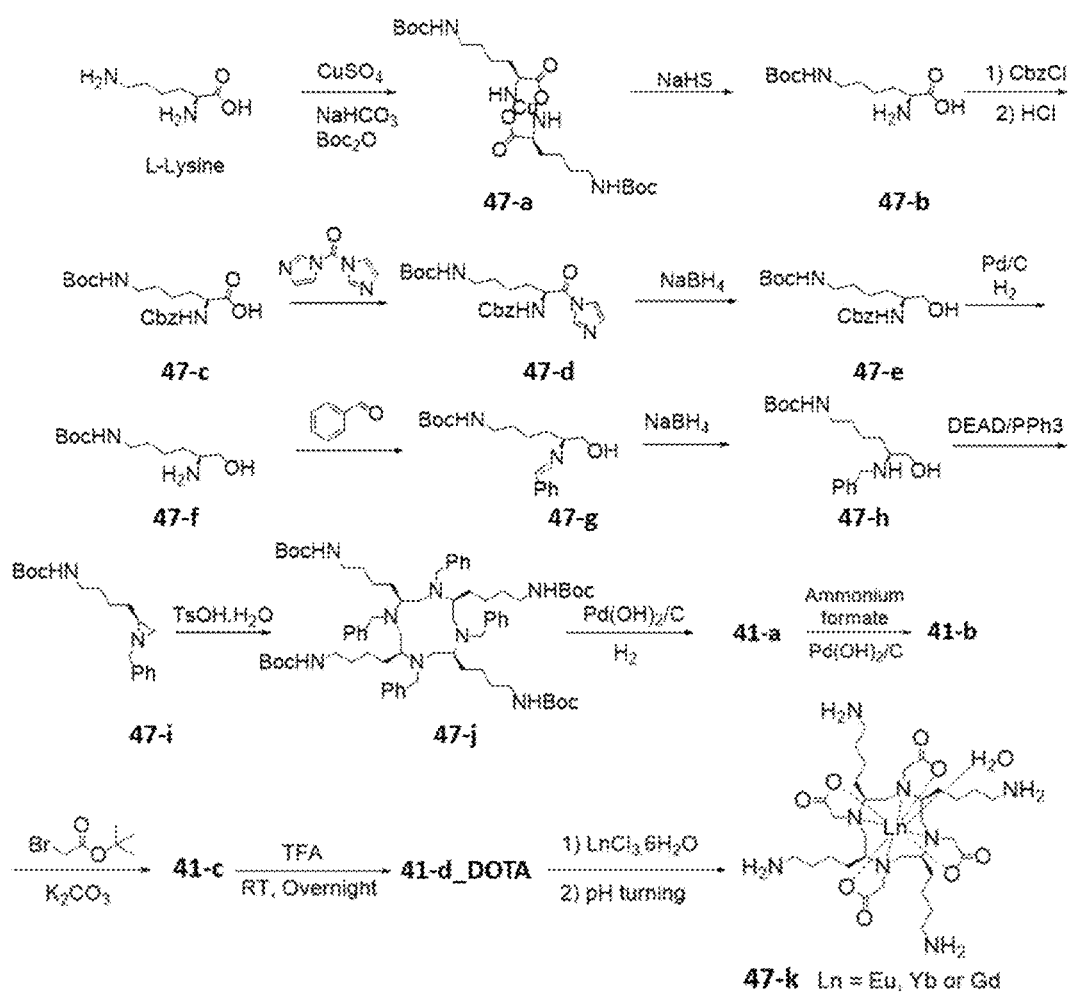
FIG. 47 shows a synthetic route of chiral DOTA-based ligand 41-d_DOTA and metal complex 47-k.

47-i was synthesized from L-lysine as the starting material (FIG. 47).

(S)-2-amino-6-((tert-butoxycarbonyl)amino)hexanoic acid (47-c): To a solution of L-lysine (40 g, 0.27 mol) and $NaHCO_3$ (23 g, 0.27 mmol) in water (600 ml) and acetone (200 ml) was added $CuSO_4.5H_2O$ (34.2 g, 0.14 mol), after stirring at room temperature for 2.5 hours, another 23 g of $NaHCO_3$ was added, then added $(Boc_2)O$ (71 g, 0.33 mol), the reaction mixture was stirring for another 16 hours. A filtration was performed, washed with water (500 ml) and ethyl acetate (200 ml). The solid was transferred into another 3 L flask, added with water (600 ml), NaHS (14 g) and $NaHCO_3$ (30 g), then CbzCl (39 g) and THF (300 ml) were added, the mixture was stirring at room temperature for another 16 hours. After that, the pH was adjusted to 4.0 by adding 2 M HCl, ethyl acetate (500 ml) was added, filtrated and the two phases were separated, the aqueous layer was extracted with ethyl acetate (500 ml) again. Combined the organic phases and washed one time with water (200 ml). Then dried with anhydrous sodium sulfate, after filtration and concentration, this resulted in 80 g of product and used to the next step reaction without any further purification.

(S)-benzyl tert-butyl (6-hydroxyhexane-1,5-diyl)dicarbamate (47-e): This reduction reaction was performed following the procedure of a patent.[59] A solution of 47-c (40 g) in dry THF (200 ml) was cooled to 0-10° C., 1,1'-carbonyldiimidazole (CDI) (17.2 g) was added and stirred at this temperature for 1 hour. Then the mixture was transferred into another solution of $NaBH_4$ (8 g) and water (100 ml) carefully (cooled with ice batch first, stirring vigorous), after stirring at room temperature for overnight, the solution was extracted with ethyl acetate (two times, each time 500 ml), combined the organic phases and washed with brine (200 ml), dried with anhydrous sodium sulfate, filtered and concentrated, the residue was purified by column chromatography on silica gel with ethyl acetate and petroleum ether (1:10 to 1:1). This resulted in a colorless oil (25 g, yield 50% from the starting material of L-lysine) which could be solidified after several days. $^1$H NMR (400 MHz, CDCl$_3$): δ7.32 (m, 5H), 5.12 (s, 1H), 5.11 (s, 2H), 4.62 (s, 1H), 3.62 (m, 3H), 3.11 (m, 2H), 2.04 (s, 1H), 1.30-1.55 (m, 15H).

(S)-tert-butyl (5-amino-6-hydroxyhexyl)carbamate (47-f): Into a solution of 47-e (30 g) in ethanol (300 ml) was added Pd/C (10%, wet) (2.5 g), the mixture was hydrogenated under an H$_2$ atmosphere at room temperature overnight. The mixture was filtrated over celite and evaporated to dryness, this resulted in the product (18 g, yield 94%) as a colorless oil. $^1$H NMR (400 MHz, CDCl$_3$) δ 4.61 (s, 1H), 3.75-3.38 (m, 1H), 3.39-3.19 (m, 1H), 3.11 (d, J=4.9 Hz, 2H), 2.80 (s, 1H), 1.99 (s, 3H), 1.57-1.18 (m, 15H).

(S)-tert-butyl (5-(benzylamino)-6-hydroxyhexyl)carbamate (47-h): A solution of benzaldehyde (8.0 g, 75.4 mmol) and 47-f (16.0 g, 68.9 mmol) in dichloromethane (208 ml) and methanol (48 ml) was stirred at room temperature under nitrogen for 16 hours. It was concentrated and the residue was pumped with oil pump for two days and washed with petroleum ether for two times (each 200 ml) before the next step reaction. The oil mixture was dissolved in methanol (400 ml) and cooled in an ice bath. Powder sodium borohydride (5.0 g, 0.13 mol) was added in portions and the solution was stirred for 2 hours, water (300 ml) was added and the solution was quenched with 4 M HCl (~4 ml), extracted with ethyl acetate (three time, each time 300 ml), combined the organic phases and washed with brine (200 ml), dried with anhydrous sodium sulfate, filtered and the filtrate was concentrated, the residue was purified by column chromatography on silica gel with ethyl acetate and petroleum ether (1:5 to 1:2). This resulted in a colorless oil (13 g, two step yield 59.1%). $^1$H NMR (400 MHz, CDCl$_3$) δ 7.41-7.09 (m, 5H), 4.68 (s, 1H), 3.91-3.66 (m, 2H), 3.66-3.49 (m, 1H), 3.31 (dd, J=10.8, 6.0 Hz, 1H), 3.07 (d, J=6.0 Hz, 2H), 2.71-2.47 (m, 1H), 1.55-1.06 (m, 15H).

(S)-tert-butyl (4-(1-benzylaziridin-2-yl)butyl)carbamate (47-i): A solution of 47-h (13 g, 40.3 mmol) in dry THF (150 ml) was cooled to 0~10° C., then added PPh$_3$ (14.8 g, 56.3 mmol) and DEAD (9.8 g, 56.3 mmol), the mixture was stirred for overnight at room temperature. Then concentrated and the residue was purified by column chromatography on silica gel with ethyl acetate and petroleum ether (1:10 to 1:1). This resulted in a colorless oil (8 g, 65.2%).

tetra-tert-butyl (((2S,5S,8S,11S)-1,4,7,10-tetrabenzyl-1,4,7,10-tetraazacyclododecane-2,5,8,11-tetrayl)tetrakis(butane-4,1-diyl))tetracarbamate (47-j): Into a solution of 47-i (5.3 g, 17.4 mmol) in acetonitrile (212 ml) was added TsOH.H$_2$O (230 mg), the solution was stirred at room temperature and added 230 mg of TsOH. H$_2$O every 24 hours, after 6 days later, the mixture was added 2% of K$_2$CO$_3$ in water (212 ml), the formed precipitate was filtered and washed with water, after drying to get the pure product as a white solid (1.3 g, yield 24.5%).

5. Experimental Procedure for Preparation of 3b-3e tetra-tert-butyl (((2S,5S,8S,11S)-1,4,7,10-tetraazacyclododecane-2,5,8,11-tetrayl)tetrakis(butane-4,1-diyl))tetracarbamate (41-b): As a light yellow solid (1.2 g, yield 92.3%). ESI-MS: 858, [M+H]$^+$.

tetra-tert-butyl 2,2',2",2"'-((2S,5S,8S,11S)-2,5,8,11-tetrakis(4-((tert-butoxycarbonyl)amino)butyl)-1,4,7,10-tetraazacyclododecane-1,4,7,10-tetrayl)tetraacetate (41-c): It was synthesized following the method of 4a. This resulted in the pure product as a white solid (1.3 g, 65.3%). ESI-MS: 1314, [M+H]$^+$.

2,2',2",2"'-((2S,5S,8S,11S)-2,5,8,11-tetrakis(4-aminobutyl)-1,4,7,10-tetraazacyclododecane-1,4,7,10-tetrayl) tetraacetic acid (41-d_DOTA): The solution of 41-c (150 mg, 0.094 mmol) in trifluoroacetic acid (2 ml) was stirring at room temperature for overnight. The mixture was concentrated to get the final ligand L5 in the form of trifluoroacetic acid salt (150 mg, yield 100%). $^1$H NMR (400 MHz, D$_2$O) δ 4.42-2.67 (m, 28H), 2.10-1.16 (m, 24H).

Figure 48:
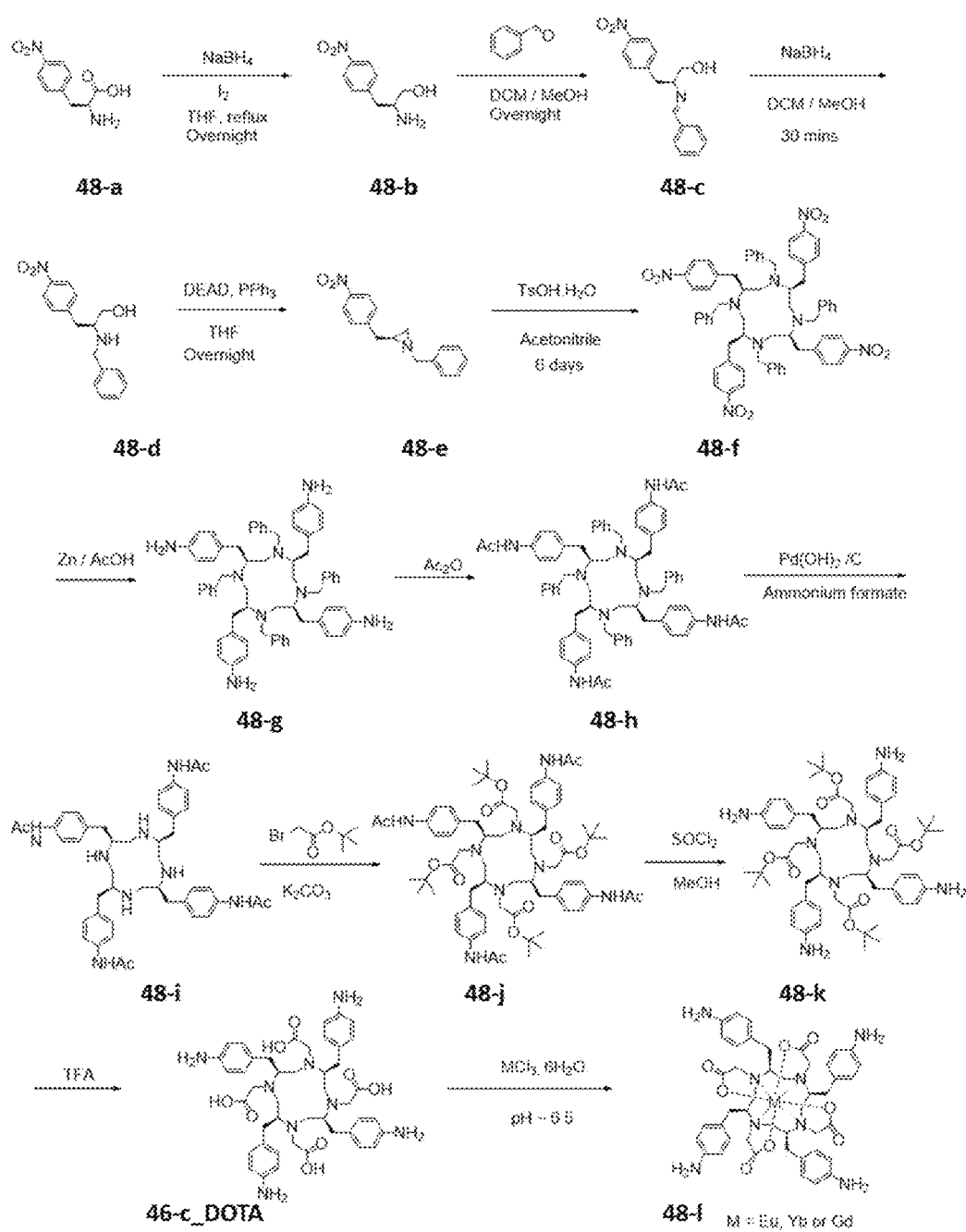
FIG. 48 shows a synthetic route of chiral DOTA-based ligand 46-e_DOTA and metal complex 48-l.
Figure 49:
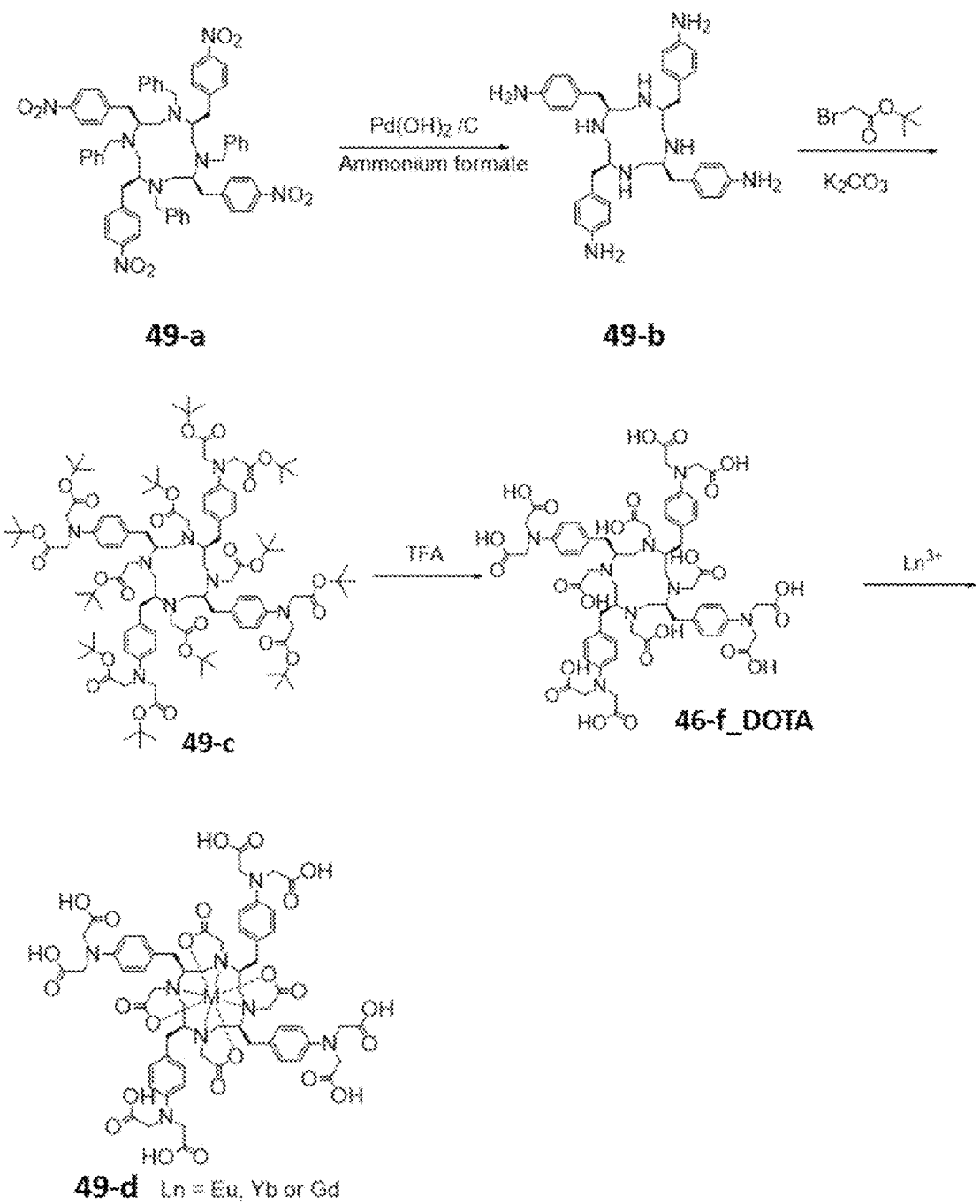
FIG. 49 shows a synthetic route of chiral DOTA-based ligand 46-f_DOTA and metal complex 49-d.

Metal complex 47-k was synthesized according to the General Method for synthesis of [GdL1]$^-$-[GdL4]$^-$ 6. Experimental Procedure for Preparation of Complexes 48-l (FIG. 48)

(S)-2-amino-3-(4-nitrophenyl)propan-1-ol (48-b): To the solution of (S)-2-amino-3-(4-nitrophenyl)propanoic acid (40 g, 0.19 mmol) in THF (300 ml) was added NaBH$_4$ (25 g, 0.66 mol), then dropped with the solution of 12 (56.8 g, 0.22 mol) in THF (50 ml) slowly while controlling the temperature below 60° C. (~2 hours). Then the reaction mixture was maintained at about 60° C. for 18 hours. The temperature was cooled down to room temperature, added methanol to make the mixture clear, concentrated, then added water (320 ml) and K$_2$CO$_3$ (42 g), heated to 80° C. for 2 hours, then took away the oil bath and stirred overnight, the solid was collected by filtration and dried to get the product as a yellow solid (25 g, yield 67.0%).

(S)-2-(benzylideneamino)-3-(4-nitrophenyl)propan-1-ol (48-c): A solution of 48-b (22.4 g, 0.11 mol) and benzaldehyde (13.3 g, 0.13 mol) in methanol (67 ml) and dichloromethane (291 ml) was stirred at room temperature for 24 hours, the solution was concentrated and the residue put under vacuum for one day, this resulted in 36 g of pale solid which was used in the next reaction without further purification.

(S)-2-(benzylamino)-3-(4-nitrophenyl)propan-1-ol (48-d): To the solid of 48-c (36 g) was added petroleum ether (100 ml), then NaHBH$_4$. (1 g) was added into the mixture. After 15 minutes, methanol (200 ml) was added and the temperature was kept below 20° C., NaHBH$_4$ (8 g) was added into the reaction mixture slowly while the formed hydrogen was removed by a stream of nitrogen. The mixture was reacted for 15 minutes and then triturated with water (500 ml). After stirring for 30 minutes, the solid was collected by filtration, washed with water (200 ml) and dried in an oven, resulting in a yellow solid (28.0 g, two steps yield 85.3%).

(S)-1-benzyl-2-(4-nitrobenzyl)aziridine (48-e): A solution of 48-d (27.5 g, 96.0 mmol) and PPh$_3$ (35.3 g, 134.3 mmol) in dry THF (300 ml) was cooled to 0~10° C., then treated with DEAD (23.4 g, 134.4 mmol) within about 30 minutes, then the mixture was stirred at room temperature overnight. After concentration, the residue was dissolved in diethyl ether (150 ml), cooled in a fridge (4° C.) for one day, and filtered. The filtered material was purified by column chromatography on silica gel using ethyl acetate and petroleum ether (1:10~2:1), resulting in a light yellow oil (14 g, 54.3%).

(2S,5S,8S,11S)-1,4,7,10-tetrabenzyl-2,5,8,11-tetrakis(4-nitrobenzyl)-1,4,7,10-tetraazacyclododecane (48-f): Into a solution of 48-e (3.4 g, 12.7 mmol) in acetonitrile (150 ml) was added TsOH.H$_2$O (199 mg). The solution was stirred at room temperature and treated with 199 mg of TsOH. H$_2$O every 24 hours. After 6 days, the mixture was treated with 2% of K$_2$CO$_3$ in water (212 ml). The resulting precipitate was filtered and washed with ethyl acetate and methanol.

The solid was purified by column chromatography on silica gel using ethyl acetate and petroleum ether (1:10~2:1). The solid was recrystallized with acetonitrile and methanol, resulting in a yellow solid (700 mg, 20.6%). ESI-MS: 1073, [M+H]$^+$.

N,N',N'',N'''-(((((2S,5S,8S,11S)-1,4,7,10-tetrabenzyl-1,4,7,10-tetraazacyclododecane-2,5,8,11-tetrayl)tetrakis(methylene))tetrakis(benzene-4,1-diyl))tetraacetamid (48-g): Into a solution of 48-f (600 mg, 0.56 mmol) in acetate acid (22 ml) was added zinc powder (200 m g). The mixture was heated at 50° C. overnight, then acetic anhydride (2 ml) was added and reacted at room temperature for another 16 hours. After water (20 ml) was added, filtration was performed and the solid was washed with water and dried in an oven, resulting in a white solid (600 mg, 95.7%). ESI-MS: 1121, [M+H]$^+$.

N,N',N'',N'''-(4(2S,5S,8S,11S)-1,4,7,10-tetraazacyclododecane-2,5,8,11-tetrayl)tetrakis(methylene))tetrakis(benzene-4,1-diyl))tetraacetamide (48-i): The solution of 48-g (480 mg, 0.43 mmol), Pd(OH)$_2$/C (dry, 20%) (240 mg) and ammonium formate (720 mg) in trifluoroethanol (30 ml) was heating at 60° C. for two days. Then cooled to room temperature, filtrated and concentrated, the solid was slurry with ethyl ether, this resulted in the product as a pale solid (250 mg, yield 76.7%). ESI-MS: 761, [M+H]$^+$.

tetra-tert-butyl 2,2',2'',2'''-((2S,5S,8S,11S)-2,5,8,11-tetrakis(4-acetamidobenzyl)-1,4,7,10-tetraazacyclododecane-1,4,7,10-tetrayl)tetraacetate (48-j): Into a solution of 48-i (325 mg) in dry DMF (10 ml) and acetonitrile (5 ml) was added K$_2$CO$_3$ (620 mg) and tert-butyl 2-bromoacetate (560 mg), after reacting at room temperature for 2 days, the solid was filtered out and the filtrate was concentrated and purified by column chromatography on silica gel with ethanol and chloroform (1:20~1:10), this resulted in the pure product as a light yellow foam solid (150 mg, 28.8%). ESI-MS: 1218, [M+H]$^+$.

Figure 50:
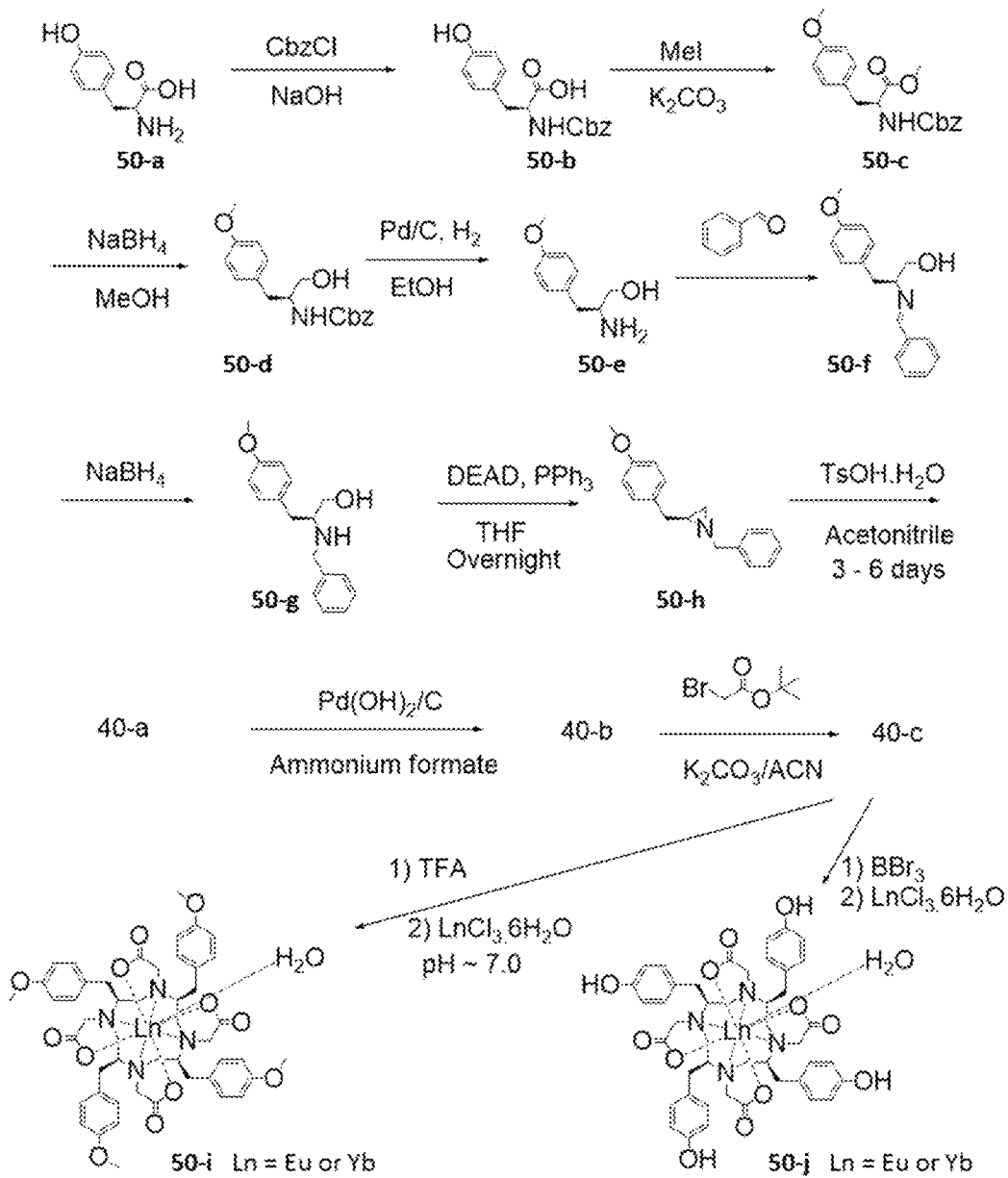
FIG. 50 shows a synthetic route of metal complexes 50-i and 50-j.
Figure 51:
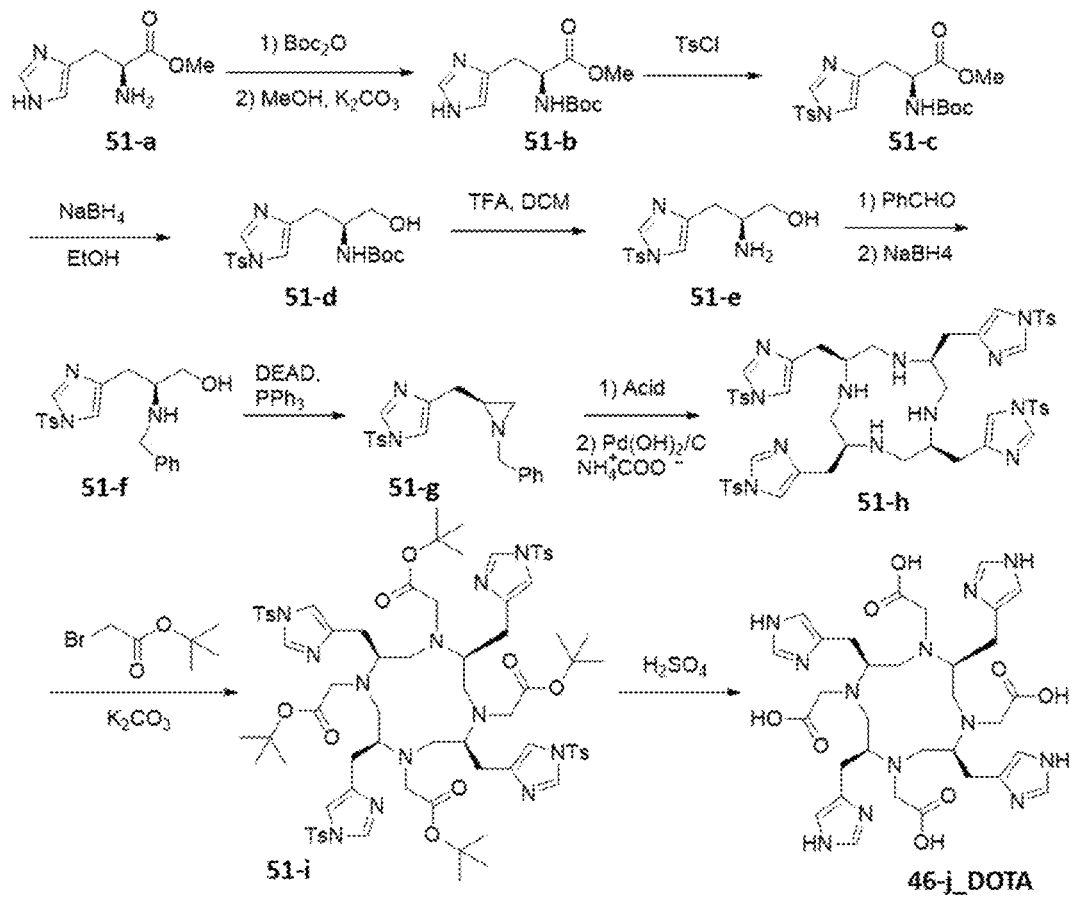
FIG. 51 shows a synthetic route of chiral DOTA-based ligand 46-j_DOTA.
Figure 52:
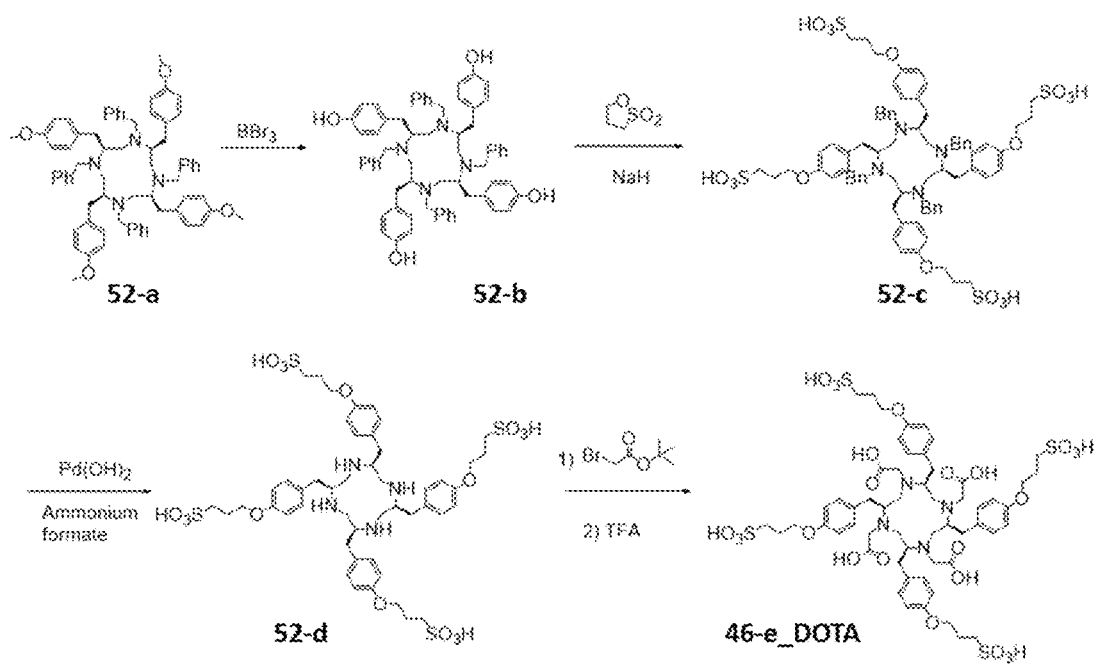
FIG. 52 shows a synthetic route of chiral DOTA-based ligand 46-e_DOTA.
Figure 53:
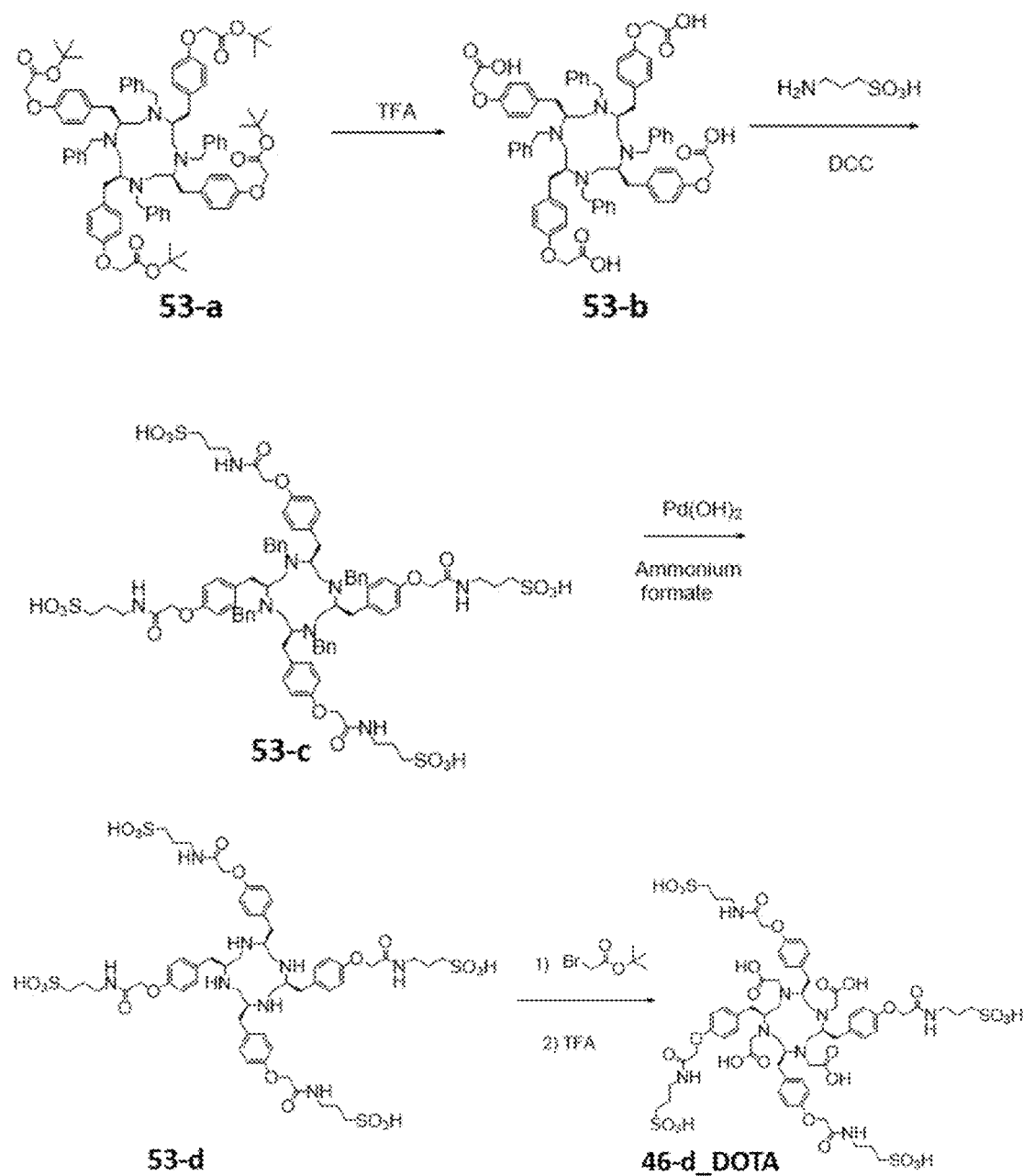
FIG. 53 shows a synthetic route of chiral DOTA-based ligand 46-d_DOTA.
Figure 54:
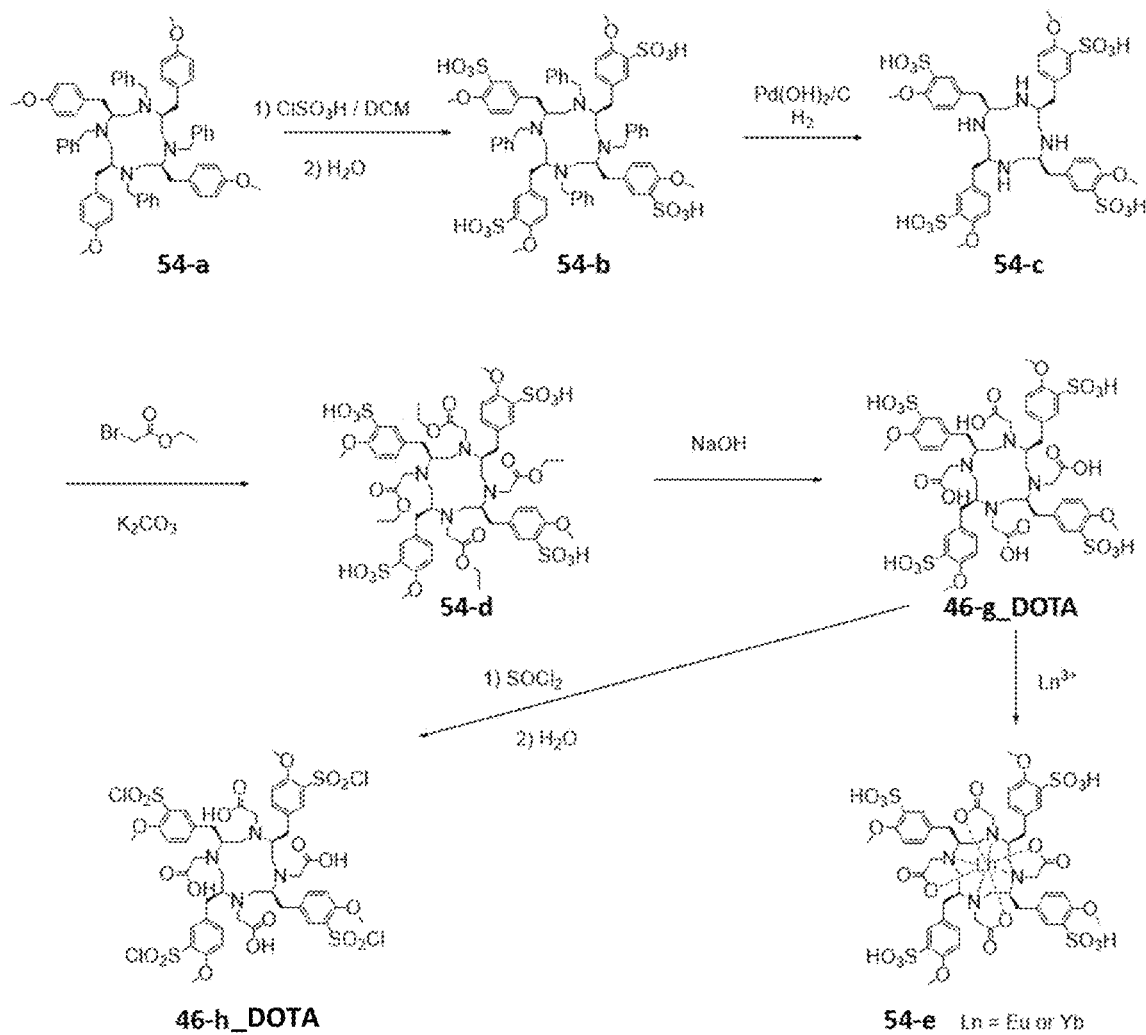
FIG. 54 shows a synthetic route of chiral DOTA-based ligands 46-g_DOTA and 46-h_DOTA, and metal complex 54-e.
Figure 55:
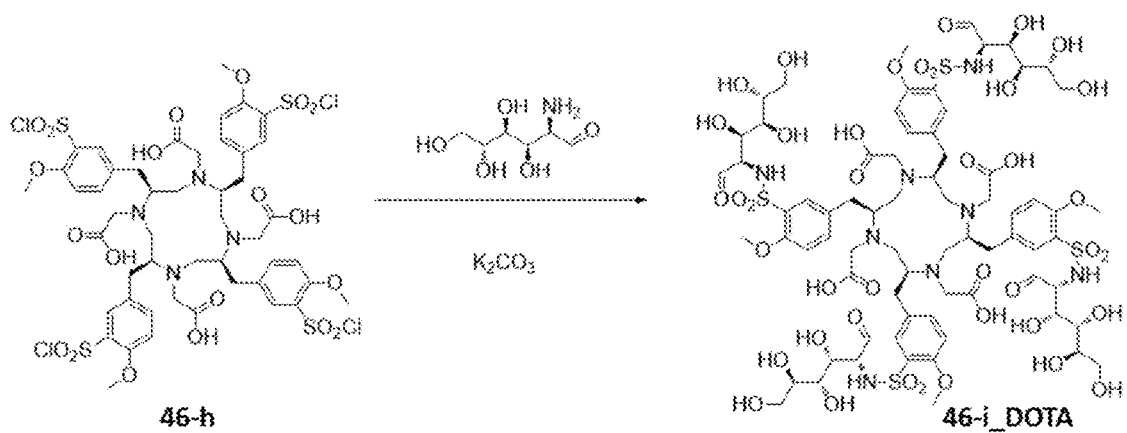
FIG. 55 shows a synthetic route of chiral DOTA-based ligand 46-i_DOTA.

2,2',2'',2'''-((2S,5S,8S,11S)-2,5,8,11-tetrakis(4-aminobenzyl)-1,4,7,10-tetraazacyclododecane-1,4,7,10-tetrayl)tetraacetic acid (46-c_DOTA): A solution of 48-j (150 mg) in methanol (4 ml) was cooled to 0~10° C., then treated with SOCl$_2$ (0.2 ml), then reacted at room temperature overnight. The intermediate was concentrated to dryness, then added TFA (3 ml) and stirred at room temperature for another 16 hours. After concentration, the residue was purified by semi-preparative HPLC. This resulted in a light yellow powder (50 mg, 38.7%). $^1$H NMR (400 MHz, D$_2$O) δ 7.09 (d, J=78.1 Hz, 8H), 6.38 (d, J=51.4 Hz, 8H), 4.03 (br, 8H), 3.01-2.02 (m, 16H). ESI-MS: 825, [M+H]$^+$, 7. Experimental Procedure for Preparation of Ligands 40d and 39f (FIGS. 50 and 51)

(S)-2-(((benzyloxy)carbonyl)amino)-3-(4-hydroxyphenyl)propanoic acid (50-b): It was synthesized from L-Tyrosine according to a reported procedure.$^{(Organic\ Letters,\ 16(1),\ 10-13;\ 2014)}$ A solution of L-Tyrosine (50 g, 0.28 mol) in THF (400 ml) was added with the solution of NaOH (22.1 g) in water (250 ml), then into the solution was dropped the solution of CbzCl (51.8 g) in THF (100 ml) at room temperature, after one night reaction, the mixture was adjusted pH to 2~3 by adding with 2 M HCl, extracted with ethyl acetate (two times, each time 500 ml), combined the organic phases and dried with anhydrous sodium sulfate, concentrated to give the product as a light yellow oil (85 g, yield 97.7%). It was used in the next reaction without further purification.

(S)-methyl 2-(((benzyloxy)carbonyl)amino)-3-(4-methoxyphenyl)propanoate (50-c): The compound of 50-b (85 g) from the previous step was dissolved into DMF (450 ml), cooled the temperature to 0~10° C., then added K$_2$CO$_3$ (115 g) and CH$_3$I (87 g), after reacting for overnight, the excess of CH$_3$I was pumped into cold trap, into the reaction solution was added water (700 ml), extracted with ethyl acetate (two times, each time 500 ml), combined the organic phases and washed with water (100 ml), then washed with brine (200 ml), dried with anhydrous sodium sulfate, concentrated to give the product as a light yellow oil (90 g, crude). It was used in the next step without further purification.

(S)-benzyl (1-hydroxy-3-(4-methoxyphenyl)propan-2-yl) carbamate (50-d): Synthesized according to a reported procedure.[68]

(S)-2-amino-3-(4-methoxyphenyl)propan-1-ol (50-e): To a solution of 50-d (80 g, 0.23 mol) in ethanol (500 ml) was added Pd/C (10%, wet) (3.3 g), the mixture was stirred under a hydrogen atmosphere and stirred overnight at room temperature. The residue was filter through celite and the filtrate was concentrated, this resulted in the product as colorless oil (44.0 g, 98%). The NMR of the product was constant to the literature reported.[69]

(S)-2-(benzylamino)-3-(4-methoxyphenyl)propan-1-ol (50-g): The synthesis of the imine compound and its reduction follow the procedure of 48-d, yield 60% for the two steps.

(S)-1-benzyl-2-(4-methoxybenzyl)aziridine (50-h): A solution of 50-g (20 g, 73.7 mmol) in dry THF (220 ml) was cooled to 0~10° C., then treated with PPh$_3$ (27.1 g, 103.1 mmol), and DEAD (18.0 g, 103.9 mmol). The mixture was stirred at room temperature overnight. Concentrated and the residue was purified by column chromatography on silica gel with ethyl and petroleum ether (1:10~1:3), this resulted in a colorless oil (16.0 g, yield 85.6%).

(2S,5S,8S,11S)-1,4,7,10-tetrabenzyl-2,5,8,11-tetrakis(4-methoxybenzyl)-1,4,7,10-tetraazacyclododecane (40-a) A solution of 50-h (10 g, 39.5 mmol) in acetonitrile (400 ml) was added TsOH.H$_2$O (435 mg), after stirred at room temperature for 48 hours, another 435 mg of TsOH.H$_2$O was added, the mixture was stirred for another 48 hours. A solution of 5% K$_2$CO$_3$ was added and filtered, dried in an oven and this resulted in the product with good purity. The NMR spectra were consistent with those reported for the compound prepared by total synthesis.[23] ESI-MS: 1013, [M+H]$^+$.

(2S,5S,8S,11S)-2,5,8,11-tetrakis(4-methoxybenzyl)-1,4,7,10-tetraazacyclododecane (40-b): A solution of 40-a (1.05 g) in trifluoroethanol (25 ml), toluene (7.5 ml) and THF (47 ml) was added Pd(OH)$_2$/C (800 mg) and ammonium formate (600 mg), the result mixture was stirred at 60° C. for two days. Then cooled and filtered through celite, concentrated to give the product (672 mg). It was used in the next step without further purification.

tetra-tert-butyl 2,2',2'',2'''-((2S,5S,8S,11S)-2,5,8,11-tetrakis(4-methoxybenzyl)-1,4,7,10-tetraazacyclododecane-1,4,7,10-tetrayl)tetraacetate (40-c): A mixture of 40-b (620 mg), K$_2$CO$_3$ (1.4 g), tert-butyl 2-bromoacetate. (1.01 g) in acetonitrile (20 ml) was stirred at room temperature for two days. Filtered and the residue was purified by column chromatography on silica gel using ethanol and chloroform (1:50~1:10). This resulted in a light yellow solid (500 mg, yield 47.6%).

2,2',2'',2'''-((2S,5S,8S,11S)-2,5,8,11-tetrakis(4-methoxybenzyl)-1,4,7,10-tetraazacyclododecane-1,4,7,10-tetrayl) tetraacetic acid (40-d_DOTA): A mixture of 40-c (55 mg) in TFA (2 ml) was stirred at room temperature overnight, concentrated and this resulted in L7 in the form of TFA salt.

¹H NMR (400 MHz, MeOD) δ 6.60 (m, 8H), 6.26-5.86 (m, 8H), 3.66 (s, 12H), 2.72 (m, 8H), 2.60-1.73 (m, 20H).

2,2',2'',2'''-((2S,5S,8S,11S)-2,5,8,11-tetrakis(4-hydroxybenzyl)-1,4,7,10-tetraazacyclododecane-1,4,7,10-tetrayl) tetraacetic acid (46-b_DOTA). A mixture of 40-d_DOTA (50 mg) in dry DCM (5 ml) was added BBr$_3$ (1 M in THF) (2 ml), the mixture was stirred at room temperature overnight. Methanol (5 ml) was dropped into the mixture and concentrated, the residue was purified by semi-preparative HPLC to give a white powder (10 mg). ¹H NMR (400 MHz, MeOD) δ 6.81 (d, J=35.3 Hz, 8H), 6.31 (d, J=35.1 Hz, 8H), 4.18 (m, 8H), 3.51 (m, 4H), 3.16 (s, 4H), 3.01-2.15 (m, 12H).

8. Synthesis of Conjugate 56-c_DO3A (FIG. 56)

The ligand 46-h was dissolved in DMSO and acetonitrile mixture, then sulfo-NHS and EDCI were added, after reacting at room temperature for 15 minutes, the reaction mixture was added with water and cooled to 0~10° C. Then, a solution of RGD peptide 56-a in water was added to the reaction mixture. After stirred for 2 hours, the mixture was quenched by adding diluted NaOH first to adjust the pH to 10, then adding diluted HCl to adjust the pH to 3~4. The resulting mixture was purified by semi-preparative HPLC and lyophilized to give the pure product as a white powder.

9. Structural Analysis of Chiral DOTA-Based Ligands L1-L4

Figure 1B:
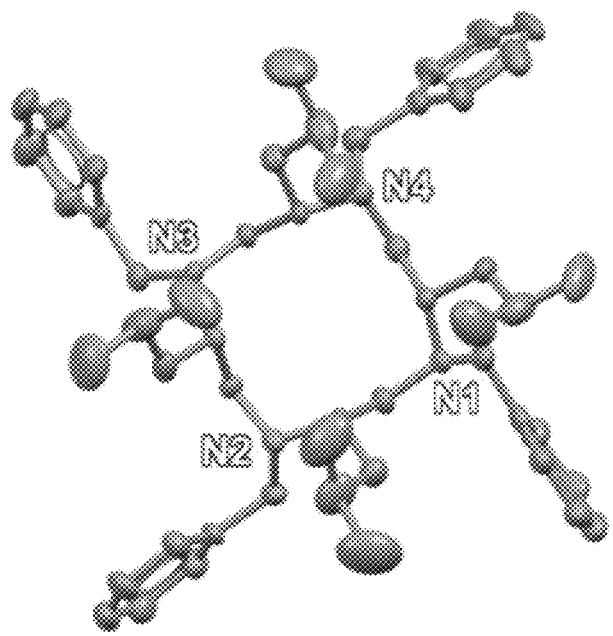
FIG. 1B shows the crystal structure of 2c. The ellipsoid is drawn in 30% probability. Hydrogen atoms are omitted for clarity.

The crystal structure (FIG. 1B) of compound 2c shows that the four iso-butyl groups are symmetrically arranged around the cyclen ring at one side of the plane, all these four substituents with S configuration indicate their absolute configuration were not changed in the process of cyclization reaction. All the compounds of 2a-2d and 3a-3d are 4-fold symmetric, ¹H NMR and ¹³C NMR spectra of these compounds show only one set of resonances. Compounds 4a-4d are dissymmetric as shown by ¹H NMR and ¹³C NMR spectra because the four tert-butyl acetate groups are too bulky for them to move freely. But after the tert-butyl groups were removed, DOTA-based ligands L1-L4 in the form of either trifluoroacetate or hydrochloride salt are 2-fold symmetric, as shown in the ¹H and ¹³C NMR spectra, wherein two sets of resonances with the ratio of 1:1 were observed (FIGS. 6-9).

10. Determination of TSA/SA Isomer Ratio of Chiral Cyclen Metal Complexes by HPLC and ¹H NMR Spectra In aqueous solution, the ratio of TSA/SA isomers of Eu(III) and Yb(III) complexes in DOTA-like systems can be easily determined by ¹H NMR as two well-defined sets of six resonances are observed for the diastereotopic protons in CH$_2$CO and NCH$_2$CH$_2$N.[13] Although the Gd(III) complexes cannot be analyzed by NMR, their ratio of isomers are expected to be similar to those of the Eu(III) and Yb(III) complexes because the ionic radius of Gd(III) is similar to the ionic radius of Eu(III) and Yb(III). The ¹H NMR measurements of these chiral complexes performed at room temperature were reproducible even after leaving the complexes at room temperature for six months; no detectable change was observed in the ratio of isomers.

Figure 3:
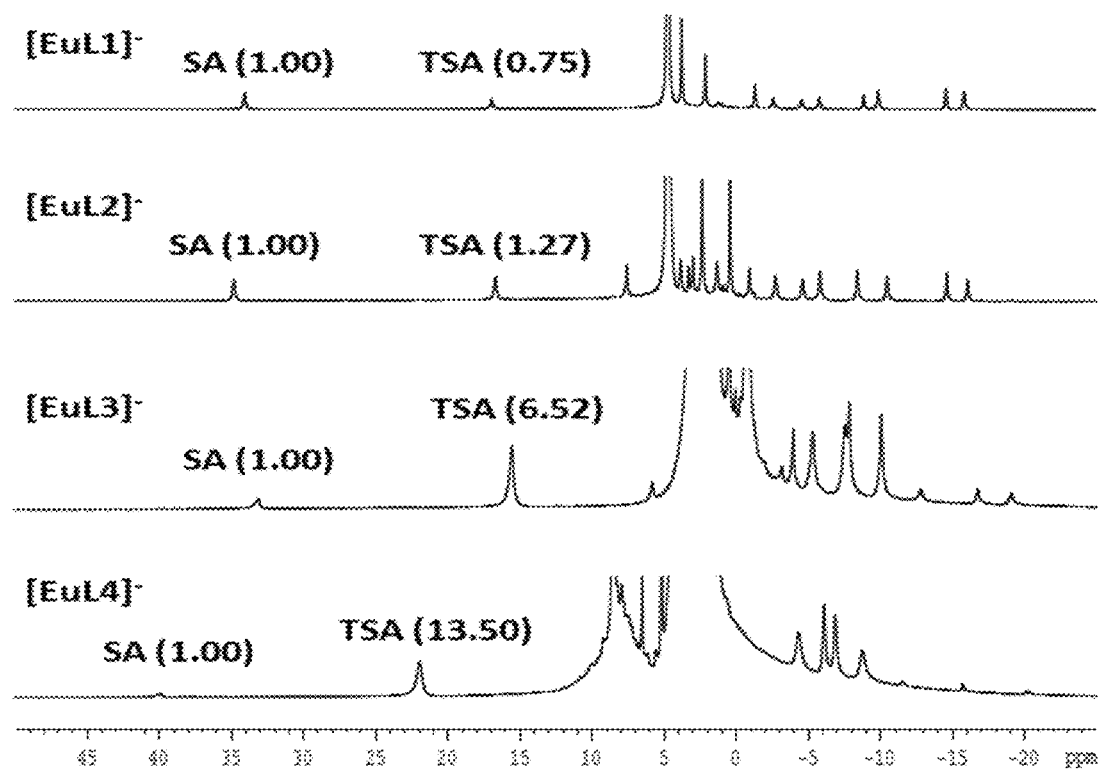
FIG. 3 shows the $^1H$ NMR spectra (25° C., 400 MHz, pD 7.0) of [EuL1]$^-$, [EuL2]$^-$, [EuL3]$^-$ and [EuL4]$^-$, including the variation in the TSA/SA isomer ratio.
Figure 4:
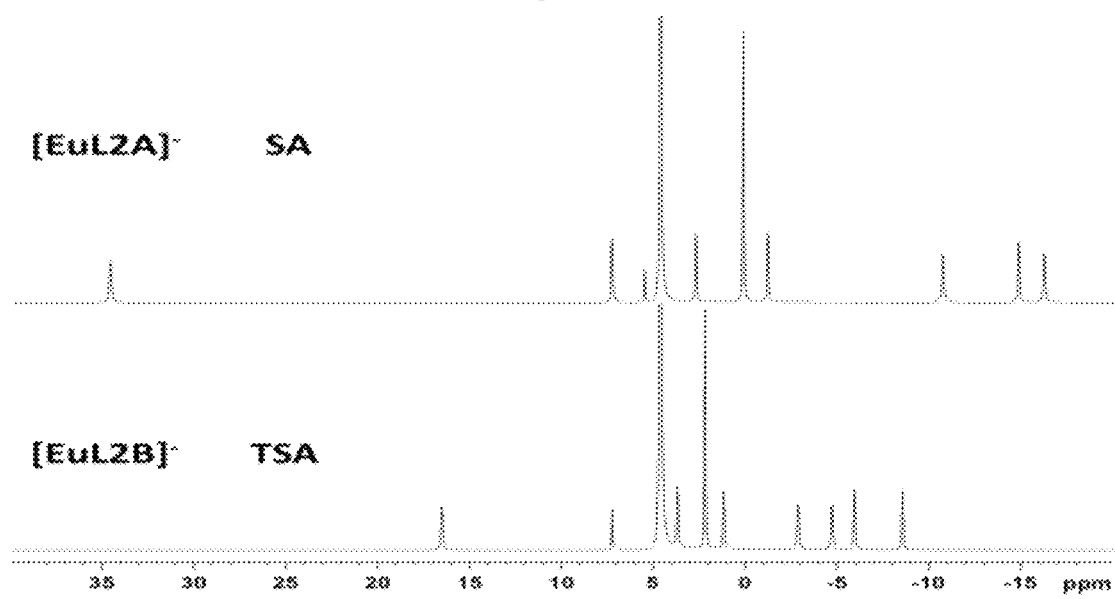
FIG. 4 shows the $^1H$ NMR spectra (25° C., 400 MHz, pD 7.0) of two isolated isomers of L2: [EuL2A]$^-$ and [EuL2B]$^-$.
Figure 10:
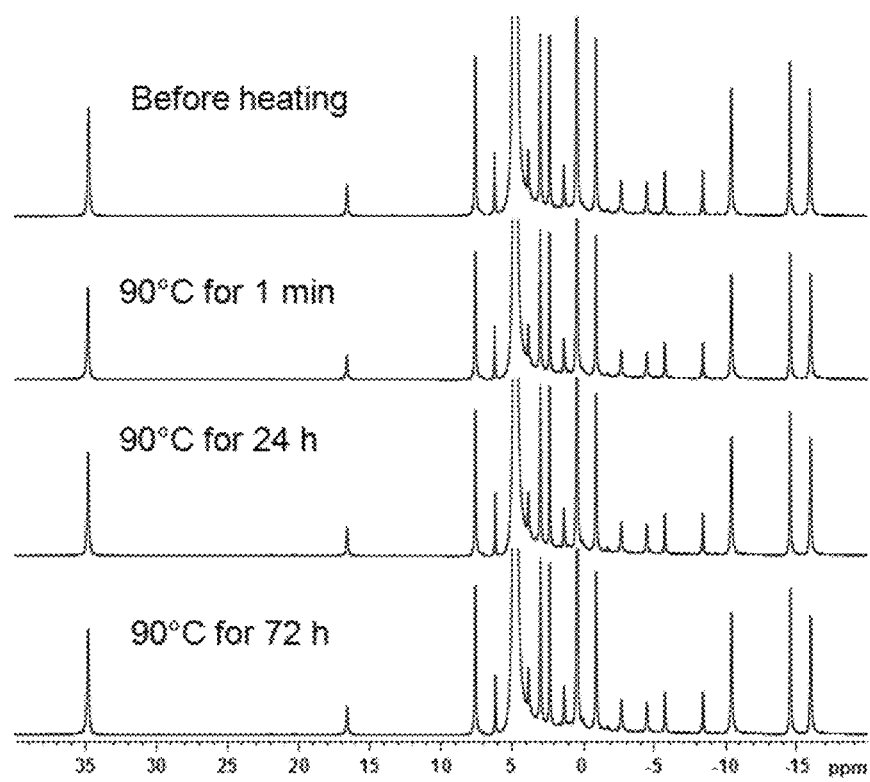
FIG. 10 shows the TSA/SA isomer ratio variation of [EuL2]$^-$ as indicated by $^1H$ NMR spectra, before heating and upon heating at 90° C. for 1 min, 24 h and 72 h.

The conformational properties of the lanthanide complexes were investigated by both HPLC and NMR spectroscopy. The ¹H NMR spectra of the four europium chiral DOTA-based complexes are compared in FIG. 3. It has been established that the isomer in solution adopts the square antiprismatic structure (SA) characterized by a shift to high frequency of the closest of the ring axial protons; the twisted square antiprism (TSA) generally exhibits less shift in the proton resonances.[15] The isomer ratio of TSA/SA increased from 0.75 for [EuL1]⁻ to 1.27 for [EuL2]⁻. In the cases of [EuL3]⁻ and [EuL4]⁻, the twisted antiprismatic isomers were more dominant, with the ratio of 6.52 for [EuL3]⁻ and 13.50 for [EuL4]⁻ observed. This variation of isomer ratio accords with the general observations that by increasing the steric demand at the bound metal ion, the twisted square antiprismatic structure is favored.[15] More significantly, these isomers detectable by NMR spectra could also be isolated easily by reversed-phase HPLC. The ¹H NMR spectra of the isolated complexes of L2 ([EuL2A]⁻ and [EuL2B]⁻) are shown in FIG. 4. No racemization was observed in the process of purification and measurement. To ensure lack of racemization, a solution of [EuL2A]⁻ and [EuL2B]⁻ at a ratio of 1:0.25 remained at the same ratio after heating at 90° C. for 3 days (FIG. 10).

Figure 5:
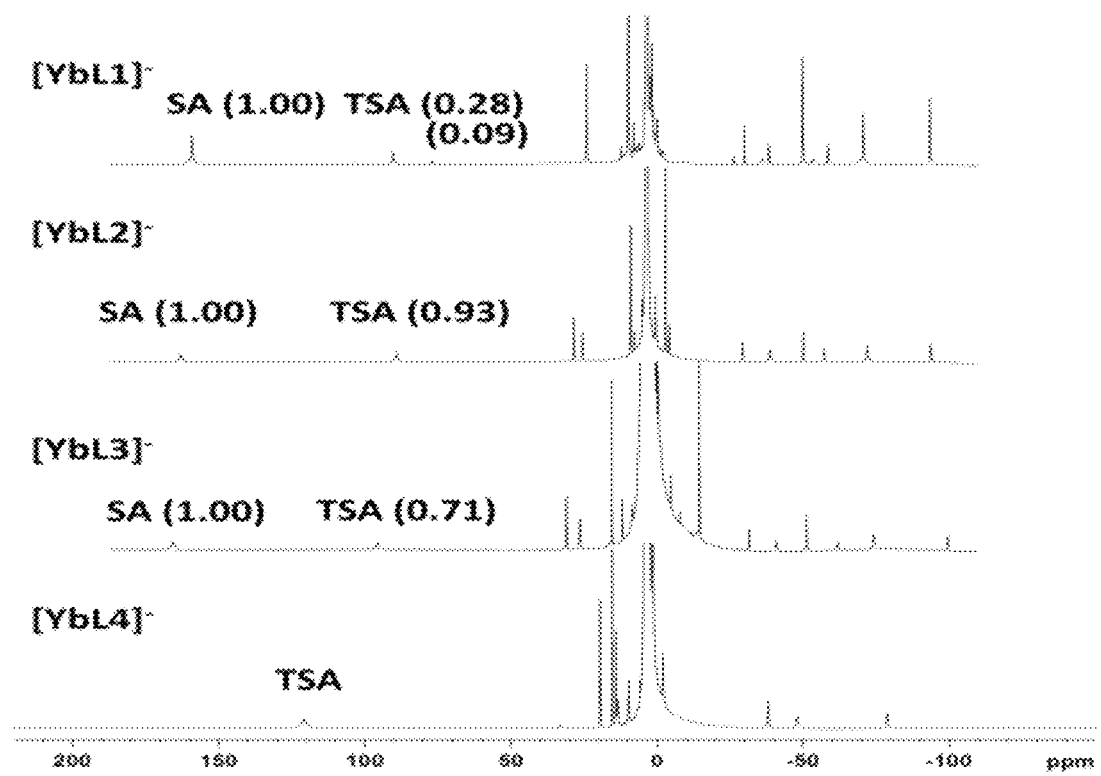
FIG. 5 shows the $^1H$ NMR spectra (25° C., 400 MHz, pD 7.0) of [YbL1]$^-$, [YbL2]$^-$, [YbL3]$^-$ and [YbL4]$^-$, including the variation in the TSA/SA isomer ratio.
Figure 6:
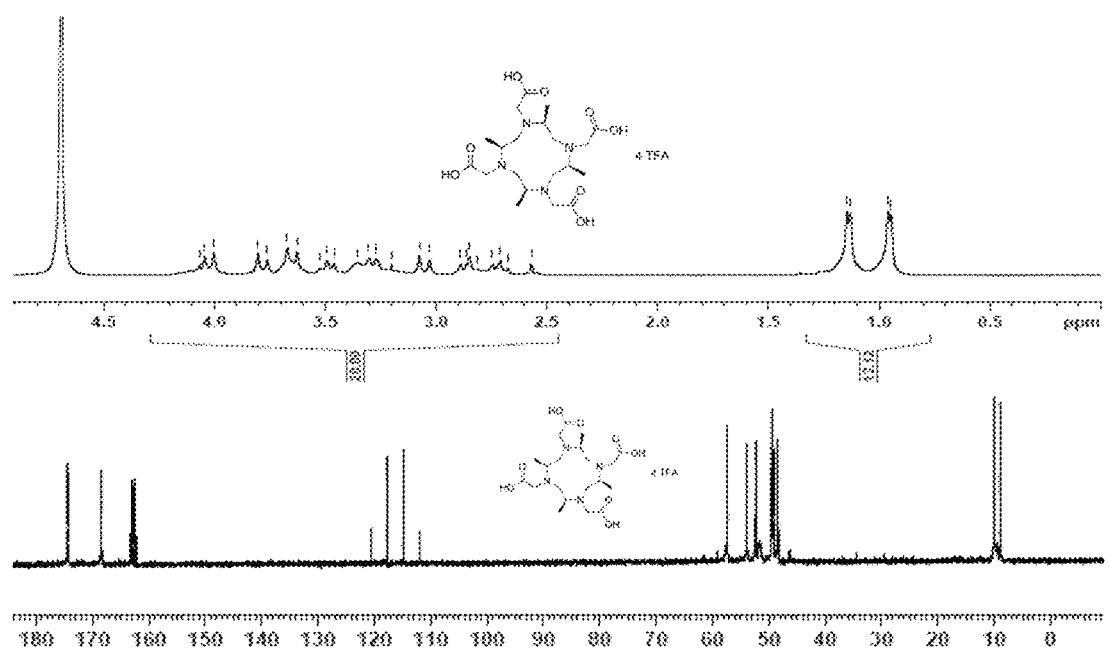
FIG. 6 shows the NMR spectra of L1. Top: $^1H$ NMR spectrum of L1 in $D_2O$. Bottom: $^{13}C$ NMR spectrum of L1 in $D_2O$.
Figure 7:
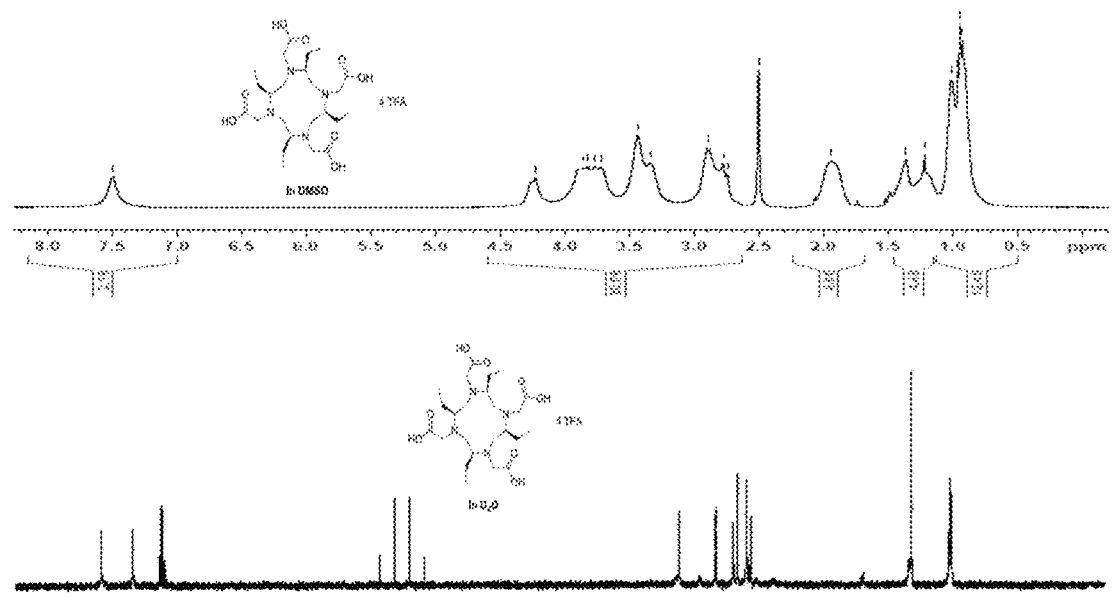
FIG. 7 shows the NMR spectra of L2. Top: $^1H$ NMR spectrum of L2 in D7-DMSO. Bottom: $^{13}C$ NMR spectrum of L2 in $D_2O$.
Figure 8:
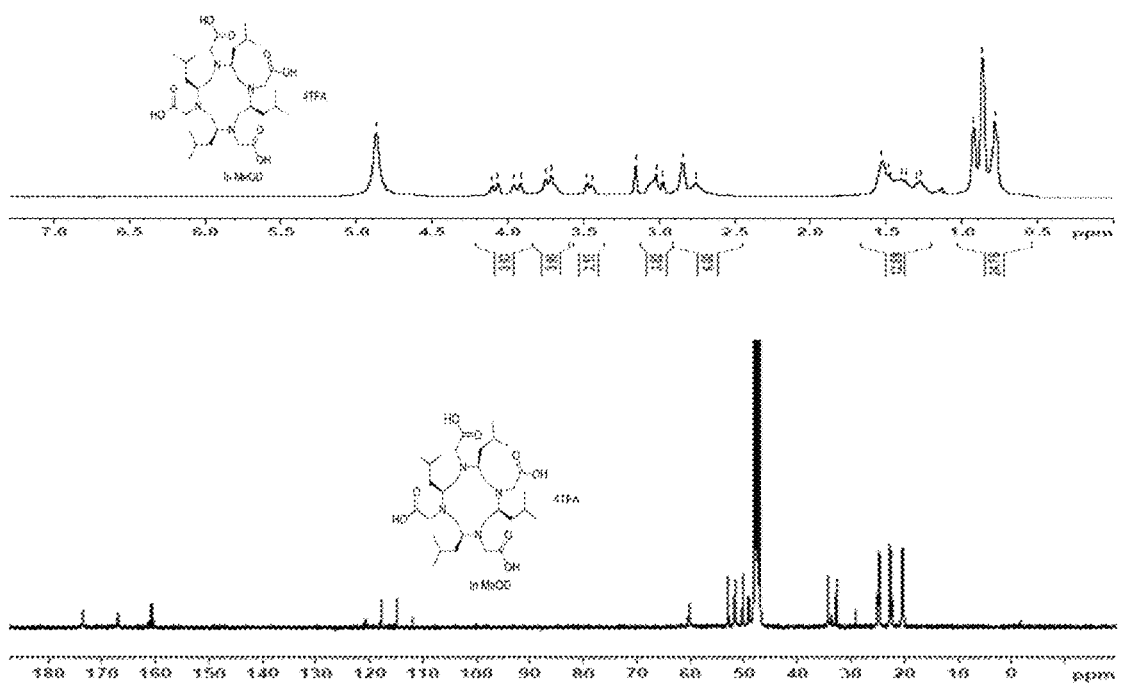
FIG. 8 shows the NMR spectra of L3. Top: $^1H$ NMR spectrum of L3 in MeOD. Bottom: $^{13}C$ NMR spectrum of L3 in MeOD.
Figure 9:
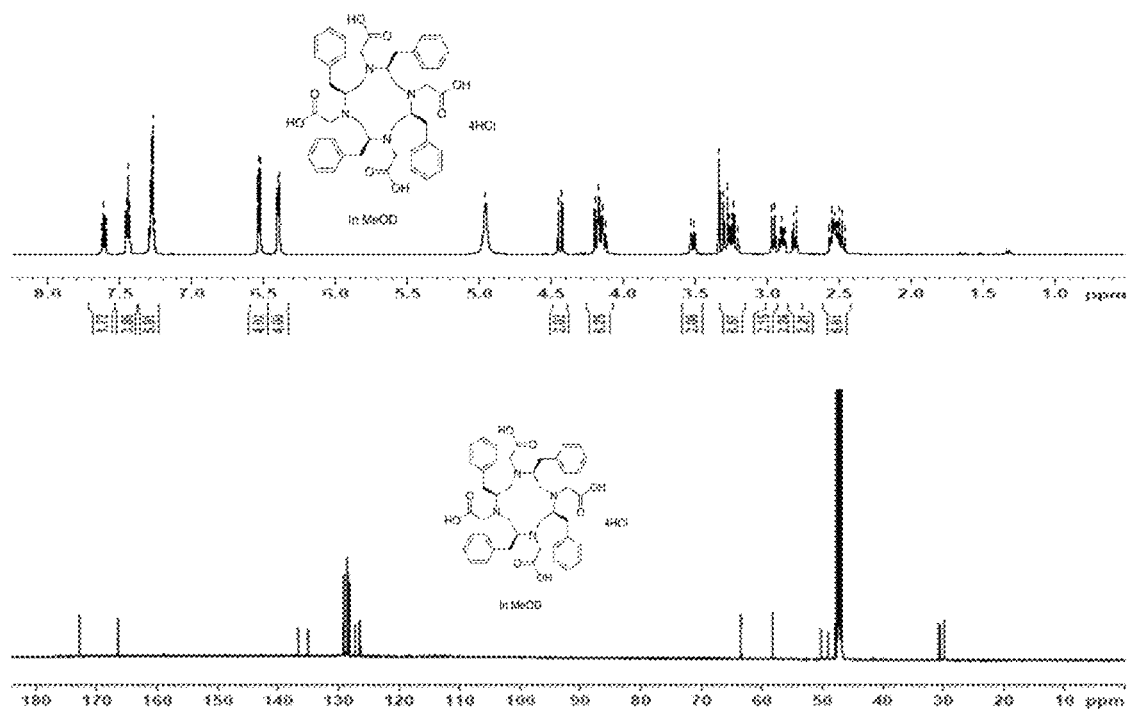
FIG. 9 shows the NMR spectra of L4. Top: $^1H$ NMR spectrum of L4 in MeOD. Bottom: $^{13}C$ NMR spectrum of L4 in MeOD.

To further demonstrate the variation in the TSA/SA isomer ratio of the ligands, the ¹H NMR spectra of the four ytterbium complexes were studied (FIG. 5). The ratio of TSA/SA isomers for [YbL1]⁻ (0.28) and [YbL2]⁻ (0.93) was relatively lower than that of the europium analogues. The ratio change from [YbL2]⁻ to [YbL3]⁻ was also not as apparent. However, for [YbL4]⁻, there was essentially one TSA isomer, the SA isomer could only be detected when the spectrum was amplified.

To check if the abundance of TSA and SA isomers of these synthesized complexes is temperature dependent and stable, variable temperature studies and stability in the presence of a competitive ligand were investigated. The high temperature ¹H NMR experiments of the Eu(III) complexes ([EuL1]⁻, [EuL2]⁻ and [EuL4]⁻), and Yb(III) complexes ([YbL1]⁻ and [YbL2]⁻) were conducted at 363 K.

Formation of Gd(III) complexes was investigated by HRMS as shown in FIG. 11.

11. Measurement of Kinetic Inertness of [GdL1]⁻ and [GdL2]⁻

Experimental procedure: Stock solution of [GdL1]⁻ and [GdL2]⁻ were prepared in 0.1 M ammonium acetate, 0~1000 equivalents of DTPA were added into the solutions, the final concentrations of the gadolinium complexes were 14.8 mM for [GdL1]⁻ and 21.6 mM for [GdL2]⁻ (6 mL). The mixtures were shaken at room temperature, and samples of 1 ml of solutions were taken out for UPLC-HRMS analysis on day 3 and day 7.

Results: Competitive bath titrations were performed with the Gd analogues, [GdL1]⁻ and [GdL2]⁻, in the presence of 0-1000 equivalents of competitive ligand DTPA (pentetic acid or diethylenetriaminepentaacetic acid) in 0.1 M ammonium acetate solution. After being shaken for 7 days (1000 eq. of DTPA, pH 5.0), the mixtures were analyzed by UPLC-HRMS. No trace of any decomplexation of these complexes was observed and the ratio of TSA/SA remained the same (FIGS. 12 and 13). This suggests that the complexes are completely stable and do not interconvert. This finding is of significant importance for future use of the complexes in biomedical applications.

12. Measurement of Relativities [GdL1]⁻, [GdL2]⁻, [GdL2A]⁻, [GdL2B]⁻ and [GdDOTA]⁻

Based on these results, it is evident that these chiral DOTAs can be synthesized with selective formation of TSA/SA isomers. This is very important because the huge difference in the inner-sphere coordinated water exchange rate between the two isomers is a key factor for applications, for example, as MRI contrast agents. To show their potential value, the two diastereomers of [GdL2]⁻ ([GdL2A]⁻ and [GdL2B]⁻) were separated and their relaxivities were measured. The relaxivities of [GdL1]⁻, [GdL2]⁻, [GdL2A]⁻, [GdL2B]⁻ and [GdDOTA]⁻ in water at different magnetic strengths (1.5 T and 11.7 T) were compared, with or without the presence of BSA and human plasma (1.5 T) (Table 1). It is clearly seen that the complexes of [GdL1]⁻, [GdL2A]⁻ and [GdL2B]⁻ have relaxivity properties similar to that of the [GdDOTA]⁻ complex.

There is no significant difference in relaxivity in water, BSA and human plasma.

TABLE 1

Summary of relaxivities of [GdL1]⁻, [GdL2]⁻, [GdL2A]⁻, [GdL2B]⁻ and [GdDOTA]⁻ in water, BSA and Human Plasma at 37° C.

| Sample | Water (1.5 T) r1 | r2 | Water (11.7 T) r1 | r2 | 4.5 w/v BSA (1.5 T) r1 | r2 | Human Plasma (1.5 T) r1 | r2 |
|---|---|---|---|---|---|---|---|---|
| [GdL1]⁻ | 3.4 | 3.6 | 2.8 | 3.3 | 4.1 | 4.7 | 3.9 | 4.1 |
| [GdL2]⁻ | 2.6 | 2.6 | 3.1 | 3.7 | 3.6 | 3.4 | 2.9 | 3.8 |
| [GdL2A]⁻ | 3.0 | 3.5 | — | — | 3.9 | 3.9 | 2.9 | 2.8 |
| [GdL2B]⁻ | 3.0 | 2.8 | — | — | 3.6 | 4.0 | 3.5 | 4.0 |
| [GdDOTA]⁻ | 3.2 | 3.2 | — | — | 4.1 | 4.8 | 4.0 | 4.0 |

13. BSA and Plasma Binding Affinity of [GdL1]⁻

The binding affinity determinations by ICP-MS showed less than 5% of complex binding with BSA and human plasma (Tables 2 and 3).

TABLE 2

Protein binding of [GdL1]⁻ at 15-320 μM.

| Sample | Conc. (mM) In BSA Before | Conc. (mM) In BSA after | Conc. (mM) In Plasma Before | Conc. (mM) In Plasma after |
|---|---|---|---|---|
| A | 0.32286251 | 0.31853386 (1.3% bound) | 0.3167862 | 0.309728 (2.2% bound) |
| B | 0.15917209 | 0.15684279 (1.5% bound) | 0.162104 | 0.1592104 (1.8% bound) |
| C | 0.02070731 | 0.01999801 (3.7% bound) | 0.021152 | 0.020152 (4.7% bound) |

TABLE 3

Protein binding of [GdL1]⁻ at 15-370 μM.

| Sample | Conc. (mM) In BSA Before | Conc. (mM) In BSA after | Conc. (mM) In Plasma Before | Conc. (mM) In Plasma after |
|---|---|---|---|---|
| A | 0.3714242 | 0.3641484 (1.9% bound) | 0.3699171 | 0.360182 (2.6% bound) |
| B | 0.1551093 | 0.1498369 (3.4% bound) | 0.134016 | 0.1310612 (2.2% bound) |
| C | 0.0251512 | 0.0245832 (2.2% bound) | 0.0189002 | 0.0181644 (3.9% bound) |

14. Complexation Reactions of L1 and L2 with Lanthanide Salts

Procedure: The ligand (~10 mg, 1.0 eq.) was dissolved in 0.5 ml of ammonium acetate buffer (1.25 M, pH 5.5) solution; the metal salt was dissolved in 0.5 ml of buffer and added into the ligand solution (another 0.5 ml of buffer was used for transferring). The resulting solution was put into a pre-heated oil bath (40 degrees C.). The reaction was monitored by mass spectra (a sample was dissolved in acetonitrile and a small amount of methanol; an injection sample was made by adding an equal volume of acetonitrile containing 0.1% of TFA).

Figure 14:
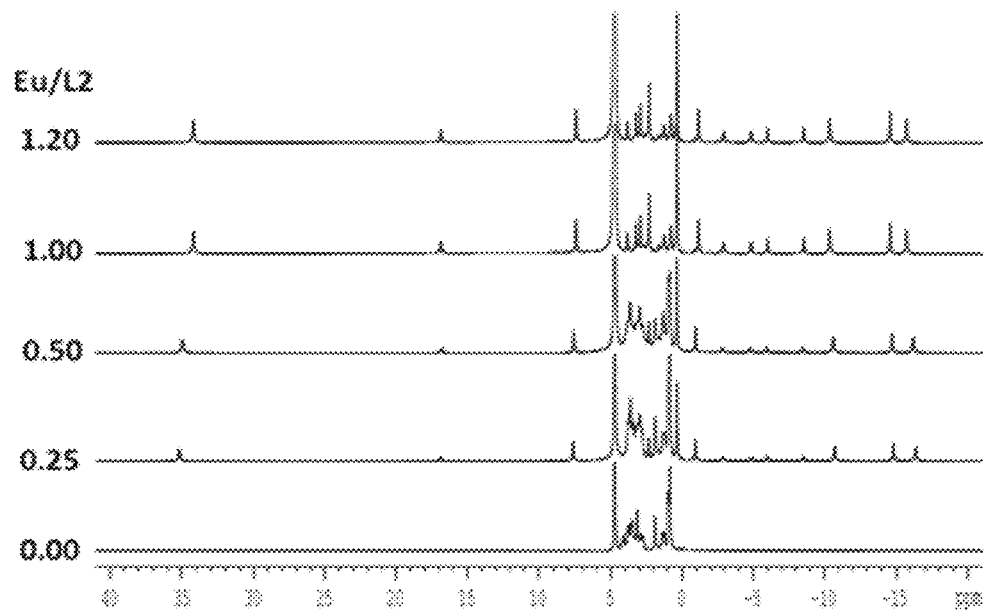
FIG. 14 are $^1$H NMR spectra taken at 298 K, showing changes after titrating L2 ($7.5\times10^{-3}$ M in $D_2O$) with different amounts of Eu(OTf)$_3$ (0.05 M in $D_2O$), and adjusting the pD to 6.0-7.0 by NaOD ($5\times10^{-3}$ M) at 323 K for 5 mins.

One more useful and important application of the ROTA-based ligands is its use as radiopharmaceutical chelates. Regarding these chelates, the free radiometal ions must be tightly sequestered from aqueous solution by chelates to obviate transchelation and hydrolysis.[19] It is believed that the chiral DOTA ligands L1-L4 with four extra substituents on one side will cause the four acetate groups to form a natural cavity, in contrast to the normal DOTA chelate whose four acetate groups are in a more disordered structure, thus having lower entropy in the process of sequestering the metal ions. The rate of complexation is expected to be much more rapid. To confirm this, $^1$H NMR (400 MHz) was used to monitor the titration of L2 with Eu(Otf)$_3$, pD adjusted to 6.0-7.0 by NaOD and heated to 50° C. for 5 minutes (FIG. 14), The spectra showed that complexation was complete within 5 minutes at 50° C. Complexation of ligands L1 and L2 with Ga(III) and Lu(III) was also performed under radiolabeling conditions reported in the literature. In ammonium acetate buffer (1.25 M, pH 5.5), the complexation reactions were complete within 30 mins at 40° C., quicker than DOTA (Table 4).

TABLE 4

Complexation reactions of Ligand and lanthanide salts (MCl$_3$)

| Complex | [LuL1]⁻ | [LuL1]⁻ | [GaL1]⁻ | [GaL2]⁻ |
|---|---|---|---|---|
| Ligand | 10.2 mg | 9.9 mg | 10.2 mg | 10.0 mg |
| MCl$_3$ | 2.96 ml | 2.63 ml | 4.73 ml | 4.25 ml |
| Buffer (overall) | 1.5 ml | 1.5 ml | 1.5 ml | 1.5 ml |
| Temperature | 40° C. | 40° C. | 40° C. | 40° C. |
| Time | 30 min | 30 min | 30 min | 30 min |

In summary, the present invention demonstrated the synthesis of a series of chiral DOTA-based chelates with four symmetrically placed substituents around the cyclen ring. The ratio of twisted square antiprism (TSA) and the square antiprism (SA) of Eu(III) and Yb(III) complexes of these chiral DOTA-based chelates are much higher than normal DOTA chelates. As the bulk of these substituents increase, the ratio of TSA/SA increases; when the substituents are benzyl groups, the TSA isomers are the dominant configurations in aqueous solutions. The high temperature experiments of $^1$H NMR confirm that the ratio of isomers is not affected by increased temperature. The relaxivities of complex [GdL1]⁻, [GdL2]⁻ and the separated diastereomers ([GdL2A]⁻ and [GdL2B]⁻) are similar to that of the parent [GdDOTA]⁻ complex. The complexation of L1 and L2 with Ga(III) and Lu(III) can be achieved under very mild conditions similar to those used for radiometal labelling, such as $^{67}$Ga and $^{177}$Lu for single photon emission computed tomography (SPECT) and $^{68}$Ga for positron emission tomography (PET). These chiral DOTA-based chelates with different substituents will serve as an excellent complementary platform to the normal DOTA compounds, and will open new doors for developing additional metal ion chelates for biomedical applications.

Example 2

Synthesis of Chiral DO3A-Based Metal Complexes

1. Materials and General Methods.

Unless noted otherwise, all chemicals were of reagent-grade and were purchased from Sigma-Aldrich or Acros Organics and used without further purification. Moisture-sensitive synthetic procedures were performed under a nitrogen atmosphere using standard Schlenk techniques. Davisil silica gel (40-63 m) was obtained from Grace Davison. Analytical-reagent grade solvents were used and acetonitrile was dried with calcium hydride and distilled under nitrogen. High-performance liquid chromatography (HPLC) was performed using an Agilent 1100 Series apparatus with an UV visible detector with UV detection from 220 to 350 nm by a Vision HT C18 HL 5 mm column. Reverse-phase semi-preparative purification was performed on the Agilent HPLC system with UV detection from 220 to 360 nm using the columns of Waters XBridge® Prep C18 5 m OBD™ (19× 250 mm) or (19×100 mm). $^1$H, $^{13}$C NMR and NOESY spectra were recorded on a Bruker Ultrashield 400 Plus NMR spectrometer (at 400 MHz and 100 MHz respectively) or a Bruker Ultrashield 600 Plus NMR spectrometer (at 600 MHz and 150 MHz respectively). The $^1$H and $^{13}$C NMR chemical shifts were referenced to solvent residual peaks. $^{31}$P NMR spectra were recorded on a Bruker Ultrashield 400 Plus NMR spectrometer (162 MHz). Mass spectra, reported as m/z, were obtained on a Micromass Q-TOF 2 mass spectrometer; HRMS were performed on an Agilent 6540 UHD Accurate-Mass Q-TOF LC/MS.

Absorption spectra of complexes were measured with HP UV-8453 spectrophotometer. Steady-state room temperature photoluminescence measurements were performed with an Edinburgh Instrument FLSP920 spectrophotometer equipped with a Xe900 continuous xenon lamp, μF920 microsecond flash lamp and a single photon counting photomultiplier tube. Spectra were corrected with the bundled F900 software. Solution-state measurements were conducted using quartz curettes of 10 mm path length. CPL measurements were conducted on a custom built spectrometer[63] (in Durham University) consisting of a laser driven light source (Energetiq EQ-99 LDLS, spectral range 170 to 2100 nm) coupled to an Acton SP2150 monochromator (600 g/nm, 300 nm Blaze) that allows excitation wavelengths to be selected with a 6 nm FWHM band-pass. The collection of the emitted light was facilitated (90° angle set up, 1 cm path length quartz curette) by a Lock-In Amplifier (Hinds Instruments Signaloc 2100) and Photoelastic Modulator (Hinds Instruments PEM-90). The differentiated light was focused onto an Acton SP2150 monochromator (1200 g/nm, 500 nm Blaze) equipped with a high sensitivity cooled Photo Multiplier Tube (H10723-20 Extended red-multialkali PMT based photosensor (5V)). Spectra were recorded using a 5 spectral average sequence in the range of 570-720 nm with 0.5 nm spectral intervals and 500 μs integration time. The recorded CPL spectrum underwent a 25% Fourier transformation smoothening protocol using Origin 8.0 Software (Origin Labs) to enhance appearance (all calculations were carried out using raw spectral data).

Figure 15:
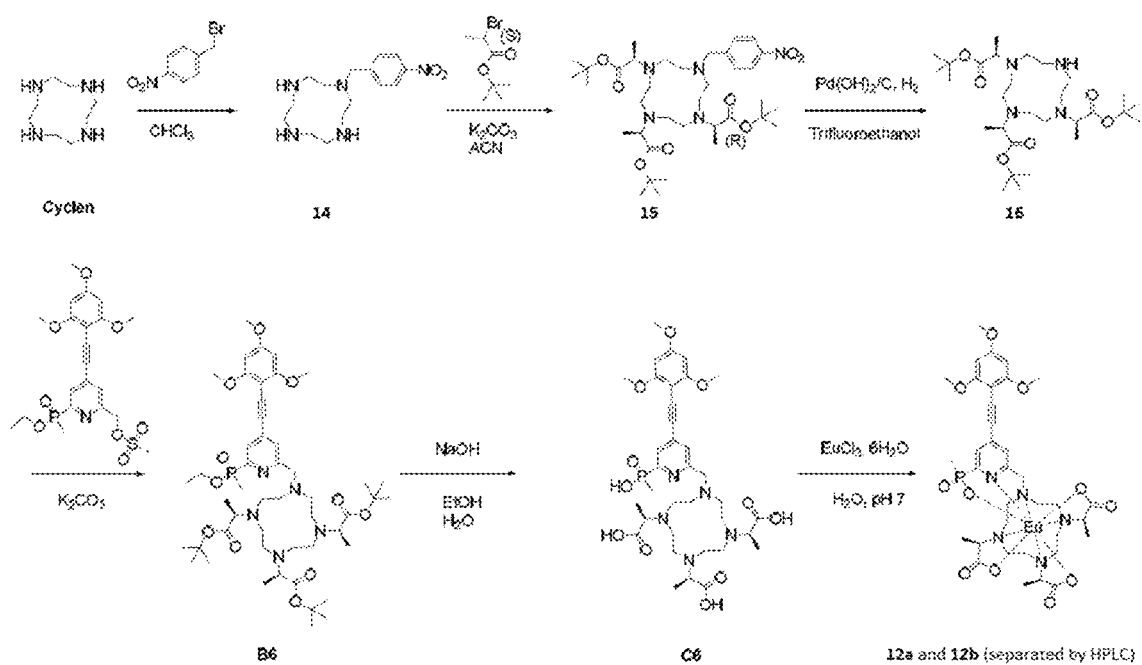
FIG. 15 shows a synthetic route of complexes 12a and 12b

2. Synthesis of Complexes 7-13 (FIGS. 2 and 15)

Following procedure shows the synthesis of complexes 7-11 (FIG. 2).

Compound 6: Compound 6 was synthesized from normal cyclen (1,4,7,10-tetraazacyclododecane) according to the procedure of literature reported.[64]

Compounds 3b, 3b(R), 3c and 3d: Cyclization reactions were similar as the literature reported procedure[18] and were described in Example 1.

Compound 5: To a solution of ethyl (6-(hydroxymethyl)-4-((2,4,6 trimethoxyphenyl)ethynyl)pyridin-2-yl)(methyl)phosphinate,[65] (1 g, 2.47 mmol) in dichloromethane (20 ml) was added DIPEA (0.96 g, 7.4 mmol), the solution was cooled to 0~10° C. and added methanesulfonyl chloride (0.42 g, 3.7 mmol), after reacting for 30 mins, the solution was quenched by added 10 ml of water, separated the organic and aqueous layers, the organic layer was washed with 10 ml water and 10 ml sat. NaCl solution, dried with magnesium sulfate, filtered and the filtrate was concentrated. The product of 5 (1.1 g, yield 92%) was used to the next step reaction without any further purification.

A1: 3b (300 mg, 1.05 mmol) was dissolved in acetonitrile (40 ml), added NaHCO$_3$ (116 mg, 1.38 mmol), then dropped the solution of 5 (308 mg, 0.64 mmol) in acetonitrile (15 ml) very slowly (over 10 hrs) at room temperature. Then stirring for another 6 hrs. The solution was filtered, concentrated under reduced pressure. The resultant crude product was purified by column chromatography on silica gel (MeOH/CH$_2$Cl$_2$: 10%) to give compound A1 as a light yellow solid (300 mg, 70%), $^{31}$P NMR (162 MHz, CDCl$_3$) δ 39.48, 38.98.

A2: (2R,5R,8R,11R)-2,5,8,11-tetraethyl-1,4,7,10-tetraazacyclododecane, 3b(R) (350 mg, 1.22 mmol) was dissolved in acetonitrile (50 ml), added NaHCO$_3$ (67 mg, 0.80 mmol), then dropped the solution of 5 (295 mg, 0.61 mmol) in acetonitrile (10 ml) very slowly (in 10 hrs) at room temperature. Then stirring for another 6 hrs. The solution was filtered, concentrated under reduced pressure. The resultant crude product was purified by column chromatography on silica gel (MeOH: CHCl$_3$, 10%~15%) to give compound A2 as a light yellow solid (320 mg, 78%). $^{31}$P NMR (162 MHz, CDCl$_3$) δ 38.89.

A3: 3c (70 mg, 0.18 mmol) was dissolved in acetonitrile (25 ml), added NaHCO$_3$ (19.3 mg, 0.23 mmol), then dropped the solution of 5 (51 mg, 0.11 mmol) in acetonitrile (9 ml) very slowly (in 9 hrs) at room temperature. Then stirring for another 6 hrs. The solution was filtered, concentrated under reduced pressure. The resultant crude product was purified by column chromatography on silica gel (MeOH/CH$_2$Cl$_2$: 10%) to give compound A3 as a light yellow solid (35 mg, 42%), $^{31}$P NMR (162 MHz, CDCl$_3$) δ 39.16.

A4: 3d (152 mg, 0.29 mmol) was dissolved into acetonitrile (50 ml), added NaHCO$_3$ (31 mg, 0.37 mmol), then dropped the solution of 5 (83 mg, 0.17 mmol) in acetonitrile (10 ml) very slowly (in 9 hrs) at room temperature. Then stirring for another 6 hrs. The solution was filtered, concentrated under reduced pressure. The resultant crude product was purified by column chromatography on silica gel (MeOH/CH$_2$Cl$_2$:10%) to give compound A4 as a white solid (80 mg, 51%). $^{31}$P NMR (162 MHz, CDCl$_3$) δ 39.32, 38.69.

Complex 7: DO3A (103 mg, 0.2 mmol) was dissolved in acetonitrile (6 ml), then K$_2$CO$_3$ (65 mg, 0.47 mmol) and compound 5 (114 mg, 0.24 mmol) were added into the reaction mixture. After reacting at room temperature for 12 hrs. The solution was filtered and the filtrate was concentrated under reduced pressure to give brown oil. This crude product was dissolved into 0.3% HCl (60 ml), then extracted with ethyl acetate (3×20 ml), the aqueous solution was then adjusted pH to 8.0 by saturated NaHCO$_3$ and extracted with CH$_2$Cl$_2$ (2×30 ml), combined the CH$_2$Cl$_2$ layers and washed with saturated NaCl (20 ml), dried over MgSO$_4$, filtered and the solvent was removed under reduced pressure. This resulted the pure product B1 (120 mg, 69%) as a yellow oil. It was dissolved into ethanol (2 ml) and 0.4 M NaOH (4 ml), after refluxing for 6 hrs, the resulting solution was cooled to 0~20° C., adjusted the pH to 7 by adding 0.5 M HCl, then EuCl$_3$.6H$_2$O (52 mg, 0.15 mmol) was added, the reaction solution was adjusted pH to 7 again by adding 0.1 M NaOH, refluxing for another 4 hrs (monitored by HPLC). Then most of solvent was removed under reduced pressure, H$_2$O (4 ml) was added into the mixture and pH was adjusted to 10 by adding 0.1 M NaOH, then filtered and pH was adjusted to 7 again. Concentrated under reduced pressure and the resultant mixture was dissolved into methanol (4 ml), filtered and the filtrate was concentrated again to give the resulted complex (100 mg, 85%) as a white solid.

Complex 8: Into a solution of compound A1 (100 mg, 0.15 mmol), $K_2CO_3$ (123.5 mg, 0.89 mmol) in acetonitrile (6 ml) was added ethyl 2-bromoacetate (87.1 mg, 0.52 mmol), stirring at 60° C. for 16 hrs. Then raised the temperature to 80° C., and added another 21 mg of ethyl 2-bromoacetate, reaction for another 42 hrs. Cooled the temperature, filtered, the solvent was removed under reduced pressure, the resultant mixture was dissolved into 0.3% HCl (60 ml), then extracted with ethyl acetate (3×20 ml), the aqueous solution was then adjusted pH to 8.0 by saturated $NaHCO_3$ and extracted with $CH_2Cl_2$ (2×30 ml), combined the $CH_2Cl_2$ layers and washed with saturated NaCl (20 ml), dried over $MgSO_4$, filtered and the solvent was removed under reduced pressure. This resulted in the product B2 with purity above 90% (HPLC and 41 NMR estimated) (120 mg, 87%) as a light yellow oil. It was dissolved into ethanol (5 ml) and 0.4 M NaOH (3 ml), after refluxing for 3 hrs, the resulting solution was cooled to 0~20° C., adjusted the pH to 7.0 by adding 0.5 M HCl, concentrated to dryness under reduced pressure, then dissolved into methanol (10 ml), filtered, the filtrate was concentrated again, and dissolved into acetone (2 ml) and added ethyl ether (20 ml), centrifuged and resulted a light yellow solid (140 mg). It was dissolved into water (5 ml), and then $EuCl_3.6H_2O$ (47 mg, 0.13 mmol) was added, the reaction solution was adjusted pH to 7.0 by adding 0.1 M NaOH, refluxing for 2 hrs. HPLC showed the relative broad peak from the ligand turned into a sharp peak in the process of complexation. Further purification by Pre-HPLC (acetonitrile/water with 0.1% formic acid, 5%~60%) was performed to remove salts. This resulted in the pure complex of 8 (30 mg, 21% three steps) as a yellow solid (with trace acid, when neutral or basic will be white).

Complex 9: Into a solution of compound A2 (160 mg, 0.24 mmol), $K_2CO_3$ (197.5 mg, 1.43 mmol) in acetonitrile (5 ml) was added ethyl 2-bromoacetate (131 mg, 0.78 mmol), stirring at room temperature for 16 hrs. Then added another 170 mg of $K_2CO_3$ and 63.6 mg of ethyl 2-bromoacetate, the resulting solution was reacting for another 2 days. After filtration, purified by column chromatography on silica gel ($EtOH/CHCl_3$: 2%~5%) to give compound B3 as a foamy solid (110 mg, 50%). $^1H$ NMR (400 MHz, $CDCl_3$) δ 7.73-7.01 (m, 2H), 5.85 (s, 2H), 4.09-3.67 (m, 8H), 3.66-3.45 (m, 11H), 3.45-1.71 (m, 18H), 1.71-1.18 (m, 7H), 1.18-0.41 (m, 28H). $^{31}P$ NMR (162 MHz, $CDCl_3$) δ 40.28, 39.55, 39.26, 38.16. Compound B3 (110 mg) was dissolved in 3 ml of ethanol and 2 ml water, added 28 mg of LiOH, then reacting at 80° C. for 1.5 hrs, after cooling and adjusting pH to ~8.0, $EuCl_3.6H_2O$ (48 mg) was added (pH ~7.0), then refluxing overnight. Purified by reversed phase Pre-HPLC (acetonitrile/water with 0.1% formic acid: 5%~60%) and lyophilized to get the pure complex 9 (25 mg, yield 25% for two steps) as a yellow solid.

Complex 10: Into a solution of compound A3 (35 mg, 0.04 mmol), $K_2CO_3$ (62 mg, 0.45 mmol) in acetonitrile (3 ml) was added ethyl 2-bromoacetate (30 mg, 0.18 mmol), stirring at room temperature for 24 hrs. After filtration, purified by column chromatography on silica gel ($EtOH/CHCl_3$: 2%~5%) to give compound B4 as a foamy solid (40 mg, 89%). $^1H$ NMR (400 MHz, $CDCl_3$) δ 8.15-7.55 (m, 2H), 6.21 (s, 2H), 4.38-4.04 (m, 8H), 3.98-3.60 (m, 11H), 3.82-1.95 (m, 18H), 1.82 (dd, J=14.8, 6.8 Hz, 3H), 1.73-1.10 (m, 24H), 1.10-0.77 (m, 24H). $^{31}P$ NMR (162 MHz, $CDCl_3$) δ 39.71, 38.56, 38.27. Compound B4 (40 mg) was dissolved in 2 ml of ethanol and 1.5 ml water, then added 15 mg of NaOH, then reacting at 80 C for 2.5 hrs, after cooling and adjusting pH to 8.0, $EuCl_3.6H_2O$ (15 mg) was added, then refluxing overnight. Cooled to room temperature and concentrated under vacuum, the purity was checked by analytical HPLC.

Complex 11: Into a solution of compound A4 (80 mg, 0.09 mmol), $K_2CO_3$ (120 mg, 0.87 mmol) in acetonitrile (3 ml) was added ethyl 2-bromoacetate (58 mg, 0.35 mmol), stirring at room temperature for 24 hrs. After filtration, purified by column chromatography on silica gel ($EtOH/CHCl_3$: 2%~5%) to give compound B5 as a foamy solid (80 mg, 78%). $^1H$ NMR (400 MHz, $CDCl_3$) δ 8.18-6.65 (m, 14H), 6.31-5.90 (m, 10H), 4.20-3.90 (m, 8H), 3.72-3.14 (m, 4H), 3.14-2.30 (m, 14H), 2.10-1.12 (m, 15H). Compound B5 (80 mg) was dissolved in 3 ml of ethanol and 1.5 ml water, then added 50 mg of NaOH, then reacting at 80° C. for 1.5 hrs, after cooling and adjusting pH to ~7.5, $EuCl_3$, $6H_2O$ (29.9 mg) was added (pH 7.0), then refluxing overnight. Cooled to room temperature and concentrated under vacuum, the purity was check by analytical HPLC.

Following procedure shows the synthesis of complexes 12a and 12b (FIG. 15).

1-(4-nitrobenzyl)-1, 4, 7, 10-tetraazacyclododecane, 14: Into a solution of 1, 4, 7, 10-tetraazacyclododecane (4 g, 23.3 mmol) in $CHCl_3$ (80 ml) was dropped with a solution of 1 (bromomethyl)-4-nitrobenzene (3.3 g, 15.3 mmol) in $CHCl_3$ (25 ml) in 2 hrs. After reacting at room temperature for 1.5 hrs, the crude product was purified by column chromatography on silica gel ($MeOH/CHCl_3$: 10%~30%) to give the product G as a light yellow solid (2.5 g, 53%).

(2R, 2'R, 2"R)-tri-tert-butyl 2,2',2"-(10-(4-nitrobenzyl)-1, 4,7,10 tetraazacyclododecane-1,4,7-triyl)tripropanoate, 15: Into a solution of 14 (210 mg, 0.54 mmol) in acetonitrile (10 ml) was added $K2CO_3$ (powder) (750 mg, 5.4 mmol) and (S)-tert-butyl 2-bromopropanoate[66] (565 mg, 2.7 mmol). After reacting at 60 C for 24 hrs, cooled the reaction mixture, filtered, the solvent was removed under reduced pressure; the resultant mixture was dissolved into 0.6 M HCl (85 ml), then extracted with ethyl acetate (3×20 ml), the aqueous solution was then adjusted pH to 8.0 by saturated $NaHCO_3$ and extracted with $CH_2Cl_2$ (3×30 ml), combined the $CH_2Cl_2$ layers and washed with saturated NaCl (20 ml), dried over $MgSO_4$, filtered and the solvent was removed under reduced pressure. This resulted in the product 15 (300 mg, yield 80%) as a light yellow solid.

(2R, 2'R, 2"R)-tri-tert-butyl 2,2',2"(1,4,7,10-tetraazacyclododecane-1,4,7 triyl)tripropanoate, 16: Into a solution of 15 (300 mg, 0.43 mmol) in trifluoroethanol (10 ml) was added 20% $Pd(OH)_2/C$ (wet) (97 mg). The solution was connected with a H2 balloon. After reacting at 50° C. for 24 hrs, cooled the reaction mixture, filtered, the solvent was removed under reduced pressure, this resulted in the product 16 (230 mg, yield 95%) as a white solid.

(2R, 2'R, 2"R)-tri-tert-butyl 2,2',2"-(10-((6-(ethoxy (methyl)phosphoryl)-4-((2,4,6-trimethoxyphenyl)ethynyl) pyridin-2-yl)methyl)-1,4,7,10-tetraazacyclododecane-1,4,7-triyl)tripropanoate, B6: Into a solution of 16 (140 mg, 0.25 mmol), $K_2CO_3$ (70 mg, 0.50 mmol) in acetonitrile (5 ml) was added (6-(ethoxy(methyl)phosphoryl)-4-((2,4,6-trimethoxyphenyl)ethynyl)pyridin-2-yl)methyl methanesulfonate, 5 (158.0 mg, 0.33 mmol), stirring at room temperature for 16 hrs. Cooled the temperature, filtered, the solvent was removed under reduced pressure, the resultant mixture was dissolved into 0.5 M HCl (60 ml), then extracted with ethyl acetate (3×20 ml), the aqueous solution was then adjusted pH to 8.0 by saturated $NaHCO_3$ and extracted with $CH_2Cl_2$ (2×30 ml), combined the $CH_2Cl_2$ layers and washed with saturated NaCl (20 ml), dried over MgSO$_4$, filtered and the solvent was removed under reduced pressure. This resulted in the product B6 (120 mg, 51%) as a light yellow foamy solid. $^{31}$P NMR (162 MHz, CDCl$_3$) δ 40.44, 40.17.

(2R, 2'R, 2"R)-2,2',2"-(10-((6-(hydroxy(methyl)phosphoryl)-4-((2,4,6-trimethoxyphenyl)ethynyl)pyridin-2-yl) methyl)-1,4,7,10-tetraazacyclododecane-1,4,7-triyl)tripropanoic acid, C6: The compound B6 (120 mg, 0.13 mmol) was dissolved in ethanol (2 ml) and water (2 ml), added NaOH (470 mg), after refluxing for 6 hrs, the resulting solution was cooled to 0~20° C., adjusted the pH to 7.0 by adding 0.5 M HCl, the crude product was purified by reversed phase Pre-HPLC (acetonitrile/water with 0.1% formic acid: 5%~50%) and lyophilized to give the pure compound C6 (50 mg, yield 53%) as a yellow powder. $^1$H NMR (400 MHz, D$_2$O) δ 8.05 (s, 1H), 7.86 (s, 1H), 6.31 (s, 2H), 4.10-2.98 (m, 30H), 1.62 (d, J=14.5 Hz, 3H), 1.52-1.20 (m, 9H). $^{31}$P NMR (162 MHz, D$_2$O) δ 24.86.

Complexes of 12a and 12b: The ligand C6 (30 mg, 0.04 mmol) was dissolved in water (2 ml), pH was adjusted to 8.0 by adding 0.1 M NaOH, and then EuCl$_3$.6H$_2$O (16 mg, 0.04 mmol) was added, the reaction mixture was refluxing for 16 hrs. The formed two isomers (~1:1 on HPLC, no any other peak was observed) were purified by reversed phase Pre-HPLC (acetonitrile/water with 0.1% formic acid, 5%~60%) and lyophilized. This resulted in the pure complexes of 12a (8 mg, yield 22%) and 12b (10 mg, yield 28%) as yellow powder.

The following procedure shows the synthesis of complex 13 (FIG. 2).

(2R, 2'R, 2"R)-tri-tart-butyl 2,2',2"-((2S,5S,8S,11S)-10-((6-(ethoxy(methyl)phosphoryl)-4-((2,4,6-trimethoxyphenyl)ethynyl)pyridin-2-yl)methyl)-2,5,8,11-tetraethyl-1,4,7,10-tetraazacyclododecane-1,4,7-triyl)tripropanoate, B7: Into a solution of compound A1 (108 mg, 0.16 mmol), K2CO$_3$ (grinded powder) (222 mg, 1.61 mmol) in dry acetonitrile (4 ml) was added new made (S)-ethyl 2-(((trifluoromethyl) sulfonyl) oxy) propanoate$^{67}$ (280 mg, 1.11 mmol), stirring at room temperature for 16 hrs. After filtration, purified by column chromatography on silica gel (EtOH/CHCl$_3$: 1%~5%) to give compound B7 as a foamy solid (50 mg, 32%).

(2R, 2'R, 2"R)-2,2',2"-((2S,5S,8S,11S)-2,5,8,11-tetraethyl-10-((6-(hydroxy(methyl)phosphoryl)-4-((2,4,6 trimethoxyphenyl)ethynyl)pyridin-2-yl)methyl)-1,4,7,10-tetraazacyclododecane-1,4,7-triyl)tripropanoic acid, C7: The compound B7 (50 mg, 0.05 mmol) was dissolved in ethanol (3 ml) and water (3 ml), added LiOH (24.7 mg), after refluxing for 8 hrs, the resulting solution was cooled to 0~20° C., adjusted the pH to 7.0 by adding 0.5 M HCl, the crude product was purified by reversed phase Pre-HPLC (acetonitrile/water with 0.1% formic acid: 5% 70%) and lyophilized to get the pure compound C7 (20 mg, yield 46%) as a yellow powder. $^1$H NMR (400 MHz, D$_2$O) δ 7.83 (d, J=15.7 Hz, 2H), 6.17 (s, 2H), 4.33-2.48 (m, 26H), 1.93 (s, 4H), 1.73-1.09 (m, 16H), 1.09-0.52 (m, 12H). $^{31}$P NMR (162 MHz, D$_2$O) δ 28.25.

Complex 13: The ligand C7 (10 mg, 0.01 mmol) was dissolved in water (2 ml), pH was adjusted to ~8.0 by adding 0.1 M NaOH, and then EuCl$_3$.6H$_2$O (4.7 mg, 0.01 mmol) was added, the reaction mixture was refluxing for 16 hrs. The formed complex was purified by reversed phase Pre-HPLC (acetonitrile/water with 0.1% formic acid, 5% 80%) and lyophilized. This resulted in the pure complexes of 13 (5 mg, yield 42%) as a light yellow powder.

HPLC Analysis

HPLC chromatograms of ligands C1-C7 and complexes 7-13 were performed under the following conditions: (a) Instrument: Agilent Analytical HPLC (1100 Series), UV-visible detector. (b) Column: Vision HT C18 HL 5 mm×250 mm; (c) Mobile phase: 0 min 90% Water (0.05% TFA)/10% ACN (0.05% TFA) ~25 mins 100% ACN (0.05% TFA).

TABLE 5

Solvent profile of HPLC analysis

| Time (mins) | Solvent A | Solvent B | Flow rate (ml/min) |
|---|---|---|---|
| 0.00 | 90 | 10 | 1.000 |
| 25.00 | 0 | 100 | 1.000 |
| 30.00 | 0 | 100 | 1.000 |

Solvent A: H$_2$O with 0.05% TFA; Solvent B: Acetonitrile (0.05% TFA).

Figure 16A:
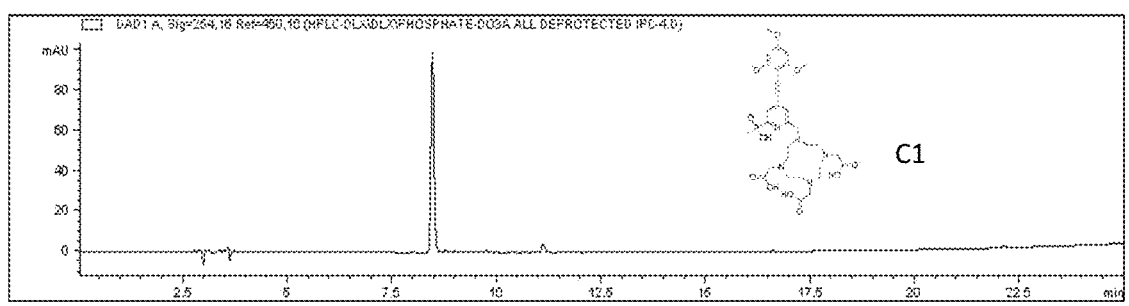
FIG. 16A shows the reversed-phase high-performance liquid chromatography (RP-HPLC) trace of compound C1 (Detection at 254 nm).
Figure 16B:
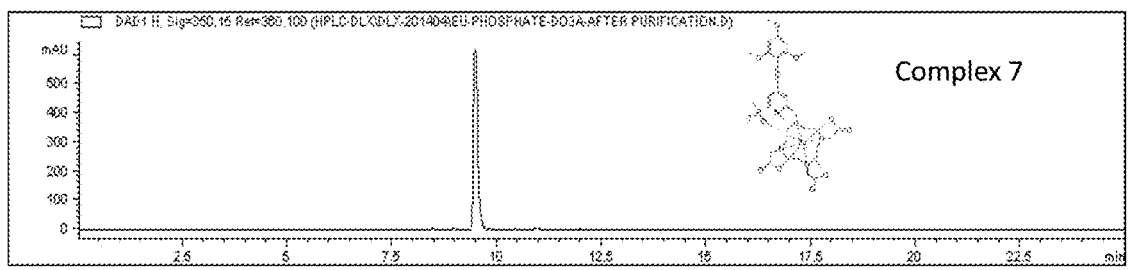
FIG. 16B shows the RP-HPLC trace of complex 7 (Detection at 350 nm).
Figure 16C:
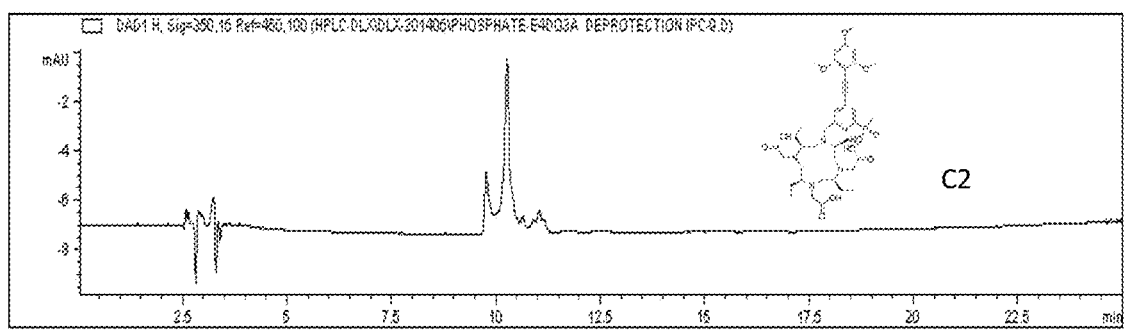
FIG. 16C shows the RP-HPLC trace of compound C2 (Detection at 350 min).
Figure 16D:
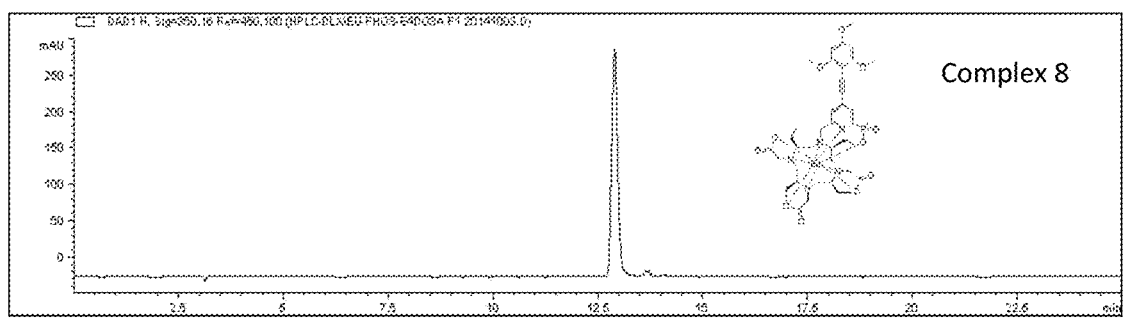
FIG. 16D shows the RP-HPLC trace of complex 8 (Detection at 350 nm).
Figure 16E:
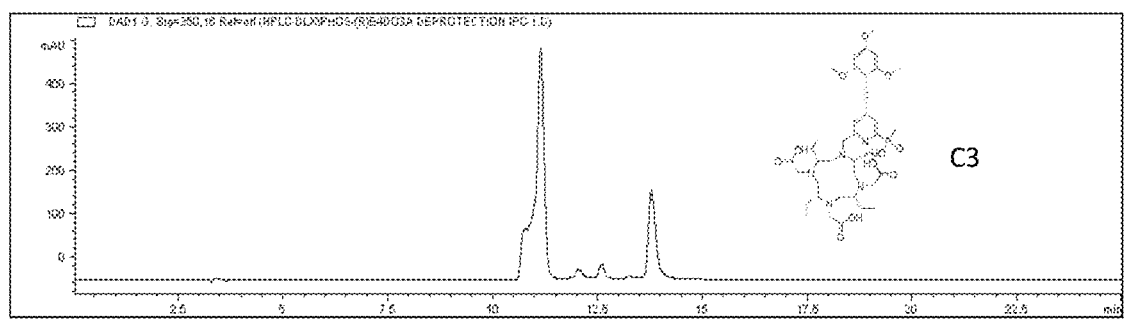
FIG. 16E shows the RP-HPLC trace of compound C3 (Detection at 350 nm).
Figure 16F:
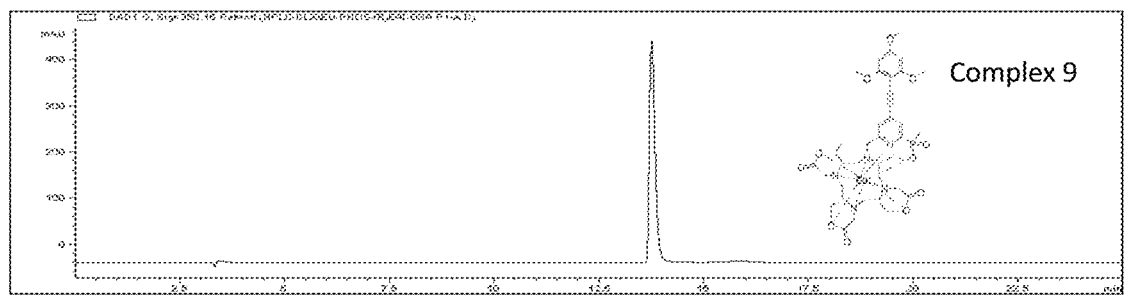
FIG. 16F shows the RP-HPLC trace of complex 9 (Detection at 350 nm).
Figure 16G:
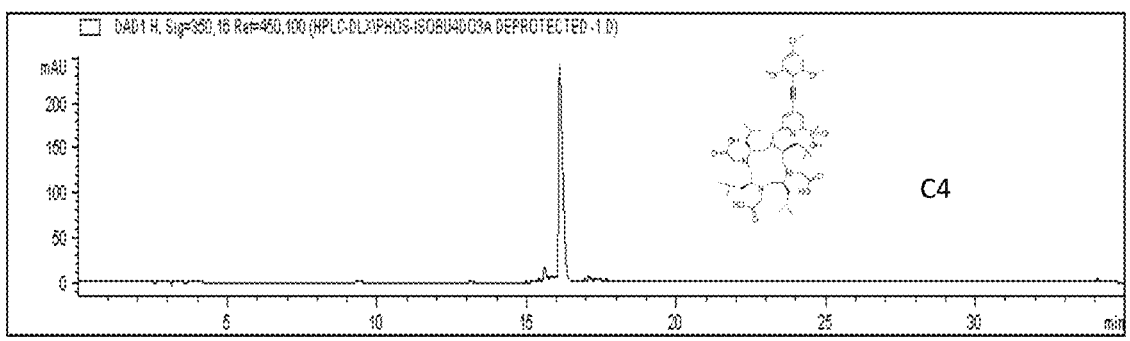
FIG. 16G shows the RP-HPLC trace of compound C4 (Detection at 350 run).
Figure 16H:
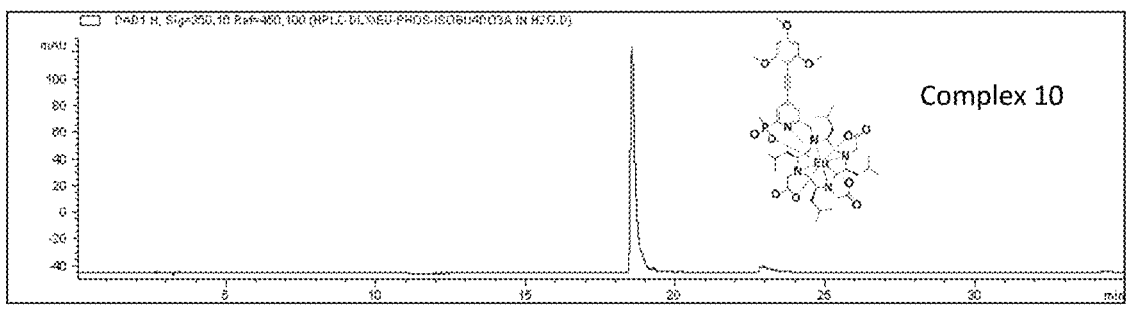
FIG. 16H shows the RP-HPLC trace of complex 10 (Detection at 350 nm).
Figure 16I:
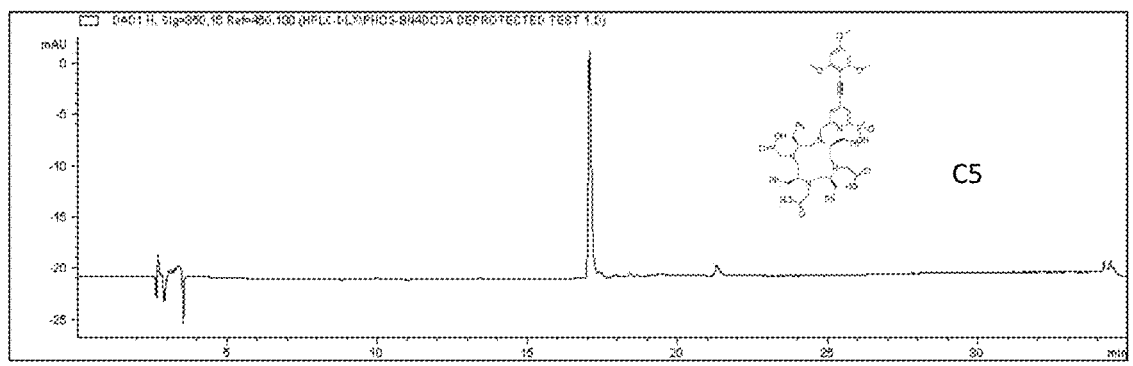
FIG. 16I shows the RP-HPLC trace of compound C5 (Detection at 350 nm).
Figure 16J:
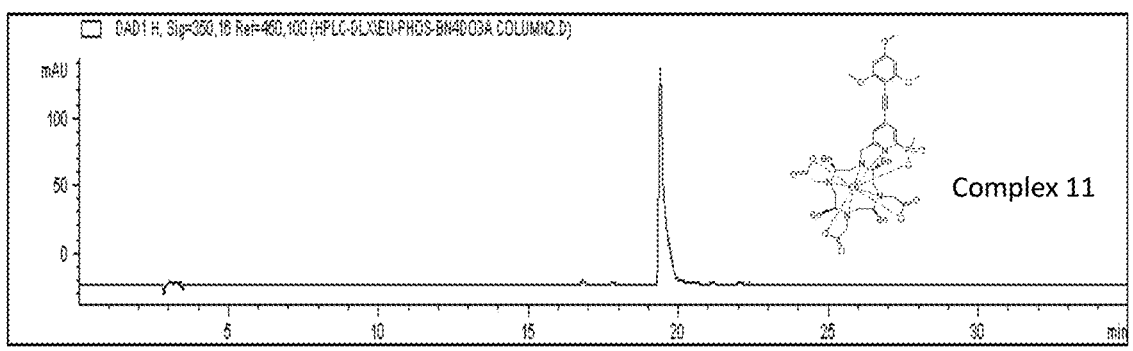
FIG. 16J shows the RP-HPLC trace of complex 11. (Detection at 350 nm).
Figure 16K:
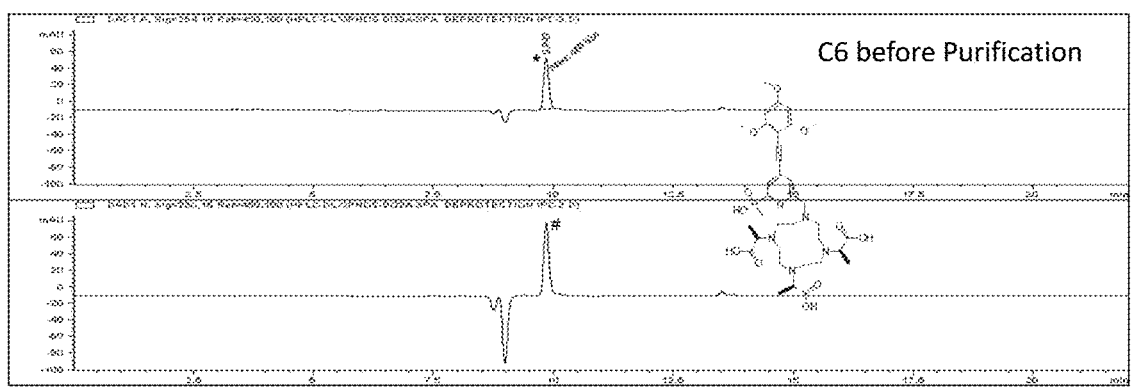
FIG. 16K shows the HPLC spectra of compound C6 before purification (Top: Detection at 254 nm; Bottom: Detection at 350 nm).
Figure 16L:
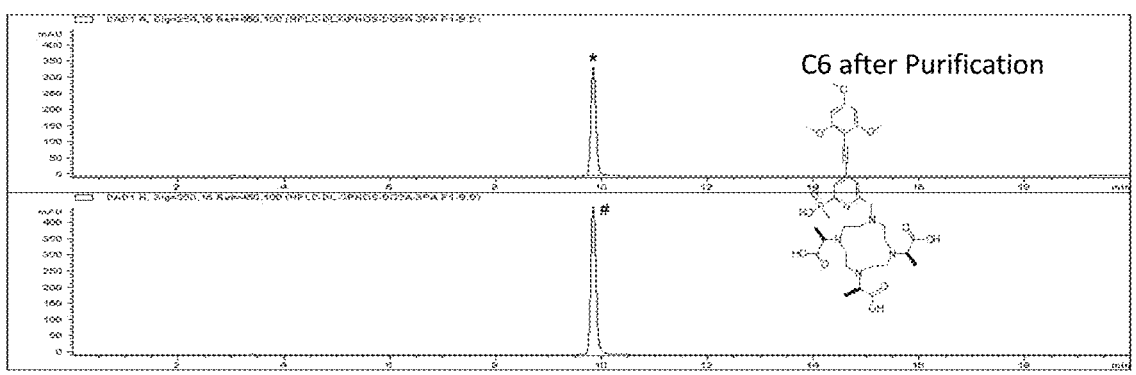
FIG. 16L shows the HPLC spectra of compound C6 after purification. (Top: Detection at 254 nm, the corresponding peak in FIG. 16K is marked '*'; Bottom: Detection at 350 nm, the corresponding peak in FIG. 16K is marked '#').
Figure 16M:
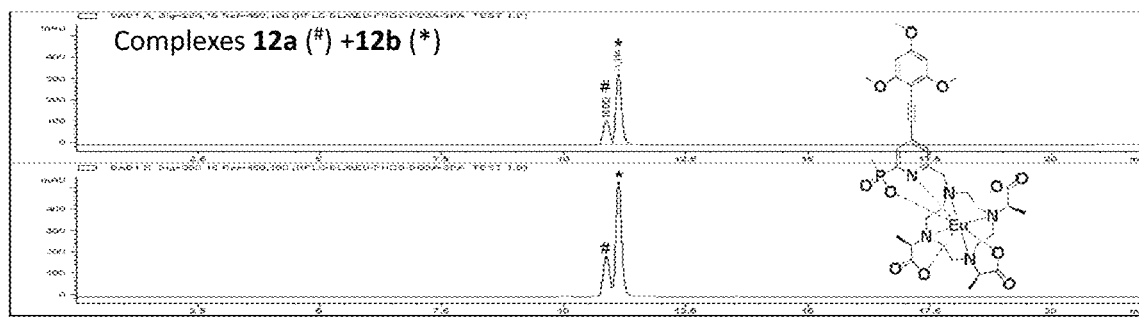
FIG. 16M shows the RP-HPLC traces of complexes 12a and 12b before purification (Top: Detection at 254 nm; Bottom: Detection at 350 nm).
Figure 16N:
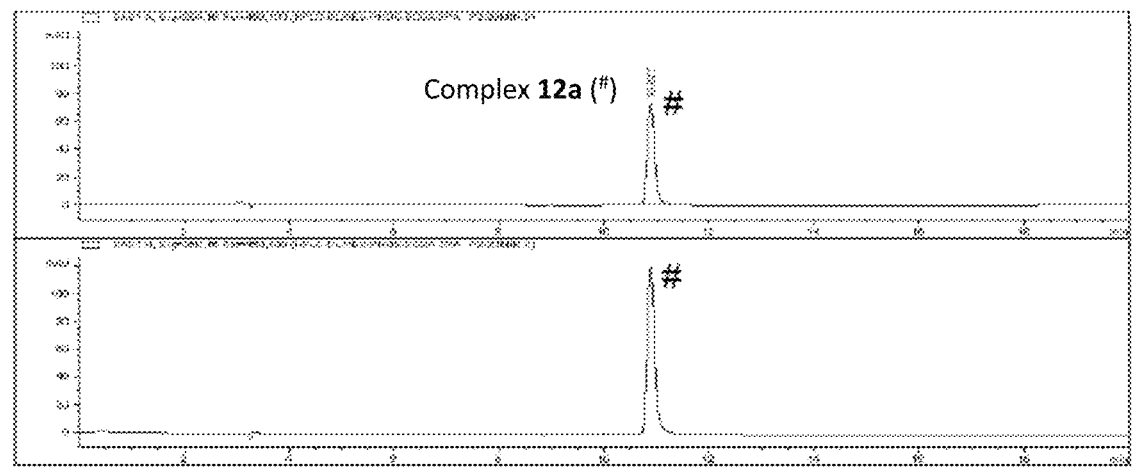
FIG. 16N shows the RP-HPLC traces of complex 12a after purification, the corresponding peak in FIG. 16M is marked '#' (Top: Detection at 254 nm; Bottom: Detection at 350 nm).
Figure 16O:
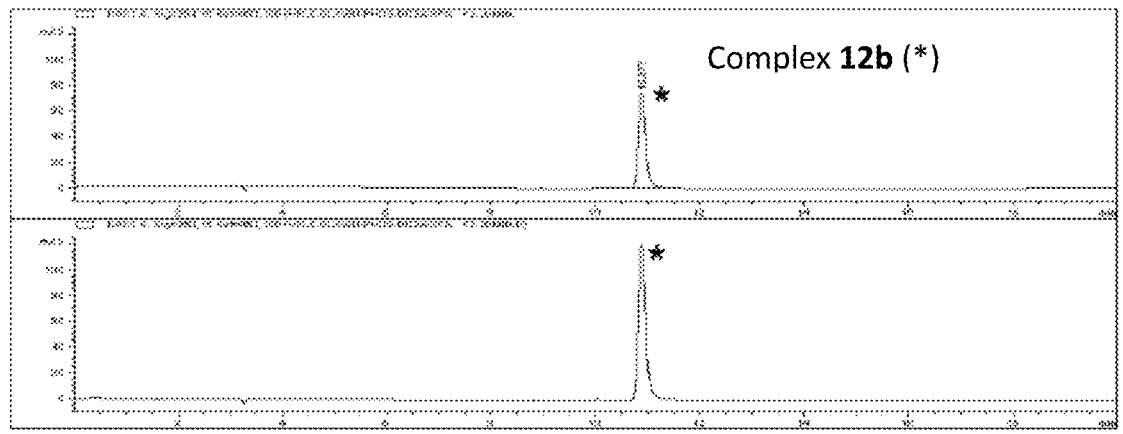
FIG. 16O shows the RP-HPLC traces of complex 12b after purification, the corresponding peak in FIG. 16M is marked '*' (Top: Detection at 254 nm; Bottom: Detection at 350 nm).
Figure 16P:
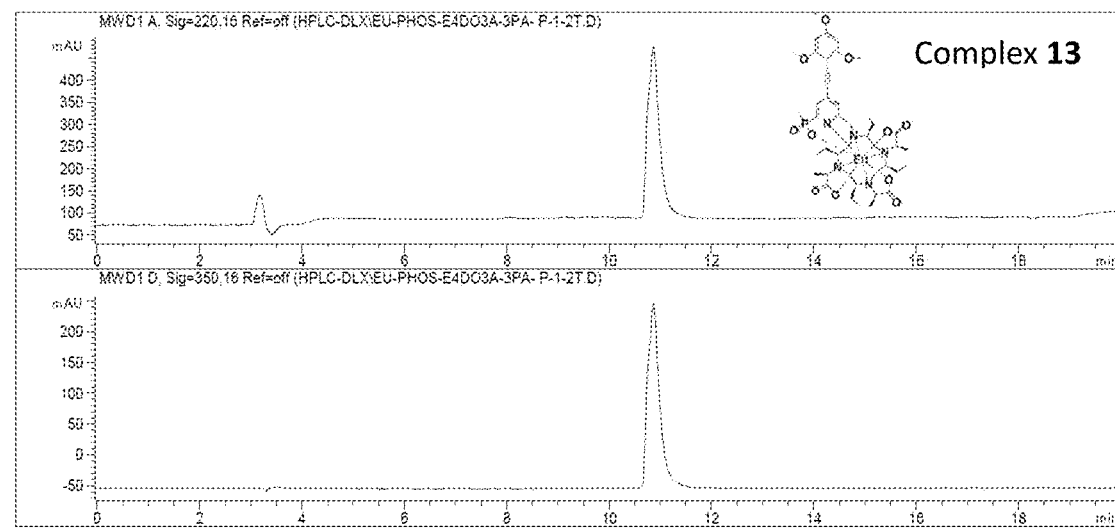
FIG. 16P shows the RP-HPLC trace of complex 13 (Detection at 220 nm and 350 nm).
Figure 17A:
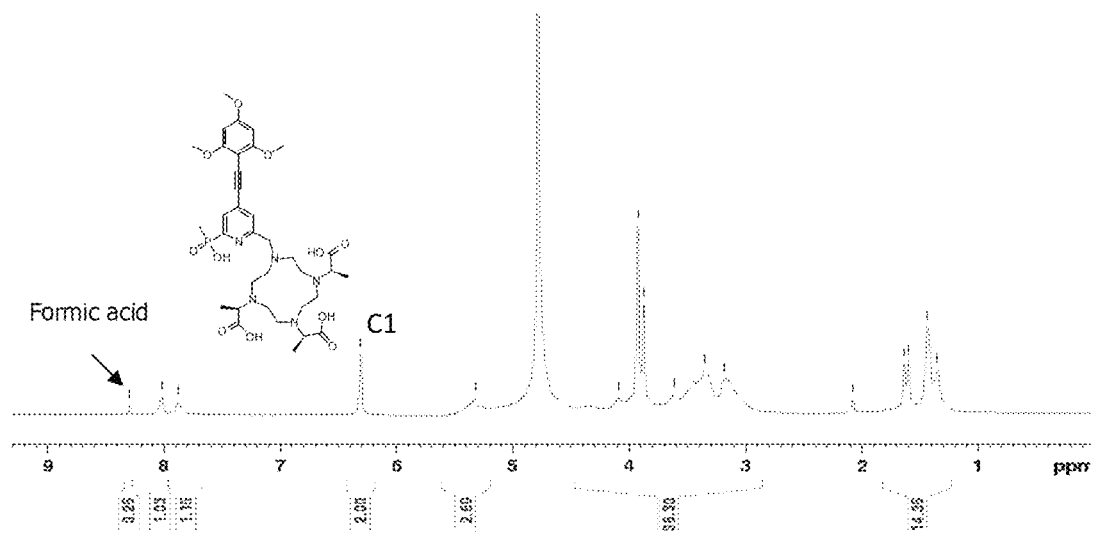
FIG. 17A shows the $^1$H NMR spectrum of C1.
Figure 17B:
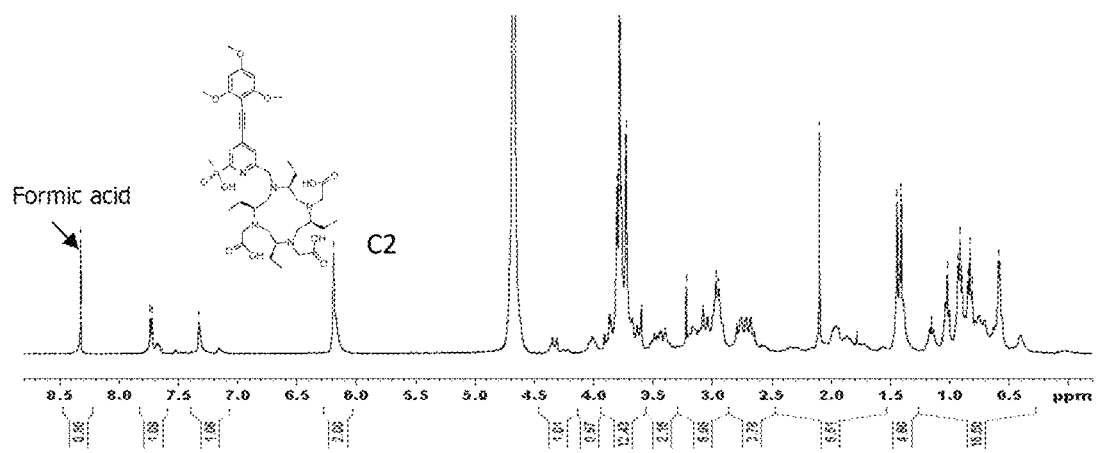
FIG. 17B shows the $^1$H NMR spectrum of C2.
Figure 17C:
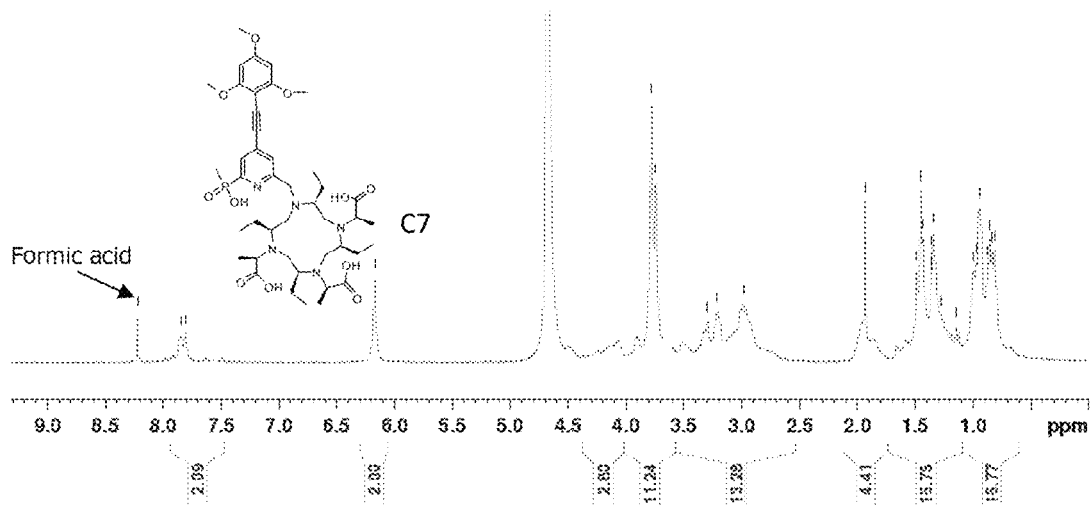
FIG. 17C shows the $^1$H NMR spectrum of C7.

HPLC analyses show that pure chiral complexes were obtained (FIGS. 16A-16O). The compounds did not racemize because the stereogenic centers were not involved in reactions and the reaction conditions of the synthetic routes were mild.

Figure 18:
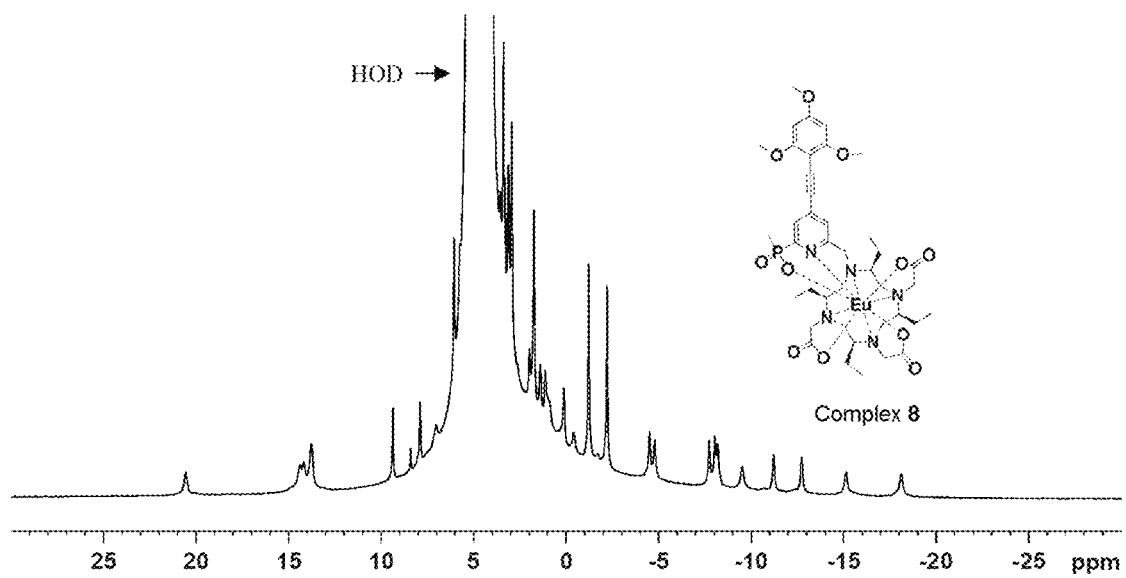
FIG. 18 shows the $^1$H NMR spectrum of complex 8 in $D_2O$.
Figure 19:
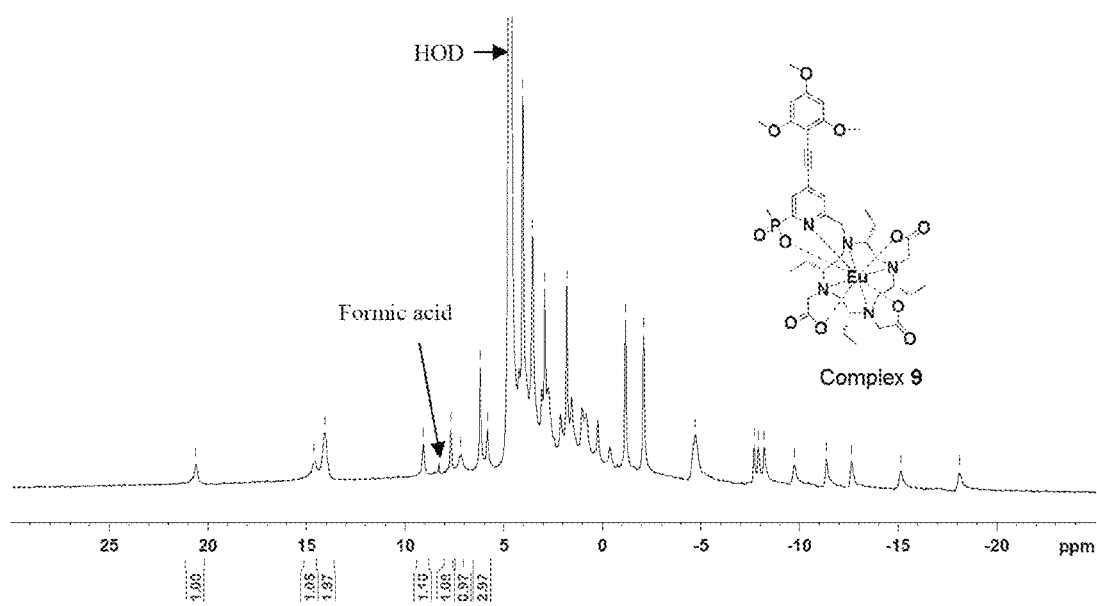
FIG. 19 shows the $^1$H NMR spectrum of complex 9 in $D_2O$.

NMR Analysis $^1$H NMR spectra were obtained to prove the purity of the ligands and complexes. (FIGS. 17A-C, 18, 19 and 21). The appearance of one set of protons beyond 10 ppm corresponding to the ring axial protons$^{53}$ on the cyclic backbone indicates that only one isomeric coordination geometry is present (FIGS. 18 and 19).

Figure 20:
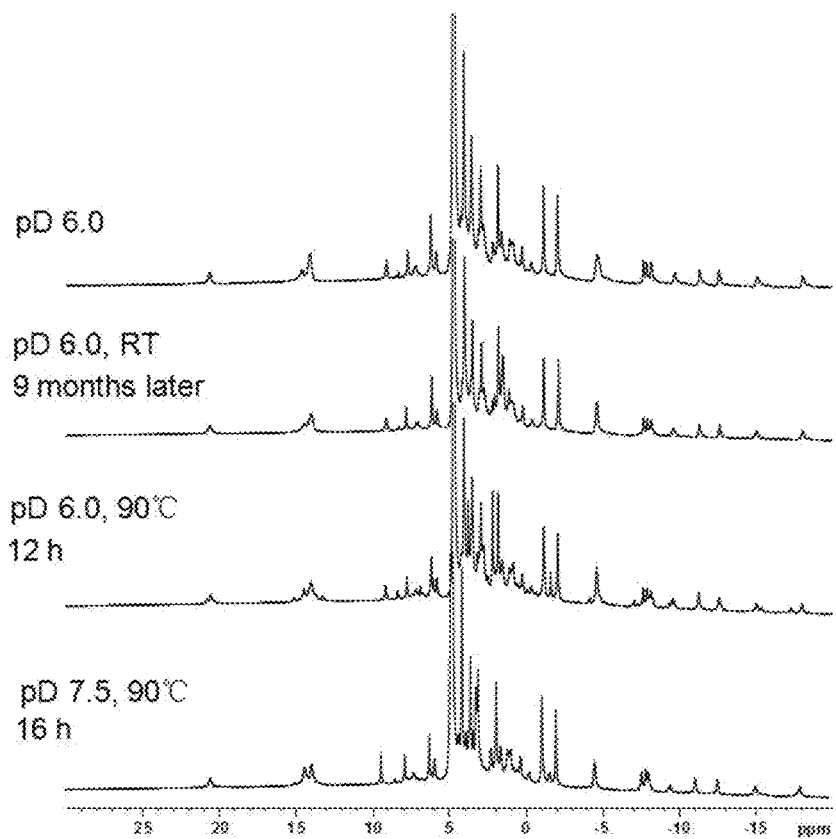
FIG. 20 shows the $^1$H NMR spectra of complex 9 in $D_2O$ at pD 6.0 (after purification by HPLC under acidic condition), after 9 months at room temperature at pD 6.0, after heating at 90° C. for 12 hours at pD 6,0, and after heating at 90° C. for 16 hours at pD 7.5. All the processes were performed in an NMR tube.
Figure 21:
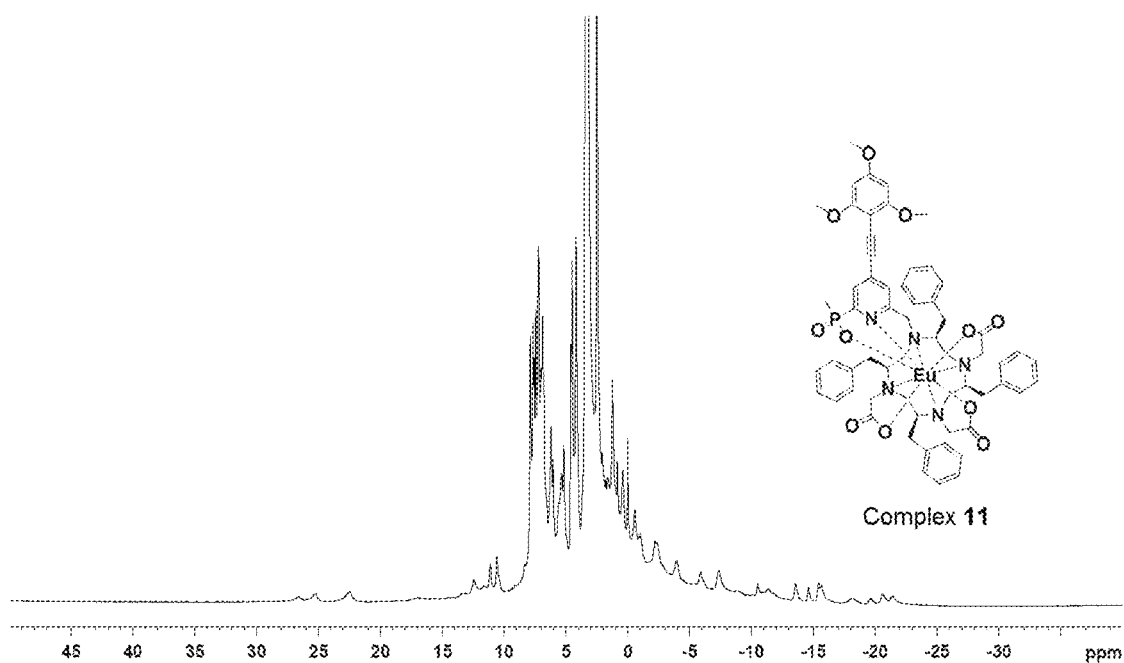
FIG. 21 shows the $^1$H NMR spectrum of complex 11 in $d_6$-DMSO

The stability of the complexes toward racemization over time was also monitored by $^1$H NMR (FIG. 20). The $^1$H NMR spectrum of complex 9 was consistent after 9 months of storage, but upon heating at 90° C., a new set of peaks appeared which may be formed because of racemization. Nevertheless, the original set of peaks existed predominately when the pD was adjusted from 6.0 to 7.5 and further heated for 12 h at 90° C. It can be observed that while the purity of the ligands may not be highly satisfactory, pure complexes could be obtained by HPLC separation after complexation. This phenomenon indicates the purification of DOTA-based ligands should be handled with care.

Two isomers of chiral DOTA-based lanthanide complexes were distinguished and separated very easily by HPLC, with its purity vindicated by $^1$H NMR; therefore it can be concluded that complexes 7-13 all exist as a single isomer.

Spectroscopic Properties

The spectroscopic properties are summarized in Table 6. The increased bulkiness of the chiral substituent in 10 and 11 contributed to their poor water solubility; hence their measurements were done in methanol and/or DMSO.

As all the complexes have the same chromophore, it is not surprising to see their absorption maxima to be at a similar position, except for 10, which showed a marked red-shift compared to the other complexes. The shift in absorption is caused by electronic communication between the electropositive lanthanide center and the chromophore. The asymmetry ratio (R)—defined as the ratio between the integrated intensities of the electric dipole $^5D_0 \rightarrow ^7F_2$ and magnetic dipole $^5D_0 \rightarrow ^7F_1$ transitions of europium(III)—is a parameter that measures the deviation from centrosymmetric geometry.$^{62}$ A marked difference in the R of 10 is consistent with the considerable shift in absorption maximum, suggesting a different coordination environment of the europium (III) in 10 among the series, which is expected due to the steric bulkiness of the isobutyl groups. These are not observed for 11, however, as we believe the steric effect of the planar phenyl ring of the benzyl group could not be alleviated by appropriate rotation, whereas that of the isobutyl group could.

regarding europium-based macrocyclic complexes. It is also worth mentioning that the more intense CPL spectrum of 11 is opposite those of 8 and 10, a result of small noncovalent

TABLE 6

Spectroscopic Properties of the Complexes 7-13 Measured at Room Temperature

| | 7 | 8 | 9 | 10 | 11 | 12a | 12b | 13 |
|---|---|---|---|---|---|---|---|---|
| $\lambda_{abs}$(max) | 353 | 356 | 356 | 364 | 354 | 352 | 355 | 356 |
| $R^c$ | 2.52 | 2.43 | 2.44 | 3.01 | 2.69 | 2.74 | 2.41 | 2.66 |
| $\Phi_{H2O/MeOH}$ (%)$^d$ | 7.6 | 14.0 | 14.9 | 11.1 | — | 12.7 | 10.2 | 21.9 |
| $\Phi_{HEPES}$ (%)$^{d,e}$ | 6.9 | 14.0 | 14.3 | — | — | 12.4 | 9.8 | 20.9 |
| $\Phi_{DMSO}$ (%)$^d$ | 47.0 | 50.0 | 53.0 | 45.3 | 40.4 | 46.4 | 44.1 | 49.7 |
| $\tau_{H2O/MeOH}$ (ms)$^f$ | 1.01 | 1.12 | 1.20 | 1.39 | — | 1.12 | 1.04 | 1.25 |
| $\tau_{D2O/MeOD}$ (ms)$^f$ | 1.44 | 1.76 | 1.77 | 1.74 | — | 1.70 | 1.77 | 1.83 |
| q(Parker's, Horrocks') | 0.06, 0.01 | 0.10, 0.02 | 0.02, 0.05 | 0.05$^g$ | — | 0.07, 0.01 | 0.11, 0.03 | 0.00, 0.06 |
| $\Phi^{Eu}_{Eu}$ (%) | 23.6 | 26.0 | 28.1 | 36.9 | — | 26.6 | 24.9 | 30.2 |
| $\eta_{sens}$ (%)$^h$ | 32.3 | 53.8 | 53.0 | 30.1 | — | 47.0 | 41.0 | 72.6 | aMeasured in MeOH, insoluble in H$_2$O.
bMeasured in DMSO, insoluble in H$_2$O and MeOH.
$^c$I($^5D_0 \rightarrow {}^7F_2$)/I($^5D_0 \rightarrow {}^7F_1$).
$^d$Relative to quinine sulfate in 0.1M H$_2$SO$_4$ ($\lambda_{exc}$ = 350 nm, $\Phi$ = 0.577). Estimated errors of quantum yield or lifetime are ±15% and ±10%, respectively.
$^e$0.1M HEPES buffer, pH 7.4.
$^f$Measuring the $^5D_0 \rightarrow {}^7F_2$ transition.
$^g$Calculated from ref 60. Errors in quantum yield or lifetime are ±15%.
$^h$Sensitization efficiency; calculated according to ref 61.

The luminescence quantum yields of the complexes are decent in water and HEPES solution, although they are much higher in DMSO, due to the nonradiative quenching by O—H oscillators of water molecules in the second coordination sphere (Table 6). The intrinsic quantum yields[61]—a calculated value evaluating the quantum yield of Eu(III) via direct metal excitation—of the complexes are calculated, and, as expected, the values are very similar, except for 10. The higher value corroborates with the shift in absorption maximum, for which we believe the reason is due to a shorter europium—chromophore distance and better interaction. On the other hand, the sensitization efficiencies of the complexes vary. The sensitization efficiency is a parameter determining the efficiency of energy transfer from the photoexcited chromophore to the emitting lanthanide center, obtained by comparing the intrinsic quantum yield and overall quantum yield.[61] As 8 and 9 are enantiomers, their structural arrangement should be identical, and hence their ηsens values are reasonably very similar; the same applies to 12a and 12b, a pair of diastereomers. The relatively remarkable ηsens of 13 is attributed to its structural rigidity, as both the tetraaza backbone and the acetate arms are modified with a chrial substituent, i.e., double chirality. The double chirality is also attributed for the increase in luminescence quantum yield compared to that of 12a/12b.

CLP Analysis

Figure 22A:
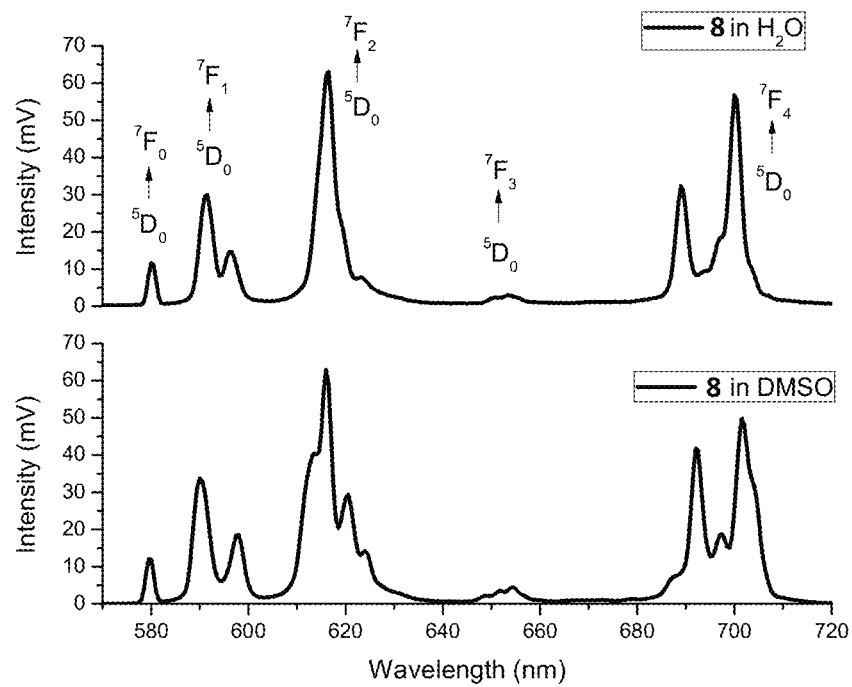
FIG. 22A shows the emission spectra of 8 in $H_2O$ and DMSO.
Figure 22B:
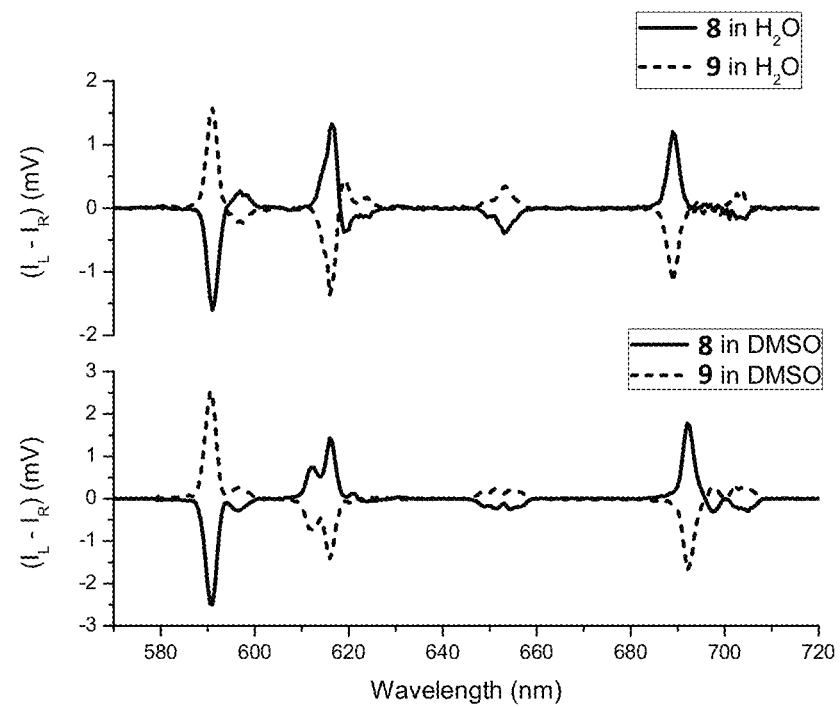
FIG. 22B shows the CPL spectra of 8 (solid) and 9 (dashed) in $H_2O$ and DMSO.
Figure 23:
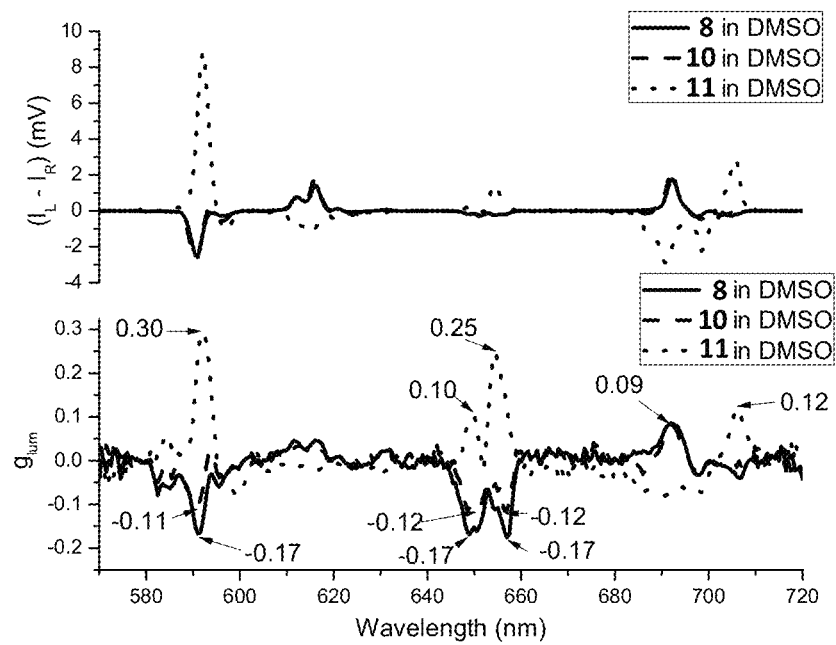
FIG. 23 shows the comparison of CPL spectra and $g_{lum}$ spectra of 8 (solid), 10 (dashed) and 11 (dotted).

The opposite CPL spectra with nearly identical absolute intensities obtained from enantiomers 8 and 9 in both H$_2$O and DMSO proved that the CPL properties were induced by the chirality of the substituents on the macrocyclic ring (FIG. 22). However, there is no necessary correlation between the bulkiness of the chiral group on the complex's dissymmetry factors, as comparison between 8, 10, and 11 gave a V-shaped trend in their $g_{lum}$ in DMSO (FIG. 23), implying that the nature of the chiral substituent—such as its freedom of rotation—and the changes in coordination environment all have influential effects on the CPL properties, rather than a straightforward relationship with bulkiness. Nevertheless, the +0.30 (ΔJ=1, 591 nm) value obtained for 11 in DMSO (Table 7) is highest among reported values interactions around the lanthanide ions from the aromatic moieties of the benzyl group thus changing the sign of the CPL signal.[49]

TABLE 7

Summary of Luminescence Dissymmetry Values ($g_{lum}$) at Specified Wavelengths

| Complex | ΔJ = 1 (λ) H$_2$O | ΔJ = 1 (λ) DMSO | ΔJ = 3 (λ) H$_2$O | ΔJ = 3 (λ) DMSO |
|---|---|---|---|---|
| 8 | −0.11 (591) | −0.18 (591) | −0.28 (653) | +0.17 (657) |
| 9 | +0.12 (591) | +0.17 (591) | +0.21 (653) | +0.13 (657) |
| 10 | — | −0.11 (591) | — | −0.12 (657) |
| 11 | — | +0.30 (591) | — | +0.25 (657) |
| 12a | −0.03 (588) | −0.04 (591) | −0.05 (653) | −0.04 (657) |
| 12b | −0.04 (591) | −0.11 (591) | −0.11 (653) | −0.10 (653) |
| 13 | −0.23 (589) | −0.17 (588) | −0.33 (652) | −0.29 (657) |

Figure 24:
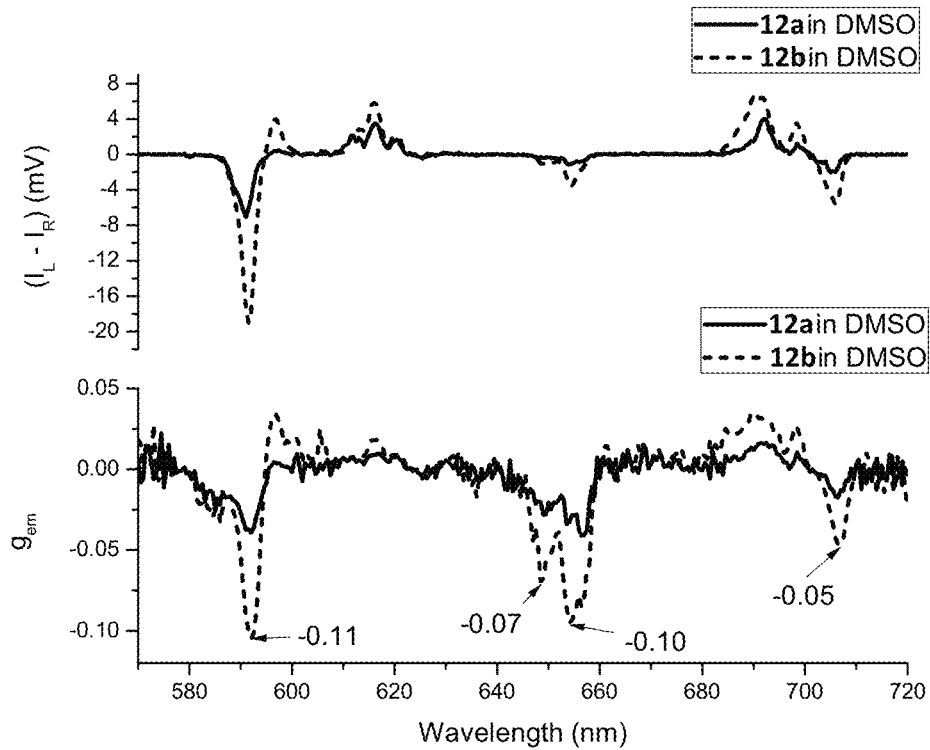
FIG. 24 shows the comparison of CPL and $g_{lem}$ spectra of 12a (solid) and 12b (dashed). Top: CPL spectra; Bottom: $g_{lum}$ spectra. (In DMSO, 295 K, $\lambda_{exc}$=352 nm, Abs. ~0.3).
Figure 26:
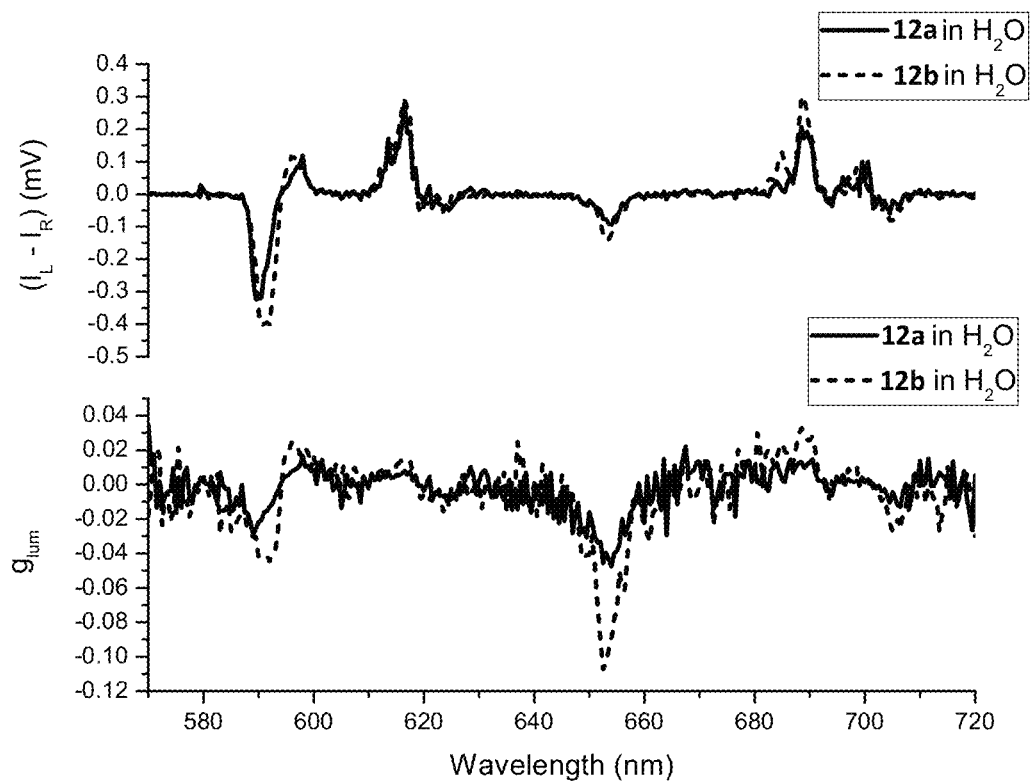
FIG. 26 shows the comparison of CPL and $g_{lum}$ spectra of 12a (solid) and 12b (dashed). Top: CPL spectra; Bottom: glum spectra. (In $H_2O$, 295 K, $\lambda_{exc}$=352 nm, Abs.=0.3).
Figure 27:
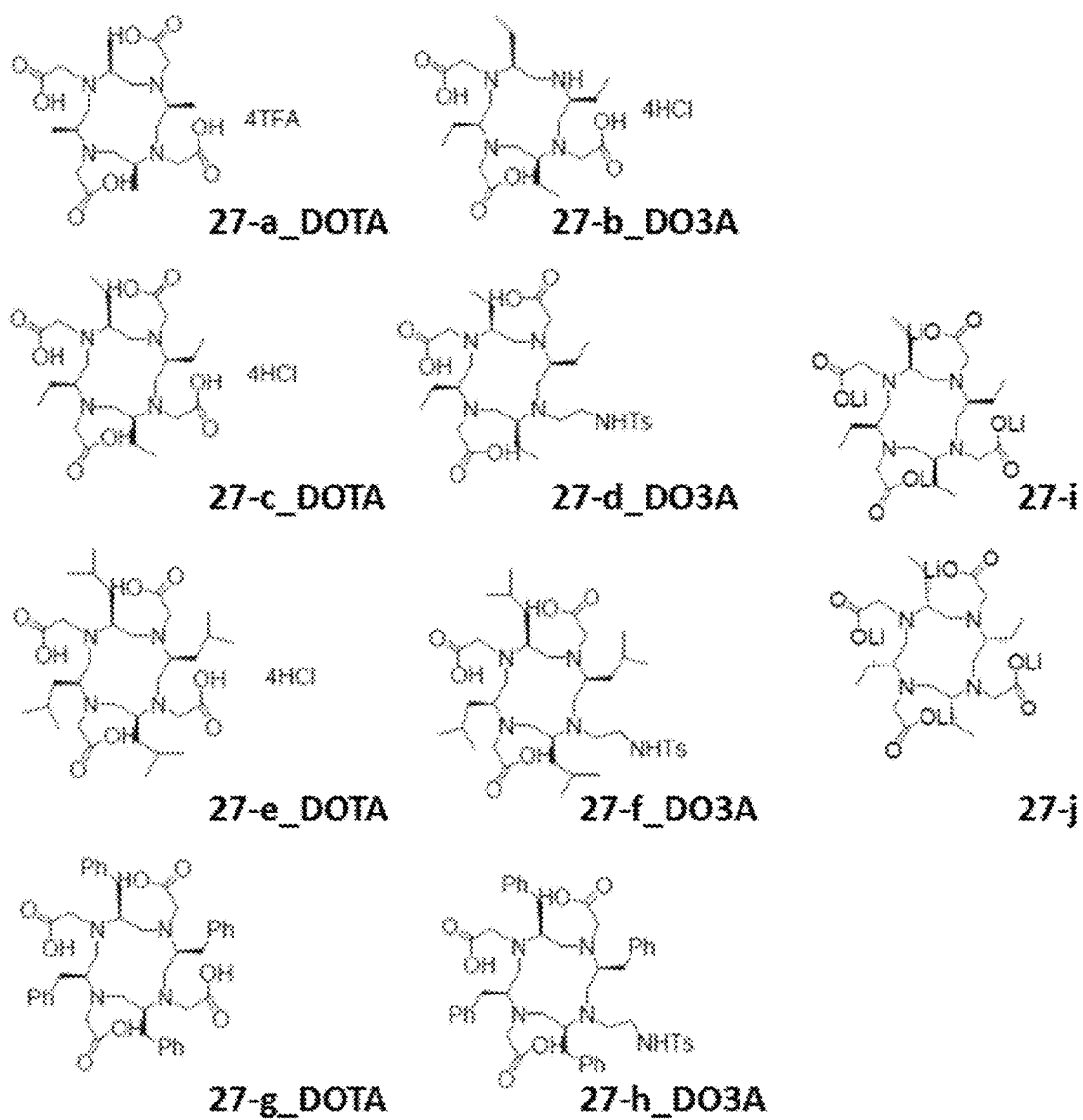
FIG. 27 shows additional examples of chiral DOTA-based ligands and chiral DO3A-based ligands.
Figure 28:
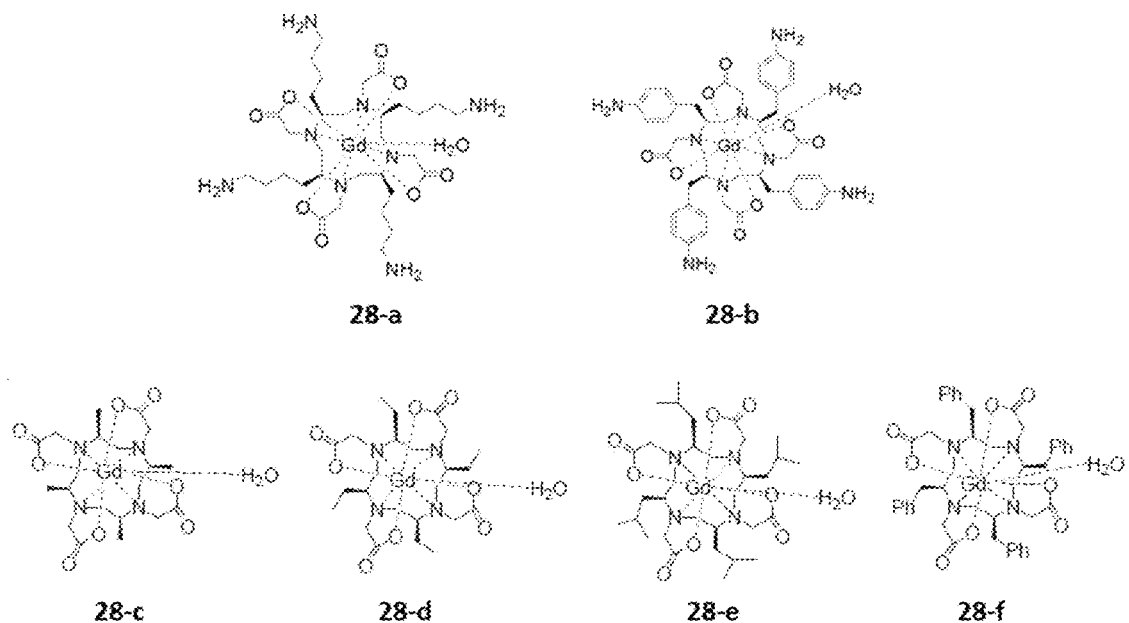
FIG. 28 shows additional examples of chiral DOTA-based metal complexes.

12a and 12b have chiral substituents incorporated onto the pendent acetate arms. It is clearly shown that the CPL signal of 12a is considerably weaker than that of 12b in DMSO (FIG. 24) and H$_2$O (FIG. 26); so are the $g_{lum}$ values. These results are not satisfactory for practical use, and while we report with confidence that 12a and 12b are optically pure, we cannot rule out any difference in their coordination environments, which is likely the reason behind the data mismatch.

Figure 25:
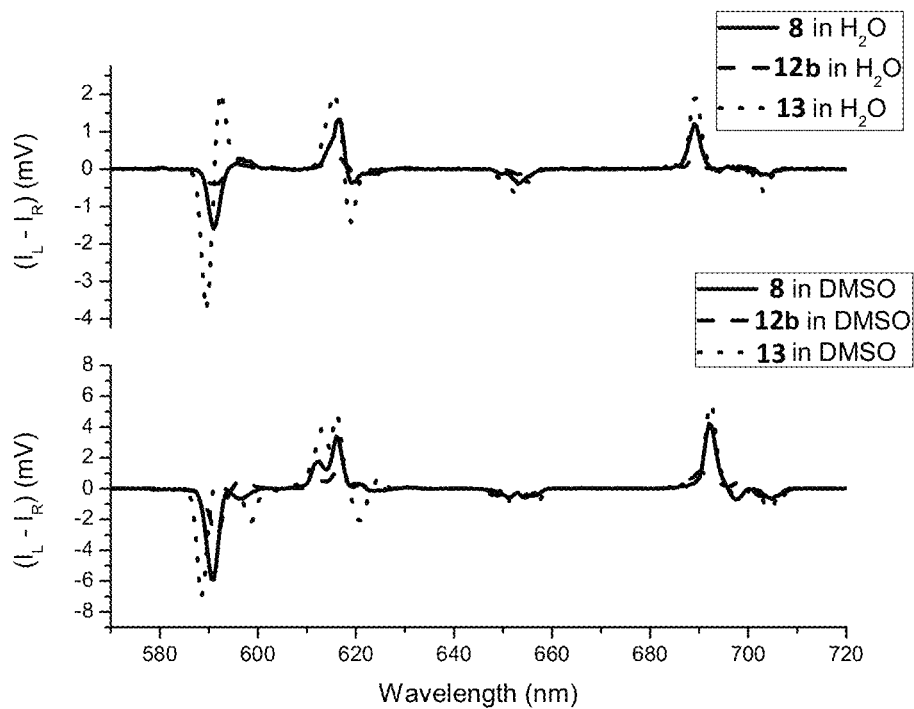
FIG. 25 shows the comparison of CPL spectra of 8 (solid), 12b (dashed) and 13 (dotted).

The CPL spectra of 13 with chiral substituents on both the macrocycle ring and acetate arms were compared with 8 (chiral substituents on macrocycle ring only) and 12 (chiral substituents on acetate arms only) (FIG. 25). The structural features of 8 and 12b were combined to give 13, and the CPL properties imparted by the substituents were also combinatory. The $g_{lum}$ values of 13 could be seen as a summation of the values of 8, 12a, and 12b, and the $g_{lum}$ of −0.23 (ΔJ=1, 589 nm) recorded in H$_2$O is comparable to the highest in aqueous solution.

Complexes 7-11 comprises a chiral cyclic backbone and a bidentate chromophore for stereocontrol, whereas complexes 12a and 12b having an achiral cyclen can be compensated with chiral acetate arms. In addition to the nine coordination sites, the rigid structures are beneficial in ensuring good protection of the lanthanide(III) emitting center from vibrational energy loss and coordination of solvent molecules, which can be evidenced by the luminescence quantum yields bring about by the antenna effect and q values (≈0), and can be obtained by the luminescence lifetimes of the complexes in $H_2O$ and $D_2O$ or MeOH and MeOD.[58-60]

In summary, stable and highly emissive lanthanide complexes based on chiral cyclen derivatives were synthesized that exhibits high luminescence quantum yields and strong CPL properties. Furthermore, the $g_{lum}$ value of 11 at the $^5D_0 \rightarrow ^7F_1$ transition (+0.3) is the highest among europium (III) complexes with high luminescence intensity and stability. The absolute $g_{lum}$ 589 nm=0.23 of 13 is also the highest among the macrocyclic europium(III) complexes in aqueous solution (Table 7). The structural-CPL-activity relationship was studied, providing a solid blueprint for developing even better chiral lanthanide complexes for studying biological chiral environments.

Example 3

Formation of Chiral DOTA-Based Copper Complexes

Figure 29:
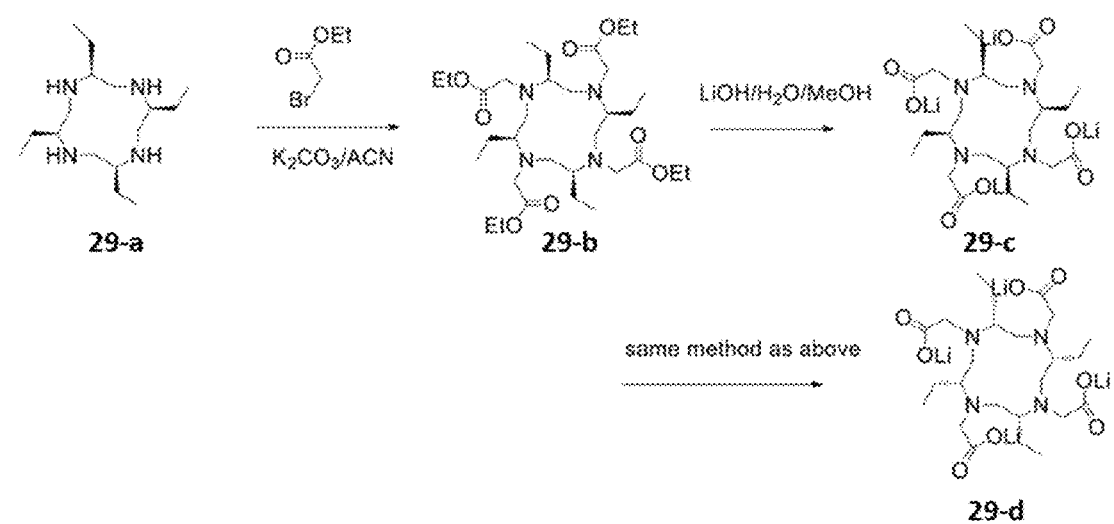
FIG. 29 shows a synthetic route of chiral DOTA-based lithium complexes 29-c and 29-d.
Figure 30:
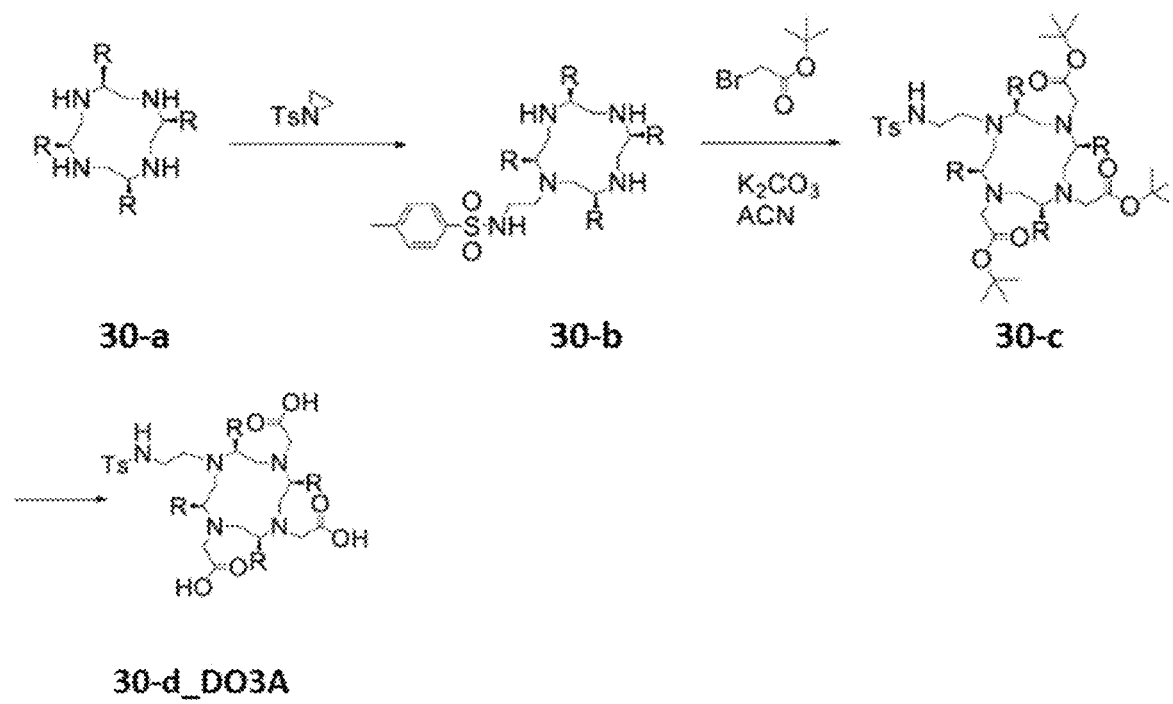
FIG. 30 shows a synthetic route of chiral DO3A-based ligands 30-d_DO3A with a linker.
Figure 31:
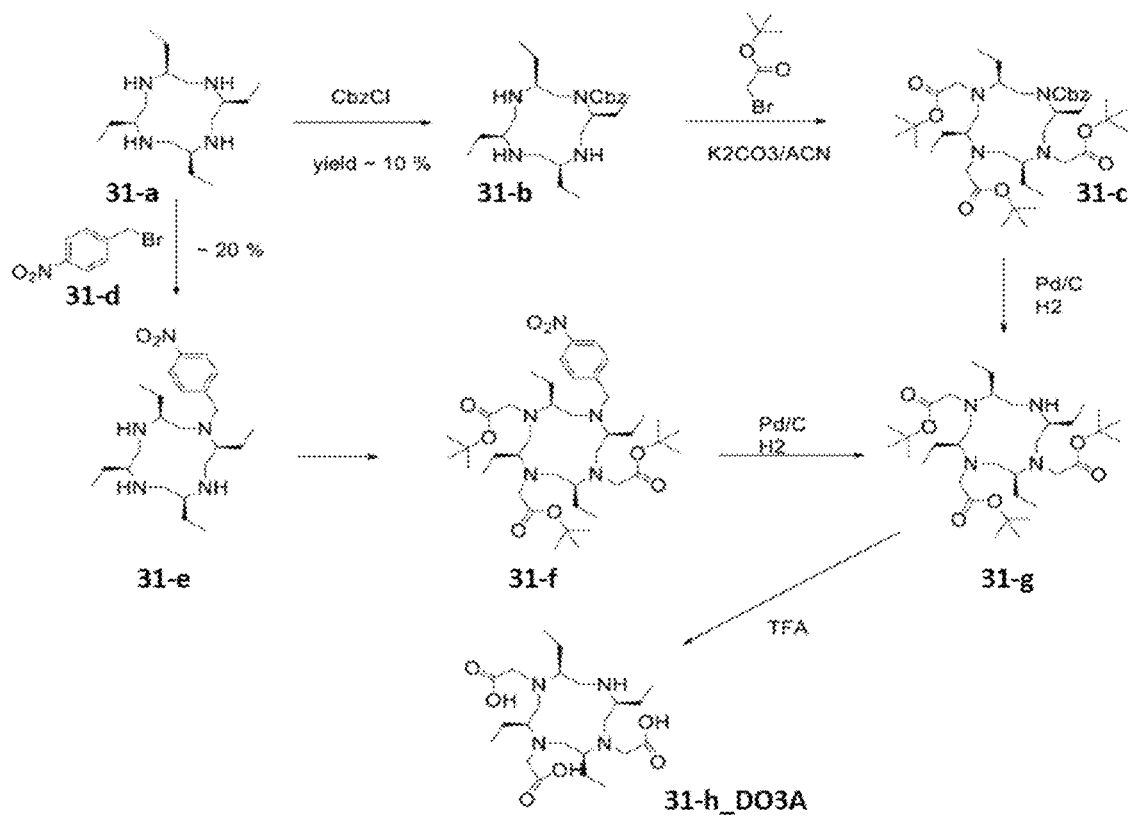
FIG. 31 shows a synthetic route of chiral DO3A-based ligand 31-h_DO3A.
Figure 32:
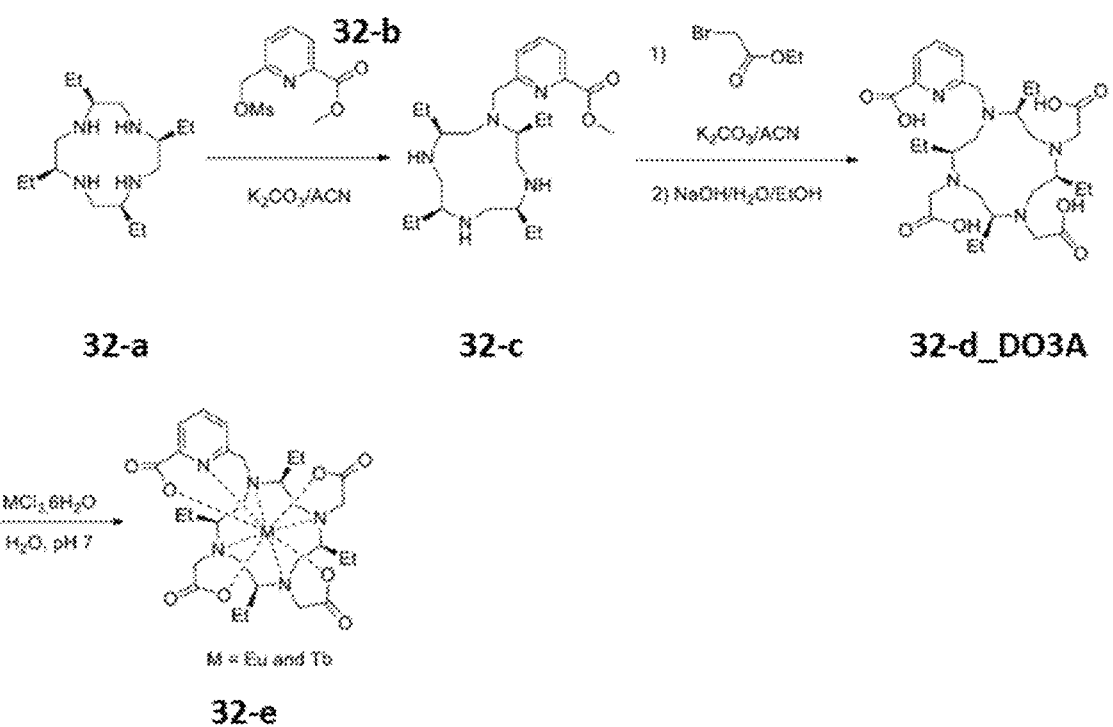
FIG. 32 shows a synthetic route of chiral DO3A-based metal complexes 32-e with a chromophore.
Figure 33:
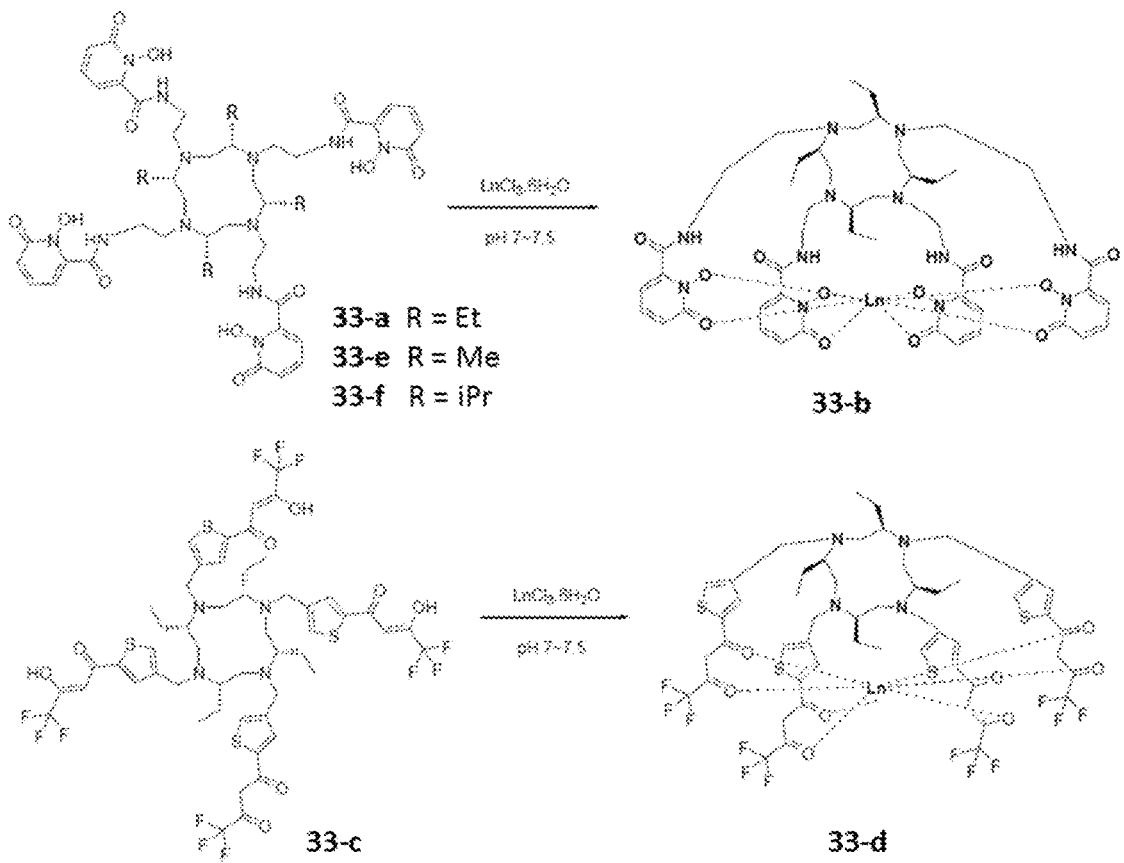
FIG. 33 shows synthetic routes of chiral cyclen metal complexes with chromophores.
Figure 36A:
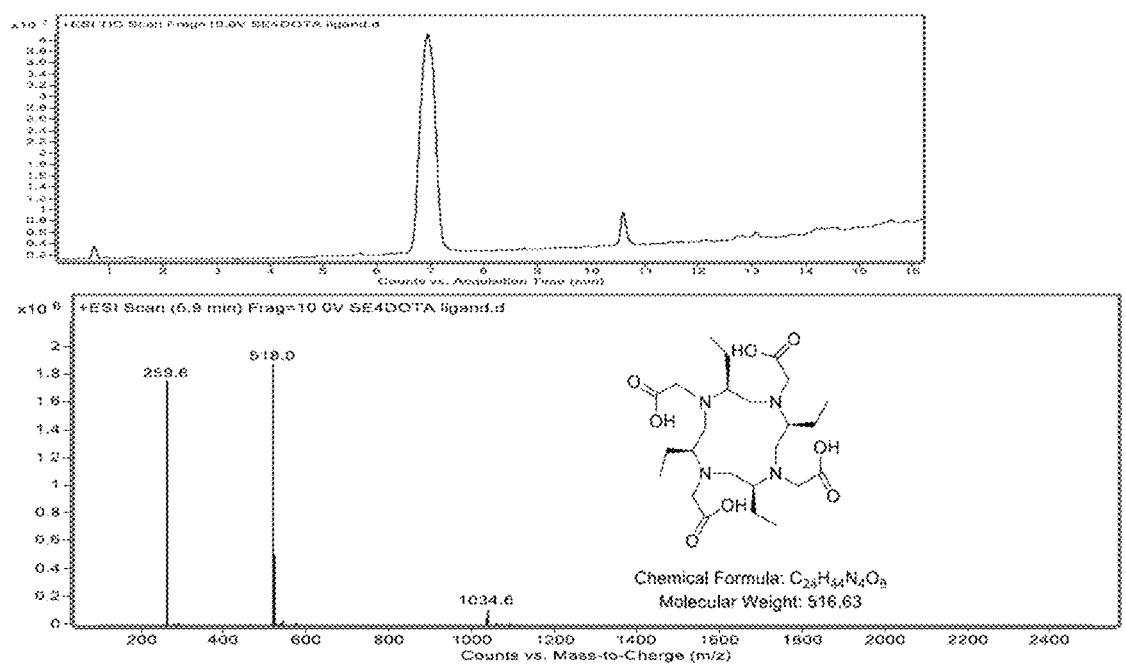
FIG. 36A shows LC-MS spectra of lithium salt 29-c.

Synthesis:
Chiral DOTA-based lithium salt 29-c and 29-d was synthesized according to similar reaction conditions as described in Examples 1 and 2 (FIG. 29).
LC-MS Analysis
Method:
LC-MS conditions: Column: Agilent Eclipse Plus C18 RRHD 1.8 μm column (50×2.1 mm), eluent A: water with 0.01% formic acid, eluent B: acetonitrile.
Gradient: 2% B from 0-2 min, 2-50% B from 2-15 min.
Experimental Procedure:
(1) The lithium salt 29-c was injected for analysis.
(2) Lithium salt 29-c (7.8 mg, 1.0 eq.) was dissolved in 3 ml of NaOAc buffer (1.0 M, pH 5.50), then $CuCl_2$ (1.94 mg, 1.0 eq.) was added.
(3) 20 uL of the reaction mixture was taken after following five conditions, and then diluted with 0.5 mL of NaOAc buffer, followed by injection of 5 uL for analysis.
  a) After adding $CuCl_2$, just stirred for several seconds;
  b) 40° C. for 30 min;
  c) 40° C. for 60 min;
  d) 40° C. for 120 min;
  e) Then 90° C. for 60 min.
Results: From MS analysis of the lithium salt 29-c, it appears that the ligand was complexed with a proton instead of lithium, as the dominated mass peak of the ligand at 518.0 m/z was observed (FIG. 36A)
The comparison of LCMS spectra is shown in FIG. 36B. According to LCMS analysis of the reaction mixture, the chiral DOTA-based copper complexes was formed immediately after addition of $CuCl_2$.

Example 4

Gallium Labeling

The comparison of LCMS spectra is shown in FIG. 36B. According to LCMS analysis of the reaction mixture, the chiral DOTA-based copper complexes was formed immediately after addition of $CuCl_2$.

Figure 37:
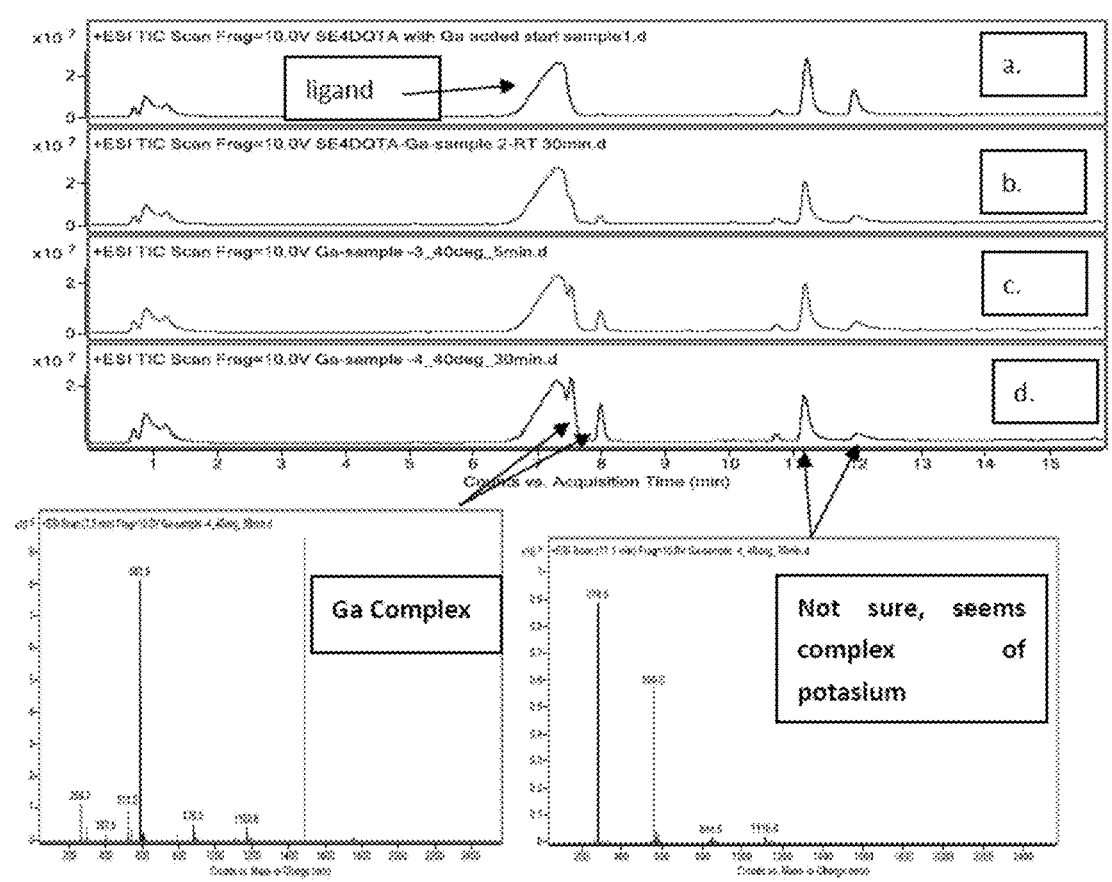
FIG. 37 shows LC-MS spectra of Gallium (III) complexation with xxx under various conditions.
Figure 39:
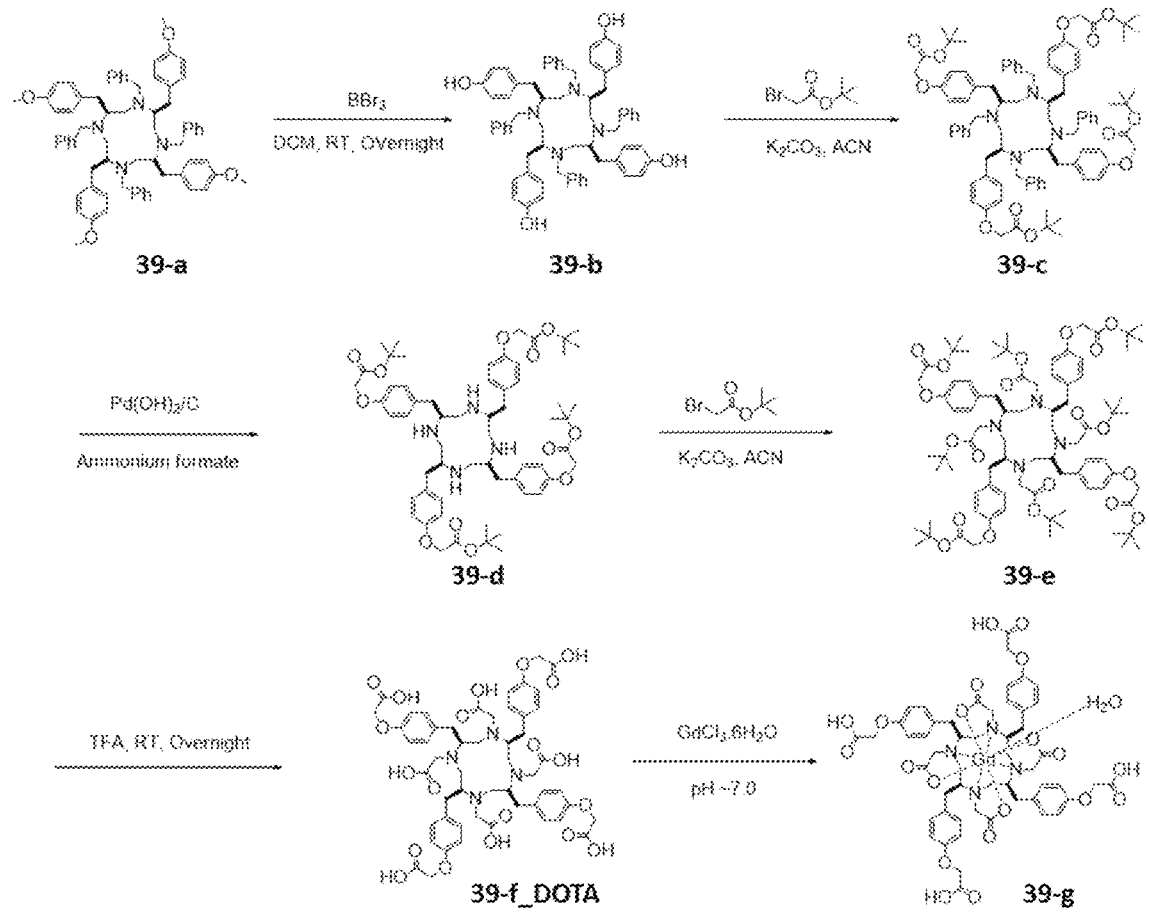
FIG. 39 shows a synthetic route of chiral DOTA-based ligand 39-f_DOTA and Gallium (III) complex 39-g.
Figure 40:
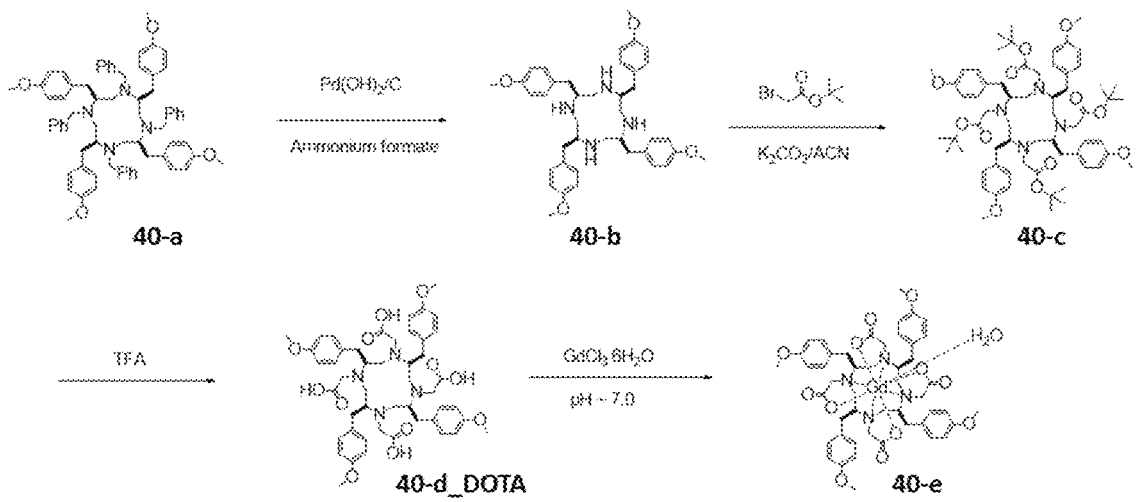
FIG. 40 shows a synthetic route of chiral DOTA-based ligand 40-d_DOTA and Gallium (III) complex 40-e.
Figure 41:
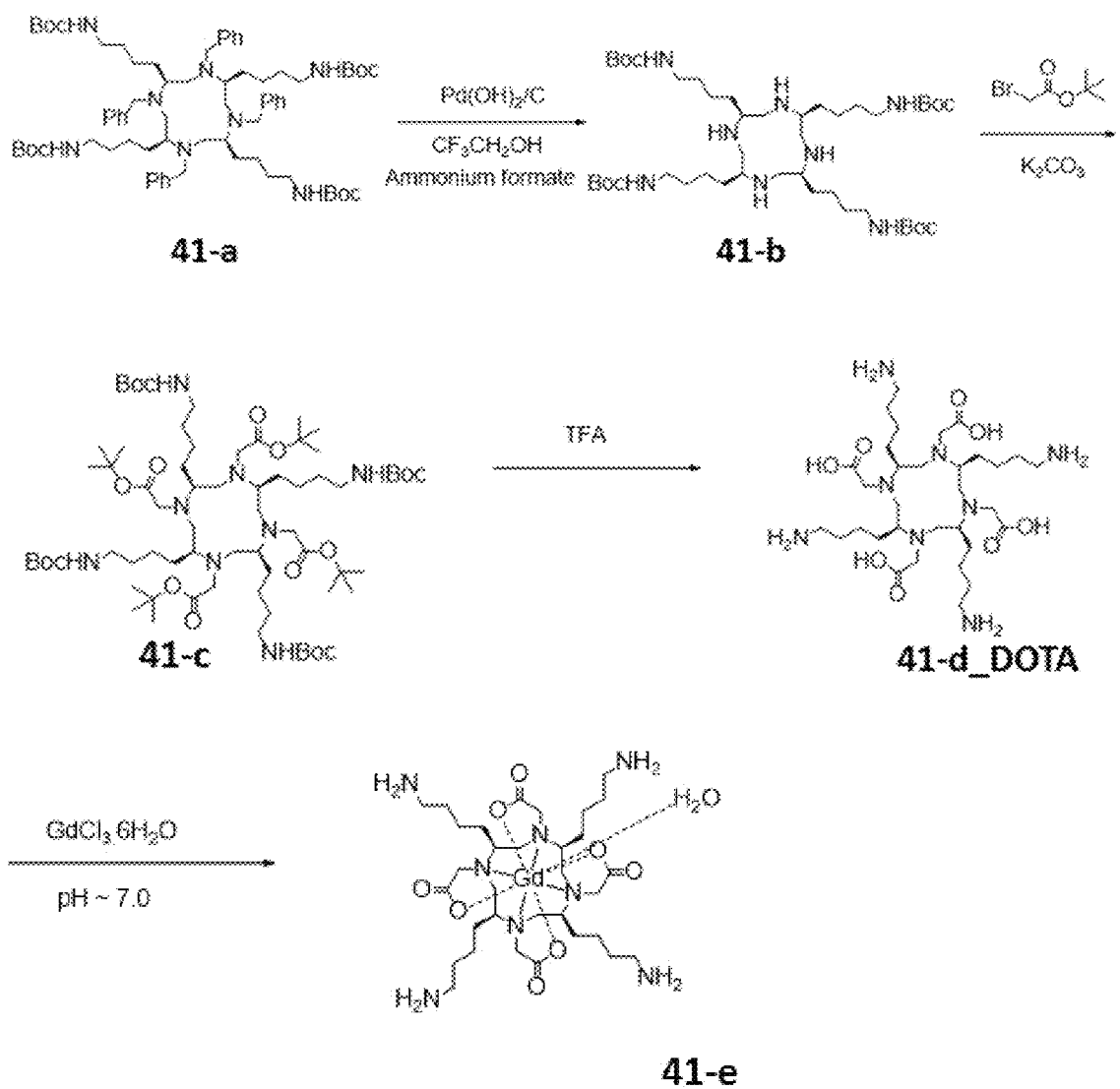
FIG. 41 shows a synthetic route of chiral DOTA-based ligand 41-d_DOTA and Gallium (III) complex 41-e.
Figure 42:
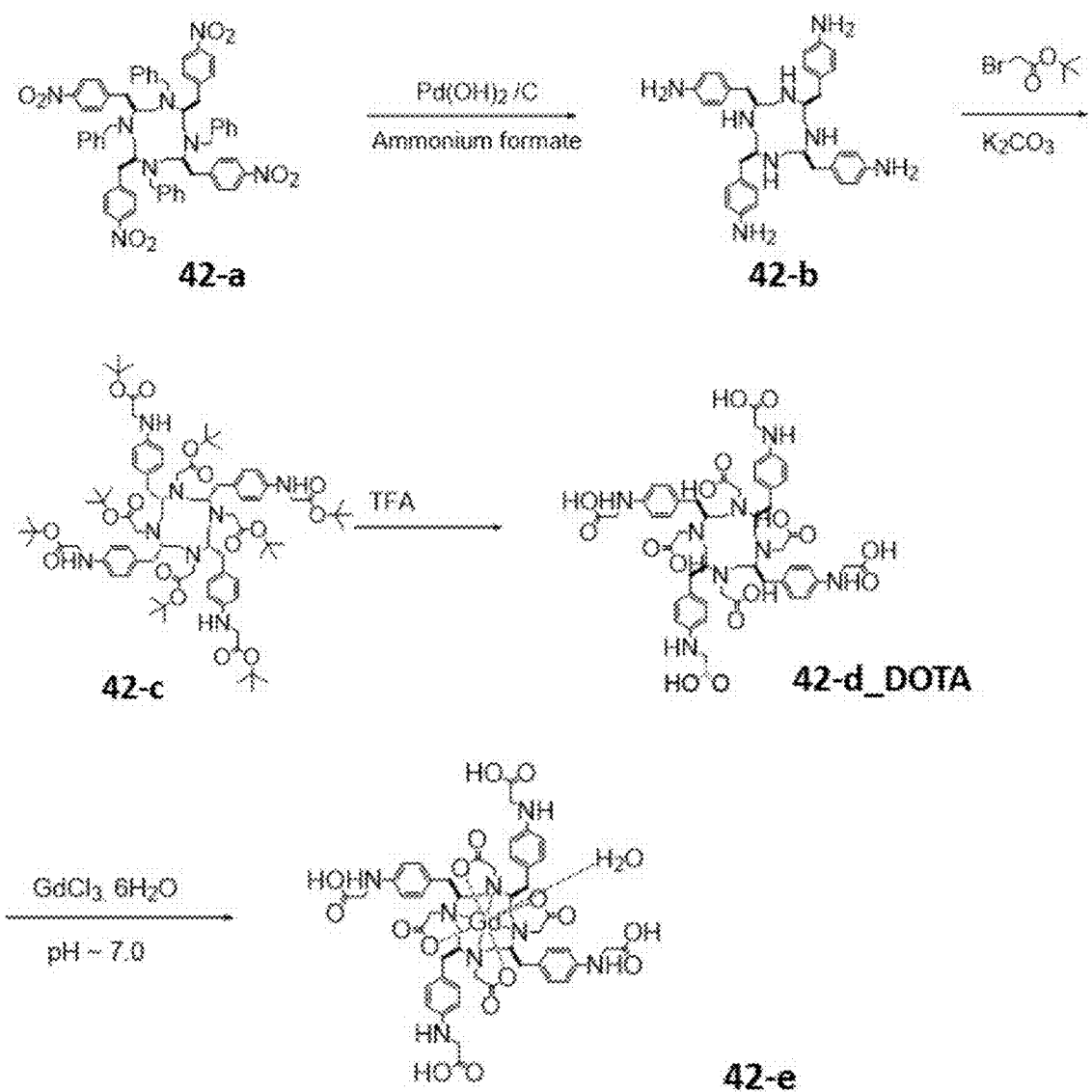
FIG. 42 shows a synthetic route of chiral DOTA-based ligand 42-d_DOTA and Gallium (III) complex 42-e.
Figure 43:
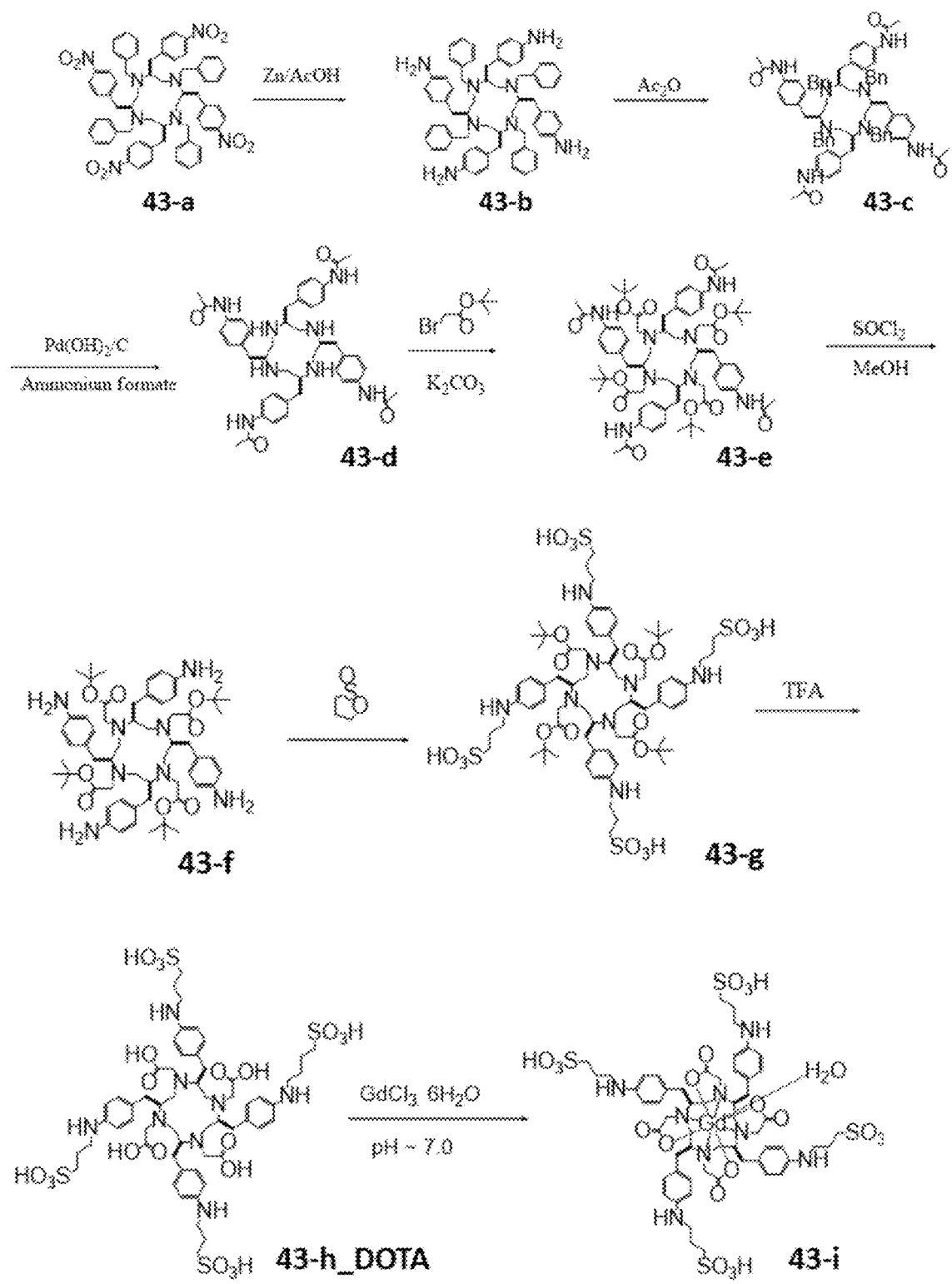
FIG. 43 shows a synthetic route of chiral DOTA-based ligand 43-h_DOTA and Gallium (III) complex 43-i.
Figure 44:
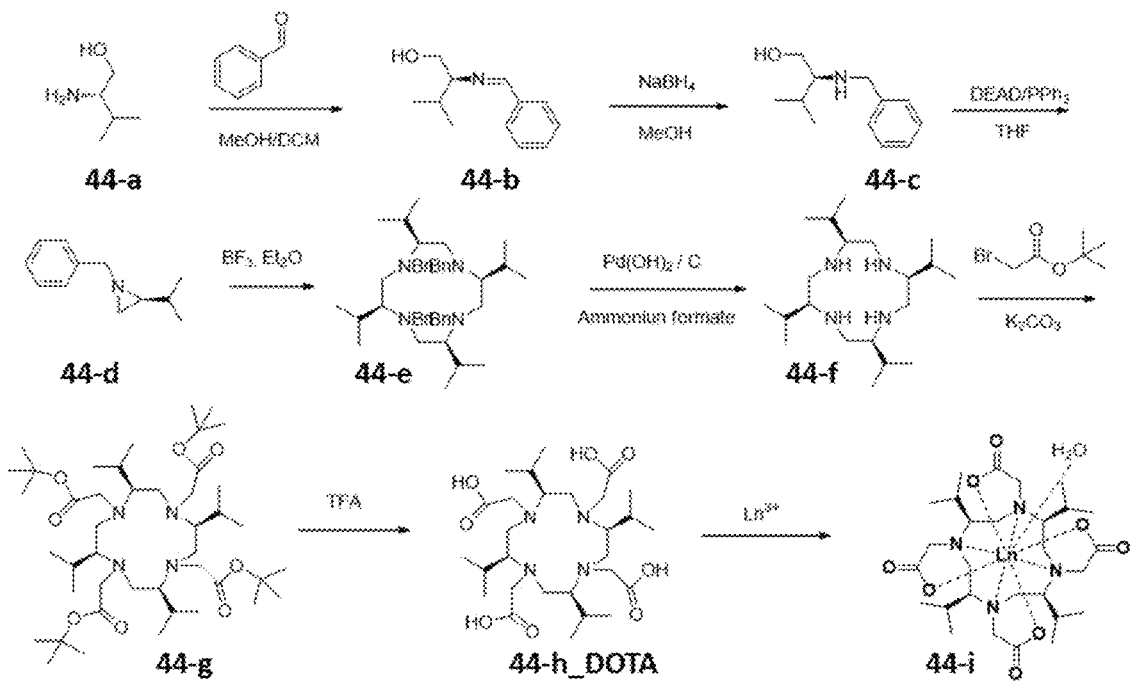
FIG. 44 shows a synthetic route of chiral DOTA-based ligand 44-h_DOTA and metal complex 44-i.
Figure 45:
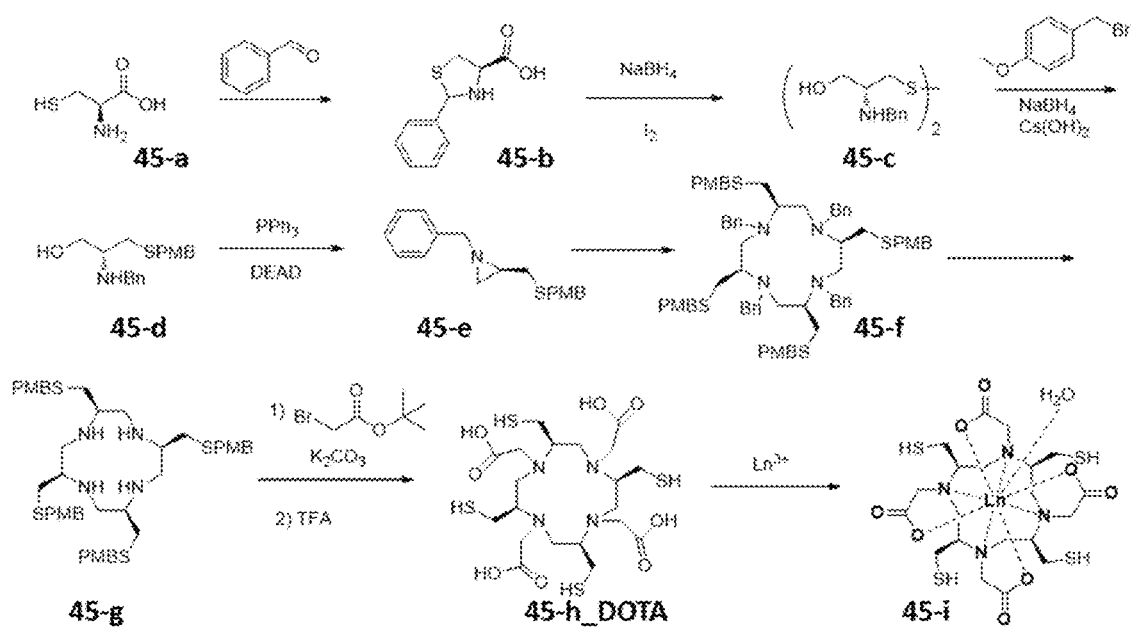
FIG. 45 shows a synthetic route of chiral DOTA-based ligand 45-h_DOTA and metal complex 45-i.

Experimental Procedure: Ligand L2 of FIG. 1A (8.0 mg) was first dissolved in sodium acetate buffer (pH 5.50, 1.0 M). Then a solution of $GaCl_3$ was added into water and heat was released with the formation of precipitate. The $GaCl_3$ solution was added to the ligand solution in buffer. The progress of Ga(III) complex formation was monitored by LCMS after the following events:
  a) After mixing the ligand and metal solution;
  b) After keeping at room temperature for 30 min;
  c) After keeping at 40° C. for 5 min;
  d) After keeping at 40° C. for 30 min;
Results: As shown in MS spectra, Ga(III) was formed (FIG. 37).

Example 5

Biodistribution

Biodistribution of the chiral cyclen Gd(III) complexes were studied and the results are shown in FIGS. 38A, 38B and 38C. According to the data, these complexes have very good biodistribution in kidney and liver.

REFERENCES 1) (a) Alexander, V. *Chem. Rev.*, 1995, 95, 273-342; (b) Wainwright, K. P. *Coord. Chem. Rev.*, 1997, 166, 35-90.
2) (a) Caravan, P.; Ellison, J. J.; McMurry, T. J.; Lauffer, R. B. *Chem. Rev,* 1999, 99, 2293-2352; (b) Viola-Villegas, N.; Doyle, R. P. *Coord. Chem. Rev.*, 2009, 253, 1906-1925.
3) (a) Merbach, A. E.; Tóth, É. *The chemistry of contrast agents in medical magnetic resonance imaging*, Wiley Online Library, 2001; (b) Parker, D.; Williams, J. G. *J. Chem. Soc., Dalton Trans.*, 1996, 3613-3628.
4) (a) Caravan, P. *Chem Soc Rev.*, 2006, 35, 512-523; (b) Caravan, P. *Acc Chem Res.*, 2009, 42, 851-862.
5) Carr, R. Evans, N. H.; Parker, D. *Chem, Soc. Rev.*, 2012, 41, 7673-7686
6) Fernando, W. S.; Martins, A. F.; Zhao, P.; Wu, Y.; Kiefer, G. E.; Platas-Iglesias, C.; Sherry, A. D. *Inorg. Chem.*, 2016, 55, 3007-3014.
7) Payne, K. M.; Woods, M. *Bioconjugate chem.*, 2015, 26, 338-344.
8) Ranganathan, R. S.; Raju, N.; Fan, H.; Zhang, X.; Tweedle, M. F.; Desreux, J. F. Jacques, V. *Inorg. Chem.*, 2002, 41, 6856-6866.
9) (a) Hajela, S.; Botta, M.; Giraudo, S.; Xu, J.; Raymond K, N.; and Aime, S. *J. Am. Chem. Soc.*, 2000, 122, 11228-11229; (b) Yu, J.; Martins, A. F.; Preihs, C.; Clavijo Jordan, V.; Chirayil, S.; Zhao, P.; Wu, Y.; Nasr, K.; Kiefer G. E.; Sherry, A. D. *J. Am. Chem. Soc.*, 2015, 137, 14173-14179.
10) Sherry A. D.; Wu, Y. *Curr. Opin. Chem. Biol.*, 2013, 17, 167-174.
11) Hermann, P.; Kotek, J.; Kubleek, V.; Lukeš, I. *Dalton Trans.*, 2008, 23, 3027-3047.
12) Woods, M. Botta, M.; Avedano, S.; Wang J.; Sherry, A. D. *Dalton Trans.*, 2005, 3829-3837.
13) Tircso, G.; Webber, B. C.; Kucera, B. E.; Young, V. G.; Woods, M. *Inorg, Chem.*, 2011, 50, 7966-7979.
14) Aime, S.; Barge, A.; Bruce, J. I.; Botta, M.; Howard, J. A.; Moloney, J. M.; Parker, D.; De Sousa A. S.; Woods, M. *J. Am. Chem. Soc.*, 1999, 121, 5762-5771.
15) (a) Brittain H. G.; Desreux, J. F. *Inorg Chem.*, 1984, 23, 4459-4466; (b) Aime, S.; Botta, M.; Fasano M. Terreno, E. *Acc. Chem. Res.*, 1999, 32, 941-949; (c) Woods, M.;

15) Aime, S.; Botta, M.; Howard, J. A.; Moloney, J. M.; Navet, M.; Parker, D.; Port M.; Rousseaux, O. J. Am. Chem. Soc., 2000, 122, 9781-9792.
16) Pasha, A.; Tircsó, G.; Benyó, E. T.; Brücher, E.; Sherry, A. D. Eur. J. Inorg. Chem., 2007, 27, 4340-4349.
17) Ranganathan, R. S.; Pillai, R. K.; Raju, N.; Fan, H.; Nguyen, H.; Tweedle, M. F.; Desreux, J. F.; Jacques, V. Inorg. Chem., 2002, 41, 6846-6855.
18) Tsuboyarna, S.; Tsuboyama, K.; Higashi, I.; Yanagita, M. Tetrahedron Lett., 1970, 11, 1367-1370,
19) Price, E. W. Orvig, C. Chem. Soc. Rev., 2014, 43, 260-290.
20) Anelli, P. L.; Beltrami, A.; Franzini, M.; Paoli, P.; Rossi, P.; Uggeri, F.; Virtuani, M. Inorganica Chimica Acta 2001, 317, 218-229.
21) Kobayashi, K.; Tsuboyama, S.; Tsuboyama, K.; Sakurai, T. Acta Cryst. (1994). C50, 306-312
22) Tsuboyama, K.; Tsuboyama, S.; Uzawa, J.; Kobayashi, K.; Sakurai, T. Tetrahedron Letters (1977), (52), 4603-6.
23) Kamioka, S; Takahashi, T.; Kawauchi, S.; Adachi, H.; Mori, Y.; Fujii, K.; Uekusa, H.; Doi, T. Organic Letters (2009), 11(11), 2289-2292;
24) Kamioka, S.; Sugiyama, S.; Takahashi T.; Doi, T. Organic & Biomolecular Chemistry (2010), 8(11), 2529-2536.
25) Tashiro, S.; Ogura, Y.; Tsuboyama, S.; Tsuboyama, K.; Shionoya, M. Inorg. Chem. 2011, 50, 4-6.
26) (a) Carr, R.; Evans, N. H.; Parker, D. Chem. Soc. Rev. 2012, 41, 7673. (b) Shen, Z.; Wang, T.; Shi, L.; Tang, Z.; Liu, M. Chem. Sci, 2015, 6, 4267. (c) Morisaki, Y.; Gon, M.; Sasamori, T.; Tokitoh, N.; Chujo, Y. J. Am. Chem. Soc. 2014, 136, 3350.
27) Xu, J.; Corneillie, T. M.; Moore, E. G.; Law, G.-L.; Butlin, N. G.; Raymond, K. N. J. Am. Chem. Soc. 2011, 133, 19900.
28) Wakabayashi, M.; Yokojima, S.; Fukaminato, T.; Shiino, K.-i.; Irie, M.; Nakamura, S. J. Phys. Chem A 2014, 118, 5046.
29) Kumar, J.; Nakashima, T.; Kawai, T. J. Phys. Chem. Lett. 2015, 6, 3445.
30) Bruce, J. I.; Parker, D.; Lopinski, S.; Peacock, R. D. Chirality 2002, 14, 562.
31) Zinna, F.; Di Bari, L. Chirality 2015, 27, 1.
32) Mason, S. F. Molecular Optical Activity and the Chiral Discriminations; Cambridge University Press, 1982.
33) (a) Sánchez-Carnerero, E. M.; Moreno, F.; Maroto, B. L.; Agarrabeitia, A. R.; Ortiz, M. J.; Vo, B. G.; Muller, G.; Moya, S. d. l. J. Am. Chem. Soc. 2014, 136, 3346. (b) Nakamura, K.; Furumi, S.; Takeuchi, M.; Shibuya, T.; Tanaka, K. J. Am. Chem. Soc. 2014, 136, 5555. (c) San Jose, B. A.; Yan, J.; Akagi, K. Angew. Chem., Int. Ed. 2014, 53, 10641. (d) Inouye, M.; Hayashi, K.; Yonenaga, Y.; Itou, T.; Fujimoto, K.; Uchida, T. a.; Iwamura, M.; Nozaki, K. Angew. Chem., Int. Ed. 2014, 53, 14392. (e) Li, H.; Zheng, X.; Su, H.; Lam, J. W.; Wong, K. S.; Xue, S.; Huang, X.; Huang, X.; Li, B. S.; Tang, B. Z. Sci. Rep. 2016, 6, 19277. (f) Feuillastre, S.; Pauton, M.; Gao, L.; Desmarchelier, A.; Riives, A. J.; Prim, D.; Tondelier, D.; Geffroy, B.; Muller, G.; Clavier, G. J. Am. Chem. Soc. 2016, 138, 3990.
34) (a) Seitz, M.; Moore, E. G.; Ingram, A. J.; Muller, G.; Raymond, K. N. J. Am. Chem. Soc. 2007, 129, 15468. (b) Lunkley, I. L.; Shirotani, D.; Yamanari, K.; Kaizaki, S.; Muller, G. J. Am. Chem. Soc. 2008, 130, 13814.
35) Muller, G. Dalton Trans. 2009, 44, 9692.
36) Caravan, P.; Ellison, J. J.; McMurry, T. J.; Lauffer, R. B. Chem. Rev. 1999, 99, 2293.
37) Mewis, R. E.; Archibald, S. J. Coord. Chem. Rev. 2010, 254, 1686.
38) Montgomery, C. P.; Murray, B. S.; New, E. J.; Pal, R.; Parker, D. Acc. Chem. Res. 2009, 42, 925.
39) (a) Aime, S.; Barge, A.; Bruce, J. I.; Botta, M.; Howard, J. A.; Moloney, J. M.; Parker, D.; De Sousa, A. S.; Woods, M. J. Am. Chem. Soc. 1999, 121, 5762. (b) Parker, D.; Dickins, R. S.; Pushmann, H.; Crossland, C.; Howard, J. A. K. Chem. Rev. 2002, 102, 1977.
40) Ranganathan, R. S.; Raju, N.; Fan, H.; Zhang, X.; Tweedle, M. F.; Desreux, J. F.; Jacques, V. Inorg. Chem. 2002, 41, 6856.
41) (16) Woods, M.; Kovacs, Z.; Zhang, S.; Sherry, A. D. Angew. Chem., Int. Ed. 2003, 42, 5889.
42) (a) Dickins, R. S.; Howard, J. A.; Lehmann, C. W.; Moloney, J.; Parker, D.; Peacock, R. D. Angew. Chem., Int. Ed. Engl. 1997, 36, 521. (b) Dickins, R. S.; Howard, J. A.; Maupin, C. L.; Moloney, J. M.; Parker, D.; Riehl, J. P.; Siligardi, G.; Williams, J. Chem.-Eur. J. 1999, 5, 1095.
43) Haussinger, D.; Huang, J.-r.; Grzesiek, S. J. Am. Chem. Soc. 2009, 131, 14761.
44) Moore, E. G.; Samuel, A. P.; Raymond, K. N. Acc. Chem. Res. 2009, 42, 542.
45) Richardson, F. S. Inorg. Chem. 1980, 19, 2806.
46) Sánchez-Carnerero, E. M.; Agarrabeitia, A. R.; Moreno, F.; Maroto, B. L.; Muller, G.; Ortiz, M. J.; de la Moya, S. Chem.-Eur. J. 2015, 21, 13488.
47) Soulié, M.; Latzko, F.; Bourrier, E.; Placide; V.; Butler, S. J.; Pal, R.; Walton, J. W.; Baldeck, P. L.; Le Guennic, B.; Andraud, C.; Zwier, J. M.; Lamarque, L.; Parker, D.; Maury, O. Chem.-Eur. J. 2014, 20,
48) 8636.
49) Yuasa, J.; Ohno, T.; Miyata, K.; Tsumatori, H.; Hasegawa, Y.; Kawai, T. J. Am. Chem. Soc. 2011, 133, 9892.
50) (a) Harada, T.; Nakano, Y.; Fujiki, M.; Naito, M.; Kawai, T.; Hasegawa, Y. Inorg. Chem. 2009, 48, 11242. (b) Harada, T.; Tsumatori, Nishiyama, K.; Yuasa, J.; Hasegawa, Y.; Kawai, T. Inorg. Chem. 2012, 51, 6476.
51) Carr, R.; Di Bari, L.; Piano, S. L.; Parker, D.; Peacock, R. D.; Sanderson, J. M. Dalton Trans. 2012, 41, 13154.
52) NOTA: 1,4,7-triazacyclononane-N,N',N"-triacetic acid; DOTA: 1,4,7,10-tetraazacyclododecane-1,4,7,10-tetraacetic acid.
53) Woods, M.; Aime, S.; Botta, M.; Howard, J. A.; Moloney, J. M.; Navet, M.; Parker, D.; Port, M.; Rousseaux, O. J. Am. Chem. Soc. 2000, 122, 9781.
54) Botta, M.; Quici, S.; Pozzi, G.; Marzanni, G.; Pagliarin, R.; Barra, S.; Crich, S. G. Org. Biomol. Chem. 2004, 2, 570.
55) Dai, L.; Lo, W.-S.; Coates, I. D.; Pal, R.; Law, G.-L. Inorg, Chem, 2016, DOI: 10.1021/acs.inorgchem.6b01546
56) Payne, K. M.; Woods, M. Bioconjugate Chem. 2015, 26, 338.
57) Evans, N. H.; Carr, R.; Delbianco, M.; Pal, R.; Yufit, D. S.; Parker, D. Dalton Trans. 2013, 42, 15610.
58) Beeby, A.; Clarkson, I. M.; Dickins, R. S.; Faulkner, S.; Parker, D.; Royle, L.; de Sousa, A. S.; Williams, J. A. G.; Woods, M. J. Chem. Soc., Perkin Trans. 2 1999, 493.
59) Supkowski, R. M.; Horrocks, W. D. Jr Inorg. Chim. Acta 2002, 340, 44.
60) Holz, R. C.; Chang, C. A.; Horrocks, W. D., Jr Inorg. Chem. 1991, 30, 3270.
61) Aebischer, A.; Gumy, F.; Bünzli, J.-C. G. Phys. Chem. Chem. Phys. 2009, 11, 1346.
62) Tanner, P. A. Chem. Soc. Rev. 2013, 42, 5090.

63) Carr, R.; Puckrin, R.; McMahon, B. K. Pal, R.; Parker, D. *Methods and Applications in Fluorescence* 2014, 2, 024007.
64) Faulkner, S.; Burton-Pye, B. P. *Chem. Commum.* 2005, 259-261.
65) Walton, J. W.; Bourdolle, A.; Butler, S. J.; Soulie, M.; Delbianco, M.; McMahon, B. K.; Pal, R.; Puschmann, H.; Zwier, J. M.; Lamarque, L.; Maury, O.; Andraud, C.; Parker, D. *Chem. Commum.* 2013, 49, 1600-1602.
66) Mishra, A.; Gottschalk, S.; Engelmann, J.; Parker, D. *Chem. Sci.* 2012, 3, 131-135.
67) Wiener, E. C.; Abadjian, M.-C.; Sengar, R.; Vander Elst, L.; Van Niekerk, C.; Grotjahn, D. B.; Leung, P. Y.; Schulte, C.; Moore, C. E.; Rheingold, A. L. *Inorg. Chem.* 2014, 53, 6554-6568.
68) Arava, V. R.; Amasa, S. R.; Bhatthula, B. K. G.; Kompella, L. S.; Matta, V. P.; Subha, M. C. S. Synthetic Communications, 2013, 43(21), 2892-2897.
69) Bosch, M. P.; Campos, F.; Niubo, I.; Rosell, G.; Diaz, J. L.; Brea, J.; Loza, M. I.; Guerrero, A. Journal of Medicinal Chemistry, 2004, 47(16), 4041-4053.

What is claimed is:

1. A method for imaging an organ selected from the group consisting of a liver and a kidney comprising the steps of
    (a) administering a cyclen metal complex to a subject in need thereof;
    (b) detecting radiation emitted by said metal complex at the organ; and
    (c) forming an image therefrom, wherein said cyclen metal complex comprises a cyclen of Formula (I):

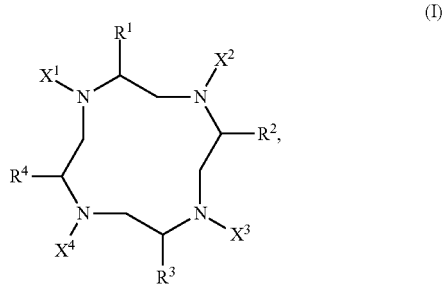

(I)

wherein each of $R^1$, $R^2$, $R^3$ and $R^4$ is ethyl; or each of $R^1$, $R^2$, $R^3$ and $R^4$ is $-(CH_2)_4NH_2$; and each of $X^1$, $X^2$, $X^3$ and $X^4$ is $-CH_2CO_2H$; and Gadolinium, wherein a metal complex is formed between said cyclen and said one or more metals.

2. The method of claim 1, wherein said imaging is magnetic resonance imaging.

3. The method of claim 1, wherein the subject is a vertebrate, a mammal or human.

4. The method of claim 1, wherein the cyclen metal complex is administered orally, nasally, aurally, ocularly, sublingually, buccally, systemically, transdermally, mucosally, via cerebral spinal fluid injection, vein injection, muscle injection, peritoneal injection, subcutaneous injection, or by inhalation.

5. The method of claim 1, wherein said imaging is in vivo.

6. The method of claim 1, wherein each of $R^1$, $R^2$, $R^3$ and $R^4$ is ethyl.

7. The method of claim 1, wherein each of $R^1$, $R^2$, $R^3$ and $R^4$ is $-(CH_2)_4NH_2$.

8. The method of claim 1, wherein said cycler of formula (I) is selected from the group consisting of:

2,2',2'',2'''-((2S,5S,8S,11S)-2,5,8,11-tetraethyl-1,4,7,10-tetraazacyclododecane-1,4,7,10-tetrayl)tetraacetic acid;

2,2',2'',2'''-((2R,5R,8R,11R)-2,5,8,11-tetraethyl-1,4,7,10-tetraazacyclododecane-1,4,7,10-tetrayl)tetraacetic acid;

2,2',2'',2'''-((2S,5S,8S,11S)-2,5,8,11-tetrakis(4-aminobutyl)-1,4,7,10-tetraazacyclododecane-1,4,7,10-tetrayl)tetraacetic acid.

9. The method of claim 1, wherein each of each of $R^1$, $R^2$, $R^3$ and $R^4$ is $-(CH_2)_4NH_2$ and the organ is a kidney; or each of $R^1$, $R^2$, $R^3$ and $R^4$ is ethyl and the organ is a liver.

* * * * *